US010443100B2

(12) United States Patent
Salomon et al.

(10) Patent No.: US 10,443,100 B2
(45) Date of Patent: *Oct. 15, 2019

(54) GENE EXPRESSION PROFILES ASSOCIATED WITH SUB-CLINICAL KIDNEY TRANSPLANT REJECTION

(71) Applicants: THE SCRIPPS RESEARCH INSTITUTE, La Jolla, CA (US); NORTHWESTERN UNIVERSITY, Evanston, IL (US)

(72) Inventors: Daniel R. Salomon, San Diego, CA (US); John Friedewald, Chicago, IL (US); Sunil Kurian, San Diego, CA (US); Michael M. Abecassis, Highland Park, IL (US); Steve Head, Lakeside, CA (US); Phillip Ordoukhanian, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/358,390

(22) Filed: Nov. 22, 2016

(65) Prior Publication Data

US 2017/0137885 A1 May 18, 2017

Related U.S. Application Data

(63) Continuation of application No. PCT/US2015/032202, filed on May 22, 2015, which is a continuation-in-part of application No. 14/481,167, filed on Sep. 9, 2014, and a continuation-in-part of application No. PCT/US2014/054735, filed on May 22, 2014.

(60) Provisional application No. 62/001,902, filed on May 22, 2014, provisional application No. 62/001,909, filed on May 22, 2014, provisional application No. 62/001,889, filed on May 22, 2014, provisional application No. 62/029,038, filed on Jul. 25, 2014.

(51) Int. Cl.
| | |
|---|---|
| *C12Q 1/6883* | (2018.01) |
| *G16H 50/30* | (2018.01) |
| *G16H 50/20* | (2018.01) |
| *G16B 20/00* | (2019.01) |
| *G16B 40/30* | (2019.01) |
| *G16B 40/20* | (2019.01) |
| *G16B 25/10* | (2019.01) |

(52) U.S. Cl.
CPC .......... *C12Q 1/6883* (2013.01); *G16B 20/00* (2019.02); *G16B 40/20* (2019.02); *G16B 40/30* (2019.02); *G16H 50/20* (2018.01); *G16H 50/30* (2018.01); *C12Q 2537/165* (2013.01); *C12Q 2600/106* (2013.01); *C12Q 2600/112* (2013.01); *C12Q 2600/118* (2013.01); *C12Q 2600/158* (2013.01); *G16B 25/10* (2019.02); *Y02A 90/26* (2018.01)

(58) Field of Classification Search
None
See application file for complete search history.

(56) References Cited

U.S. PATENT DOCUMENTS

| | | |
|---|---|---|
| 5,210,015 A | 5/1993 | Gelfand et al. |
| 5,458,852 A | 10/1995 | Buechler |
| 5,480,792 A | 1/1996 | Buechler et al. |
| 5,525,524 A | 6/1996 | Buechler et al. |
| 5,538,848 A | 7/1996 | Livak et al. |
| 5,578,832 A | 11/1996 | Trulson et al. |
| 5,631,734 A | 5/1997 | Stern et al. |
| 5,679,526 A | 10/1997 | Buechler et al. |
| 5,824,799 A | 10/1998 | Buechler et al. |
| 5,851,776 A | 12/1998 | Valkirs |
| 5,855,527 A | 1/1999 | Koole |
| 5,863,736 A | 1/1999 | Haaland |
| 5,922,615 A | 7/1999 | Nowakowski et al. |
| 5,939,272 A | 8/1999 | Buechler et al. |
| 5,947,124 A | 9/1999 | Buechler et al. |
| 5,985,579 A | 11/1999 | Buechler et al. |
| 6,019,944 A | 2/2000 | Buechler |
| 6,020,165 A | 2/2000 | Yue et al. |
| 6,113,855 A | 9/2000 | Buechler |
| 6,143,576 A | 11/2000 | Buechler |
| 6,187,534 B1 | 2/2001 | Strom et al. |
| 6,623,738 B1 | 9/2003 | Tessier-Lavigne et al. |
| 6,878,518 B2 | 4/2005 | Whitehead |

(Continued)

FOREIGN PATENT DOCUMENTS

| | | |
|---|---|---|
| EP | 1850130 B1 | 11/2011 |
| EP | 2209916 B1 | 12/2011 |

(Continued)

OTHER PUBLICATIONS

First, M. Roy. Renal function as a predictor of long-term graft survival in renal transplant patients. Nephrol. Dial. Transplant. vol. 18, Suppl. 1, pp. i3-i6. (Year: 2003).*

(Continued)

*Primary Examiner* — Channing S Mahatan
(74) *Attorney, Agent, or Firm* — Hugh Wang; Thomas Fitting; Kimberly Stopak

(57) ABSTRACT

By a genome-wide gene analysis of expression profiles of over 50,000 known or putative gene sequences in peripheral blood, the present inventors have identified a consensus set of gene expression-based molecular biomarkers associated with subclinical acute rejection (subAR). These genes sets are useful for diagnosis, prognosis, monitoring of subAR.

20 Claims, 7 Drawing Sheets

(56) References Cited

U.S. PATENT DOCUMENTS

| | | | |
|---|---|---|---|
| 6,927,028 | B2 | 8/2005 | Dennis et al. |
| RE39,920 | E | 11/2007 | Umansky et al. |
| 7,415,358 | B2 | 8/2008 | Mendrick et al. |
| 7,426,441 | B2 | 9/2008 | Mendrick et al. |
| 7,615,355 | B2 | 11/2009 | Papadopoulos et al. |
| 7,645,575 | B2 | 1/2010 | Wohlgemuth et al. |
| 7,741,038 | B2 | 6/2010 | Sarwal et al. |
| 7,785,797 | B2 | 8/2010 | Wohlgemuth et al. |
| 7,811,767 | B2 | 10/2010 | Raulf et al. |
| 7,883,858 | B2 | 2/2011 | Hood et al. |
| 7,994,286 | B2 | 8/2011 | Watts et al. |
| 7,998,687 | B2 | 8/2011 | Grass |
| 8,003,333 | B2 | 8/2011 | Charlton |
| 8,333,970 | B2 | 12/2012 | Aukerman et al. |
| 8,486,626 | B2 | 7/2013 | Umansky et al. |
| 8,512,953 | B2 | 8/2013 | Saito et al. |
| 8,586,006 | B2 | 11/2013 | Hood et al. |
| 8,735,080 | B2 | 5/2014 | Labrie et al. |
| 9,102,983 | B2 | 8/2015 | Winkler et al. |
| 2004/0126767 | A1 | 7/2004 | Anderberg et al. |
| 2006/0216722 | A1 | 9/2006 | Betsholtz et al. |
| 2006/0263813 | A1 | 11/2006 | Rosenberg et al. |
| 2006/0281122 | A1 | 12/2006 | Bryant et al. |
| 2007/0099251 | A1 | 5/2007 | Zhang et al. |
| 2007/0122806 | A1 | 5/2007 | Strom et al. |
| 2008/0044403 | A1 | 2/2008 | Sawitzki et al. |
| 2008/0131441 | A1 | 6/2008 | Suthanthiran |
| 2009/0053195 | A1 | 2/2009 | Raulf et al. |
| 2009/0053695 | A1 | 2/2009 | Tanigawara et al. |
| 2009/0202531 | A1 | 8/2009 | Aukerman et al. |
| 2009/0311745 | A1 | 12/2009 | Liebeton et al. |
| 2010/0022627 | A1 | 1/2010 | Scherer |
| 2010/0068711 | A1 | 3/2010 | Umansky et al. |
| 2010/0086928 | A1 | 4/2010 | Feinberg |
| 2010/0120041 | A1 | 5/2010 | Quaggin |
| 2010/0151467 | A1 | 6/2010 | Wohlgemuth et al. |
| 2010/0196426 | A1 | 8/2010 | Skog et al. |
| 2010/0233716 | A1 | 9/2010 | Saint-Mezard et al. |
| 2010/0266579 | A1 | 10/2010 | Cook et al. |
| 2010/0305000 | A1 | 12/2010 | Mathew et al. |
| 2011/0003708 | A1 | 1/2011 | Kinar et al. |
| 2011/0034532 | A1 | 2/2011 | Li et al. |
| 2011/0039710 | A1 | 2/2011 | Tibbetts |
| 2011/0065599 | A1 | 3/2011 | Labrie et al. |
| 2011/0086051 | A1 | 4/2011 | Zuckerman et al. |
| 2011/0171750 | A1 | 7/2011 | Struck et al. |
| 2011/0189680 | A1* | 8/2011 | Keown ............... C12Q 1/6883 435/6.12 |
| 2012/0003633 | A1 | 1/2012 | Kuijpers et al. |
| 2012/0094853 | A1 | 4/2012 | Clark et al. |
| 2012/0101001 | A1 | 4/2012 | Suthanthiran |
| 2012/0135882 | A1 | 5/2012 | Bottinger |
| 2012/0165207 | A1* | 6/2012 | Butte ............... G01N 33/6893 506/9 |
| 2012/0178642 | A1 | 7/2012 | Salomon et al. |
| 2012/0192878 | A1 | 8/2012 | Toyoda |
| 2012/0219542 | A1 | 8/2012 | Reiser |
| 2012/0251527 | A1 | 10/2012 | Reiser |
| 2013/0012860 | A1 | 1/2013 | Suthanthiran et al. |
| 2013/0040301 | A1 | 2/2013 | Strom et al. |
| 2013/0045873 | A1 | 2/2013 | Hood et al. |
| 2013/0115232 | A1 | 5/2013 | Ferrara et al. |
| 2013/0143223 | A1 | 6/2013 | Hernandez-Fuentes et al. |
| 2013/0143755 | A1 | 6/2013 | Sarwal et al. |
| 2013/0216557 | A1 | 8/2013 | Bienkowska et al. |
| 2013/0236437 | A1 | 9/2013 | Bishopric et al. |
| 2014/0030266 | A1 | 1/2014 | Bucala et al. |
| 2014/0045915 | A1 | 2/2014 | Skog et al. |
| 2014/0121126 | A1 | 5/2014 | Bivona et al. |
| 2015/0011401 | A1 | 1/2015 | Davicioni et al. |
| 2015/0167085 | A1 | 6/2015 | Salomon et al. |

FOREIGN PATENT DOCUMENTS

| | | |
|---|---|---|
| GB | 1603464.7 | 2/2016 |
| WO | WO-9710365 A1 | 3/1997 |
| WO | WO-9727317 A1 | 7/1997 |
| WO | WO-0238561 A1 | 5/2002 |
| WO | WO-03082859 A1 | 10/2003 |
| WO | WO-2004052359 A1 | 6/2004 |
| WO | WO-2004059293 A2 | 7/2004 |
| WO | WO-2005066156 A1 | 7/2005 |
| WO | WO-2007104537 A2 | 9/2007 |
| WO | WO-2008021290 A2 | 2/2008 |
| WO | WO-2008048970 A2 | 4/2008 |
| WO | WO-2009060035 A1 | 5/2009 |
| WO | WO-2009151600 A2 | 12/2009 |
| WO | WO-2011066380 A1 | 6/2011 |
| WO | WO-2013049892 A1 | 4/2013 |
| WO | PCT/US2013/068456 | 5/2014 |
| WO | WO-2014074501 A1 | 5/2014 |

OTHER PUBLICATIONS

Anglicheau; et al. Noninvasive prediction of organ graft rejection and outcome using gene expression patterns. Transplantation. Jul. 27, 2008;86(2):192-9. doi: 10.1097/TP.0b013e31817eef7b.

Banasik, et al. Chronic allograft nephropathy—immunologic and nonimmunologic factors. Ann Transplant. 2006;11(1):7-10.

Bao, et al. A novel accurate rapid ELISA for detection of urinary connective tissue growth factor, a biomarker of chronic allograft nephropathy. Transplant Proc. Sep. 2008;40(7):2361-4. doi: 10.1016/j.transproceed.2008.07.122.

Bolstad, et al. A comparison of normalization methods for high density oligonucleotide array data based on variance and bias. Bioinformatics. Jan. 22, 2003;19(2):185-93.

Brouard, et al. Identification of peripheral blood transcriptional biomarker panel associated with operational renal allograft tolerance. Proc Natl Acad Sci U S A. Sep. 25, 2007;104(39):15448-53. Epud Sep. 14, 2007.

Brown, et al. Knowledge-based analysis of microarray gene expression data by using support vector machines. Proc Natl Acad Sci U S A. 2000; 97(1): 262-7.

Calne, et al. Cyclosporin A in patients receiving renal allografts from cadaver donors. Lancet. Dec. 23-30, 1978;2(8104-5):1323-7.

Cardinale; et al. Transcriptome profiling of human ulcerative colitis mucosa reveals altered expression of pathways enriched in genetic susceptibility loci. PLoS One. May 1, 2014;9(5):e96153. doi: 10.1371/journal.pone.0096153. eCollection 2014.

Chang, et al. Prediction of chronic allograft damage index of renal allografts using serum level of plasminogen activator inhibitor-1. Clin Transplant. Mar.-Apr. 2009;23(2):206-12. doi: 10.1111/j.1399-0012.2009.00970.x. Epub Feb. 11, 2009.

Chapman. Longitudinal analysis of chronic allograft nephropathy: clinicopathologic correlations. Kidney Int Suppl. 2005; (99): S108-12.

Chau, et al. Validation of analytic methods for biomarkers used in drug development. Clin Cancer Res. Oct. 1, 2008;14(19):5967-76. doi: 10.1158/1078-0432.CCR-07-4535.

Clarke, et al. Characterization of renal allograft rejection by urinary proteomic analysis. Ann Surg. May 2003;237(5):660-4; discussion 664-5.

Colvin, RB. Chronic allograft nephropathy. N Engl J Med Dec. 11, 2003;349(24):2288-90.

Dabney, AR. Classification of microarrays to nearest centroids. Bioinformatics. Nov. 15, 2005;21(22):4148-54. Epub Sep. 20, 2005.

De Mattos, et al. Nephrotoxicity of immunosuppressive drugs: long-term consequences and challenges for the future. Am J Kidney Dis. Feb. 2000;35(2):333-46.

Deng, et al. Noninvasive discrimination of rejection in cardiac allograft recipients using gene expression profiling. Am J Transplant. Jan. 2006;6(1):150-60.

Derisi, et al. Use of a cDNA microarray to analyse gene expression patterns in human cancer. Nat Genet. Dec. 1996;14(4):457-60.

(56) References Cited

OTHER PUBLICATIONS

Diaz-Uriarte, et al. Gene selection and classification of microarray data using random forest. BMC bioinformatics. 2006; 7: 3.

Dudoit. Comparison of discrimination methods for the classification of tumors using gene expression data. Journal of the American Statistical Association 97: 77-87, 2002.

Eisen, et al. Cluster analysis and display of genome-wide expression patterns. Proc Natl Acad Sci U S A. Dec. 8, 1998;95(25):14863-8.

Flechner, et al. De novo kidney transplantation without use of calcineurin inhibitors preserves renal structure and function at two years. Am J Transplant. Nov. 2004;4(11):1776-85.

Flechner, et al. Kidney transplant rejection and tissue injury by gene profiling of biopsies and peripheral blood lymphocytes. Am J Transplant. Sep. 2004;4(9):1475-89.

Flechner, et al. Kidney transplantation with sirolimus and mycophenolate mofetil-based immunosuppression: 5-year results of a randomized prospective trial compared to calcineurin inhibitor drugs. Transplantation. Apr. 15, 2007;83(7):883-92.

Gibbs, et al. Quantitative detection of changed in cytokine gene expression in peripheral blood mononuclear cells correlates with and precedes acute rejection in renal transplant recipients. Transpl Immunol. Jun. 2005;14(2):99-108. Epub Mar. 29, 2005.

Gibson, et al. A novel method for real time quantitative RT-PCR. Genome Res. Oct. 1996;6(10):995-1001.

GP. GraphPad QuickCalcs: free statistical calculators. GraphPad Software. 2014. Accessed Dec. 9, 2014 http://www.graphpad.com/quickcalcs/index.cfm.

Guo, et al. Regularized linear discriminant analysis and its application in microarrays. Biostatistics. Jan. 2007;8(1):86-100. Epub Apr. 7, 2006.

Harrell, et al. Multivariable prognostic models: issues in developing models, evaluating assumptions and adequacy, and measuring and reducing errors. Statistics in medicine. 1996;15(4): 361-87.

Harrell. Regression Modeling Strategies: with applications to linear models, logistic regression, and survival anaysis. Springer, New York 2001.

Heid, et al. Real time quantitative PCR. Genome Res. Oct. 1996;6(10):986-94.

Holland, et al. Detection of specific polymerase chain reaction product by utilizing the 5'—3' exonuclease activity of Thermus aquaticus DNA polymerase. Proc Natl Acad Sci U S A. Aug. 15, 1991;88(16):7276-80.

Horwitz, et al. Detection of cardiac allograft rejection and response to immunosuppressive therapy with peripheral blood gene expression. Circulation. Dec. 21, 2004;110(25):3815-21. Epub Dec. 6, 2004.

Hsu, et al. A comparison of methods for multiclass support vector machines. IEEE Trans Neural Netw. 2002;13(2):415-25. doi: 10.1109/72.991427.

Huang, et al. Classification of malignant pediatric renal tumors by gene expression. Pediatr Blood Cancer. Jun. 2006;46(7):728-38.

Hymes, et al. Prevalence of clinical rejection after surveillance biopsies in pediatric renal transplants: does early subclinical rejection predispose to subsequent rejection episodes? Pediatr Transplant. Nov. 2009;13(7):823-6. doi: 10.1111/j.1399-3046.2009.01200.x. Epub Jun. 8, 2009.

International search report and written opinion dated May 24, 2011 for PCT Application No. PCT/US2010/041598.

International search report and written opinion dated Oct. 19, 2015 for PCT Application No. US2015/032191.

International search report and written opinion dated Oct. 26, 2015 for PCT Application No. US2015/032195.

International search report and written opinion dated Nov. 4, 2015 for PCT Application No. US2015/032202.

International search report and written opinion dated Dec. 23, 2014 for PCT Application No. PCT/US2014/054735.

Jevnikar, et al. Late kidney allograft loss: what we know about it, and what we can do about it. Clin J Am Soc Nephrol. Mar. 2008;3 Suppl 2:S56-67. doi: 10.2215/CJN.03040707.

Kurian, et al. Applying genomics to organ transplantation medicine in both discovery and validation of biomarkers. Int Immunopharmacol. Dec. 20, 2007;7(14):1948-60. Epub Aug. 9, 2007.

Kurian, et al. Biomarkers for early and late stage chronic allograft nephropathy by proteogenomic profiling of peripheral blood. PLoS One. Jul. 10, 2009;4(7):e6212. doi: 10.1371/journal.pone.0006212.

Kurian, et al. Molecular classifiers for acute kidney transplant rejection in peripheral blood by whole genome gene expression profiling. Am J Transplant. May 2014;14(5):1164-72. doi: 10.1111/ajt.12671. Epub Apr. 11, 2014.

Kurian. Genomics and proteomics in transplantation. Current opinion in organ transplantation. 2005, 10: 193-197.

Lachenbruch, et al. Biomarkers and surrogate endpoints in renal transplantation: present status and considerations for clinical trial design. Am J Transplant. Apr. 2004;4(4):451-7.

Lee, et al. Fit-for-purpose method development and validation for successful biomarker measurement. Pharm Res. Feb. 2006;23(2):312-28. Epub Jan. 12, 2006.

Lerut, et al. Acute rejection in non-compliant renal allograft recipients: a distinct morphology. Clin Transplant. 2007; 21(3): 344-51.

Levitsky; et al. Clinical and plasma proteomic markers correlating with chronic kidney disease after liver transplantation. Am J Transplant. Sep. 2011;11(9):1972-8. doi: 10.1111/j.1600-6143.2011.03669.x. Epub Jul. 27, 2011.

Li, et al. A peripheral blood diagnostic test for acute rejection in renal transplantation. Am J Transplant. Oct. 2012;12(10):2710-8. doi: 10.1111/j.1600-6143.2012.04253.x.

Lipshutz, et al. High density synthetic oligonucleotide arrays. Nat Genet. Jan. 1999;21(1 Suppl):20-4.

Liu, et al. A model for random sampling and estimation of relative protein abundance in shotgun proteomics. Anal Chem. Jul. 15, 2004;76(14):4193-201.

Livak, et al. Oligonucleotides with fluorescent dyes at opposite ends provide a quenched probe system useful for detecting PCR product and nucleic acid hybridization. PCR Methods Appl. Jun. 1995;4(6):357-62.

Lockhart, et al. Expression monitoring by hybridization to high-density oligonucleotide arrays. Nat Biotechnol. Dec. 1996;14(13):1675-80.

Maluf, et al. Molecular pathways involved in loss of kidney graft function with tubular atrophy and interstitial fibrosis. Mol Med. May-Jun. 2008;14(5-6):276-85. doi: 10.2119/2007-00111.Maluf.

Mannon, et al. Chronic rejection of mouse kidney allografts. Kidney Int. May 1999;55(5):1935-44.

Mas, et al. Establishing the molecular pathways involved in chronic allograft nephropathy for testing new noninvasive diagnostic markers. Transplantation. Feb. 27, 2007;83(4):448-57.

McCall, et al. Frozen robust multiarray analysis (fRMA). Biostatistics. Apr. 2010;11(2):242-53. doi: 10.1093/biostatistics/kxp059. Epub Jan. 22, 2010.

McCall, et al. Thawing Frozen Robust Multi-array Analysis (fRMA). BMC Bioinformatics. Sep. 16, 2011;12:369. doi: 10.1186/1471-2105-12-369.

Meier-Kriesche, et al. Lack of improvement in renal allograft survival despite a marked decrease in acute rejection rates over the most recent era. Am J Transplant. Mar. 2004;4(3):378-83.

Meier-Kriesche, et al. Survival improvement among patients with end-stage renal disease: trends over time for transplant recipients and wait-listed patients. J Am Soc Nephrol. Jun. 2001;12(6):1293-6.

Mengel, et al. Infiltrates in protocol biopsies from renal allografts. Am J Transplant. 2007; 7(2):356-65.

Mengel, et al. SWOT analysis of Banff: strengths, weaknesses, opportunities and threats of the international Banff consensus process and classification system for renal allograft pathology. Am J Transplant. Oct. 2007;7(10):2221-6.

Miao, et al. Estimating Harrells's Optimism on Predictive Indices Using Bootstrap Samples. SAS Global Forum, San Francisco; 2013.

Moreso, et al. Early subclinical rejection as a risk factor for late chronic humoral rejection. Transplantation. 2012; 93(1):41-6.

Moreso, et al. Subclinical rejection associated with chronic allograft nephropathy in protocol biopsies as a risk factor for late graft loss. Am J Transplant. Apr. 2006;6(4):747-52.

(56) References Cited

OTHER PUBLICATIONS

Morrissey, et al. Factors contributing to acute rejection in renal transplantation: the role of noncompliance. Transplant Proc. 2005; 37(5): 2044-7.

Mueller, et al. Assessment of kidney organ quality and prediction of outcome at time of transplantation. 2011. Semin Immunopathol. vol. 33, pp. 185-199.

Nankivell, et al. Chronic allograft nephropathy: current concepts and future directions. Transplantation. Mar. 15, 2006;81(5):643-54.

Nankivell, et al. The natural history of chronic allograft nephropathy. N Engl J Med. Dec. 11, 2003;349(24):2326-33.

Nankivell. Subclinical renal allograft rejection and protocol biopsies: quo vadis? Nat Clin Pract Nephrol. 2008; 4(3): 134-5.

Nielsen, et al. Sequence-selective recognition of DNA by strand displacement with a thymine-substituted polyamide. Science. Dec. 6, 1991;254(5037):1497-500.

Oetting, et al. Urinary beta2-microglobulin is associated with acute renal allograft rejection. Am J Kidney Dis. May 2006;47(5):898-904.

Office Action dated Jan. 9, 2017 for U.S. Appl. No. 14/481,167.
Office Action dated Mar. 12, 2015 for U.S. Appl. No. 13/261,130.
Office Action dated Jun. 15, 2016 for U.S. Appl. No. 14/481,167.
Office Action dated Nov. 13, 2015 for U.S. Appl. No. 13/261,130.
Office Action dated Dec. 2, 2016 for U.S. Appl. No. 13/261,130.
PA. Power Atlas. 2007. Accessed Dec. 9, 2014 http://www.poweratlas.org/.

Pascual, et al. Chronic rejection and chronic cyclosporin toxicity in renal allografts. Immunol Today. Nov. 1998;19(11):514-9.

Pascual, et al. Strategies to improve long-term outcomes after renal transplantation. N Engl J Med. Feb. 21, 2002;346(8):580-90.

Pascual, et al. The clinical usefulness of the renal allograft biopsy in the cyclosporine era: a prospective study. Transplantation. Mar. 15, 1999;67(5):737-41.

Powell, et al. Managing renal transplant ischemia reperfusion injury: novel therapies in the pipeline. Clin Transplant. Jul.-Aug. 2013;27(4):484-91. doi: 10.1111/ctr.12121. Epub Apr. 25, 2013.

Racusen, et al. The Banff 97 working classification of renal allograft pathology. Kidney Int. Feb. 1999;55(2):713-23.

Robin, et al. pROC: an open-source package for R and S+ to analyze and compare ROC curves. BMC Bioinformatics. Mar. 17, 2011;12:77. doi: 10.1186/1471-2105-12-77.

Rodder, et al. Renal allografts with IF/TA display distinct expression profiles of metzincins and related genes. American Journal of Transplantation, vol. 9, No. 3, pp. 517-526, Feb. 2009.

Rush, et al. Subclinical rejection—a potential surrogate marker for chronic rejection—may be diagnosed by protocol biopsy or urine spectroscopy. Ann Transplant. 2000; 5(2): 44-9.

Sabek, et al. Quantitative detection of T-cell activation markers by real-time PCR in renal transplant rejection and correlation with histopathologic evaluation. Transplantation. Sep. 15, 2002; 74(5):701-7.

Sadygov, et al. Code developments to improve the efficiency of automated MS/MS spectra interpretation. J Proteome Res. May-Jun. 2002;1(3):211-5.

Salvadori, et al. Update on ischemia-reperfusion injury in kidney transplantation: Pathogenesis and treatment. World J Transplant. Jun. 24, 2015;5(2):52-67. doi: 10.5500/wjt.v5.i2.52.

Sarwal, et al. Molecular heterogeneity in acute renal allograft rejection identified by DNA microarray profiling. N Engl J Med. Jul. 10, 2003;349(2):125-38.

Schena, et al. Quantitative monitoring of gene expression patterns with a complementary DNA microarray. Science. Oct. 20, 1995;270(5235):467-70.

Scherer, et al. Transcriptome changes in renal allograft protocol biopsies at 3 months precede the onset of interstitial fibrosis/tubular atrophy (IF/TA) at 6 months. Nephrol Dial Transplant. Aug. 2009;24(8):2567-75. doi: 10.1093/ndt/gfp183. Epub Apr. 27, 2009.

Schuab, et al. Proteomic-based identification of cleaved urinary beta2-microglobulin as a potential marker for acute tubular injury in renal allografts. Am J Transplant. Apr. 2005;5(4 Pt 1):729-38.

Schwarz, et al. Risk factors for chronic allograft nephropathy after renal transplantation: a protocol biopsy study. Kidney Int. 2005; 67(1): 341-8.

Shapiro, et al. An analysis of early renal transplant protocol biopsies—the high incidence of subclinical tubulitis. Am J Transplant. May 2001;1(1):47-50.

Shen, et al. Eigengene-based linear discriminant model for tumor classification using gene expression microarray data. Bioinformatics. Nov. 1, 2006;22(21):2635-42. Epub Aug. 22, 2006.

Simon, et al. Serial peripheral blood perforin and granzyme B gene expression measurements for prediction of acute rejection in kidney graft recipients. Am J Transplant. Sep. 2003;3(9):1121-7.

Sis, et al. Endothelial gene expression in kidney transplants with alloantibody indicates antibody-mediated damage despite lack of C4d staining. Am J Transplant. Oct. 2009;9(10):2312-23. doi: 10.1111/j.1600-6143.2009.02761.x. Epub Jul. 22, 2009.

Solez, et al. Banff '05 Meeting Report: differential diagnosis of chronic allograft injury and elimination of chronic allograft nephropathy ('CAN'). Am J Transplant. Mar. 2007;7(3):518-26.

Solez, et al. Banff 07 classification of renal allograft pathology: updates and future directions. Am J Transplant. Apr. 2008;8(4):753-60. doi: 10.1111/j.1600-6143.2008.02159.x. Epub Feb. 19, 2008.

Tabb, et al. DTASelect and Contrast: tools for assembling and comparing protein identifications from shotgun proteomics. J Proteome Res. Jan.-Feb. 2002;1(1):21-6.

Thomas, et al. Chronic kidney disease and its complications. Prim Care. Jun. 2008;35(2):329-44, vii. doi: 10.1016/j.pop.2008.01.008. Review.

Tibshirani, et al. Class prediction by nearest shrunken centroids with applications to DNA microarrays. Statist. Sci. vol. 18 (1): 104-117.

Tibshirani, et al. Diagnosis of multiple cancer types by shrunken centroids of gene expression. Proc Natl Acad Sci U S A. May 14, 2002;99(10):6567-72.

Tijssen, P. Chapter 3 of Laboratory Techniques in Biochemistry and Molecular Biology: Hybridization With Nucleic Acid Probes, Part I. Theory and Nucleic Acid Preparation, Elsevier, N.Y. 1993.

Tonelli, et al. Chronic kidney disease and mortality risk: a systematic review. J Am Soc Nephrol. Jul. 2006;17(7):2034-47. Epub May 31, 2006.

Tou, et al. Pattern Recognition Principals, Addison-Wesley, Reading, Massachusetts. 1974.

U.S. Department of Health and Human Services. OPTN/SRTR Annual Report. Source: OPTN/SRTR Data as of May 4, 2009. http://www.ustransplant.org/annual_reports/current/509a_ki.htm.

Vasconcellos, et al. Cytotoxic lymphocyte gene expression in peripheral blood leukocytes correlates with rejecting renal allografts. Transplantation. Sep. 15, 1998;66(5):562-6.

Washburn et al. Large-scale analysis of the yeast proteome by multidimensional protein identification technology. Nat Biotechnol 19(3):242-247 (2001).

Wiebe, et al. Evolution and clinical pathologic correlations of de novo donor-specific HLA antibody post kidney transplant. Am J Transplant. May 2012;12(5):1157-67. doi: 10.1111/j.1600-6143. 2012.04013.x. Epub Mar. 19, 2012.

Woolf, SH. Screening for prostate cancer with prostate-specific antigen. An examination of the evidence. N Engl J Med. Nov. 23, 1995;333(21):1401-5.

Yates, et al. The aetiology and pathogenesis of chronic allograft nephropathy. Transpl Immunol. Nov. 2006;16(3-4):148-57. Epub Nov. 2, 2006.

Yilmaz, et al. Evaluating the accuracy of functional biomarkers for detecting histological changes in chronic allograft nephropathy. Transpl Int. Jul. 2007;20(7):608-15. Epub May 22, 2007.

Yilmaz, et al. Protocol core needle biopsy and histologic Chronic Allograft Damage Index (CADI) as surrogate end point for long-term graft survival in multicenter studies. J Am Soc Nephrol. Mar. 2003;14(3):773-9.

Zhu, et al. Network-based support vector machine for classification of microarry samples. BMC Bioinformatics. Jan. 30, 2009;10 Suppl 1:S21. doi: 10.1186/1471-2105-10-S1-S21.

Nankivell et al., The Significance of Subclinical Rejection and the Value of Protocol Biopsies, American Journal of Transplantation 2006: 6: 2006-2012.

(56) References Cited

OTHER PUBLICATIONS

Lipman, et al., Immune-Activation Gene Expression in Clinically Stable Renal Allograft Biopsies: Molecular Evidence for Subclinical Rejection, Dec. 27, 1998, vol. 66, 1673-1681, No. 12.
Examination Report under Section 18(3) dated Oct. 17, 2018 for GB Application No. 1609984.8.
EP15795436.7 European Communication dated May 2, 2019.

* cited by examiner

A schematic overview of certain methods in the disclosure.
110. Obtain sample from a transplant recipient 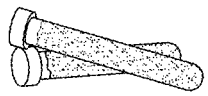
120. Perform assay to determine gene expression level 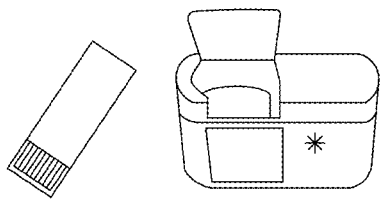
130. Apply computer algorithm to the gene expression level 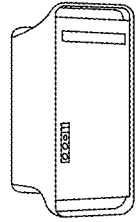
140. Classification based on the results 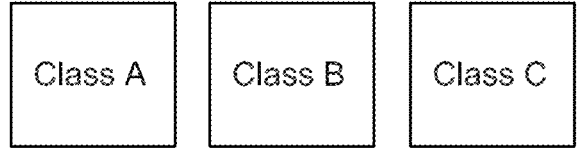
FIG. 1

GENE EXPRESSION PROFILES ASSOCIATED WITH SUB-CLINICAL KIDNEY TRANSPLANT REJECTION

CROSS-REFERENCE TO RELATED APPLICATIONS

This application claims the benefit of priority to International Application No. PCT/US2015/032202, filed May 22, 2015; to U.S. application Ser. No. 14/481,167, filed Sep. 9, 2014; to International Application No. PCT/US2014/054735, filed Sep. 9, 2014; to U.S. Provisional Application No. 62/029,038, filed Jul. 25, 2014; to U.S. Provisional Application No. 62/001,889, filed May 22, 2014; to U.S. Provisional Application No. 62/001,902, filed May 22, 2014; and to U.S. Provisional Application No. 62/001,909, filed May 22, 2014, each of which is incorporated by reference herein in their entirety.

STATEMENT CONCERNING GOVERNMENT SUPPORT

This invention was made with government support under AI063603 awarded by the National Institutes of Health. government has certain rights in the invention.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Kidney transplantation offers a significant improvement in life expectancy and quality of life for patients with end stage renal disease. Unfortunately, graft losses due to allograft dysfunction or other uncertain etiologies have greatly hampered the therapeutic potential of kidney transplantation. Among various types of graft losses, subclinical acute rejection (subAR or SCAR) is histologically defined as acute rejection characterized by tubule-interstitial mononuclear infiltration identified from a biopsy specimen, but without concurrent functional deterioration (variably defined as a serum creatinine not exceeding 10%, 20% or 25% of baseline values).

A critically important challenge for the future of molecular diagnostics in transplantation based on peripheral blood profiling is to predict a state of adequate immunosuppression with immune mediated kidney injury before there is a change in the serum creatinine. This is the challenge of identifying subclinical acute rejection, which at this time is only occasionally and accidentally picked up by protocol biopsies done at arbitrary time points.

The terms subAR and SCAR are used interchangeably herein to refer to subclinical acute rejection. SubAR (or SCAR) is distinct from clinical acute rejection, which is characterized by acute functional renal impairment. The differences between subAR or SCAR and acute rejection (which may appear histologically indistinguishable on a limited sample) can be explained by real quantitative differences of renal cortex affected, qualitative differences (such as increased perforin, granzyme, c-Bet expression or macrophage markers), or by an increased ability of the allograft to withstand immune injury ('accommodation'). SubAR or SCAR is often diagnosed only on biopsies taken as per protocol at a fixed time after transplantation, rather than driven by clinical indication. Its diagnosis cannot rely on traditional kidney function measurements like serum creatinine and glomerular filtration rates. Predicting graft outcomes strictly based on the kidney biopsy is difficult and this invasive procedure has significant costs and risks for patients. Organ biopsy results can also be inaccurate, particularly if the area biopsied is not representative of the health of the organ as a whole (e.g., as a result of sampling error). There can be significant differences between individual observers when they read the same biopsies independently and these discrepancies are particularly an issue for complex histologies that can be challenging for clinicians. In addition, the early detection of rejection of a transplant organ may require serial monitoring by obtaining multiple biopsies, thereby multiplying the risks to the patients, as well as the associated costs.

Transplant rejection is a marker of ineffective immunosuppression and ultimately if it cannot be resolved, a failure of the chosen therapy. The fact that 50% of kidney transplant patients will lose their grafts by ten years post-transplant reveals the difficulty of maintaining adequate and effective long-term immunosuppression. Currently, there are no other effective and reliable blood-based or any other tests for subAR or SCAR diagnosis. Thus, there is a pressing medical need to identify minimally invasive biomarkers that are able to identify subAR or SCAR at a time that changes in therapy may alter outcomes. The present invention addresses this and other unfulfilled needs in the art.

SUMMARY OF THE INVENTION

In one aspect, the disclosure provides methods of detecting, prognosing, diagnosing or monitoring subclinical acute rejection (subAR or SCAR). These methods typically entail obtaining nucleic acids of interest, and then (a) determining or detecting expression levels in a subject of at least 5 genes (e.g., at least 10 genes, at least 20 genes, at least 50 genes, at least 100 genes, at least 300 genes, at least 500 genes, etc.); and (b) detecting, prognosing, diagnosing or monitoring subAR or SCAR in the subject from the expression levels. In some methods, the nucleic acids of interest comprise mRNA extracted from a sample from the subject or nucleic acids derived from the mRNA extracted from the sample from the subject. The methods are particularly useful for analysis of blood samples.

Some of the methods are directed to subjects who have or are at risk of developing subAR or SCAR or acute rejection (AR), or have well-functioning normal transplant (TX). In some of the methods, the subject has a serum creatinine level of less than 3 mg/dL, less than 2.5 mg/dL, less than 2.0 mg/dL, or less than 1.5 mg/dL. In some methods, the subject has a normal serum creatinine level. In some of the methods, for each of the at least five genes, step (b) involves comparing the expression level of the gene in the subject to one or more reference expression levels of the gene associated with subAR or SCAR, acute rejection (AR) or lack of transplant rejection (TX). In some of these methods, step (b) further includes, for each of the at least five genes, assigning the expression level of the gene in the subject a value or other designation providing an indication whether the subject has or is at risk of developing SCAR, has acute rejection (AR), or has well-functioning normal transplant (TX). In some methods, the expression level of each of the at least five genes is assigned a value on a normalized scale of values associated with a range of expression levels in kidney transplant patients with SCAR, with AR, or with TX. In some methods, the expression level of each of the at least five genes is assigned a value or other designation providing an indication that the subject has or is at risk of SCAR, has or is at risk of AR, has well-functioning normal transplant, or that the expression level is uninformative. In some methods, step (b) further includes combining the values or designations for each of the genes to provide a combined value or designation providing an indication whether the subject has or is at risk of SCAR, has acute rejection (AR), or has well-functioning normal transplant (TX). In some embodiments, the method can be repeated at different times on the subject. Some of these methods are directed to subjects who have been receiving a drug, and a change in the combined value or designation over time provides an indication of the effectiveness of the drug.

In some embodiments, the expression level is determined in a subject of at least five genes selected from the genes in one or more of Tables 2, 3, 4, 7, 8, 11, 12, 14, 15, 17, or 18. In another aspect, the methods comprise detecting or determining the expression level of at least 2, 3, 4, 5, 6, 7, 8, 9, 10, 20, 30, 40, 50, 60, 70, 80, 90, 100, 200, 300, 400, 500, 600, 700, 800, 900, 1000, 1500, or 2000 genes selected from at least one of Tables 2, 3, 4, 7, 8, 11, 12, 14, 15, 17, and 18.

In some embodiments, the detection of expression levels comprises applying a two-step classifier to the gene expression levels. In some embodiments, one step in the two-step classifier distinguishes between normal transplant (TX) and AR+subAR. In some embodiments, one step in the two-step classifier distinguishes between AR and subAR.

In various embodiments, the subjects suitable for methods of the invention are patients who have undergone a kidney transplant. Often, the subject has received the kidney transplant within 1 month, 3 months, 1 year, 2 years, 3 years or 5 years of performing step (a). In some methods of the invention, step (a) is performed on a blood sample of the subject. In some methods, the sample is a blood sample and comprises whole blood, peripheral blood, serum, plasma, PBLs, PBMCs, T cells, CD4 T cells CD8 T cells, or macrophages. In some methods, step (a) is performed on a urine sample of the subject. In some methods, step (a) is performed on a biopsy from the subject, preferably a kidney biopsy. In some methods, step (a) is performed on at least 10, 20, 40, 50, 70, 100, 150, 200, 250, 300, 400, or 500 genes from one or more of Tables 2, 3, 4, 7, 8, 11, 12, 14, 15, 17, or 18. Some methods further include changing the treatment regime of the patient responsive to the detecting, prognosing, diagnosing or monitoring step. In these methods, the subject can be one who has received a drug before performing the methods, and the change comprises administering an additional drug or administering a higher dose of the same drug or administering a lower dose of the same drug, or stopping administering the same drug.

Some methods of the invention further include performing an additional procedure to detect SCAR or risk thereof if the determining step provides an indication the subject has or is at risk of SCAR. The additional procedure can be, e.g., examination of a kidney biopsy sample. In some methods of the invention, expression levels of the genes are determined at the mRNA level or at the protein level. In some methods, step (b) can be performed by a computer. In some preferred embodiments, the at least five genes are selected from one or more of Tables 2, 3, 4, 7, 8, 11, 12, 14, 15, 17, or 18.

In a related aspect, the invention provides methods of detecting, prognosing, diagnosing or monitoring subclinical acute rejection (subAR or SCAR) in a subject having normal serum creatinine level. These methods involve obtaining nucleic acids of interest, and then (a) determining or detecting expression levels in the subject of at least 2 genes; and (b) detecting, prognosing, diagnosing or monitoring subAR or SCAR in the subject from the expression levels. In some of these methods, the methods comprise determining or detecting the expression levels in the subject of at least five genes. In some of these methods, the at least two genes or the at least five genes are selected from the genes in one or more of Tables 2, 3, 4, 7, 8, 11, 12, 14, 15, 17, or 18. In some of these methods, the nucleic acids of interest comprise mRNA extracted from a sample from a subject or nucleic acids derived from the mRNA extracted from the sample from the subject. In some methods, the sample is a blood sample. In some methods, the nucleic acids of interest are contacted with probes, wherein the probes are specific for the at least two genes or the at least five genes. In some of these methods, for each of the at least two genes or the at least five genes, step (b) entails comparing the expression level of the gene in the subject to one or more reference expression levels of the gene associated with SCAR, or lack of transplant rejection (TX). In some of these methods, step (b) further includes, for each of the at least two genes or the at least five genes, assigning the expression level of the gene in the subject a value or other designation providing an indication whether the subject has or is at risk of developing SCAR. In some methods, the expression level of each of the at least two genes or the at least five genes is assigned a value on a normalized scale of values associated with a range of expression levels in kidney transplant patients with and without SCAR. In some methods, the expression level of each of the at least two genes or at least five genes is assigned a value or other designation providing an indication that the subject has or is at risk of SCAR, lacks and is not at risk of SCAR, or that the expression level is uninformative. In some of these methods, step (b) further includes combining the values or designations for each of the genes to provide a combined value or designation providing an indication whether the subject has or is at risk of subAR or SCAR.

In various embodiments, the method can be repeated at different times on the subject. In some methods, the subject can be one who is receiving a drug, and a change in the combined value or designation over time provides an indication of the effectiveness of the drug. Some methods of the invention are directed to subjects who have undergone a kidney transplant within 1 month, 3 months, 1 year, 2 years, 3 years or 5 years of performing step (a). In some methods, step (a) is performed on a blood sample of the subject. In some methods, the sample is a blood sample and comprises whole blood, peripheral blood, serum, plasma, PBLs, PBMCs, T cells, CD4 T cells CD8 T cells, or macrophages. In some methods, step (a) is performed on a urine sample of the subject. In some methods, step (a) is performed on at least 3, 4, 5, 10, 15, 20, 30 or more genes. In some methods, step (a) is performed on at least 10, 20, 40, or 100 or more genes selected from at least one of Tables 2, 3, 4, 7, 8, 11, 12, 14, 15, 17, and 18. Some of the methods further include changing the treatment regime of the patient responsive to the detecting, prognosing, diagnosing or monitoring step. In some of these methods, the subject is one who has received a drug before performing the methods, and the change comprises administering an additional drug or administering a higher dose of the same drug, or administering a lower dose of the same drug, or stopping administering the same drug. Some other methods can further include performing an additional procedure to detect SCAR or risk thereof if the determining step provides an indication the subject has or is at risk of SCAR, e.g., a kidney biopsy. In various embodiments, expression levels of the genes can be determined at the mRNA level or at the protein level. In some methods, step (b) is performed by a computer.

In various embodiments, the methods provided herein compare the gene expression profile in the peripheral blood of patients with acute cellular rejection (AR) on a surveillance protocol biopsy (SCAR-normal creatinine) with that of patients with normal protocol surveillance biopsies (TX—normal creatinine), or with a previously validated peripheral blood profile for patients with clinical acute cellular rejection (CAR-elevated creatinine) found on a "for cause" biopsy.

In another aspect, the invention provides arrays which contain a support or supports bearing a plurality of nucleic acid probes complementary to a plurality of mRNAs fewer than 5000 in number. Typically, the plurality of mRNAs includes mRNAs expressed by at least five genes selected from one or more of Tables 2, 3, 4, 7, 8, 11, 12, 14, 15, 17, or 18. In some embodiments, the plurality of mRNAs are fewer than 1000 or fewer than 100 in number. In some embodiments, the plurality of nucleic acid probes are attached to a planar support or to beads. In some embodiments, the at least five genes are selected from one or more of Tables 2, 3, 4, 7, 8, 11, 12, 14, 15, 17, or 18. In a related aspect, the invention provides arrays that contain a support or supports bearing a plurality of ligands that specifically bind to a plurality of proteins fewer than 5000 in number. The plurality of proteins typically includes at least five proteins encoded by genes selected from one or more of Tables 2, 3, 4, 7, 8, 11, 12, 14, 15, 17, or 18. In some embodiments, the plurality of proteins are fewer than 1000 or fewer than 100 in number. In some embodiments, the plurality of ligands are attached to a planar support or to beads. In some embodiments, the at least five proteins are encoded by genes selected from one or more of Tables 2, 3, 4, 7, 8, 11, 12, 14, 15, 17, or 18. In some embodiments, the ligands are different antibodies that bind to different proteins of the plurality of proteins.

In still another aspect, the invention provides methods of expression analysis. These methods involve determining expression levels of up to 2,000 genes (including at least 5 genes selected from one or more of Tables 2, 3, 4, 7, 8, 11, 12, 14, 15, 17, or 18) in a sample from a subject having a kidney transplant. In some methods, the expression levels of up to 100 or 1000 genes are determined. The gene expression levels can be determined at the mRNA level or at the protein level. For example, the expression levels can be determined by quantitative PCR or hybridization to an array or sequencing.

The invention additionally provides methods of screening a compound for activity in inhibiting or treating SCAR. The methods involve (a) administering the compound to a subject having or at risk of SCAR; (b) determining, before and after administering the compound to the subject, expression levels of at least five genes in the subject selected from one or more of Tables 2, 3, 4, 7, 8, 11, 12, 14, 15, 17, or 18 and species variants thereof and (c) determining whether the compound has activity in inhibiting or treating SCAR from a change in expression levels of the genes after administering the compound. In some methods, step (c) entails, for each of the at least five changes, assigning a value or designation depending on whether the change in the expression level of the gene relative to one or more reference levels indicating presence or absence of SCAR. Some methods further include determining a combined value or designation for the at least five genes from the values or designations determined for each gene. In some preferred embodiments, the subject is human or a nonhuman animal model of SCAR.

In another aspect, the methods disclosed herein have an error rate of less than about 40%. In some embodiments, the method has an error rate of less than about 40%, 35%, 30%, 25%, 20%, 15%, 10%, 5%, 3%, 2%, or 1%. For example, the method has an error rate of less than about 10%. In some embodiments, the methods disclosed herein have an accuracy of at least about 60%, 65%, 70%, 75%, 80%, 85%, 90%, 95%, or 99%. For example, the method has an accuracy of at least about 70%. In some embodiments, the methods disclosed herein have a sensitivity of at least about 60%, 65%, 70%, 75%, 80%, 85%, 90%, 95%, or 99%. For example, the method has a sensitivity of at least about 80%. In some embodiments, the methods disclosed herein have a positive predictive value of at least about 60%, 65%, 70%, 75%, 80%, 85%, 90%, 95%, or 99%. In some embodiments, the methods disclosed herein have a negative predictive value of at least about 60%, 65%, 70%, 75%, 80%, 85%, 90%, 95%, or 99%.

In some embodiments, the gene expression products described herein are RNA (e.g., mRNA). In some embodiments, the gene expression products are polypeptides. In some embodiments, the gene expression products are DNA complements of RNA expression products from the transplant recipient.

In an embodiment, the algorithm described herein is a trained algorithm. In another embodiment, the trained algorithm is trained with gene expression data from biological samples from at least three different cohorts. In another embodiment, the trained algorithm comprises a linear classifier. In another embodiment, the linear classifier comprises one or more linear discriminant analysis, Fisher's linear discriminant, Naïve Bayes classifier, Logistic regression, Perceptron, Support vector machine (SVM) or a combination thereof. In another embodiment, the algorithm comprises a Diagonal Linear Discriminant Analysis (DLDA) algorithm. In another embodiment, the algorithm comprises a Nearest Centroid algorithm. In another embodiment, the algorithm comprises a Random Forest algorithm or statistical bootstrapping. In another embodiment, the algorithm comprises a Prediction Analysis of Microarrays (PAM) algorithm. In another embodiment, the algorithm is not validated by a cohort-based analysis of an entire cohort. In another embodiment, the algorithm is validated by a combined analysis with an unknown phenotype and a subset of a cohort with known phenotypes.

In another aspect, the sample is a blood sample or is derived from a blood sample. In another embodiment, the blood sample is a peripheral blood sample. In another embodiment, the blood sample is a whole blood sample. In another embodiment, the sample does not comprise tissue from a biopsy of a transplanted organ of the transplant recipient. In another embodiment, the sample is not derived from tissue from a biopsy of a transplanted organ of the transplant recipient.

In another aspect, the assay is a microarray, SAGE, blotting, RT-PCR, sequencing and/or quantitative PCR assay. In another embodiment, the assay is a microarray assay. In another embodiment, the microarray assay comprises the use of an Affymetrix Human Genome U133 Plus 2.0 GeneChip. In another embodiment, the mircroarray uses the Hu133 Plus 2.0 cartridge arrays plates. In another embodiment, the microarray uses the HT HG-U133+PM array plates. In another embodiment, determining the assay is a sequencing assay. In another embodiment, the assay is a RNA sequencing assay.

In some embodiments, the subject or transplant recipient has a serum creatinine level of less than 3.0 mg/dL, less than 2.5 mg/dL, less than 2.0 mg/dL, or less than 1.5 mg/dL. The subject may have a serum creatinine level that is stable over time. In some cases, the subject or transplant recipient has a serum creatinine level of at least 0.4 mg/dL, 0.6 mg/dL, 0.8 mg/dL, 1.0 mg/dL, 1.2 mg/dL, 1.4 mg/dL, 1.6 mg/dL, 1.8 mg/dL, 2.0 mg/dL, 2.2 mg/dL, 2.4 mg/dL, 2.6 mg/dL, 2.8 mg/dL, 3.0 mg/dL, 3.2 mg/dL, 3.4 mg/dL, 3.6 mg/dL, 3.8 mg/dL, or 4.0 mg/dL. For example, the transplant recipient has a serum creatinine level of at least 1.5 mg/dl. In another example, the transplant recipient has a serum creatinine level of at least 3 mg/dL.

In one aspect, the invention provides methods of detecting subclinical acute rejection (subAR) in a subject comprising: (a) obtaining nucleic acids of interest, wherein the nucleic acids of interest comprise mRNA extracted from a sample from the subject or nucleic acids derived from the mRNA extracted from the sample from the subject; (b) detecting expression levels in the subject of at least five genes using the nucleic acids of interest obtained in step (a); and (c) detecting subAR in the subject from the expression levels detected in step (b). In an example, the sample from the subject is a blood sample.

In another aspect, the method detects subAR with an accuracy of greater than 50%, 55%, 60%, 65%, 70%, 75%, 80%, 85%, 90% or 95%. In another aspect, the method detects subAR with a sensitivity of greater than 50%, 55%, 60%, 65%, 70%, 75%, 80%, 85%, 90% or 95%. For example, the method detects subAR with an accuracy of greater than 75% or a sensitivity of greater than 75%.

In another aspect, the method further comprises contacting the nucleic acids of interest with probes, wherein the probes are specific for the at least 2, 3, 4, 5, 6, 7, 8, 9, 10, 20, 30, 40, 50, 60, 70, 80, 90, 100, 200, 300, 400, 500, 600, 700, 800, 900, 1000, 1500, or 2000 genes selected in step (b).

In another aspect, detecting subAR comprises detecting a risk of developing subAR, detecting acute rejection (AR), detecting a risk of having acute rejection (AR), or detecting a well-functioning normal transplant (TX). In another aspect, for each of at least 2, 3, 4, 5, 6, 7, 8, 9, 10, 20, 30, 40, 50, 60, 70, 80, 90, 100, 200, 300, 400, 500, 600, 700, 800, 900, 1000, 1500, or 2000 genes, step (c) of the method comprises comparing the expression level of the gene in the subject to one or more reference expression levels of genes associated with subAR, acute rejection (AR) or lack of transplant rejection (TX).

A further understanding of the nature and advantages of the present invention may be realized by reference to the remaining portions of the specification and claims.

BRIEF DESCRIPTION OF THE DRAWINGS

FIG. 1 shows a schematic overview of certain methods in the disclosure.

DETAILED DESCRIPTION

Figure 2:
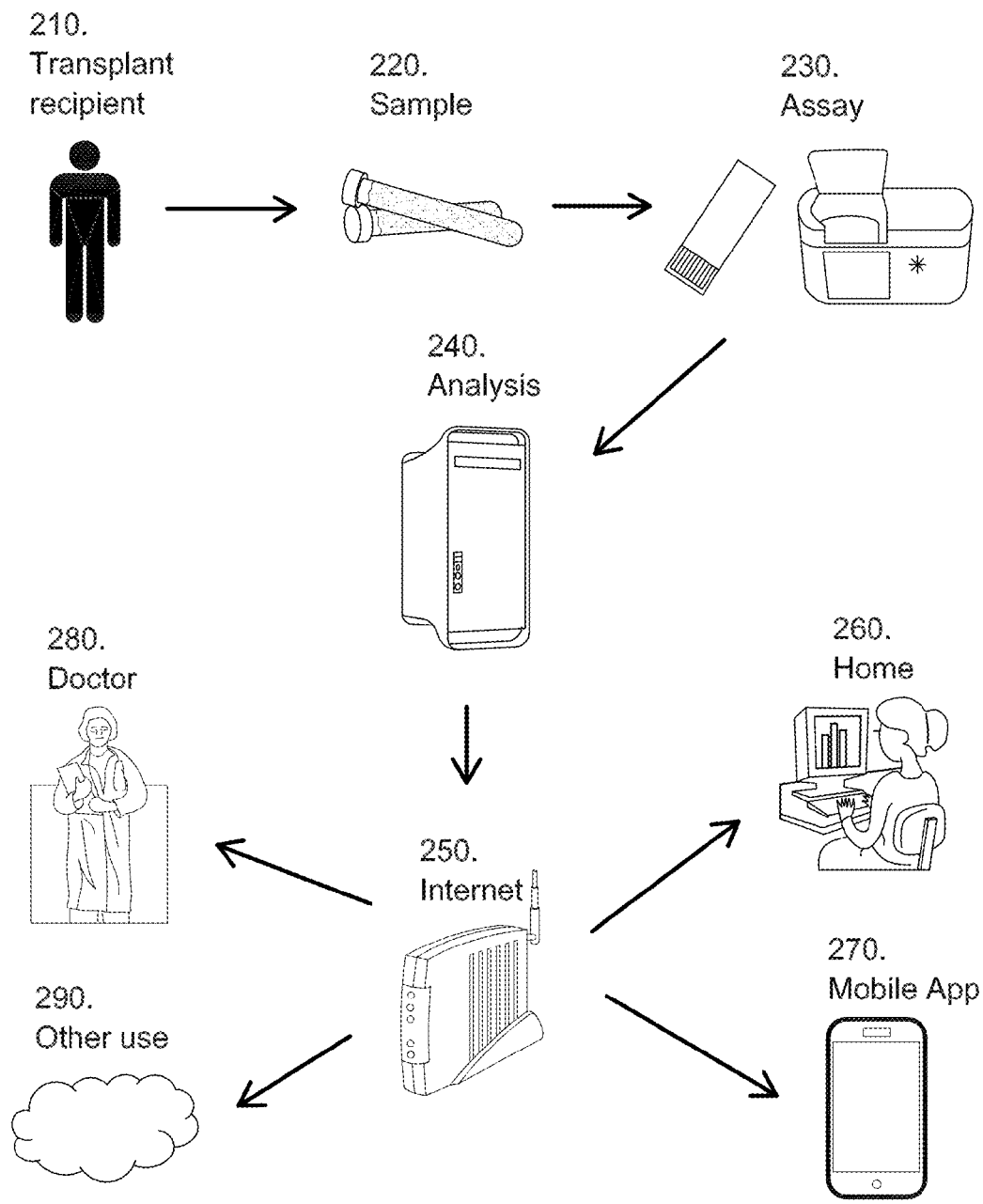
FIG. 2 shows a schematic overview of certain methods of acquiring samples, analyzing results, and transmitting reports over a computer network.

Sub-clinical acute rejection (referred to herein as "subAR" or "SCAR," interchangeably) is normally defined as histologic kidney rejection (e.g., histologic acute cellular rejection) with normal serum creatinine, and is associated with worse long term graft survival. In some cases, creatinine can be a lagging indicator of renal injury. Most times acute rejection (AR) of kidney graft is detected only after the initial injury has started. Early detection of subAR or SCAR can avoid unnecessary complications later in the course of graft life. However, normally subAR or SCAR is detected using a protocol kidney biopsy which is invasive, expensive and involves substantial risk. The present invention is predicated in part on the development by the inventors of a peripheral blood gene expression profiling signature that can distinguish Sub-Clinical Acute Rejection (subAR or SCAR), well-functioning normal transplant (TX) and Acute Rejection (AR). As detailed herein, the present inventors have identified consensus sets of gene expression-based molecular biomarkers associated with SCAR. This was accomplished via a genome-wide gene analysis of expression profiles of over 50,000 known or putative gene sequences in peripheral blood. More than 2,000 sequences were found to have differential expressions among the 3 different patient groups (Table 4). Among these sequences, the inventors further identified the top 200 differentially expressed probesets (Table 2), which can provide more focused and better expression profiles for differentiating the three classes of patients. In addition, a set of genes with differential expression levels only between SCAR and non-rejected transplants (TX) were also identified (Table 3). Expression rotocs based on the genes in this set are predictive in differentiating between transplant patients who will develop SCAR and patients who will maintain non-rejected transplants.

Results from the present inventors' studies provide the basis of a molecular test that can diagnose subAR or SCAR, and also enables minimally invasive methods for monitoring kidney transplant recipients. The value of a blood test for subAR or SCAR is that it allows detection of subclinical immune-mediated transplant rejection prior to clinical evidence of kidney injury and dysfunction. This blood-based test is minimally invasive and amenable to serial monitoring. Moreover, peripheral blood gene expression profiling may be used to inform when to perform a biopsy in patients with normal renal function and/or to replace surveillance protocol biopsies. Therefore, the invention is useful for post-transplant management of kidney recipients. Additional advantages of the test is that serial monitoring of all patients with a blood test for SCAR and treatment of all patients with SCAR by increasing the level of effective immunosuppression may significantly improve long term graft function and survival.

An overview of certain methods in the disclosure is provided in FIG. 1. In some instances, a method comprises obtaining a sample from a transplant recipient in a minimally invasive manner (110), such as via a blood draw. The sample may comprise gene expression products (e.g., polypeptides, RNA, mRNA isolated from within cells or a cell-free source) associated with the status of the transplant (e.g., subAR.). In some instances, the method may involve reverse-transcribing RNA within the sample to obtain cDNA that can be analyzed using the methods described herein. The method may also comprise assaying the level of the gene expression products (or the corresponding DNA) using methods such as microarray or sequencing technology (120). The method may also comprise applying an algorithm to the assayed gene expression levels (130) in order to detect subAR. After detection of the presence or absence of subAR, a treatment decision may be made. In some cases, the treatment decision may be that the transplant recipient should be treated more aggressively to mitigate the risk of acute rejection. In some cases, the treatment decision may be to reduce an existing treatment regimen, particularly if subAR is not detected. In the event that no subAR is detected, the treatment decision may involve a decision to forego or delay obtaining a kidney biopsy from the patient.

The following sections provide guidance for carrying out the methods of the invention.

I. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Illustrated Dictionary of Immunology*, Cruse (Ed.), CRC Pr I LIc (2$^{nd}$ ed., 2002); *Oxford Dictionary of Biochemistry and Molecular Biology*, Smith et al. (Eds.), Oxford University Press (revised ed., 2000); *Encyclopedic Dictionary of Chemistry*, Kumar (Ed.), Anmol Publications Pvt. Ltd. (2002); *Dictionary of Microbiology and Molecular Biology*, Singleton at al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology (Oxford Paperback Reference)*, Martin and Hine (Eds.), Oxford University Press (4$^{th}$ ed., 2000). In addition, the following definitions are provided to assist the reader in the practice of the invention.

Transplantation is the transfer of tissues, cells or an organ from a donor into a recipient. If the donor and recipient as the same person, the graft is referred to as an autograft and as is usually the case between different individuals of the same species an allograft. Transfer of tissue between species is referred to as a xenograft.

A biopsy is a specimen obtained from a living patient for diagnostic or prognostic evaluation. Kidney biopsies can be obtained with a needle.

An average value can refer to any of a mean, median or mode.

A gene expression level is associated with a particular phenotype e.g., presence of subAR (SCAR) or AR if the gene is differentially expressed in a patient having the phenotype relative to a patient lacking the phenotype to a statistically significant extent. Unless otherwise apparent from the context a gene expression level can be measured at the mRNA and/or protein level.

A target nucleic acid may be a nucleic acid (often derived from a biological sample), to which a polynucleotide probe is designed to specifically hybridize. The probe can detect presence, absence and/or amount of the target. The term target nucleic acid can refer to the specific subsequence of a larger nucleic acid to which the probe is directed or to the overall sequence (e.g., cDNA or mRNA) whose expression level is to be detected. The term target nucleic acid can also refer to a nucleic acid that is analyzed by any method, including by sequencing, PCR, microarray, or other method known in the art.

The term subject or patient can include human or non-human animals. Thus, the methods and described herein are applicable to both human and veterinary disease and animal models. Preferred subjects are "patients," i.e., living humans that are receiving medical care for a disease or condition. This includes persons with no defined illness who are being investigated for signs of pathology. The term subject or patient can include transplant recipients or donors or healthy subjects. The methods can be particularly useful for human subjects who have undergone a kidney transplant although they can also be used for subjects who have gone other types of transplant (e.g., heart, liver, lung, stem cell, etc.). The subjects may be mammals or non-mammals. Preferably, the subject is a human but in some cases, the subject is a non-human mammal, such as a non-human primate (e.g., ape, monkey, chimpanzee), cat, dog, rabbit, goat, horse, cow, pig, rodent, mouse, SCID mouse, rat, guinea pig or sheep. The subject may be male or female; the subject may be and, in some cases, the subject may be an infant, child, adolescent, teenager or adult. In some cases, the methods provided herein are used on a subject who has not yet received a transplant, such as a subject who is awaiting a tissue or organ transplant. In other cases, the subject is a transplant donor. In some cases, the subject has not received a transplant and is not expected to receive such transplant. In some cases, the subject may be a subject who is suffering from diseases requiring monitoring of certain organs for potential failure or dysfunction. In some cases, the subject may be a healthy subject.

Often, the subject is a patient or other individual undergoing a treatment regimen, or being evaluated for a treatment regimen (e.g., immunosuppressive therapy). However, in some instances, the subject is not undergoing a treatment regimen. A feature of the graft tolerant phenotype detected or identified by the subject methods is that it is a phenotype which occurs without immunosuppressive therapy, e.g., it is present in a subject that is not receiving immunosuppressive therapy.

A transplant recipient may be a recipient of a solid organ or a fragment of a solid organ such as a kidney. Preferably, the transplant recipient is a kidney transplant or allograft recipient. In some instances, the transplant recipient may be a recipient of a tissue or cell. In some particular examples, the transplanted kidney may be a kidney differentiated in vitro from pluripotent stem cell(s) (e.g., induced pluripotent stem cells or embryonic stem cells).

The donor organ, tissue, or cells may be derived from a subject who has certain similarities or compatibilities with the recipient subject. For example, the donor organ, tissue, or cells may be derived from a donor subject who is age-matched, ethnicity-matched, gender-matched, blood-type compatible, or HLA-type compatible with the recipient subject.

In various embodiments, the subjects suitable for methods of the invention are patients who have undergone an organ transplant within 6 hours, 12 hours, 1 day, 2 days, 3 days, 4 days, 5 days, 10 days, 15 days, 20 days, 25 days, 1 month, 2 months, 3 months, 4 months, 5 months, 7 months, 9 months, 11 months, 1 year, 2 years, 4 years, 5 years, 10 years, 15 years, 20 years or longer of prior to receiving a classification obtained by the methods disclosed herein, such as detection of subAR.

Diagnosis refers to methods of estimating or determining whether or not a patient is suffering from a given disease or condition or severity of the condition. Diagnosis does not require ability to determine the presence or absence of a particular disease with 100% accuracy, or even that a given course or outcome is more likely to occur than not. Instead, the "diagnosis" refers to an increased probability that a certain disease or condition is present in the subject compared to the probability before the diagnostic test was performed. Similarly, a prognosis signals an increased probability that a given course or outcome will occur in a patient relative to the probability before the prognostic test.

A probe or polynucleotide probe is a nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." A probe can include natural (e.g., A, G, C, U, or T) or modified bases (e.g., 7-deazaguanosine, inosine.). A probe can be an oligonucleotide and may be a single-stranded DNA or RNA. Polynucleotide probes can be synthesized or produced from naturally occurring polynucleotides. In addition, the bases in a probe can be joined by a linkage other than a phosphodiester bond, so long as it does not interfere with hybridization. Thus, probes can include, for example, peptide nucleic acids in which the constituent bases are joined by peptide bonds rather than phosphodiester linkages (see, e.g., Nielsen et al., *Science* 254, 1497-1500 (1991)). Some probes can have leading and/or trailing sequences of noncomplementarity flanking a region of complementarity.

A perfectly matched probe has a sequence perfectly complementary to a particular target sequence. The probe is typically perfectly complementary to a portion (subsequence) of a target sequence. The term "mismatch probe" refer to probes whose sequence is deliberately selected not to be perfectly complementary to a particular target sequence.

The term "isolated," "purified" or "substantially pure" means an object species (e.g., a nucleic acid sequence described herein or a polypeptide encoded thereby) has been at least partially separated from the components with which it is naturally associated.

Differential expression refers to a statistically significant difference in expression levels of a gene between two populations of samples (e.g., samples with and without SCAR). The expression levels can differ for example by at least a factor of 1.5 or 2 between such populations of samples. Differential expression includes genes that are expressed in one population and are not expressed (at least at detectable levels) in the other populations. Unique expression refers to detectable expression in one population and undetectable expression (i.e., insignificantly different from background) in the other population using the same technique (e.g., as in the present example for detection).

Control populations for comparison with populations undergoing SCAR are usually referred to as being without SCAR. In some embodiments, such a control population also means subjects without acute kidney rejection.

Hybridization reactions are preferably performed under stringent conditions in which probes or primers hybridize to their intended target with which they have perfect complementarity and not to or at least to a reduced extent to other targets. An example of stringent hybridization conditions are hybridization in 6× sodium chloride/sodium citrate (SSC) at about 45° C., followed by one or more washes in 0.2×SSC, 0.1% SDS at 50° C., 55° C., 60° C., and even more or 65° C.

Statistical significance means $p<0.05$ or $<0.01$ or even $<0.001$ level.

II. Genes in Profiles

Table 4 lists more than 2000 probesets with corresponding genes whose expression changes significantly between kidney transplant patients undergoing SCAR compared with patients not undergoing rejection (TX) and also patients undergoing acute rejection (AR) (3-way prediction). The columns in the table have the following meanings: column 1 is a number assigned to a gene, column 2 is an Affymetrix number indicating a set of probes suitable for measuring expression of the gene, column 3 is a gene name (recognized names of HUGO or similar bodies are used when available), column 4 is a further description of the gene, column 5 is a raw uncorrected measure of the statistical significance of change in gene expression between the above patient populations, column 6 corresponds to a value of the statistical significance after correction for the false discovery rate (FDR), and columns 7-9 respectively show mean expression levels of AR, SCAR, and TX patients. Table 2 similarly provides a subset of 200 preferred genes from Table 4. Table 3 provides similar information for a subset of genes from Table 4 which show differential expression between kidney transplant patients undergoing SCAR with kidney transplant patients not undergoing rejection (TX) (2-way prediction).

The genes referred to in the above tables are human genes. In some methods, species variants or homologs of these genes are used in a non-human animal model. Species variants are the genes in different species having greatest sequence identity and similarity in functional properties to one another. Many species variants of the above human genes are listed in the Swiss-Prot database.

To identify differentially expressed genes, raw gene expression levels are comparable between different genes in the same sample but not necessarily between different samples. As noted above, values given for gene expression levels can be normalized so that values for particular genes are comparable within and between the populations being analyzed. The normalization eliminates or at least reduces to acceptable levels any sample to sample differences arising from factors other than SCAR (e.g. differences in overall transcription levels of patients due to general state of health and differences in sample preparation or nucleic acid amplification between samples). The normalization effectively applies a correction factor to the measured expression levels from a given array such that a profile of many expression levels in the array are the same between different patient samples. Software for normalizing overall expression patterns between different samples is both commercially and publically available (e.g., XRAY from Biotique Systems or BRB ArrayTools from the National Cancer Institute). After applying appropriate normalizing factors to the measured expression value of a particular gene in different samples, an average or mean value of the expression level is determined for the samples in a population. The average or mean values between different populations are then compared to determine whether expression level has changed significantly between the populations. The changes in expression level indicated for a given gene represent the relative expression level of that gene in samples from a population of individuals with a defined condition (e.g., transplant patients with SCAR) relative to samples from a control population (kidney transplant patients not undergoing rejection). In some cases, the population of individuals with a defined condition may be transplant recipients with SCAR identified by acute cellular rejection (AR) on a surveillance protocol biopsy (SCAR-normal creatinine) and the control population is patients (e.g., transplant recipients) with normal protocol surveillance biopsies (TX-normal creatine). In some cases, this SCAR gene expression profile is compared with a previously validated peripheral blood profile/signature for patients with clinical acute cellular rejection (CAR-elevated creatinine), such as a CAR identified with a "for cause" biopsy.

Similar principles apply in normalizing gene expression levels at the mRNA and protein levels. Comparisons between populations are made at the same level (e.g., mRNA levels in one population are compared with mRNA levels in another population or protein levels in one population with protein levels in another population).

III. Subject Populations

The methods are suitable for detecting subAR or SCAR in transplant patients, and are particularly useful for detecting subAR or SCAR without relying on a histologic analysis or obtaining a biopsy. Subclinical rejection (SCR) including subAR generally refers to histologically defined acute rejection—particularly, histologically defined acute cellular rejection—characterized by tubule-interstitial mononuclear infiltration identified from a biopsy specimen, but without concurrent functional deterioration (variably defined as a serum creatinine not exceeding 10%, 20% or 25% of baseline values). Some instances of SCR or subAR may represent the beginning or conclusion of an alloimmune infiltrate diagnosed fortuitously by protocol sampling, and some episodes of clinical rejection may actually represent subAR or SCAR with an alternative cause of functional decline, such as concurrent calcineurin inhibitor (CNI) nephrotoxicity A subAR subject may have normal and stable organ function. For example, a subAR subject typically shows normal and/or stable serum creatinine levels or eGFR. SubAR is usually diagnosed through biopsies that are taken at a fixed time after transplantation (e.g., protocol biopsies or serial monitoring biopsies) which are not driven by clinical indications but rather by standards of care. The biopsies may be analyzed histologically in order to detect the subAR. SubAR may be subclassified by some into acute subAR (subAR) or a milder form called borderline subAR (suspicious for acute rejection) based on the biopsy histology.). A failure to recognize, diagnose and treat subclinical AR before significant tissue injury has occurred and the transplant shows clinical signs of dysfunction could be a major cause of irreversible organ damage. Moreover, a failure to recognize a chronic, subclinical immune-mediated organ damage and a failure to make appropriate changes in immunosuppressive therapy to restore a state of effective immunosuppression in that patient could contribute to late organ transplant failure. The methods disclosed herein can reduce or eliminate these and other problems associated with transplant rejection or failure.

In some instances, a normal serum creatinine level and/or a normal estimated glomerular filtration rate (eGFR) may indicate or correlate with healthy transplant (TX) or subclinical rejection (SCAR). For example, typical reference ranges for serum creatinine are 0.5 to 1.0 mg/dL for women and 0.7 to 1.2 mg/dL for men, though typical kidney transplant patients have creatinines in the 0.8 to 1.5 mg/dL range for women and 1.0 to 1.9 mg/dL range for men. This may be due to the fact that most kidney transplant patients have a single kidney. In some instances, the trend of serum creatinine levels over time can be used to evaluate the recipient's organ function. This is why it may be important to consider both "normal" serum creatinine levels and "stable" serum creatinine levels in making clinical judgments, interpreting testing results, deciding to do a biopsy or making therapy change decisions including changing immunosuppressive drugs. For example, the transplant recipient may show signs of a transplant dysfunction or rejection as indicated by an elevated serum creatinine level and/or a decreased eGFR. In some instances, a transplant subject with a particular transplant condition (e.g., AR, ADNR) may have an increase of a serum creatinine level of at least 0.1 mg/dL, 0.2 mg/dL, 0.3 mg/dL, 0.4 mg/dL, 0.5 mg/dL, 0.6 mg/dL, 0.7 mg/dL 0.8 mg/dL, 0.9 mg/dL, 1.0 mg/dL, 1.1 mg/dL, 1.2 mg/dL, 1.3 mg/dL, 1.4 mg/dL, 1.5 mg/dL, 1.6 mg/dL, 1.7 mg/dL, 1.8 mg/dL, 1.9 mg/dL, 2.0 mg/dL, 2.1 mg/dL, 2.2 mg/dL, 23 mg/dL, 2.4 mg/dL, 2.5 mg/dL, 2.6 mg/dL, 2.7 mg/dL, 2.8 mg/dL, 2.9 mg/dL, 3.0 mg/dL, 3.1 mg/dL, 3.2 mg/dL, 3.3 mg/dL, 3.4 mg/dL, 3.5 mg/dL, 3.6 mg/dL, 3.7 mg/dL, 3.8 mg/dL, 3.9 mg/dL, or 4.0 mg/dL. In some instances, a transplant subject with a certain transplant condition (e.g., AR, ADNR,) may have an increase of a serum creatinine level of at least 10%, 20%, 30%, 40%, 50%, 60%, 70%, 80%, 90%4 or 100% from baseline. In some instances, a transplant subject with a certain transplant condition (e.g., AR. ADNR, etc.) may have an increase of a serum creatinine level of at least 1-fold, 2-fold, 3-fold, 4-fold, 5-fold, 6-fold, 7-fold, 8-fold, 9-fold, or 10-fold from baseline. In some cases, the increase in serum creatinine (e.g., any increase in the concentration of serum creatinine described herein) may occur over about 0.25 days, 0.5 days, 0.75 days, 1 day, 1.25 days, 1.5 days, 1.75 days, 2.0 days, 3.0 days, 4.0 days, 5.0 days, 6.0 days, 7.0 days, 8.0 days, 9.0 days, 10.0 days, 15 days, 30 days, 1 month, 2 months, 3 months, 4 months, 5 months, or 6 months, or more. In some instances, a transplant subject with a particular transplant condition (e.g., AR, ADNR, CAN, etc.) may have a decrease of a eGFR of at least 10%, 20%, 30%, 40%, 50%, 60%, 70%, 80%, 90%, or 100% from baseline. In some cases, the decrease in eGFR may occur over 0.25 days, 0.5 days, 0.75 days, 1 day, 1.25 days, 1.5 days, 1.75 days, 2.0 days, 3.0 days, 4.0 days, 5.0 days, 6.0 days, 7.0 days, 8.0 days, 9.0 days, 10.0 days, 15 days, 30 days, 1 month, 2 months, 3 months, 4 months, 5 months, or 6 months, or more. In some instances, diagnosing, predicting, or monitoring the status or outcome of a transplant or condition comprises determining transplant recipient-specific baselines and/or thresholds. The methods are particularly useful on human subjects who have undergone a kidney transplant although can also be used on subjects who have undergone other types of transplant (e.g., heart, liver, lungs, stem cell) or on non-humans who have undergone kidney or other transplant. As detailed herein, the methods can be employed to distinguish transplant patients who (1) have or are at risk of having acute rejection (AR), (2) have or are at risk of having SCAR, and (3) have normal functional transplant (TX). In some other applications, the methods are more practically employed to distinguish patients who either are either transplant excellent (TX) or have existing SCAR (or risk of developing SCAR). This is because patients with acute rejections can usually be easily diagnosed via conventional assays, e.g., those based on serum creatinine level.

As such, the methods of the invention can be used in patients who have normal and stable creatinine levels to diagnose or prognose hidden SCAR without depending on invasive biopsies. In some cases, the serum creatinine levels of the transplant recipient are stable over at least 10 days, 20 days, 30 days, 40 days, 50 days, 60 days, 90 days, 100 days, 200 days, 300 days, 400 days or longer. In some cases, the transplant recipient has a serum creatinine level of less than 0.2 mg/dL, less than 0.3 mg/dL, less than 0.4 mg/dL, less than 0.5 mg/dL, less than 0.6 mg/dL, less than 0.7 mg/dL less than 0.8 mg/dL, less than 0.9 mg/dL, less than 1.0 mg/dL, less than 1.1 mg/dL, less than 1.2 mg/dL, less than 1.3 mg/dL, 1.4 mg/dL, less than 1.5 mg/dL, less than 1.6 mg/dL, less than 1.7 mg/dL, less than 1.8 mg/dL, less than 1.9 mg/dL, less than 2.0 mg/dL, less than 2.1 mg/dL, less than 2.2 mg/dL, less than 2.3 mg/dL, less than 2.4 mg/dL, less than 2.5 mg/dL, less than 2.6 mg/dL, less than 2.7 mg/dL, less than 2.8 mg/dL, less than 2.9 mg/dL, or less than 3.0 mg/dL.

As mentioned, often the methods provided herein can be used to detect subAR as opposed to a condition such as acute rejection (AR), or to predict whether the subject is at risk of having AR. Acute rejection (AR) or clinical acute rejection may occur when transplanted tissue is rejected by the recipient's immune system, which damages or destroys the transplanted tissue unless immunosuppression is achieved. T-cells, B-cells and other immune cells as well as possibly antibodies of the recipient may cause the graft cells to lyse or produce cytokines that recruit other inflammatory cells, eventually causing necrosis of allograft tissue. In some instances, AR may be diagnosed by a biopsy of the transplanted organ. In the case of kidney transplant recipients, AR may be associated with an increase in serum creatinine levels. The treatment of AR may include using immunosuppressive agents, corticosteroids, polyclonal and monoclonal antibodies, engineered and naturally occurring biological molecules, and antiproliferatives. AR more frequently occurs in the first three to 12 months after transplantation but there is a continued risk and incidence of AR for the first five years post transplant and whenever a patient's immunosuppression becomes inadequate for any reason for the life of the transplant.

The methods herein may also be used to distinguish between a kidney transplant patient with subAR and a normally functioning kidney transplant. Typically, when the patient does not exhibit symptoms or test results of organ dysfunction or rejection, the transplant is considered a normal functioning transplant (TX: Transplant eXcellent). An unhealthy transplant recipient may exhibit signs of organ dysfunction and/or rejection (e.g., an increasing serum creatinine Regardless of the specific subject population, gene expression levels in the patients can be measured, for example, within, one month, three months, six months, one year, two years, five years or ten years after a kidney transplant. In some methods, gene expression levels are determined at regular intervals, e.g., every 3 months, 6 months or every year posttransplant, either indefinitely, or until evidence of SCAR is observed, in which case the frequency of monitoring is sometimes increased. In some methods, baseline values of expression levels are determined in a subject before a kidney transplant in combination with determining expression levels at one or more time points thereafter. Similar methods can be practiced in non-human species, in which cases, the expression levels measured are the species equivalent of the human genes referenced above.

IV. Methods of Measuring Profiles

Samples

The preferred sample type for analysis is a blood sample, which refers to whole blood or fractions thereof such as plasma, or lymphocytes. Other samples that can be analyzed include urine, feces, saliva, and a kidney biopsy. The samples are typically isolated from a subject, particularly as a peripheral blood sample, and not returned to the subject. The analytes of interests in the samples can be analyzed with or without further processing of the sample, such as purification and amplification. Samples not requiring biopsy to obtain, particularly peripheral blood, are preferred. However, a sample may be any material containing tissues, cells, nucleic acids, genes, gene fragments, expression products, polypeptides, exosomes, gene expression products, or gene expression product fragments of a subject to be tested. In some cases, the sample is from a single patient. In some cases, the method comprises analyzing multiple samples at once, e.g., via massively parallel sequencing.

The sample is preferably blood. In some cases, the sample comprises whole blood, plasma, peripheral blood lymphocytes (PBLs), peripheral blood mononuclear cells (PBMCs), serum, T cells, B Cells, CD3 cells, CD8 cells, CD4 cells, or other immune cells.

The methods, kits, and systems disclosed herein may comprise specifically detecting, profiling, or quantitating molecules (e.g., nucleic acids, DNA, RNA, polypeptides, etc.) that are within the biological samples. In some instances, genomic expression products, including RNA, or polypeptides, may be isolated from the biological samples. In some cases, nucleic acids, DNA, RNA, polypeptides may be isolated from a cell-free source. In some cases, nucleic acids, DNA, RNA, polypeptides may be isolated from cells derived from the transplant recipient.

The sample may be obtained using any method known to the art that can provide a sample suitable for the analytical methods described herein. The sample may be obtained by a non-invasive method such as a throat swab, buccal swab, bronchial lavage, urine collection, scraping of the skin or cervix, swabbing of the cheek, saliva collection, feces collection, menses collection, or semen collection.

The sample may be obtained by a minimally-invasive method such as a blood draw. The sample may be obtained by venipuncture. In other instances, the sample is obtained by an invasive procedure including but not limited to: biopsy, alveolar or pulmonary lavage, or needle aspiration. The method of biopsy may include surgical biopsy, incisional biopsy, excisional biopsy, punch biopsy, shave biopsy, or skin biopsy. The sample may be formalin fixed sections. The method of needle aspiration may further include fine needle aspiration, core needle biopsy, vacuum assisted biopsy, or large core biopsy. In some embodiments, multiple samples may be obtained by the methods herein to ensure a sufficient amount of biological material. In some instances, the sample is not obtained by biopsy. In some instances, the sample is not a kidney biopsy.

Expression Profiles

For prognosis or diagnosis of SCAR in patients as opposed to both patients with acute rejection (AR) and patients without rejection (TX), the profiles can contain genes selected from at least one of Tables 2, 3, 4, 7, 8, 11, 12, 14, 15, 17, and 18, for example, from Table 2. In some other methods, when the prognosis or diagnosis is intended to distinguish between patients having or at risk of developing SCAR and patients without rejection (TX), the genes in the profiles can be selected from at least one of Tables 2, 3, 4, 7, 8, 11, 12, 14, 15, 17, and 18, for example, from Table 3.

Expression profiles are preferably measured at the nucleic acid level, meaning that levels of mRNA or nucleic acid derived therefrom (e.g., cDNA or cRNA). An expression profile refers to the expression levels of a plurality of genes in a sample. A nucleic acid derived from mRNA means a nucleic acid synthesized using mRNA as a template. Methods of isolation and amplification of mRNA are well known in the art, e.g., as described in WO 97/10365, WO 97/27317, Chapter 3 of Laboratory Techniques in Biochemistry and Molecular Biology: Hybridization With Nucleic Acid Probes, Part 1. Theory and Nucleic Acid Preparation, (P. Tijssen, ad.) Elsevier, N.Y. (1993). If mRNA or a nucleic acid therefrom is amplified, the amplification is performed under conditions that approximately preserve the relative proportions of mRNA in the original samples, such that the levels of the amplified nucleic acids can be used to establish phenotypic associations representative of the mRNAs.

A variety of approaches are available for determining mRNA levels including probe arrays and quantitative PCR. A number of distinct array formats are available. Some arrays, such as an Affymetrix HG-U133 PM microarray or other Affymetrix GeneChip® array, have different probes occupying discrete known areas of a contiguous support. Exemplary microarrays include but are not limited to the Affymetrix Human Genome U133 Plus 2.0 GeneChip or the HT HG-U133+PM Array Plate.

Other arrays, such as arrays from Illumina, have different probes attached to different particles or beads. In such arrays, the identity of which probe is attached to which particle or beads is usually determinable from an encoding system. The probes can be oligonucleotides. In such case, typically several match probes are included with perfect complementarity to a given target mRNA together, optionally together with mismatch probes differing from the match probes are a known number of oligonucleotides (Lockhart, at al., Nature Biotechnology 14:1675-1680 (1996); and Lipschutz, et al., Nature Genetics Supplement 21: 20-24, 1999). Other arrays including full length cDNA sequences with perfect or near perfect complementarity to a particular cDNA (Schena et al. (Science 270:467-470 (1995); and DeRisi et al. (Nature Genetics 14:457-460 (1996)). Such arrays can also include various control probes, such as a probe complementarity with a house keeping gene likely to be expressed in most samples. Regardless of the specifics of array design, an array contains one or more probes either perfectly complementary to a particular target mRNA or sufficiently complementary to the target mRNA to distinguish it from other mRNAs in the sample, and the presence of such a target mRNA can be determined from the hybridization signal of such probes, optionally by comparison with mismatch or other control probes included in the array. Typically, the target bears a fluorescent label, in which case hybridization intensity can be determined by, for example, a scanning confocal microscope in photon counting mode. Appropriate scanning devices are described by e.g., U.S. Pat. Nos. 5,578,832, and 5,631,734. The intensity of labeling of probes hybridizing to a particular mRNA or its amplification product provides a raw measure of expression level.

In other methods, expression levels are determined by so-called "real time amplification" methods also known as quantitative PCR or Taqman (see, e.g., U.S. Pat. No. 5,210, 015 to Gelfand, U.S. Pat. No. 5,538,848 to Livak, et al., and U.S. Pat. No. 5,863,736 to Haaland, as well as Held, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified. mRNA levels can also be measured without amplification by hybridization to a probe, for example, using a branched nucleic acid probe, such as a QuantiGene® Reagent System from Panomics.

In certain preferred embodiments, the expression level of the gene products (e.g., RNA) is determined by sequencing, such as by RNA sequencing or by DNA sequencing (e.g., of cDNA generated from reverse-transcribing RNA (e.g., mRNA) from a sample). Sequencing may be performed by any available method or technique. Sequencing methods may include: Next Generation sequencing, high-throughput sequencing, pyrosequencing, classic Sangar sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/ Thermo-Fisher), massively-parallel sequencing, clonal single molecule Array (Solexa), shotgun sequencing, Maxim-Gilbert sequencing, primer walking, and any other sequencing methods known in the art.

Measuring gene expression levels may comprise reverse transcribing RNA (e.g., mRNA) within a sample in order to produce cDNA. The cDNA may then be measured using any of the methods described herein (e.g., PCR, digital PCR, qPCR, microarray, SAGE, blotting, sequencing etc.).

Alternatively or additionally, expression levels of genes can be determined at the protein level, meaning that levels of proteins encoded by the genes discussed above are measured. Several methods and devices are well known for determining levels of proteins including immunoassays such as described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. These assays include various sandwich, competitive, or non-competitive assay formats, to generate a signal that is related to the presence or amount of an protein analyte of interest. Any suitable immunoassay may be utilized, for example, lateral flow, enzyme-linked immunoassays (ELISA), radioimmunoassays (RIAs), competitive binding assays, and the like. Numerous formats for antibody arrays have been described proposed employing antibodies. Such arrays typically include different antibodies having specificity for different proteins intended to be detected. For example, usually at least one hundred different antibodies are used to detect one hundred different protein targets, each antibody being specific for one target. Other ligands having specificity for a particular protein target can also be used, such as the synthetic antibodies disclosed in WO/2008/048970. Other compounds with a desired binding specificity can be selected from random libraries of peptides or small molecules. U.S. Pat. No. 5,922,615 describes a device that utilizes multiple discrete zones of immobilized antibodies on membranes to detect multiple target antigens in an array. U.S. Pat. Nos. 5,458,852, 6,019,944, U.S. Pat. No. 6,143,576. Microtiter plates or automation can be used to facilitate detection of large numbers of different proteins. Protein levels can also be determined by mass spectrometry as described in the examples.

The selection of genes for determination of expression levels depends on the particular application. In general, the genes are selected from one of the tables indicated above as appropriate for the application. In some methods, expression levels of at least 2, 3, 4, 5, 10, 20, 25, 50, 100, 150, 250 (e.g. 100-250) genes shown in any of Tables 2, 3, 4, 7, 8, 11, 12, 14, 15, 17, or 18 are determined. In some methods, expression levels of 1, 2, 3, 4, 5, 6, 7, 8, 9, 10, 11, 12, 13, 14, 15, 16, 17, 18, 19, 20, 50, 100, 200, 300, 400, 500, 1000 or more genes found in Tables 2, 3, 4, 7, 8, 11, 12, 14, 15, 17, or 18 are determined. In some methods, genes are selected such that genes from several different pathways are represented. The genes within a pathway tend to be expressed in a coordinated expression whereas genes from different pathways tend to be expressed more independently. Thus, changes in expression based on the aggregate changes of genes from different pathways can have greater statistical significance than aggregate changes of genes within a pathway. In some cases, expression levels of the top 5, top 10, top 15, top 20, top 25, top 30, top 35, top 40, top 45, top 50, top 55, top 60, top 65, top 70, top 75, top 80, top 85, top 90, top 95, top 100, top 150, top 200, top 250 or top 300 genes listed in Tables 2, 3, 4, 7, 8, 11, 12, 14, 15, 17, or 18 are determined.

Expression levels of the present genes and/or proteins can be combined with or without determination of expression levels of any other genes or proteins of interest (e.g., genes or proteins associated with rejection of kidneys or other organs in WO 2007/104537, WO 2009/060035), Anglicheau et al., PNAS 106, 5330-5335 (2009)) and references, 16, 20, 21, 22, 23, 25, 26, 37 and 39. In some methods, the genes in the expression profiles to be measured do not include at least one or all of the genes encoding urinary granzyme A, granzyme B, glyceraldehyde 3-phospate dehydrogenase (GAPDH), perforin, Fas ligand, CXCL9, CXCL10, and other proteins involved in patients' cytolytic attack against the transplant.

Regardless of the format adopted, the present methods can (but need not) be practiced by detection expression levels of a relatively small number of genes or proteins compared with the whole genome level expression analysis described in the Examples. In some methods, the total number of genes whose expression levels are determined is less than 5000, 1000, 500, 200, 100, 50, 25, 10, 5 or 3. In some methods, the total number of genes whose expression level is determined is 100-1500, 100-250, 500-1500 or 750-1250. In some methods, the total number of proteins whose expression levels are determined is less than 5000, 1000, 500, 200, 100, 50, 25, 10, 5 or 3. In some methods, the total number of proteins whose expression level is determined is 100-1500, 100-250, 500-1500 or 750-1250. Correspondingly, when an array form is used for detection of expression levels, the array includes probes or probes sets for less than 5000, 1000, 500, 200, 100, 50, 25, 10, 5 or 3 genes. Thus, for example, an Affymetrix GeneChip® expression monitoring array contains a set of about 20-50 oligonucleotide probes (half match and half-mismatch) for monitoring each gene of interest. Such an array design would include less than 5000, 1000, 500, 200, 100, 50, 25, 10, 5 or 3 such probes sets for detecting less than 5000, 1000, 500, 200, 100, 50, 25, 10, 5 or 3 genes. By further example, an alternative array including one cDNA for each gene whose expression level is to be detected would contain less than 5000, 1000, 500, 200, 100, 50, 25, 10, 5 or 3 such cDNAs for analyzing less than 5000, 1000, 500, 200, 100, 50, 25, 10, 5 or 3 genes. By further example, an array containing a different antibody for each protein to be detected would containing less than 5000, 1000, 500, 200, 100, 50, 25, 10, 5 or 3 different antibodies for analyzing less than 5000, 1000, 500, 200, 100, 50, 25, 10, 5 or 3 gene products.

As described herein, in some cases the methods involve obtaining or analyzing a biopsy sample (e.g., kidney biopsy). The biopsy sample may be used for different purposes including to develop an expression profile signature. In some cases, an analysis described herein may be performed on a biopsy obtained from a transplant recipient in order to predict, monitor, or detect SCAR in the transplant recipient. In cases where biopsies are obtained, the biopsies may be processed included by placing the samples in a vessel (e.g., tube, PAX tube, vial, microfuge tube, etc.) and storing them at a specific location such as a biorepository. The samples may also be processed by treatment with a specific agent, such as an agent that prevents nucleic acid degradation or deterioration, particularly an agent that protects RNA (e.g., RNALater) or DNA. In some cases, biopsies subjected to histologic analysis including staining (e.g., hematoxylin and eosin (H&E) stain) probing (e.g., a probe attached to a dye, a probe attached to a fluorescent label). In some cases, the staining (e.g., H&E) may be analyzed by a blinded physician such as a blinded pathologist, or at least two blinded pathologists, using criteria such as BANFF criteria. In some cases, a histologic diagnosis is reconciled with laboratory data and clinical courses by one or more clinicians (e.g., at least two clinicians) prior to biomarker analyses.

V. Analysis of Expression Levels

Analysis of expression levels initially provides a measurement of the expression level of each of several individual genes. The expression level can be absolute in terms of a concentration of an expression product, or relative in terms of a relative concentration of an expression product of interest to another expression product in the sample. For example, relative expression levels of genes can be expressed with respect to the expression level of a housekeeping gene in the sample. Relative expression levels can also be determined by simultaneously analyzing differentially labeled samples hybridized to the same array. Expression levels can also be expressed in arbitrary units, for example, related to signal intensity.

The individual expression levels, whether absolute or relative, can be converted into values or other designations providing an indication of presence or risk of SCAR by comparison with one or more reference points. Preferably, genes in Table 2 and/or one or more of Tables 2, 3, 4, 7, 8, 11, 12, 14, 15, 17, or 18 are used for such analysis. The reference points can include a measure of an average or mean expression level of a gene in subjects having had a kidney transplant without SCAR, an average or mean value of expression levels in subjects having had a kidney transplant with SCAR, and/or an average/mean value of expression levels in subjects having had a kidney transplant with acute rejection. The reference points can also include a scale of values found in kidney transplant patients including patients having and not having SCAR. The reference points can also or alternatively include a reference value in the subject before kidney transplant, or a reference value in a population of patients who have not undergone kidney transplant Such reference points can be expressed in terms of absolute or relative concentrations of gene products as for measured values in a sample.

For comparison between a measured expression level and reference level(s), the measured level sometimes needs to be normalized for comparison with the reference level(s) or vice versa. The normalization serves to eliminate or at least minimize changes in expression level unrelated to SCAR (e.g., from differences in overall health of the patient or sample preparation). Normalization can be performed by determining what factor is needed to equalize a profile of expression levels measured from different genes in a sample with expression levels of these genes in a set of reference samples from which the reference levels were determined. Commercial software is available for performing such normalizations between different sets of expression levels.

Comparison of the measured expression level of a gene with one or more of the above reference points provides a value (i.e., numerical) or other designation (e.g., symbol or word(s)) of presence or susceptibility to SCAR. In some methods, a binary system is used; that is a measured expression level of a gene is assigned a value or other designation indicating presence or susceptibility to SCAR or lack thereof without regard to degree. For example, the expression level can be assigned a value of 1 to indicate presence or susceptibility to SCAR and −1 to indicate absence or lack of susceptibility to SCAR. Such assignment can be based on whether the measured expression level is closer to an average or mean level in kidney transplant patients having or not having SCAR. In other methods, a ternary system is used in which an expression level is assigned a value or other designation indicating presence or susceptibility to SCAR or lack thereof or that the expression level is uninformative. Such assignment can be based on whether the expression level is closer to the average or mean level in kidney transplant patient undergoing SCAR, closer to an average or mean level in kidney transplant patients lacking SCAR or intermediate between such levels. For example, the expression level can be assigned a value of +1, −1 or 0 depending on whether it is closer to the average or mean level in patients undergoing SCAR, is closer to the average or mean level in patients not undergoing SCAR or is intermediate. In other methods, a particular expression level is assigned a value on a scale, where the upper level is a measure of the highest expression level found in kidney transplant patients and the lowest level of the scale is a measure of the lowest expression level found in kidney transplant patients at a defined time point at which patients may be susceptible to SCAR (e.g., one year post transplant). Preferably, such a scale is normalized scale (e.g., from 0-1) such that the same scale can be used for different genes. Optionally, the value of a measured expression level on such a scale is indicated as being positive or negative depending on whether the upper level of the scale associates with presence or susceptibility to SCAR or lack thereof. It does not matter whether a positive or negative sign is used for SCAR or lack thereof as long as the usage is consistent for different genes.

Values or other designation can also be assigned based on a change in expression level of a gene relative to a previous measurement of the expression level of gene in the same patient. Here as elsewhere expression level of a gene can be measured at the protein or nucleic acid level. Such a change can be characterized as being toward, away from or neutral with respect to average or mean expression levels of the gene in kidney transplant patients undergoing or not undergoing SCAR. For example, a gene whose expression level changes toward an average or mean expression level in kidney transplant patients undergoing SCAR can be assigned a value of 1 and a gene whose express level changes way from an average or mean expression level in kidney transplant patients undergoing SCAR and toward an average or mean expression level in kidney transplant patients not undergoing SCAR can be assigned a value −1. Of course, more sophisticated systems of assigning values are possible based on the magnitude of changes in expression of a gene in a patient.

Having determined values or other designations of expression levels of individual genes providing an indication of presence or susceptibility to subAR (or SCAR) or lack thereof, the values or designations may be combined to provide an aggregate value for all of the genes in the signature being analyzed. If each gene is assigned a score of +1 if its expression level indicates presence or susceptibility to subAR (or SCAR) and −1 if its expression level indicates absence or lack of susceptibility to subAR and optionally zero if uninformative, the different values can be combined by addition. The same approach can be used if each gene is assigned a value on the same normalized scale and assigned as being positive or negative depending whether the upper point of the scale is associate with presence or susceptibility to subAR or lack thereof. In some cases, the signal intensity for each gene is obtained and used to compute a score. The score may be obtained by adding up the values for the upregulated genes to obtain an upregulated gene value and adding up the values of the downregulated genes to obtain a downregulated gene value; the downregulated gene value may be compared with the upregulated value (e.g., by calculating a ratio) to determine the score. Other methods of combining values for individual markers of disease into a composite value that can be used as a single marker are described in US20040126767 and WO/2004/059293. In some cases, the score may be used to evaluate severity of a transplant condition, such as by comparing the score with a score normally associated with subAR. In some cases, the score may be used to monitor a subject transplant recipient over time. In such case, scores at a plurality of timepoints may be compared in order to assess the relative condition of the subject. For example, if the subject's score rises over time, that may indicate that the subject has subAR and that his or her condition is worsening over time.

Sample Data

The data pertaining to the sample may be compared to data pertaining to one or more control samples, which may be samples from the same patient at different times. In some cases, the one or more control samples may comprise one or more samples from healthy subjects, unhealthy subjects, or a combination thereof. The one or more control samples may comprise one or more samples from healthy subjects, subjects suffering from transplant dysfunction with no rejection, subjects suffering from transplant rejection, or a combination thereof. The healthy subjects may be subjects with normal transplant function. The data pertaining to the sample may be sequentially compared to two or more classes of samples. The data pertaining to the sample may be sequentially compared to three or more classes of samples. The classes of samples may comprise control samples classified as being from subjects with normal transplant function, control samples classified as being from subjects suffering from transplant dysfunction with no rejection, control samples classified as being from subjects suffering from transplant rejection, or a combination thereof.

Classifiers

The methods include using a trained classifier or algorithm to analyze sample data, particularly to detect subAR. In some instances, the expression levels from sample are used to develop or train an algorithm or classifier provided herein. In some instances, gene expression levels are measured in a sample from a transplant recipient (or a healthy or transplant excellent control) and a classifier or algorithm (e.g., trained algorithm) is applied to the resulting data in order to detect, predict, monitor, or estimate the risk of a transplant condition (e.g., subAR).

Training of multi-dimensional classifiers (e.g., algorithms) may be performed using numerous samples. For example, training of the multi-dimensional classifier may be performed using at least about 10, 20, 30, 40, 50, 60, 70, 80, 90, 100, 110, 120, 130, 140, 150, 160, 170, 180, 190, 200 or more samples. In some cases, training of the multi-dimensional classifier may be performed using at least about 200, 210, 220, 230, 240, 250, 260, 270, 280, 290, 300, 350, 400, 450, 500 or more samples. In some cases, training of the multi-dimensional classifier may be performed using at least about 525, 550, 600, 650, 700, 750, 800, 850, 900, 950, 1000, 1100, 1200, 1300, 1400, 1500, 1600, 1700, 1800, 2000 or more samples.

Further disclosed herein are classifier sets and methods of producing one or more classifier sets. The classifier set may comprise one or more genes, particularly genes from Tables 2, 3, 4, 7, 8, 11, 12, 14, 15, 17, or 18. In some cases, the classifier set may comprise 1, 2, 3, 4, 5, 6, 7, 8, 9, 10, 11, 12, 13, 14, 15, 16, 17, 18, 19, 20, 50, 100, 150, 200, 300 or more genes from Tables 2, 3, 4, 7, 8, 11, 12, 14, 15, 17, or 18. Disclosed herein is the use of a classification system comprises one or more classifiers. In some instances, the classifier is a 2-, 3-, 4-, 5-, 6-, 7-, 8-, 9-, or 10-way classifier. In some instances, the classifier is a 15-, 20-, 25-, 30-, 35-, 40-, 45-, 50-, 55-, 60-, 65-, 70-, 75-, 80-, 85-, 90-, 95-, or 100-way classifier. In some preferred embodiments, the classifier is a three-way classifier. In some embodiments, the classifier is a four-way classifier.

A two-way classifier may classify a sample from a subject into one of two classes. In some instances, a two-way classifier may classify a sample from an organ transplant recipient into one of two classes comprising subAR and normal transplant function (TX). In some instances, a three-way classifier may classify a sample from a subject into one of three classes. A three-way classifier may classify a sample from an organ transplant recipient into one of three classes comprising AR, subAR, and TX In some cases, the classifier may work by applying two or more classifiers sequentially. For example, the first classifier may classify AR+subAR and TX, which results in a set of samples that are classified either as (1) TX or (2) AR or subAR. In some cases, a second classifier capable of distinguishing between AR and subAR is applied to the samples classified as having AR or subAR in order to detect the subAR samples.

Classifiers and/or classifier probe sets may be used to either rule-in or rule-out a sample as healthy. For example, a classifier may be used to classify a sample as being from a healthy subject. Alternatively, a classifier may be used to classify a sample as being from an unhealthy subject. Alternatively, or additionally, classifiers may be used to either rule-in or rule-out a sample as transplant rejection. For example, a classifier may be used to classify a sample as being from a subject suffering from a transplant rejection. In another example, a classifier may be used to classify a sample as being from a subject that is not suffering from a transplant rejection. Classifiers may be used to either rule-in or rule-out a sample as transplant dysfunction with no rejection. For example, a classifier may be used to classify a sample as being from a subject with subAR. In another example, a classifier may be used to classify a sample as not being from a subject suffering from transplant dysfunction with no rejection.

The samples may be classified simultaneously. In some cases, the samples may be classified sequentially. The two or more samples may be classified at two or more time points. The samples may be obtained at 1, 2, 3, 4, 5, 6, 7, 8, 9, 10, 11, 12, 13, 14, 15, 16, 17, 18, 19, 20, 100 or more time points. The two or more time points may be 1 day, 10 days, 30 days, 60 days, 100 days, 200 days, 1 year, 2 years or more apart.

Methods of simultaneous classifier-based analysis of one or more samples may comprise applying one or more algorithm to data from one or more samples to simultaneously produce one or more lists, wherein the lists comprise one or more samples classified as being from healthy subjects (e.g. subjects with a normal functioning transplant (TX)), unhealthy subjects, subjects suffering from transplant rejection, subjects suffering from transplant dysfunction, subjects with AR, or subjects with subAR.

The methods, kits, and systems disclosed herein may comprise one or more algorithms or uses thereof. The one or more algorithms may be used to classify one or more samples from one or more subjects. The one or more algorithms may be applied to data from one or more samples. The data may comprise gene expression data. The data may comprise sequencing data. The data may comprise array hybridization data.

The methods disclosed herein may comprise assigning a classification to one or more samples from one or more subjects. Assigning the classification to the sample may comprise applying an algorithm to the expression level. In some cases, the gene expression levels are inputted to a trained algorithm for classifying the sample as one of the conditions comprising subAR, AR, TX, subAR+AR, or other condition.

The algorithm may provide a record of its output including a classification of a sample and/or a confidence level. In some instances, the output of the algorithm can be the possibility of the subject of having a condition, such as subAR. In some instances, the output of the algorithm can be the risk of the subject of having a condition, such as AR. In some instances, the output of the algorithm can be the possibility of the subject of developing into a condition in the future, such as AR.

The algorithm may be a trained algorithm. The algorithm may comprise a linear classifier. The linear classifier may comprise one or more linear discriminant analysis, Fisher's linear discriminant, Naïve Bayes classifier, Logistic regression, Perceptron, Support vector machine, or a combination thereof. The linear classifier may be a Support vector machine (SVM) algorithm.

The algorithm may comprise one or more linear discriminant analysis (LDA), Basic perceptron, Elastic Net, logistic regression, (Kernel) Support Vector Machines (SVM), Diagonal Linear Discriminant Analysis (DLDA), Golub Classifier, Parzen-based, (kernel) Fisher Discriminant Classifier, k-nearest neighbor, Iterative RELIEF, Classification Tree, Maximum Likelihood Classifier, Random Forest, Nearest Centroid, Prediction Analysis of Microarrays (PAM), k-medians clustering, Fuzzy C-Means Clustering, Gaussian mixture models, or a combination thereof. The algorithm may comprise a Diagonal Linear Discriminant Analysis (DLDA) algorithm. The algorithm may comprise a Nearest Centroid algorithm. The algorithm may comprise a Random Forest algorithm. The algorithm may comprise a Prediction Analysis of Microarrays (PAM) algorithm.

The methods disclosed herein may comprise use of one or more classifier equations. Classifying the sample may comprise a classifier equation. The classifier equation may be Equation 1:

$$\delta_k(x^*) = \sum_{i=1}^{p} \frac{(x_i^* - \overline{x}_{ik}')^2}{(s_i + s_0)^2} - 2\log\pi_k,$$

wherein:
k is a number of possible classes;
$\delta_k$ may be the discriminant score for class k;
$x_i^*$ represents the expression level of gene i;
$x^*$ represents a vector of expression levels for all p genes to be used for classification drawn from the sample to be classified;
$\overline{x}_k'$ may be a shrunken centroid calculated from a training data and a shrinkage factor,
$\overline{x}_{ik}'$ may be a component of $\overline{x}_k'$ corresponding to gene i;
$s_i$ is a pooled within-class standard deviation for gene i in the training data;
$s_0$ is a specified positive constant; and
$\pi_k$ represents a prior probability of a sample belonging to class k.

Assigning the classification may comprise calculating a class probability. Calculating the class probability $\hat{p}_k(x^*)$ may be calculated by Equation 2:

$$\hat{p}_k(x^*) = \frac{e^{-\frac{1}{2}\delta_k(x^*)}}{\sum_{l=1}^{K} e^{-\frac{1}{2}\delta_l(x^*)}}.$$

Assigning the classification may comprise a classification rule. The classification rule C(x*) may be expressed by Equation 3:

$$C(x^*) = \underset{k \in \{1,K\}}{\operatorname{argmax}} \hat{p}_k(x^*).$$

VI. Diagnosis, Prognosis and Monitoring

The above described methods can provide a composite or aggregate value or other designation for a patient, which indicates whether the patient either has or is at enhanced risk of SCAR (or AR), or conversely does not have or is at reduced risk of SCAR (or AR). Risk is a relative term in which risk of one patient is compared with risk of other patients either qualitatively or quantitatively. For example, the value of one patient can be compared with a scale of values for a population of patients having undergone kidney transplant to determine whether the patient's risk relative to that of other patients. In general, diagnosis is the determination of the present condition of a patient (e.g., presence or absence of SCAR) and prognosis is developing future course of the patient (e.g., risk of developing SCAR in the future or likelihood of improvement in response to treatment); however, the analyses contemplated by these terms may overlap or even be the same. For example, the present methods alone do not necessarily distinguish between presence and enhanced risk of SCAR. However, these possibilities can be distinguished by additional testing.

The methods provided herein can help determine whether the patient either has or is at enhanced risk of subAR/SCAR (or AR) with a high degree of accuracy, sensitivity, and/or specificity. In some cases, the predictive accuracy (e.g., for predicting subAR/SCAR, for detecting subAR/SCAR, or for distinguishing SCAR versus TX, SCAR versus AR, AR versus TX, and/or any combination thereof) is greater than 75%, 85%, 90%, 91%, 92%, 93%, 94%, 95%, 96%, 97%, 98%, 98.5%, 99.0%, 99.1%, 99.2%, 99.3%, 99.4%, 99.5%, 99.6%, 99.7%, 99.8%, 99.9%, 99.95%, or 99.99%. In some embodiments, the predictive accuracy is 100%. In some cases, the sensitivity (e.g., for detecting or predicting SCAR or for distinguishing SCAR versus TX, SCAR versus AR, AR versus TX, and/or any combination thereof) is greater than 75%, 85%, 90%, 91%, 92%, 93%, 94%, 95° %, 96%, 97%, 98%, 98.5%, 99.0%, 99.1%, 99.2%, 99.3%, 99.4%, 99.5%, 99.6%, 99.7%, 99.8%, 99.9%, 99.95%, or 99.99%. In some embodiments the sensitivity is 100%. In some cases, the specificity (e.g., for detecting or predicting SCAR or for distinguishing SCAR versus TX, SCAR versus AR, AR versus TX, and/or any combination thereof) is greater than 75%, 85%, 90%, 91%, 92%, 93%, 94%, 95%, 96%, 97%, 98%, 98.5%, 99.0%, 99.1%, 99.2%, 99.3%, 99.4%, 99.5/%, 99.6%, 99.7%, 99.8%, 99.9%, 99.95%, or 99.99%. In some cases, the specificity is 100%. In some cases, the positive predictive value (e.g., for detecting or predicting SCAR or for distinguishing SCAR versus TX, SCAR versus AR, AR versus TX, and/or any combination thereof) of the method is greater than 75%, 85%, 90%, 91%, 92%, 93%, 94%, 95%, 96%, 97%, 98%, 98.5%, 99.0%, 99.1%, 99.2%, 99.3%, 99.4%, 99.5/%, 99.6/%, 99.7%, 99.8%, 99.9%, 99.95%, or 99.99%. In some cases the positive predictive value is 100%. The AUC after thresholding in any of the methods provided herein may be greater than 0.9, 0.91, 0.92, 0.93, 0.94, 0.95, 0.96, 0.97, 0.98, 0.99, 0.995, or 0.999. Conversely, the method may predict or determine whether a transplant recipient does not have or is at reduced risk of SCAR (or AR). The negative predictive value (e.g., for predicting or determining that transplant recipient does not have SCAR or is at reduced risk for SCAR or for distinguishing SCAR versus TX, SCAR versus AR, AR versus TX, and/or any combination thereof) may be greater than 85%, 90%, 91%, 92%, 93%, 94%, 95%, 96%, 97%, 98%, 98.5%, 99.0%, 99.1%, 99.2%, 99.3%, 99.4%, 99.5%, 99.6%, 99.7%, 99.8%, 99.9%, 99.95%, or 99.99%. In some cases, the negative predictive value is 100%.

In some instances, the methods, compositions, systems and kits described herein provide information to a medical practitioner that can be useful in making a therapeutic decision. Therapeutic decisions may include decisions to: continue with a particular therapy, modify a particular therapy, alter the dosage of a particular therapy, stop or terminate a particular therapy, altering the frequency of a therapy, introduce a new therapy, introduce a new therapy to be used in combination with a current therapy, or any combination of the above. In some instances, the results of diagnosing, predicting, or monitoring a condition of a transplant recipient may be useful for informing a therapeutic decision such as removal of the transplant. In some instances, the removal of the transplant can be an immediate removal. In other instances, the therapeutic decision can be a retransplant. Other examples of therapeutic regimen can include a blood transfusion in instances where the transplant recipient is refractory to immunosuppressive or antibody therapy.

If a patient is indicated as having or being at enhanced risk of subAR or SCAR, the physician can subject the patient to additional testing including performing a kidney biopsy or performing other analyses such as creatinine, BUN or glomerular filtration rate at increased frequency. Additionally or alternatively, the physician can change the treatment regime being administered to the patient. A change in treatment regime can include administering an additional or different drug to a patient, or administering a higher dosage or frequency of a drug already being administered to the patient. Many different drugs are available for treating rejection, such as immunosuppressive drugs used to treat transplant rejection calcineurin inhibitors (e.g., cyclosporine, tacrolimus), mTOR inhibitors (e.g., sirolimus and everolimus) anti-proliferatives (e.g., azathioprine, mycophenolic acid), corticosteroids (e.g., prednisolone and hydrocortisone) and antibodies (e.g., basiliximab, daclizumab, Orthoclone, anti-thymocyte globulin and anti-lymphocyte globulin).

Conversely, if the value or other designation of aggregate expression levels of a patient indicates the patient does not have or is at reduced risk of SCAR, the physician need not order further diagnostic procedures, particularly not invasive ones such as biopsy. Further, the physician can continue an existing treatment regime, or even decrease the dose or frequency of an administered drug.

In some methods, expression levels are determined at intervals in a particular patient (i.e., monitoring). Preferably, the monitoring is conducted by serial minimally-invasive tests such as blood draws; but, in some cases, the monitoring may also involve analyzing a kidney biopsy, either histologically or by analyzing a molecular profile. The monitoring may occur at different intervals, for example the monitoring may be hourly, daily, weekly, monthly, yearly, or some other time period, such as twice a month, three times a month, every two months, every three months, etc.

Such methods can provide a series of values changing over time indicating whether the aggregate expression levels in a particular patient are more like the expression levels in patients undergoing subAR or SCAR or not undergoing subAR or SCAR. Movement in value toward or away from subAR or SCAR can provide an indication whether an existing immunosuppressive regime is working, whether the immunosuppressive regime should be changed or whether a biopsy or increased monitoring by markers such as creatinine or glomerular filtration rate should be performed.

The methods provided herein include administering a blood test (e.g., a test to detect subclinical acute rejection) to a transplant recipient who has already undergone a surveillance or protocol biopsy of the kidney and received a biopsy result in the form of a histological analysis or a molecular profiling analysis. In some particular instances, the analysis of the kidney biopsy (e.g., by histology or molecular profiling) may result in ambiguous, inconclusive or borderline results. In such cases, a blood test provided herein may assist a caregiver with determining whether the transplant recipient has subclinical acute rejection or with interpreting the biopsy. In other cases the biopsy itself may be inconclusive or ambiguous, and in such cases the molecular analysis of the biopsy may be used in adjunct with the histology to confirm a diagnosis. In some instances, the analysis of the kidney biopsy may yield a negative result. In such cases, the subject may receive a blood test provided herein in order to confirm the negative result, or to detect subclinical acute rejection. In some cases, after receiving any type of biopsy result (e.g., negative result, ambiguous, inconclusive, borderline, positive), the patient may receive multiple, serial blood tests to monitor changes in molecular markers correlated with subclinical acute rejection.

The methods provided herein also include administering a biopsy test (e.g., histology or molecular profiling) to a transplant recipient who has received a molecular blood profiling test. For example, the transplant recipient may receive an ambiguous, inconclusive or borderline result on a blood molecular profiling test. In such cases, the patient's healthcare worker may use the results of a kidney biopsy test as a complement to the blood test to determine whether the subject is experiencing subclinical acute rejection. In another example, the transplant recipient may have received a positive result on a blood molecular profiling test, indicating that the transplant recipient has, or likely has, subclinical acute rejection, or even multiple positive results over time. In such cases, the patient's physician or other healthcare worker may decide to biopsy the patient's kidney in order to detect subAR. Such kidney biopsy test may be a molecular profiling analysis of the patient's kidney, as described herein. In some cases, a histological analysis of the kidney biopsy may be performed instead of, or in addition to, the molecular analysis of the biopsy. In some cases, the physician may decide to wait a certain period of time after receiving the positive blood result to perform the biopsy test.

The methods provided herein may often provide early detection of subAR and may help a patient to obtain early treatment such as receiving immunosuppressive therapy or increasing an existing immunosuppressive regimen. Such early treatment may enable the patient to avoid more serious consequences associated with acute rejection later in time, such as allograft loss or procedures such as kidney dialysis. In some cases, such early treatments may be administered after the patient receives both a molecular profiling blood test and a biopsy analyzed either by molecular profiling or histologically.

The diagnosis or detection of condition of a transplant recipient may be particularly useful in limiting the number of invasive diagnostic interventions that are administered to the patient. For example, the methods provided herein may limit or eliminate the need for a transplant recipient (e.g., kidney transplant recipient) to receive a biopsy (e.g., kidney biopsies) or to receive multiple biopsies. In a further embodiment, the methods provided herein can be used alone or in combination with other standard diagnosis methods currently used to detect or diagnose a condition of a transplant recipient, such as but not limited to results of biopsy analysis for kidney allograft rejection, results of histopathology of the biopsy sample, serum creatinine level, creatinine clearance, ultrasound, radiological imaging results for the kidney, urinalysis results, elevated levels of inflammatory molecules such as neopterin, and lymphokines, elevated plasma interleukin (IL)-1 in azathioprine-treated patients, elevated IL-2 in cyclosporine-treated patients, elevated IL-6 in serum and urine, intrarenal expression of cytotoxic molecules (granzyme B and perforin) and immunoregulatory cytokines (IL-2, -4, -10, interferon gamma and transforming growth factor-b1).

The methods herein may be used in conjunction with kidney function tests, such as complete blood count (CBC), serum electrolytes tests (including sodium, potassium, chloride, bicarbonate, calcium, and phosphorus), blood urea test, blood nitrogen test, serum creatinine test, urine electrolytes tests, urine creatinine test, urine protein test, urine fractional excretion of sodium (FENA) test, glomerular filtration rate (GFR) test. Kidney function may also be assessed by a renal biopsy. Kidney function may also be assessed by one or more gene expression tests.

VII. Drug Screening

The expression profiles associated with SCAR or lack thereof (TX) provided by the invention are useful in screening drugs, either in clinical trials or in animal models of SCAR. A clinical trial can be performed on a drug in similar fashion to the monitoring of an individual patient described above, except that drug is administered in parallel to a population of kidney transplant patients, usually in comparison with a control population administered a placebo.

The changes in expression levels of genes can be analyzed in individual patients and across a treated or control population. Analysis at the level of an individual patient provides an indication of the overall status of the patient at the end of the trial (i.e., whether gene expression profile indicates presence or enhanced susceptibility to SCAR) and/or an indication whether that profile has changed toward or away from such indication in the course of the trial. Results for individual patients can be aggregated for a population allowing comparison between treated and control population.

Similar trials can be performed in non-human animal models of chronic kidney disease, e.g., the mouse model of Mannon et al., Kidney International 55: 1935-1944, 1999. In this case, the expression levels of genes detected are the species variants or homologs of the human genes referenced above in whatever species of non-human animal on which tests are being conducted. Although the average or mean expression levels of human genes determined in human kidney transplant patients undergoing or not undergoing SCAR are not necessarily directly comparable to those of homolog genes in an animal model, the human values can nevertheless be used to provide an indication whether a change in expression level of a non-human homolog is In a direction toward or away from SCAR or susceptibility thereto. The expression profile of individual animals in a trial can provide an indication of the status of the animal at the end of the trial with respect to presence or susceptibility to SCAR and/or change in such status during the trial. Results from individual animals can be aggregated across a population and treated and control populations compared. Average changes in the expression levels of genes can then be compared between the two populations.

VIII. Computer Implemented Methods

Expression levels can be analyzed and associated with status of a subject (e.g., presence or susceptibility to SCAR) in a digital computer. Optionally, such a computer is directly linked to a scanner or the like receiving experimentally determined signals related to expression levels. Alternatively, expression levels can be input by other means. The computer can be programmed to convert raw signals into expression levels (absolute or relative), compare measured expression levels with one or more reference expression levels, or a scale of such values, as described above. The computer can also be programmed to assign values or other designations to expression levels based on the comparison with one or more reference expression levels, and to aggregate such values or designations for multiple genes in an expression profile. The computer can also be programmed to output a value or other designation providing an indication of presence or susceptibility to SCAR as well as any of the raw or intermediate data used in determining such a value or designation.

A typically computer (see U.S. Pat. No. 6,785,613 FIGS. 4 and 5) includes a bus which interconnects major subsystems such as a central processor, a system memory, an input/output controller, an external device such as a printer via a parallel port, a display screen via a display adapter, a serial port, a keyboard, a fixed disk drive and a floppy disk drive operative to receive a floppy disk. Many other devices can be connected such as a scanner via I/O controller, a mouse connected to serial port or a network interface. The computer contains computer readable media holding codes to allow the computer to perform a variety of functions. These functions include controlling automated apparatus, receiving input and delivering output as described above. The automated apparatus can include a robotic arm for delivering reagents for determining expression levels, as well as small vessels, e.g., microtiter wells for performing the expression analysis.

The methods, systems, kits and compositions provided herein may also be capable of generating and transmitting results through a computer network. As shown in FIG. 2, a sample (220) is first collected from a subject (e.g. transplant recipient, 210). The sample is assayed (230) and gene expression products are generated. A computer system (240) is used in analyzing the data and making classification of the sample. The result is capable of being transmitted to different types of end users via a computer network (250). In some instances, the subject (e.g. patient) may be able to access the result by using a standalone software and/or a web-based application on a local computer capable of accessing the internet (260). In some instances, the result can be accessed via a mobile application (270) provided to a mobile digital processing device (e.g. mobile phone, tablet, etc.). In some instances, the result may be accessed by physicians and help them identify and track conditions of their patients (280). In some instances, the result may be used for other purposes (290) such as education and research.

Computer Program

The methods, kits, and systems disclosed herein may include at least one computer program, or use of the same. A computer program may include a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. The computer program will normally provide a sequence of instructions from one location or a plurality of locations. In various embodiments, a computer program includes, in part or in whole, one or more web applications, one or more mobile applications, one or more standalone applications, one or more web browser plug-ins, extensions, add-ins, or add-ons, or combinations thereof.

Further disclosed herein are systems for classifying one or more samples and uses thereof. The system may comprise (a) a digital processing device comprising an operating system configured to perform executable instructions and a memory device; (b) a computer program including instructions executable by the digital processing device to classify a sample from a subject comprising: (i) a first software module configured to receive a gene expression profile of one or more genes from the sample from the subject; (ii) a second software module configured to analyze the gene expression profile from the subject; and (iii) a third software module configured to classify the sample from the subject based on a classification system comprising three or more classes. At least one of the classes may be selected from transplant rejection, transplant dysfunction with no rejection and normal transplant function. At least two of the classes may be selected from transplant rejection, transplant dysfunction with no rejection and normal transplant function. All three of the classes may be selected from transplant rejection, transplant dysfunction with no rejection and normal transplant function. Analyzing the gene expression profile from the subject may comprise applying an algorithm. Analyzing the gene expression profile may comprise normalizing the gene expression profile from the subject. In some instances, normalizing the gene expression profile does not comprise quantile normalization.

Figure 4:
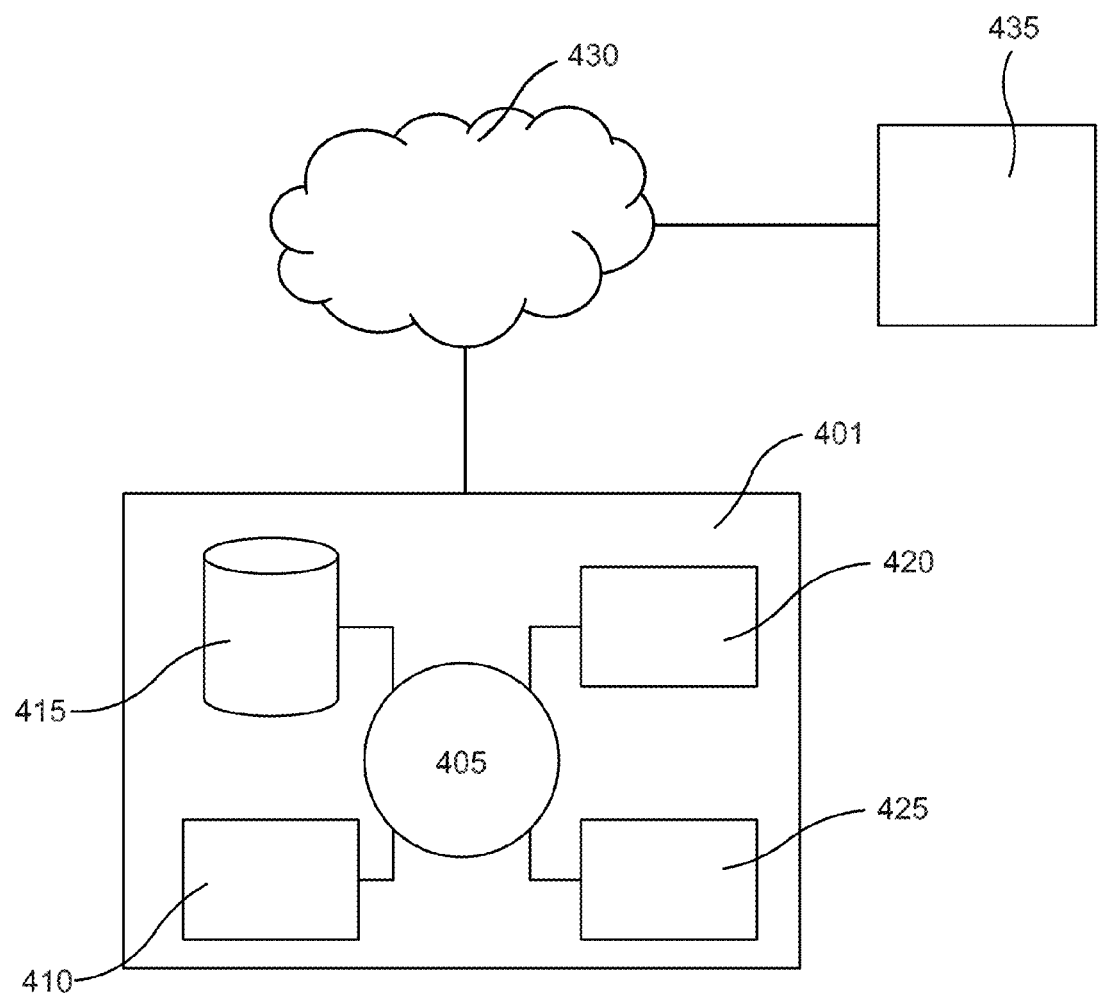
FIG. 4 shows a computer system for implementing the methods of the disclosure.
Figure 5:
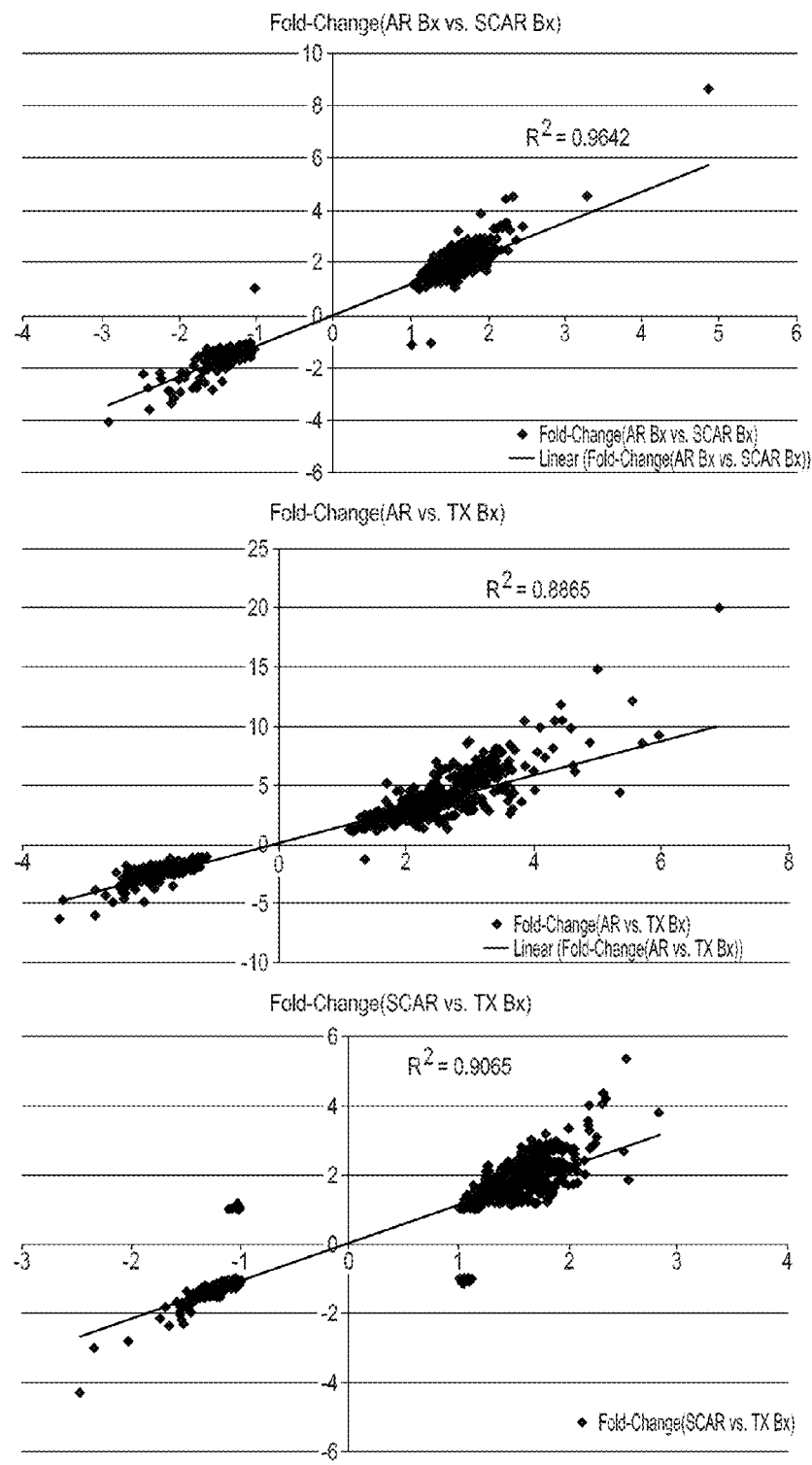
FIG. 5 shows a correlation of fold-change between microarray and NGS analyses (1066 common genes).

FIG. 4 shows a computer system (also "system" herein) 401 programmed or otherwise configured for implementing the methods of the disclosure, such as producing a selector set and/or for data analysis. The system 401 includes a central processing unit (CPU, also "processor" and "computer processor" herein) 405, which can be a single core or multi core processor, or a plurality of processors for parallel processing. The system 401 also includes memory 410 (e.g., random-access memory, read-only memory, flash memory), electronic storage unit 415 (e.g., hard disk), communications interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communications bus (solid lines), such as a motherboard. The storage unit 415 can be a data storage unit (or data repository) for storing data. The system 401 is operatively coupled to a computer network ("network") 430 with the aid of the communications interface 420. The network 430 can be the Internet, an internet and/or extranet, or an intranet and/or extranet that is in communication with the Internet. The network 430 in some instances is a telecommunication and/or data network. The network 430 can include one or more computer servers, which can enable distributed computing, such as cloud computing. The network 430 in some instances, with the aid of the system 401, can implement a peer-to-peer network, which may enable devices coupled to the system 401 to behave as a client or a server.

The system 401 is in communication with a processing system 435. The processing system 435 can be configured to implement the methods disclosed herein. In some examples, the processing system 435 is a nucleic acid sequencing system, such as, for example, a next generation sequencing system (e.g., Illumina sequencer, Ion Torrent sequencer, Pacific Biosciences sequencer). The processing system 435 can be in communication with the system 401 through the network 430, or by direct (e.g., wired, wireless) connection. The processing system 435 can be configured for analysis, such as nucleic acid sequence analysis.

Methods as described herein can be implemented by way of machine (or computer processor) executable code (or software) stored on an electronic storage location of the system 401, such as, for example, on the memory 410 or electronic storage unit 415. During use, the code can be executed by the processor 405. In some examples, the code can be retrieved from the storage unit 415 and stored on the memory 410 for ready access by the processor 405. In some situations, the electronic storage unit 415 can be precluded, and machine-executable instructions are stored on memory 410.

Digital Processing Device

The methods, kits, and systems disclosed herein may include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

The digital processing device will normally include an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

The device generally includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

A display to send visual information to a user will normally be initialized. Examples of displays include a cathode ray tube (CRT, a liquid crystal display (LCD), a thin film transistor liquid crystal display (TFT-LCD, an organic light emitting diode (OLED) display. In various further embodiments, on OLED display is a passive-matrix OLED (PMOLED) or active-matrix OLED (AMOLED) display. In some embodiments, the display may be a plasma display, a video projector or a combination of devices such as those disclosed herein.

The digital processing device would normally include an input device to receive information from a user. The input device may be, for example, a keyboard, a pointing device including, by way of non-limiting examples, a mouse, trackball, track pad, joystick, game controller, or stylus; a touch screen, or a multi-touch screen, a microphone to capture voice or other sound input, a video camera to capture motion or visual input or a combination of devices such as those disclosed herein.

Non-Transitory Computer Readable Storage Medium

The methods, kits, and systems disclosed herein may include one or more non-transitory computer readable storage media encoded with a program including instructions executable by the operating system to perform and analyze the test described herein; preferably connected to a networked digital processing device. The computer readable storage medium is a tangible component of a digital that is optionally removable from the digital processing device. The computer readable storage medium includes, by way of non-limiting examples, CD-ROMs, DVDs, flash memory devices, solid state memory, magnetic disk drives, magnetic tape drives, optical disk drives, cloud computing systems and services, and the like. In some instances, the program and instructions are permanently, substantially permanently, semi-permanently, or non-transitorily encoded on the media.

A non-transitory computer-readable storage media may be encoded with a computer program including instructions executable by a processor to create or use a classification system. The storage media may comprise (a) a database, in a computer memory, of one or more clinical features of two or more control samples, wherein (i) the two or more control samples may be from two or more subjects; and (ii) the two or more control samples may be differentially classified based on a classification system comprising three or more classes; (b) a first software module configured to compare the one or more clinical features of the two or more control samples; and (c) a second software module configured to produce a classifier set based on the comparison of the one or more clinical features.

At least two of the classes may be selected from transplant rejection, transplant dysfunction with no rejection and normal transplant function. All three classes may be selected from transplant rejection, transplant dysfunction with no rejection and normal transplant function. The storage media may further comprise one or more additional software modules configured to classify a sample from a subject. Classifying the sample from the subject may comprise a classification system comprising three or more classes. At least two of the classes may be selected from transplant rejection, transplant dysfunction with no rejection and normal transplant function. All three classes may be selected from transplant rejection, transplant dysfunction with no rejection and normal transplant function.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The methods, kits, and systems disclosed herein may include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

The methods, kits, and systems disclosed herein may comprise one or more databases, or use of the same. In view of the disclosure provided herein, those of skill in the art will recognize that many databases are suitable for storage and retrieval of information pertaining to gene expression profiles, sequencing data, classifiers, classification systems, therapeutic regimens, or a combination thereof. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Data Transmission

The methods, kits, and systems disclosed herein may be used to transmit one or more reports. The one or more reports may comprise information pertaining to the classification and/or identification of one or more samples from one or more subjects. The one or more reports may comprise information pertaining to a status or outcome of a transplant in a subject. The one or more reports may comprise information pertaining to therapeutic regimens for use in treating transplant rejection in a subject in need thereof. The one or more reports may comprise information pertaining to therapeutic regimens for use in treating transplant dysfunction in a subject in need thereof. The one or more reports may comprise information pertaining to therapeutic regimens for use in suppressing an immune response in a subject in need thereof.

The one or more reports may be transmitted to a subject or a medical representative of the subject. The medical representative of the subject may be a physician, physician's assistant, nurse, or other medical personnel. The medical representative of the subject may be a family member of the subject. A family member of the subject may be a parent, guardian, child, sibling, aunt, uncle, cousin, or spouse. The medical representative of the subject may be a legal representative of the subject.

EXAMPLES

The following examples are offered to illustrate, but not to limit the present invention.

Example 1 Materials and Methods

This Example describes some of the materials and methods employed in identification of differentially expressed genes in SCAR.

The discovery set of samples consisted of the following biopsy-documented peripheral blood samples. 69 PAXgene whole blood samples were collected from kidney transplant patients. The samples were histology confirmed, and comprised 3 different phenotypes: (1) Acute Rejection (AR; n=21); (2) Sub-Clinical Acute Rejection (SCAR; n=23); and (3) Transplant Excellent (TX; n=25). Specifically, SCAR was defined by a protocol biopsy done on a patient with totally stable kidney function and the light histology revealed unexpected evidence of acute rejection (16 "Borderline", 7 Banff 1A). The SCAR samples consisted of 3 month and 1 year protocol biopsies, whereas the TXs were predominantly 3 month protocol biopsies. The mean age of the patients is 49.3 years (ranging from 22-71); 35% female; 52% deceased donors. Table 5 presents time to biopsies where time is defined as days post transplantation. All the AR biopsies were "for cause" where clinical indications like a rise in serum creatinine prompted the need for a biopsy. All patients were induced with Thymoglobulin.

Example 2 Gone Expression Profiling and Data Analysis

All samples were processed on the Affymetrix HG-U133 PM only peg microarrays. To eliminate low expressed signals we used a signal filter cut-off that was data dependent, and therefore expression signals <$Log_2$ 3.74 (median signals on all arrays) in all samples were eliminated leaving us with 48734 probe sets from a total of 54721 probe sets. We performed a 3-way ANOVA analysis of AR vs. ADNR vs. TX. This yielded over 6000 differentially expressed probesets at a p-value <0.001. Even when a False Discovery rate cut-off of (FDR <10%), was used it gave us over 2700 probesets. The corresponding genes for 2156 probes are listed in Table 4. Therefore for the purpose of a diagnostic signature we used the top 200 differentially expressed probe sets (Table 2) to build predictive models that could differentiate the three classes. The top 200 probesets have FDR values of <0.05%. We used three different predictive algorithms, namely Diagonal Linear Discriminant Analysis (DLDA), Nearest Centroid (NC) and Support Vector Machines (SVM) to build the predictive models. We ran the predictive models using two different methodologies and calculated the Area Under the Curve (AUC). SVM, DLDA and NC picked classifier sets of 200, 192 and 188 probesets as the best classifiers. Since there was very little difference in the AUC's we decided to use all 200 probesets as classifiers for all methods. We also demonstrated that these results were not the consequence of statistical over-fitting by using the replacement method of Harrell to perform a version of 1000-test cross-validation. Table 1 shows the performance of these classifier sets using both one-level cross validation as well as the Optimism Corrected Bootstrapping (1000 data sets).

Figure 3:
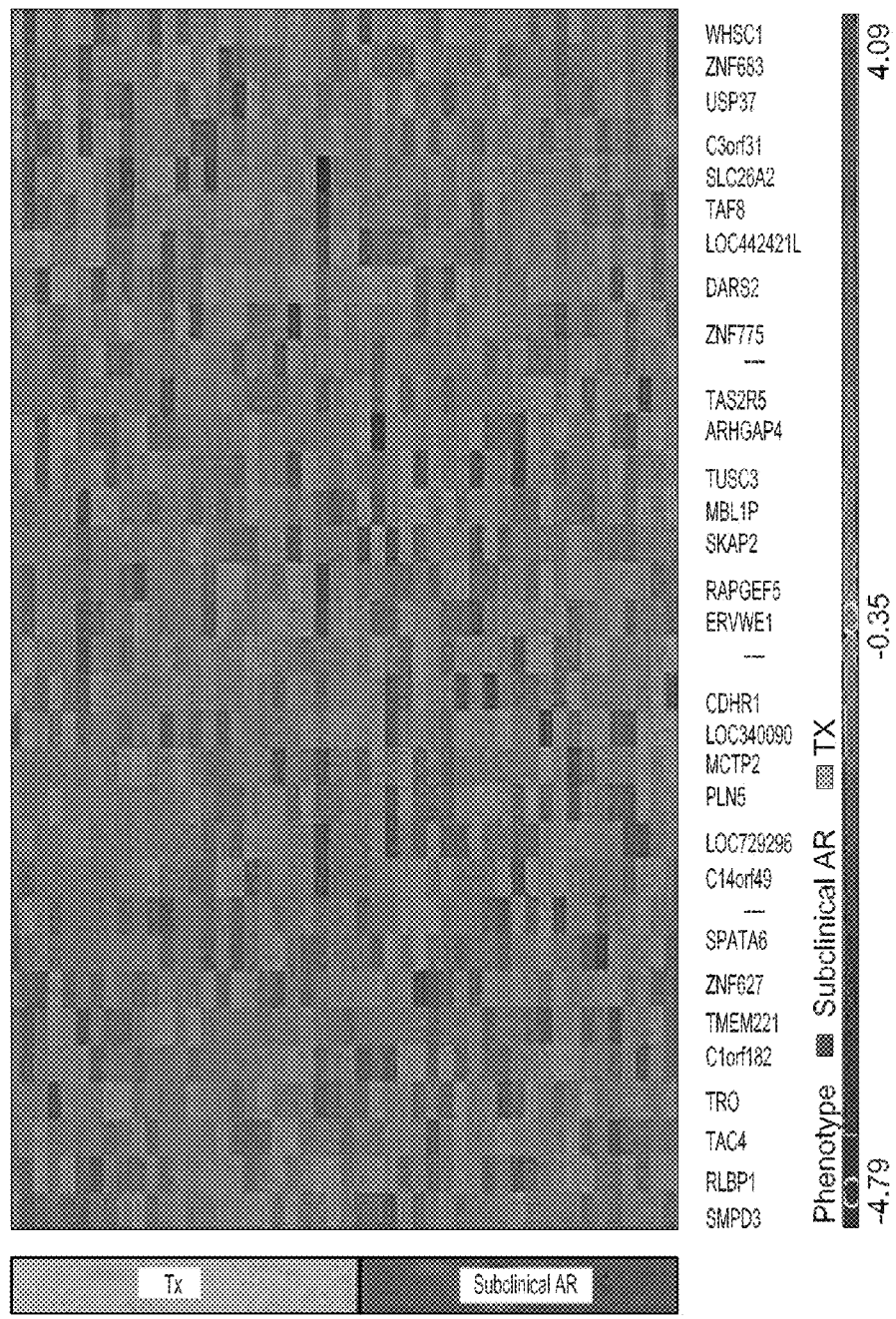
FIG. 3 is an illustration of hierarchical clustering of gene expression signals of 33 probesets used to differentiate SCAR versus TX.

An important point here is that in real clinical practice the challenge is actually not to distinguish SCAR from AR because generally only AR presents with a significant increase in baseline serum creatinine. The real challenge is to take a patient with normal and stable creatinine and diagnose the hidden SCAR without having to depend on invasive and expensive protocol biopsies that cannot be done frequently in any case. Though we have already successfully done this using our 3-way analysis, we also tested a 2-way prediction of SCAR vs. TX. The point was to further validate that a phenotype as potentially subtle clinically as SCAR can be truly distinguished from TX. At a p-value <0.001, there were 33 probesets whose expression signals highly differentiated SCAR and TX, a result in marked contrast with the >2500 probesets differentially expressed between AR vs. TX at that same p-value. (FIG. 3 shows the hierarchical clustering of gene expression profiling of these 33 probesets.) However, when these 33 probesets (Table 3) were used in NC to predict SCAR and TX creating a 2-way classifier, the predictive accuracies with a one-level cross-validation was 96% and with the Harrell 1000 test optimism correction it was 94%. Thus, we are confident that we can distinguish SCAR, TX and AR by peripheral blood gene expression profiling using this proof of principle data set.

Example 3 Microarray and NGS Analyses

This Example describes the identification of differentially expressed genes in SCAR using microarray and next-generation sequencing (NGS) analyses.

Biopsy Samples

To compare the methods using blood and biopsy samples, we performed microarray and NGS analyses on the blood and biopsy samples from the same kidney transplant patients. The discovery set of blood samples consisted of the following biopsy samples. 68 biopsy samples were collected from kidney transplant patients. The samples were histology confirmed, and comprised 3 different phenotypes: (1) Acute Rejection (AR; n=21); (2) Sub-Clinical Acute Rejection (SCAR; n=22); and (3) Transplant Excellent (TX; n=25). The specific sample characterizations and methods were described in Example 1.

Microarray Analyses—Biopsy Samples

All samples were processed on the HG-U133 Plus PM microarrays. All samples were normalized using RMA in Partek Genomics Suite 6.6. To facilitate biomarker discovery by removing probe sets with low signal intensities we used a signal filter cut-off that was data dependent, and therefore expression signals <$Log_2$ 4.14 (median signals on all arrays) in all samples were eliminated leaving us with 27980 probe sets representing about 13900 genes.

We first performed a 3-way 1-step ANOVA analysis of AR vs. SCAR (subAR) vs. TX. A False Discovery rate cut-off of (FDR) 1% was set, and after Bonferroni correction of Phenotype (AR vs. SCAR vs. TX) p-values, 1195 genes were selected. Nearest Centroid Algorithm in Partek were used to identify best classifier set that can distinguish all three phenotypes. We demonstrated that the method has an overall predictive accuracy of 85%. As shown in Table 6, the method correctly classified most samples. When Nearest Centroid (NC) was used to predict TX vs. AR, the results showed predictive accuracy of 100%, sensitivity of 100%, specificity of 100%, positive predictive value of 100%, negative predictive value of 100%, and AUC of 1.0. In TX vs. SCAR (subAR), the results showed predictive accuracy of 78%, sensitivity of 81%, specificity of 75%, positive predictive value of 84%, negative predictive value of 71%, and AUC of 0.785. Similarly, in AR vs. SCAR (subAR) 2-way classifier, the results showed predictive accuracy of 76%, sensitivity of 76%, specificity of 75%, positive predictive value of 80%, negative predictive value of 71%, and AUC of 0.768. Thus, we are confident that we can distinguish SCAR, TX and AR by biopsy sample gene expression profiling using the 3-way 1-step analysis.

We then performed a 2-way 2-step ANOVA analysis. Because of the disproportionate distribution (only 46 probesets that differentiate SCAR from TX compared to AR vs. TX (10834 probesets) and AR vs. SCAR (2067 probesets)), we decided to test a 2-step approach where we combined SCAR+AR vs. TX to clearly separate a SCAR or AR from TX as the first step. The second step was using the SCAR vs AR genes to separate the SCARs from the ARs.

We used the 4598 (SCAR+AR vs TX) and the 745 (SCAR vs. AR) unique genes (1322 genes were common between the two groups) to build 2-way classifiers. Nearest Centroid (NC) was used as a two-step prediction. The top 300 genes (based on p-value) for the first step (AR+subAR vs. TX) are listed in Table 7. The top 300 genes (based on p-value) for the second step (AR vs. subAR) are listed in Table 8.

The method correctly classified most samples with an overall predictive accuracy of 94%. As shown in Table 9, in TX vs. AR, the results showed predictive accuracy of 97%, sensitivity of 100%, specificity of 94%, positive predictive value of 95%, negative predictive value of 100%, and AUC of 0.965. In TX vs. SCAR (subAR), the results showed predictive accuracy of 95%, sensitivity of 100%, specificity of 90%, positive predictive value of 91%, negative predictive value of 100%, and AUC of 0.947. Similarly, in AR vs. SCAR (subAR) 2-way classifier, the results showed predictive accuracy of 86%, sensitivity of 90%, specificity of 81%, positive predictive value of 81%, negative predictive value of 90%, and AUC of 0.862. Thus, we are confident that we can distinguish SCAR, TX and AR by biopsy sample gene expression profiling using the 2-way 2-step analysis.

NGS Analyses—Biopsy Samples

All samples were processed on the ION PROTON™ System. Only runs with >10 million reads were used for analysis. There was an average of 16 million reads across all samples. Samples were aligned using the STAR aligner (Dobin et al, Bioinformatics 2012). Differential expression of noramlized (DESeq2 Values) was done using ANOVA in Partek. Samples were first filtered for a minimum of 5 cpm per gene. After filtering, 13191 genes (56%) were eligible for analysis. The same 1 and 2 step methodologies described in the microarray section were tested. When comparing microarray with NGS analyses using biopsy samples at FDR <10% in both cases, 8862 probe sets were identified in microarray analysis, while only 2058 probe sets were identified.

Briefly, the 3-way 1-step method has an overall predictive accuracy of 81%. As shown in Table 10, the method correctly classified most samples. In TX v. AR a, the results showed predictive accuracy of 97%, sensitivity of 100%, specificity of 92%, positive predictive value of 95%, negative predictive value of 100%, and AUC of 0.967. In TX vs. SCAR (subAR), the results showed predictive accuracy of 80%, sensitivity of 72%, specificity of 83%, positive predictive value of 72%, negative predictive value of 91%, and AUC of 0.795. Similarly, in AR vs. SCAR (subAR), the results showed predictive accuracy of 69%, sensitivity of 58%, specificity of 79% positive predictive value of 79%, negative predictive value of 59%, and AUC of 0.689. Thus, we are confident that we can distinguish SCAR, TX and AR from biopsy samples using the next-generation sequencing 3-way 1-step analysis.

We then performed a 2-way 2-step analysis. Similar to the microarray 2-way 2-step analysis, there was a disproportionate distribution: there are only 5 genes that differentiate SCAR from TX compared to AR vs. TX (1510 genes) and AR vs. SCAR (132 genes). And thus, we decided to test a 2-step approach where we combined SCAR+AR vs. TX to clearly separate a SCAR or AR from TX as the first step. The top 200 probe sets (ranked on p-value) of the biopsy NGS signatures for the first step (SCAR+AR vs. TX) is listed in Table 11. The second step was using the SCAR vs AR genes to separate the SCARs from the ARs. The top 160 probe sets (ranked on p-value) of the biopsy NGS signatures for the second step (SCAR vs. AR) is listed in Table 12. As shown in Table 13, when Nearest Centroid (NC) was used as a two-step prediction in the AR and TX 2-way classifier, the results showed predictive accuracy of 95%, sensitivity of 100%, specificity of 88%, positive predictive value of 92%, negative predictive value of 100%, and AUC of 0.943. In the SCAR (subAR) and TX 2-way classifier, the results showed predictive accuracy of 100%, sensitivity of 100%, specificity of 100%, positive predictive value of 100%, negative predictive value of 100%, and AUC of 1.000. Similarly, in the AR and SCAR (subAR) 2-way classifier, the results showed predictive accuracy of 79%, sensitivity of 76%, specificity of 83%, positive predictive value of 83%, negative predictive value of 72%, and AUC of 0.792. The method correctly classified most samples with an overall predictive accuracy of 91%. Thus, we are confident that we can distinguish SCAR, TX and AR by biopsy sample gene expression profiling using the 2-way 2-step analysis.

Next, to show the correlation between the probe sets identified in microarray and NGS analyses, we performed correlation analyses on 1) the 1066 genes common to both microarray and NGS (both differentially expressed at FDR <1%); and 2) all the 7076 NGS expressed genes (above threshold).

Figure 6:
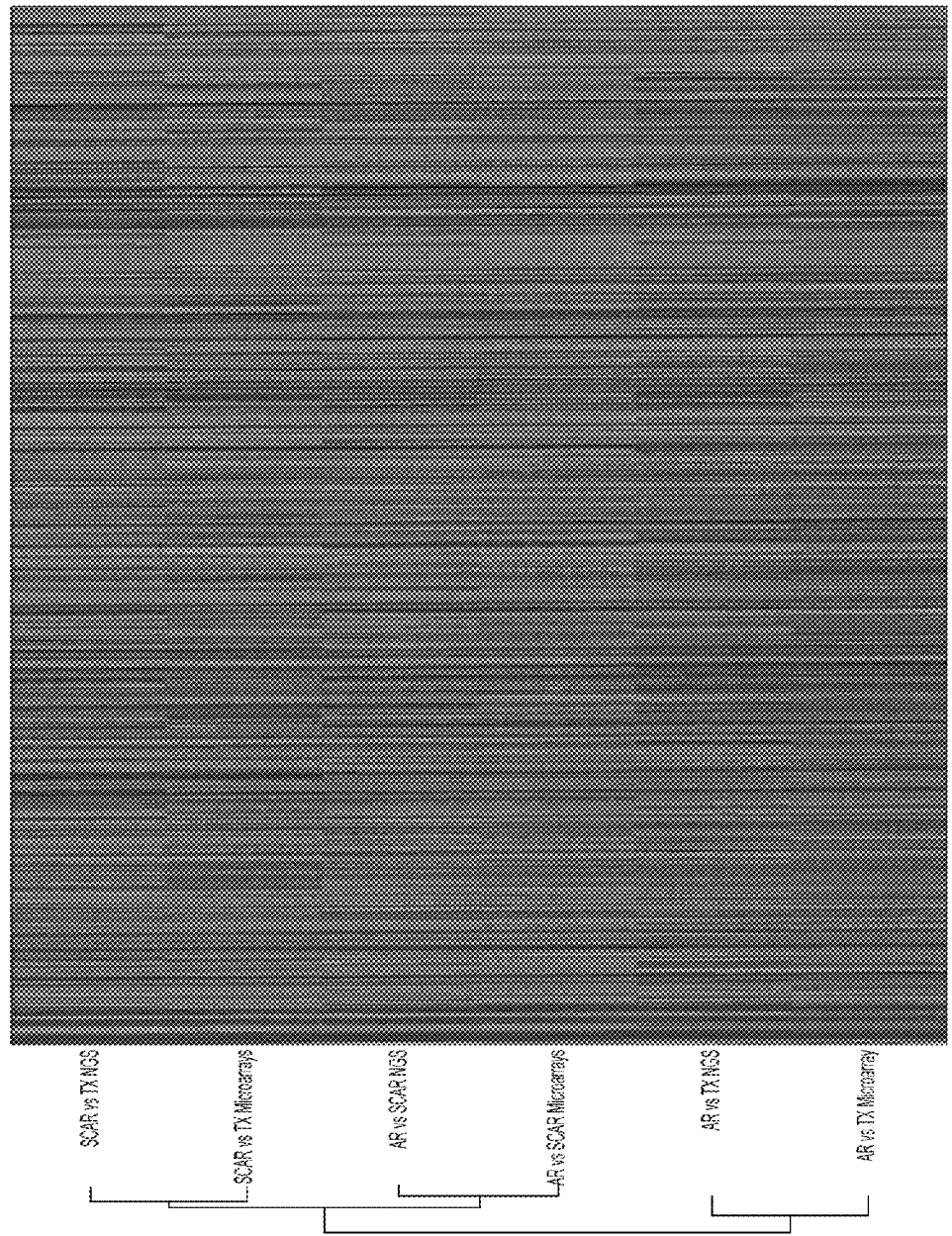
FIG. 6 shows a heat map and clustering of fold changes (Microarrays vs NGS) of 1066 genes.

We first performed correlation analyses on the 1066 genes common to both microarray and NGS. The genes were found to be highly correlated in correlation of fold-change in directionality analysis, 1063 out of the 1066 genes (99.8%) were found in agreement for AR vs. TX; 1063 out of the 1066 genes (99.8%) were found in agreement for AR vs. SCAR; 1042 out of the 1066 genes (97.8%) were found in agreement for AR vs. TX. We also plotted correlation of absolute fold changes of the 1066 genes in FIG. 5 and generated the heat map showing the clustering of this high correlation in FIG. 6.

Figure 7:
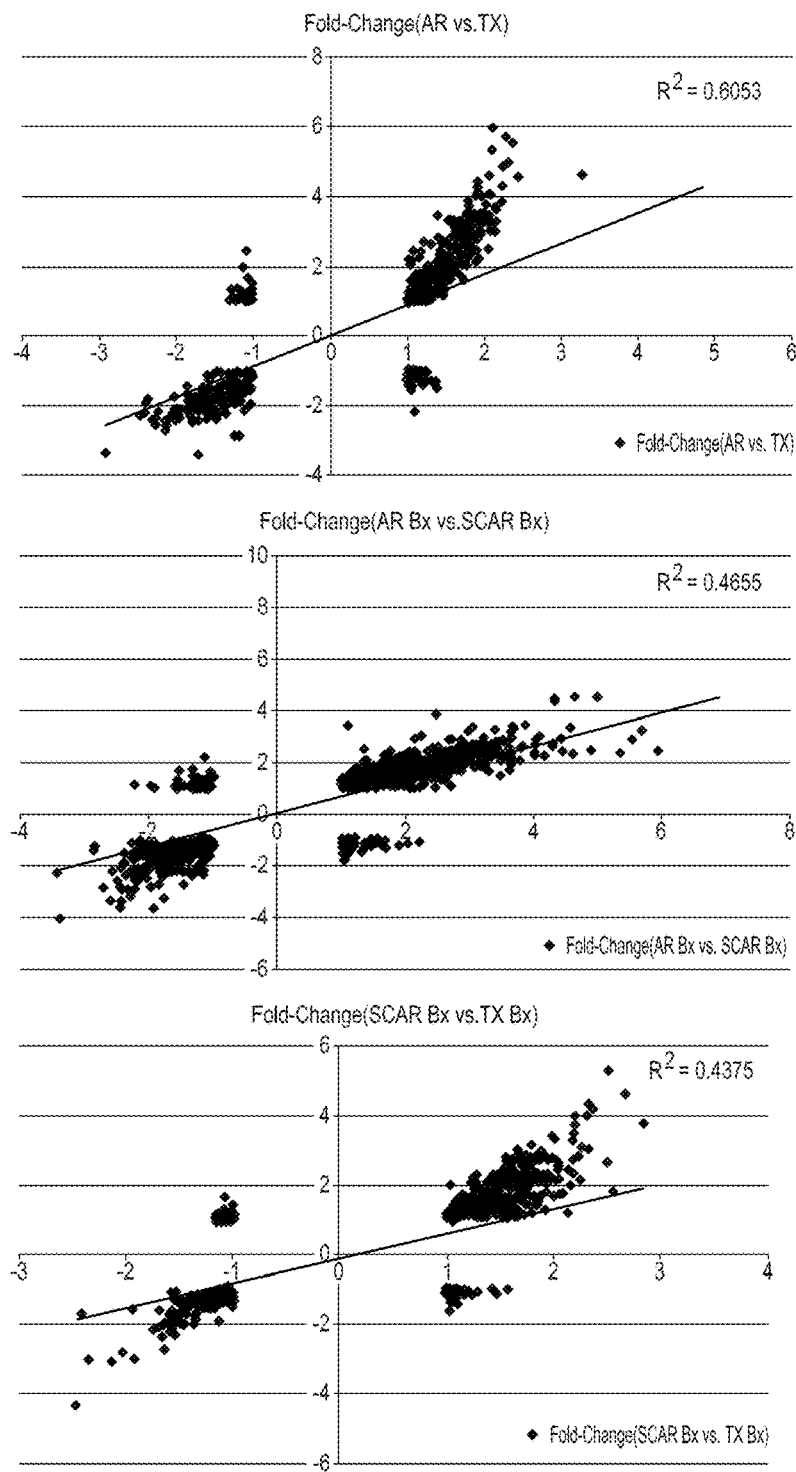
FIG. 7 shows correlation of fold-change between microarray and NGS analyses (all expressed NGS 7076 genes).

We then performed correlation analyses on all the 7076 NGS expressed genes. In correlation of fold-change in directionality analysis, 5747 out of the 7076 genes (81.2%) were found in agreement for AR vs. TX; 6080 out of the 7076 genes (85.9%) were found in agreement for AR vs. SCAR; 5652 out of the 7076 genes (79.8%) were found in agreement for AR vs. TX. We also plotted correlation of absolute fold changes of the 7076 NGS expressed genes in FIG. 7.

Blood Samples

To compare the methods using blood and biopsy samples, we also performed the microarray and NGS analyses on the blood samples from the same kidney transplant patients. Specifically, 68 PAXgene whole blood samples were collected from kidney transplant patients. As described earlier, the samples were histology confirmed, and comprised 3 different phenotypes: (1) Acute Rejection (AR; n=21); (2) Sub-Clinical Acute Rejection (SCAR; n=22); and (3) Transplant Excellent (TX; n=25).

Microarray Analyses—Blood Samples

All samples were processed the same way as the biopsy microarray samples. We first performed a 3-way 1-step ANOVA analysis of AR vs. SCAR (subAR) vs. TX. Nearest Centroid Algorithm in Partek were used to identify best classifier set that can distinguish all three phenotypes. The full 818 probe sets ranked by p-value are listed in Table 14 and the best performing 61 probe sets gene signature picked by the Nearest Centroid Algorithm are listed in Table 15.

We demonstrated that the 3-way 1-step analysis has an overall predictive accuracy of 91%. As shown in Table 16, the method correctly classified most samples. In the AR and TX 2-way classifier, the results showed predictive accuracy of 90%, sensitivity of 95%, specificity of 85%, positive predictive value of 86%, negative predictive value of 94%, and AUC of 0.898. In the SCAR (subAR) and TX 2-way classifier, the results showed predictive accuracy of 91%, sensitivity of 95%, specificity of 87%, positive predictive value of 86%, negative predictive value of 95%, and AUC of 0.912. Similarly, in the AR and SCAR (subAR) 2-way classifier, the results showed predictive accuracy of 91%, sensitivity of 88%, specificity of 94%, positive predictive value of 95%, negative predictive value of 85%, and AUC of 0.905. Thus, we are confident that we can distinguish SCAR, TX and AR by peripheral blood gene expression profiling using this data set.

NGS Analyses—Blood Samples

All samples were processed the same way as the biopsy NGS samples. We first performed a 3-way 1-step ANOVA analysis of AR vs. SCAR (subAR) vs. TX. Nearest Centroid Algorithm in Partek were used to identify best classifier set that can distinguish all three phenotypes. The full 123 probe sets (p<0.01) ranked by p-value are listed in Table 17 and the best performing 53 probe sets gene signature picked by the Nearest Centroid Algorithm are listed in Table IS. Among the gene signatures in Table 18, JUP, XCL1, CRADD, XCL1/XCL2, PRNP, HHEX, FAM43A, and PSMD6-AS2 Were also differentially expressed (p<0.05) in the microarray comparisons.

We demonstrated that the 3-way 1-step analysis has an overall predictive accuracy of 89%. As shown in Table 19, the method correctly classified most samples. In the AR and TX 2-way classifier, the results showed predictive accuracy of 92%, sensitivity of 95%, specificity of 90%, positive predictive value of 90%, negative predictive value of 95%, and AUC of 0.921. In the SCAR (subAR) and TX 2-way classifier, the results showed predictive accuracy of 83%, sensitivity of 83%, specificity of 82%, positive predictive value of 83%, negative predictive value of 82%, and AUC of 0.829. Similarly, in the AR and SCAR (subAR) 2-way classifier, the results showed predictive accuracy of 93%, sensitivity of 94%, specificity of 95%, positive predictive value of 94%, negative predictive value of 95%, and AUC of 0.943. Thus, we are confident that we can distinguish SCAR, TX and AR by peripheral blood gene expression profiling using this data set.

Next, similar to the biopsy sample analyses, to show the correlation between the probe sets identified in microarray and NGS analyses, we performed correlation analyses on 1) the 101 genes differentially expressed in both microarray and NGS; and 2) all the 7076 NGS expressed genes (above threshold).

We performed correlation analyses on the 101 genes common to both microarray and NGS. The genes were found to be highly correlated in correlation of fold-change in directionality analysis, 94 out of the 101 genes (93.8%) were found in agreement for AR vs. TX; 100 out of the 101 genes (99.0%) were found in agreement for AR vs. SCAR; 79 out of the 101 genes (78.2%) were found in agreement for AR vs. TX.

CONCLUSIONS—MICROARRAY VS. NGS

The comparison demonstrated that microarrays and NGS perform similarly with respect to predictions of phenotypes. Both methods have very high correlation with fold-change especially amongst significantly differentially expressed genes.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used In the practice or testing of the present invention, the preferred methods and materials are described.

All publications, GenBank sequences, ATCC deposits, patents and patent applications cited herein are hereby expressly incorporated by reference in their entirety and for all purposes as if each is individually so denoted.

TABLE 1

Blood Expression Profiling of Kidney Transplants: 3-Way Classifier AR vs. SCAR vs. TX

| Algorithm | Predictors | Comparison | AUC after Thresholding | Predictive Accuracy (%) | Sensitivity (%) | Specificity (%) | Positive Predictive Value (%) | Negative Predictive Value (%) |
|---|---|---|---|---|---|---|---|---|
| Nearest Centroid | 200 | SCAR vs. TX | 1.000 | 100 | 100 | 100 | 100 | 100 |
| Nearest Centroid | 200 | SCAR vs. AR | 0.953 | 95 | 92 | 100 | 100 | 90 |
| Nearest Centroid | 200 | AR vs. TX | 0.932 | 93 | 96 | 90 | 92 | 95 |

TABLE 2

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1 | 238108_PM_at | — | — | 1.70E-10 | 8.27E-06 | 73.3 | 45.4 | 44.4 |
| 2 | 243524_PM_at | — | — | 3.98E-10 | 9.70E-06 | 72.3 | 41.3 | 37.7 |
| 3 | 1558831_PM_x_at | — | — | 5.11E-09 | 8.30E-05 | 48.1 | 30.8 | 31.4 |
| 4 | 229858_PM_at | — | — | 7.49E-09 | 8.31E-05 | 576.2 | 359.3 | 348.4 |
| 5 | 236685_PM_at | — | — | 8.53E-09 | 8.31E-05 | 409.1 | 213.3 | 211.0 |
| 6 | 213546_PM_at | DKFZP586I1420 | hypothetical protein DKFZP586I1420 | 3.52E-08 | 2.60E-04 | 619.2 | 453.7 | 446.0 |
| 7 | 231958_PM_at | C3orf31 | Chromosome 3 open reading frame 31 | 4.35E-08 | 2.60E-04 | 22.8 | 20.1 | 16.4 |
| 8 | 210275_PM_s_at | ZFAND5 | zinc finger, AN1-type domain 5 | 4.96E-08 | 2.60E-04 | 1045.9 | 1513.6 | 1553.8 |
| 9 | 244341_PM_at | — | — | 5.75E-08 | 2.60E-04 | 398.3 | 270.7 | 262.8 |
| 10 | 1558822_PM_at | — | — | 5.84E-08 | 2.60E-04 | 108.6 | 62.9 | 56.8 |
| 11 | 242175_PM_at | — | — | 5.87E-08 | 2.60E-04 | 69.1 | 37.2 | 40.0 |
| 12 | 222357_PM_at | ZBTB20 | zinc finger and BTB domain containing 20 | 6.97E-08 | 2.83E-04 | 237.4 | 127.4 | 109.8 |
| 13 | 206288_PM_at | PGGT1B | protein geranylgeranyltransferase type I, beta subunit | 9.42E-08 | 3.53E-04 | 20.8 | 34.7 | 34.2 |
| 14 | 222306_PM_at | — | — | 1.03E-07 | 3.59E-04 | 23.3 | 15.8 | 16.0 |
| 15 | 1569601_PM_at | — | — | 1.67E-07 | 4.80E-04 | 49.5 | 34.1 | 29.7 |
| 16 | 235138_PM_at | — | — | 1.69E-07 | 4.80E-04 | 1169.9 | 780.0 | 829.7 |
| 17 | 240452_PM_at | GSPT1 | G1 to S phase transition 1 | 1.74E-07 | 4.80E-04 | 97.7 | 54.4 | 48.6 |
| 18 | 243003_PM_at | — | — | 1.77E-07 | 4.80E-04 | 92.5 | 52.5 | 51.3 |
| 19 | 218109_PM_s_at | MFSD1 | major facilitator superfamily domain containing 1 | 1.90E-07 | 4.87E-04 | 1464.0 | 1881.0 | 1886.4 |
| 20 | 241681_PM_at | — | — | 2.00E-07 | 4.87E-04 | 1565.7 | 845.7 | 794.6 |
| 21 | 243878_PM_at | — | — | 2.19E-07 | 5.08E-04 | 76.1 | 39.7 | 39.5 |
| 22 | 233296_PM_x_at | — | — | 2.33E-07 | 5.17E-04 | 347.7 | 251.5 | 244.7 |
| 23 | 243318_PM_at | DCAF8 | DDB1 and CUL4 associated factor 8 | 2.52E-07 | 5.34E-04 | 326.2 | 229.5 | 230.2 |
| 24 | 236354_PM_at | — | — | 3.23E-07 | 6.39E-04 | 47.1 | 31.2 | 27.8 |
| 25 | 243768_PM_at | — | — | 3.35E-07 | 6.39E-04 | 1142.0 | 730.6 | 768.5 |
| 26 | 238558_PM_at | — | — | 3.65E-07 | 6.39E-04 | 728.5 | 409.4 | 358.4 |
| 27 | 237825_PM_x_at | — | — | 3.66E-07 | 6.39E-04 | 34.2 | 20.9 | 19.9 |
| 28 | 244414_PM_at | — | — | 3.67E-07 | 6.39E-04 | 548.7 | 275.2 | 284.0 |
| 29 | 215221_PM_at | — | — | 4.06E-07 | 6.83E-04 | 327.2 | 176.7 | 171.9 |
| 30 | 235912_PM_at | — | — | 4.46E-07 | 7.25E-04 | 114.1 | 71.4 | 59.5 |
| 31 | 239348_PM_at | — | — | 4.87E-07 | 7.54E-04 | 20.1 | 14.5 | 13.4 |
| 32 | 240499_PM_at | — | — | 5.06E-07 | 7.54E-04 | 271.4 | 180.1 | 150.2 |
| 33 | 208054_PM_at | HERC4 | hect domain and RLD 4 | 5.11E-07 | 7.54E-04 | 114.9 | 57.6 | 60.0 |
| 34 | 240263_PM_at | — | — | 5.46E-07 | 7.81E-04 | 120.9 | 78.7 | 66.6 |
| 35 | 241303_PM_x_at | — | — | 5.78E-07 | 7.81E-04 | 334.5 | 250.3 | 261.5 |
| 36 | 233692_PM_at | — | — | 5.92E-07 | 7.81E-04 | 22.4 | 15.5 | 15.0 |
| 37 | 243561_PM_at | — | — | 5.93E-07 | 7.81E-04 | 341.1 | 215.1 | 207.3 |
| 38 | 232778_PM_at | — | — | 6.91E-07 | 8.86E-04 | 46.5 | 31.0 | 28.5 |
| 39 | 237632_PM_at | — | — | 7.09E-07 | 8.86E-04 | 108.8 | 61.0 | 57.6 |
| 40 | 233690_PM_at | — | — | 7.30E-07 | 8.89E-04 | 351.1 | 222.7 | 178.1 |
| 41 | 220221_PM_at | VPS13D | vacuolar protein sorting 13 homolog D (S. cerevisiae) | 7.50E-07 | 8.89E-04 | 93.5 | 60.0 | 59.9 |
| 42 | 242877_PM_at | — | — | 7.72E-07 | 8.89E-04 | 173.8 | 108.1 | 104.0 |
| 43 | 218155_PM_x_at | TSR1 | TSR1, 20S rRNA accumulation, homolog (S. cerevisiae) | 7.86E-07 | 8.89E-04 | 217.2 | 165.6 | 164.7 |
| 44 | 239603_PM_x_at | — | — | 8.24E-07 | 8.89E-04 | 120.9 | 75.5 | 81.1 |
| 45 | 242859_PM_at | — | — | 8.48E-07 | 8.89E-04 | 221.1 | 135.4 | 138.3 |

TABLE 2-continued

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 46 | 240866_PM_at | — | — | 8.54E−07 | 8.89E−04 | 65.7 | 33.8 | 35.2 |
| 47 | 239661_PM_at | — | — | 8.72E−07 | 8.89E−04 | 100.5 | 48.3 | 45.2 |
| 48 | 224493_PM_x_at | C18orf45 | chromosome 18 open reading frame 45 | 8.77E−07 | 8.89E−04 | 101.8 | 78.0 | 89.7 |
| 49 | 1569202_PM_x_at | — | — | 8.98E−07 | 8.89E−04 | 23.3 | 18.5 | 16.6 |
| 50 | 1560474_PM_at | — | — | 9.12E−07 | 8.89E−04 | 25.2 | 17.8 | 18.5 |
| 51 | 232511_PM_at | — | — | 9.48E−07 | 9.06E−04 | 77.2 | 46.1 | 49.9 |
| 52 | 228119_PM_at | LRCH3 | leucine-rich repeats and calponin homology (CH) domain containing 3 | 1.01E−06 | 9.51E−04 | 117.2 | 84.2 | 76.1 |
| 53 | 228545_PM_at | ZNF148 | zinc finger protein 148 | 1.17E−06 | 9.99E−04 | 789.9 | 571.1 | 579.7 |
| 54 | 232779_PM_at | — | — | 1.17E−06 | 9.99E−04 | 36.7 | 26.0 | 20.7 |
| 55 | 239005_PM_at | FLJ39739 | Hypothetical FLJ39739 | 1.18E−06 | 9.99E−04 | 339.1 | 203.7 | 177.7 |
| 56 | 244478_PM_at | LRRC37A3 | leucine rich repeat containing 37, member A3 | 1.20E−06 | 9.99E−04 | 15.7 | 12.6 | 12.7 |
| 57 | 244535_PM_at | — | — | 1.28E−06 | 9.99E−04 | 261.5 | 139.5 | 137.8 |
| 58 | 1562673_PM_at | — | — | 1.28E−06 | 9.99E−04 | 77.4 | 46.5 | 51.8 |
| 59 | 240601_PM_at | — | — | 1.29E−06 | 9.99E−04 | 212.6 | 107.7 | 97.7 |
| 60 | 239533_PM_at | GPR155 | G protein-coupled receptor 155 | 1.30E−06 | 9.99E−04 | 656.3 | 396.7 | 500.1 |
| 61 | 222358_PM_x_at | — | — | 1.32E−06 | 9.99E−04 | 355.2 | 263.1 | 273.7 |
| 62 | 214707_PM_x_at | ALMS1 | Alstrom syndrome 1 | 1.32E−06 | 9.99E−04 | 340.2 | 255.9 | 266.0 |
| 63 | 236435_PM_at | — | — | 1.32E−06 | 9.99E−04 | 144.0 | 92.6 | 91.1 |
| 64 | 232333_PM_at | — | — | 1.33E−06 | 9.99E−04 | 487.7 | 243.7 | 244.3 |
| 65 | 222366_PM_at | — | — | 1.33E−06 | 9.99E−04 | 289.1 | 186.1 | 192.8 |
| 66 | 215611_PM_at | TCF12 | transcription factor 12 | 1.38E−06 | 1.02E−03 | 45.5 | 32.4 | 30.8 |
| 67 | 1558002_PM_at | STRAP | Serine/threonine kinase receptor associated protein | 1.40E−06 | 1.02E−03 | 199.6 | 146.7 | 139.7 |
| 68 | 239716_PM_at | — | — | 1.43E−06 | 1.02E−03 | 77.6 | 49.5 | 45.5 |
| 69 | 239091_PM_at | — | — | 1.45E−06 | 1.02E−03 | 76.9 | 44.0 | 45.0 |
| 70 | 238883_PM_at | — | — | 1.68E−06 | 1.15E−03 | 857.1 | 475.5 | 495.1 |
| 71 | 235615_PM_at | PGGT1B | protein geranylgeranyltransferase type I, beta subunit | 1.72E−06 | 1.15E−03 | 127.0 | 235.0 | 245.6 |
| 72 | 204055_PM_s_at | CTAGE5 | CTAGE family, member 5 | 1.77E−06 | 1.15E−03 | 178.8 | 115.2 | 105.9 |
| 73 | 239757_PM_at | ZFAND6 | Zinc finger, AN1-type domain 6 | 1.81E−06 | 1.15E−03 | 769.6 | 483.3 | 481.9 |
| 74 | 1558409_PM_at | — | — | 1.82E−06 | 1.15E−03 | 14.8 | 10.9 | 11.8 |
| 75 | 242688_PM_at | — | — | 1.85E−06 | 1.15E−03 | 610.5 | 338.4 | 363.4 |
| 76 | 242377_PM_x_at | THUMPD3 | THUMP domain containing 3 | 1.87E−06 | 1.15E−03 | 95.5 | 79.0 | 81.3 |
| 77 | 242650_PM_at | — | — | 1.88E−06 | 1.15E−03 | 86.0 | 55.5 | 47.4 |
| 78 | 243589_PM_at | KIAA1267 /// LOC100294337 | KIAA1267 /// hypothetical LOC100294337 | 1.89E−06 | 1.15E−03 | 377.8 | 220.3 | 210.4 |
| 79 | 227384_PM_s_at | — | — | 1.90E−06 | 1.15E−03 | 3257.0 | 2255.5 | 2139.7 |
| 80 | 237864_PM_at | — | — | 1.91E−06 | 1.15E−03 | 121.0 | 69.2 | 73.4 |
| 81 | 243490_PM_at | — | — | 1.92E−06 | 1.15E−03 | 24.6 | 17.5 | 16.5 |
| 82 | 244383_PM_at | — | — | 1.96E−06 | 1.17E−03 | 141.7 | 93.0 | 77.5 |
| 83 | 215908_PM_at | — | — | 2.06E−06 | 1.19E−03 | 98.5 | 67.9 | 67.5 |
| 84 | 230651_PM_at | — | — | 2.09E−06 | 1.19E−03 | 125.9 | 74.3 | 71.5 |
| 85 | 1561195_PM_at | — | — | 2.14E−06 | 1.19E−03 | 86.6 | 45.1 | 43.9 |
| 86 | 239268_PM_at | NDUFS1 | NADH dehydrogenase (ubiquinone) Fe—S protein 1, 75 kDa (NADH-coenzyme Q reductase) | 2.14E−06 | 1.19E−03 | 14.0 | 12.0 | 11.3 |
| 87 | 236431_PM_at | SR140 | U2-associated SR140 protein | 2.16E−06 | 1.19E−03 | 69.4 | 47.9 | 43.9 |
| 88 | 236978_PM_at | — | — | 2.19E−06 | 1.19E−03 | 142.4 | 88.6 | 88.1 |
| 89 | 1562957_PM_at | — | — | 2.21E−06 | 1.19E−03 | 268.3 | 181.8 | 165.4 |
| 90 | 238913_PM_at | — | — | 2.21E−06 | 1.19E−03 | 30.9 | 20.2 | 20.1 |
| 91 | 239646_PM_at | — | — | 2.23E−06 | 1.19E−03 | 100.3 | 63.1 | 60.8 |
| 92 | 235701_PM_at | — | — | 2.34E−06 | 1.24E−03 | 133.2 | 66.1 | 60.0 |
| 93 | 235601_PM_at | — | — | 2.37E−06 | 1.24E−03 | 121.9 | 75.5 | 79.0 |
| 94 | 230918_PM_at | — | — | 2.42E−06 | 1.25E−03 | 170.4 | 114.5 | 94.4 |
| 95 | 219112_PM_at | FNIP1 /// RAPGEF6 | folliculin interacting protein 1 /// Rap guanine nuctotide exchange factor (GEF) 6 | 2.49E−06 | 1.28E−03 | 568.2 | 400.2 | 393.4 |

TABLE 2-continued

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 96 | 202228_PM_s_at | NPTN | neuroplastin | 2.52E-06 | 1.28E-03 | 1017.7 | 1331.5 | 1366.4 |
| 97 | 242839_PM_at | — | — | 2.78E-06 | 1.39E-03 | 17.9 | 14.0 | 13.6 |
| 98 | 244778_PM_x_at | — | — | 2.85E-06 | 1.42E-03 | 105.1 | 66.0 | 65.9 |
| 99 | 237388_PM_at | — | — | 2.91E-06 | 1.42E-03 | 59.3 | 38.0 | 33.0 |
| 100 | 202770_PM_s_at | CCNG2 | cyclin G2 | 2.92E-06 | 1.42E-03 | 142.2 | 269.0 | 270.0 |
| 101 | 240008_PM_at | — | — | 2.96E-06 | 1.42E-03 | 96.2 | 65.6 | 56.2 |
| 102 | 1557718_PM_at | PPP2R5C | protein phosphatase 2, regulatory subunit B', gamma | 2.97E-06 | 1.42E-03 | 615.2 | 399.8 | 399.7 |
| 103 | 215528_PM_at | — | — | 3.01E-06 | 1.42E-03 | 126.8 | 62.6 | 69.0 |
| 104 | 204689_PM_at | HHEX | hematopoietically expressed homeobox | 3.08E-06 | 1.44E-03 | 381.0 | 499.9 | 567.9 |
| 105 | 213718_PM_at | RBM4 | RNA binding motif protein 4 | 3.21E-06 | 1.46E-03 | 199.3 | 140.6 | 132.2 |
| 106 | 243233_PM_at | — | — | 3.22E-06 | 1.46E-03 | 582.3 | 343.0 | 337.1 |
| 107 | 239597_PM_at | — | — | 3.23E-06 | 1.46E-03 | 1142.9 | 706.6 | 720.8 |
| 108 | 232890_PM_at | — | — | 3.24E-06 | 1.46E-03 | 218.0 | 148.7 | 139.9 |
| 109 | 232883_PM_at | — | — | 3.42E-06 | 1.53E-03 | 127.5 | 79.0 | 73.1 |
| 110 | 241391_PM_at | — | — | 3.67E-06 | 1.62E-03 | 103.8 | 51.9 | 48.3 |
| 111 | 244197_PM_x_at | — | — | 3.71E-06 | 1.62E-03 | 558.0 | 397.3 | 418.8 |
| 112 | 205434_PM_s_at | AAK1 | AP2 associated kinase 1 | 3.75E-06 | 1.62E-03 | 495.2 | 339.9 | 301.2 |
| 113 | 235725_PM_at | SMAD4 | SMAD family member 4 | 3.75E-06 | 1.62E-03 | 147.1 | 102.1 | 112.0 |
| 114 | 203137_PM_at | WTAP | Wilms tumor 1 associated protein | 3.89E-06 | 1.66E-03 | 424.1 | 609.4 | 555.8 |
| 115 | 231075_PM_x_at | RAPH1 | Ras association (RalGDS/AF-6) and pleckstrin homology domains 1 | 3.91E-06 | 1.66E-03 | 30.4 | 19.3 | 18.2 |
| 116 | 236043_PM_at | LOC100130175 | hypothetical protein LOC100130175 | 3.98E-06 | 1.67E-03 | 220.6 | 146.2 | 146.5 |
| 117 | 238299_PM_at | — | — | 4.09E-06 | 1.70E-03 | 217.1 | 130.4 | 130.3 |
| 118 | 243667_PM_at | — | — | 4.12E-06 | 1.70E-03 | 314.5 | 225.3 | 232.8 |
| 119 | 223937_PM_at | FOXP1 | forkhead box P1 | 4.20E-06 | 1.72E-03 | 147.7 | 85.5 | 90.9 |
| 120 | 238666_PM_at | — | — | 4.25E-06 | 1.72E-03 | 219.1 | 148.3 | 145.5 |
| 121 | 1554771_PM_at | — | — | 4.28E-06 | 1.72E-03 | 67.2 | 41.5 | 40.8 |
| 122 | 202379_PM_s_at | NKTR | natural killer-tumor recognition sequence | 4.34E-06 | 1.73E-03 | 1498.2 | 1170.6 | 1042.6 |
| 123 | 244695_PM_at | GHRLOS | ghrelin opposite strand (non-protein coding) | 4.56E-06 | 1.79E-03 | 78.0 | 53.0 | 52.5 |
| 124 | 239393_PM_at | — | — | 4.58E-06 | 1.79E-03 | 852.0 | 554.2 | 591.7 |
| 125 | 242920_PM_at | — | — | 4.60E-06 | 1.79E-03 | 392.8 | 220.9 | 251.8 |
| 126 | 242405_PM_at | — | — | 4.66E-06 | 1.80E-03 | 415.8 | 193.8 | 207.4 |
| 127 | 1556432_PM_at | — | — | 4.69E-06 | 1.80E-03 | 61.5 | 43.1 | 38.1 |
| 128 | 1570299_PM_at | — | — | 4.77E-06 | 1.81E-03 | 27.0 | 18.0 | 19.8 |
| 129 | 225198_PM_at | VAPA | VAMP (vesicle-associated membrane protein)-associated protein A, 33 kDa | 4.85E-06 | 1.83E-03 | 192.0 | 258.3 | 273.9 |
| 130 | 230702_PM_at | — | — | 4.94E-06 | 1.85E-03 | 28.2 | 18.4 | 17.5 |
| 131 | 240262_PM_at | — | — | 5.07E-06 | 1.88E-03 | 46.9 | 22.8 | 28.0 |
| 132 | 232216_PM_at | YME1L1 | YME1-like 1 (S. cerevisiae) | 5.14E-06 | 1.89E-03 | 208.6 | 146.6 | 130.1 |
| 133 | 225171_PM_at | ARHGAP18 | Rho GTPase activating protein 18 | 5.16E-06 | 1.89E-03 | 65.9 | 109.1 | 121.5 |
| 134 | 243992_PM_at | — | — | 5.28E-06 | 1.92E-03 | 187.1 | 116.0 | 125.6 |
| 135 | 227082_PM_at | — | — | 5.45E-06 | 1.96E-03 | 203.8 | 140.4 | 123.0 |
| 136 | 239948_PM_at | NUP153 | nucleoporin 153 kDa | 5.50E-06 | 1.96E-03 | 39.6 | 26.5 | 27.8 |
| 137 | 221905_PM_at | CYLD | cylindromatosis (turban tumor syndrome) | 5.51E-06 | 1.96E-03 | 433.0 | 316.8 | 315.1 |
| 138 | 242578_PM_x_at | SLC22A3 | Solute carrier family 22 (extraneuronal monoamine transporter), member 3 | 5.56E-06 | 1.96E-03 | 148.4 | 109.2 | 120.1 |
| 139 | 1569238_PM_a_at | — | — | 5.73E-06 | 1.99E-03 | 71.0 | 33.0 | 36.1 |
| 140 | 201453_PM_x_at | RHEB | Ras homolog enriched in brain | 5.76E-06 | 1.99E-03 | 453.3 | 600.0 | 599.0 |
| 141 | 236802_PM_at | — | — | 5.76E-06 | 1.99E-03 | 47.9 | 29.1 | 29.6 |
| 142 | 232615_PM_at | — | — | 5.82E-06 | 1.99E-03 | 4068.5 | 3073.4 | 2907.4 |
| 143 | 237179_PM_at | PCMTD2 | protein-L-isoaspartate (D-aspartate) O-methyltransferase domain containing 2 | 5.84E-06 | 1.99E-03 | 48.7 | 30.2 | 26.8 |

TABLE 2-continued

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 144 | 203255_PM_at | FBXO11 | F-box protein 11 | 5.98E−06 | 2.02E−03 | 748.3 | 529.4 | 539.6 |
| 145 | 212989_PM_at | SGMS1 | sphingomyelin synthase 1 | 6.04E−06 | 2.03E−03 | 57.2 | 93.1 | 107.9 |
| 146 | 236754_PM_at | PPP1R2 | protein phosphatase 1, regulatory (inhibitor) subunit 2 | 6.17E−06 | 2.05E−03 | 505.3 | 380.7 | 370.1 |
| 147 | 1559496_PM_at | PPA2 | pyrophosphatase (inorganic) 2 | 6.24E−06 | 2.05E−03 | 68.8 | 39.7 | 39.3 |
| 148 | 236494_PM_x_at | — | — | 6.26E−06 | 2.05E−03 | 135.0 | 91.1 | 82.9 |
| 149 | 237554_PM_at | — | — | 6.30E−06 | 2.05E−03 | 53.4 | 31.5 | 30.1 |
| 150 | 243469_PM_at | — | — | 6.37E−06 | 2.05E−03 | 635.2 | 308.1 | 341.5 |
| 151 | 240155_PM_x_at | ZNF493 /// ZNF738 | zinc finger protein 493 /// zinc finger protein 738 | 6.45E−06 | 2.05E−03 | 483.9 | 299.9 | 316.6 |
| 152 | 222442_PM_s_at | ARL8B | ADP-ribosylation factor-like 8B | 6.47E−06 | 2.05E−03 | 201.5 | 292.6 | 268.3 |
| 153 | 240307_PM_at | — | — | 6.48E−06 | 2.05E−03 | 55.4 | 36.8 | 33.1 |
| 154 | 200864_PM_s_at | RAB11A | RAB11A, member RAS oncogene family | 6.50E−06 | 2.05E−03 | 142.1 | 210.9 | 233.0 |
| 155 | 235757_PM_at | — | — | 6.53E−06 | 2.05E−03 | 261.4 | 185.2 | 158.9 |
| 156 | 222351_PM_at | PPP2R1B | protein phosphatase 2, regulatory subunit A, beta | 6.58E−06 | 2.06E−03 | 75.8 | 51.1 | 45.4 |
| 157 | 222788_PM_s_at | RSBN1 | round spermatid basic protein 1 | 6.63E−06 | 2.06E−03 | 389.9 | 302.7 | 288.2 |
| 158 | 239815_PM_at | — | — | 6.70E−06 | 2.06E−03 | 216.9 | 171.4 | 159.5 |
| 159 | 219392_PM_x_at | PRR11 | proline rich 11 | 6.77E−06 | 2.07E−03 | 1065.3 | 827.5 | 913.2 |
| 160 | 240458_PM_at | — | — | 6.80E−06 | 2.07E−03 | 414.3 | 244.6 | 242.0 |
| 161 | 235879_PM_at | MBNL1 | Muscleblind-like (Drosophila) | 6.88E−06 | 2.08E−03 | 1709.2 | 1165.5 | 1098.0 |
| 162 | 230529_PM_at | HECA | headcase homolog (Drosophila) | 7.08E−06 | 2.13E−03 | 585.1 | 364.3 | 418.4 |
| 163 | 1562063_PM_x_at | KIAA1245 /// NBPF1 /// NBPF10 /// NBPF11 /// NBPF12 /// NBPF24 /// NBPF8 /// NBPF9 | KIAA1245 /// neuroblastoma breakpoint family, member 1 /// neuroblastoma breakpoint fam | 7.35E−06 | 2.20E−03 | 350.4 | 238.8 | 260.8 |
| 164 | 202769_PM_at | CCNG2 | cyclin G2 | 7.42E−06 | 2.20E−03 | 697.1 | 1164.0 | 1264.6 |
| 165 | 1556493_PM_a_at | KDM4C | lysine (K)-specific demethylase 4C | 7.64E−06 | 2.24E−03 | 81.4 | 49.0 | 44.5 |
| 166 | 216509_PM_x_at | MLLT10 | myeloid/lymphoid or mixed-lineage leukemia (trithorax homolog, Drosophila); translocate | 7.64E−06 | 2.24E−03 | 22.4 | 17.9 | 19.3 |
| 167 | 223697_PM_x_at | C9orf64 | chromosome 9 open reading frame 64 | 7.70E−06 | 2.25E−03 | 1013.6 | 771.2 | 836.8 |
| 168 | 235999_PM_at | — | — | 7.77E−06 | 2.25E−03 | 227.6 | 174.1 | 182.1 |
| 169 | 244766_PM_at | LOC100271836 /// LOC440354 /// LOC595101 /// LOC641298 /// SMG1 | SMG1 homolog, phosphatidylinositol 3-kinase-related kinase pseudogene /// PI-3-kinase-r | 8.03E−06 | 2.31E−03 | 133.4 | 99.4 | 87.5 |
| 170 | 230332_PM_at | ZCCHC7 | Zinc finger, CCHC domain containing 7 | 8.07E−06 | 2.31E−03 | 467.4 | 265.1 | 263.2 |
| 171 | 235308_PM_at | ZBTB20 | zinc finger and BTB domain containing 20 | 8.17E−06 | 2.32E−03 | 256.7 | 184.2 | 167.3 |
| 172 | 242492_PM_at | CLNS1A | Chloride channel, nucleotide-sensitive, 1A | 8.19E−06 | 2.32E−03 | 128.5 | 82.8 | 79.2 |
| 173 | 215898_PM_at | TTLL5 | tubulin tyrosine ligase-like family, member 5 | 8.24E−06 | 2.32E−03 | 20.9 | 14.0 | 13.8 |
| 174 | 244840_PM_x_at | DOCK4 | dedicator of cytokinesis 4 | 8.65E−05 | 2.42E−03 | 43.1 | 16.5 | 21.5 |
| 175 | 220235_PM_s_at | C1orf103 | chromosome 1 open reading frame 103 | 8.72E−06 | 2.43E−03 | 88.4 | 130.5 | 143.3 |
| 176 | 229467_PM_at | PCBP2 | Poly(rC) binding protein 2 | 8.80E−06 | 2.44E−03 | 186.5 | 125.4 | 135.8 |
| 177 | 232527_PM_at | — | — | 8.99E−06 | 2.48E−03 | 667.4 | 453.9 | 461.3 |
| 178 | 243286_PM_at | — | — | 9.24E−06 | 2.53E−03 | 142.6 | 98.2 | 87.2 |
| 179 | 215628_PM_x_at | — | — | 9.28E−06 | 2.53E−03 | 49.6 | 36.3 | 39.4 |
| 180 | 1556412_PM_at | — | — | 9.45E−06 | 2.56E−03 | 34.9 | 24.7 | 23.8 |
| 181 | 204786_PM_s_at | IFNAR2 | Interferon (alpha, beta and omega) receptor 2 | 9.64E−06 | 2.59E−03 | 795.6 | 573.0 | 639.2 |

TABLE 2-continued

200 Probeset classifer for distinguishing AR, SCAR and TX based on a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 182 | 234258_PM_at | — | — | 9.73E−06 | 2.60E−03 | 27.4 | 17.8 | 20.3 |
| 183 | 233274_PM_at | — | — | 9.76E−06 | 2.60E−03 | 109.9 | 77.5 | 79.4 |
| 184 | 239784_PM_at | — | — | 9.82E−06 | 2.60E−03 | 137.0 | 80.1 | 70.1 |
| 185 | 242498_PM_x_at | — | — | 1.01E−05 | 2.65E−03 | 59.2 | 40.4 | 38.9 |
| 186 | 231351_PM_at | — | — | 1.02E−05 | 2.67E−03 | 124.8 | 70.8 | 60.6 |
| 187 | 222368_PM_at | — | — | 1.03E−05 | 2.67E−03 | 89.9 | 54.5 | 44.3 |
| 188 | 236524_PM_at | — | — | 1.03E−05 | 2.67E−03 | 313.2 | 234.7 | 214.2 |
| 189 | 243834_PM_at | TNRC6A | trinucleotide repeat containing 6A | 1.04E−05 | 2.67E−03 | 211.8 | 145.1 | 146.9 |
| 190 | 239167_PM_at | — | — | 1.04E−05 | 2.67E−03 | 287.4 | 150.2 | 160.3 |
| 191 | 239238_PM_at | — | — | 1.05E−05 | 2.67E−03 | 136.0 | 81.6 | 92.0 |
| 192 | 237194_PM_at | — | — | 1.05E−05 | 2.67E−03 | 57.2 | 34.4 | 27.9 |
| 193 | 242772_PM_x_at | — | — | 1.06E−05 | 2.67E−03 | 299.2 | 185.2 | 189.4 |
| 194 | 243827_PM_at | — | — | 1.06E−05 | 2.67E−03 | 115.9 | 50.1 | 56.4 |
| 195 | 1552536_PM_at | VTI1A | vesicle transport through interaction with t-SNAREs homolog 1A (yeast) | 1.10E−05 | 2.75E−03 | 61.7 | 35.1 | 34.6 |
| 196 | 243696_PM_at | KIAA0562 | KIAA0562 | 1.12E−05 | 2.77E−03 | 19.0 | 14.8 | 15.0 |
| 197 | 233648_PM_at | — | — | 1.12E−05 | 2.77E−03 | 33.9 | 21.0 | 24.1 |
| 198 | 225858_PM_s_at | XIAP | X-linked Inhibitor of apoptosis | 1.16E−05 | 2.85E−03 | 1020.7 | 760.3 | 772.6 |
| 199 | 238736_PM_at | REV3L | REV3-like, catalytic subunit of DNA polymerase zeta (yeast) | 1.19E−05 | 2.91E−03 | 214.2 | 135.8 | 151.6 |
| 200 | 221192_PM_x_at | MFSD11 | major facilitator superfamily domain containing 11 | 1.20E−05 | 2.92E−03 | 100.4 | 74.5 | 81.2 |

TABLE 3

33 probesets that differentiate SCAR and TX at p-value < 0.001 in PAXGene blood tubes

| Probeset ID | Gene Symbol | Gene Title | p-value (Phenotype) | Fold-Change (SCAR vs. TX) | ID | SCAR - Mean | TX - Mean |
|---|---|---|---|---|---|---|---|
| 1553094_PM_at | TAC4 | tachykinin 4 (hemokinin) | 0.000375027 | −1.1 | 1553094_PM_at | 8.7 | 9.6 |
| 1553352_PM_x_at | ERVWE1 | endogenous retroviral family W, env(C7), member 1 | 0.000494742 | −1.26 | 1553352_PM_x_at | 15.5 | 19.6 |
| 1553644_PM_at | C14orf49 | chromosome 14 open reading frame 49 | 0.000868817 | −1.16 | 1553644_PM_at | 10.1 | 11.7 |
| 1556178_PM_x_at | TAF8 | TAF8 RNA polymerase II, TATA box binding protein (TBP)-associated factor, 43 kDa | 0.000431074 | 1.24 | 1556178_PM_x_at | 39.2 | 31.7 |
| 1559687_PM_at | TMEM221 | transmembrane protein 221 | 8.09E−05 | −1.16 | 1559687_PM_at | 13.0 | 15.1 |
| 1562492_PM_at | LOC340090 | hypothetical LOC340090 | 0.00081096 | −1.1 | 1562492_PM_at | 8.8 | 9.7 |
| 1563204_PM_at | ZNF627 | Zinc finger protein 627 | 0.000784254 | −1.15 | 1563204_PM_at | 10.6 | 12.2 |
| 1570124_PM_at | — | — | 0.000824814 | −1.14 | 1570124_PM_at | 10.6 | 12.2 |
| 204681_PM_s_at | RAPGEF5 | Rap guanine nucleotide exchange factor (GEF) 5 | 0.000717727 | −1.18 | 204681_PM_s_at | 9.6 | 11.3 |
| 206154_PM_at | RLBP1 | retinaldehyde binding protein 1 | 0.000211941 | −1.13 | 206154_PM_at | 11.0 | 12.4 |
| 209053_PM_s_at | WHSC1 | Wolf-Hirschhorn syndrome candidate 1 | 0.000772412 | 1.23 | 209053_PM_s_at | 15.1 | 12.3 |
| 209228_PM_x_at | TUSC3 | tumor suppressor candidate 3 | 0.000954529 | −1.13 | 209228_PM_x_at | 8.9 | 10.1 |
| 211701_PM_s_at | TRO | trophinin | 0.000684486 | −1.13 | 211701_PM_s_at | 10.0 | 11.3 |
| 213369_PM_at | CDHR1 | cadherin-related family member 1 | 0.000556648 | −1.14 | 213369_PM_at | 10.8 | 12.3 |

TABLE 3-continued

33 probesets that differentiate SCAR and TX at p-value < 0.001 in PAXGene blood tubes

| Probeset ID | Gene Symbol | Gene Title | p-value (Phenotype) | Fold-Change (SCAR vs. TX) | ID | SCAR - Mean | TX - Mean |
|---|---|---|---|---|---|---|---|
| 215110_PM_at | MBL1P | mannose-binding lectin (protein A) 1, pseudogene | 0.000989176 | −1.13 | 215110_PM_at | 9.2 | 10.4 |
| 215232_PM_at | ARHGAP44 | Rho GTPase activating protein 44 | 0.000332776 | −1.18 | 215232_PM_at | 11.1 | 13.1 |
| 217158_PM_at | LOC442421 | hypothetical LOC442421 /// prostaglandin E2 receptor EP4 subtype-like | 2.98E−05 | 1.18 | 217158_PM_at | 14.2 | 12.0 |
| 218365_PM_s_at | DARS2 | aspartyl-tRNA synthetase 2, mitochondrial | 0.000716035 | 1.18 | 218365_PM_s_at | 17.2 | 14.5 |
| 219695_PM_at | SMPD3 | sphingomyelin phosphodiesterase 3, neutral membrane (neutral sphingomyelinase II) | 0.000377151 | −1.47 | 219695_PM_at | 12.0 | 17.6 |
| 220603_PM_s_at | MCTP2 | multiple C2 domains, transmembrane 2 | 0.000933412 | −1.38 | 220603_PM_s_at | 338.5 | 465.8 |
| 224963_PM_at | SLC26A2 | solute carrier family 26 (sulfate transporter), member 2 | 0.000961242 | 1.47 | 224963_PM_at | 94.3 | 64.0 |
| 226729_PM_at | USP37 | ubiquitin specific peptidase 37 | 0.000891038 | 1.24 | 226729_PM_at | 32.9 | 26.6 |
| 228226_PM_s_at | ZNF775 | zinc finger protein 775 | 0.000589512 | 1.2 | 228226_PM_s_at | 20.5 | 17.1 |
| 230608_PM_at | C1orf182 | chromosome 1 open reading frame 182 | 0.000153478 | −1.18 | 230608_PM_at | 15.9 | 18.8 |
| 230756_PM_at | ZNF683 | zinc finger protein 683 | 0.00044751 | 1.52 | 230756_PM_at | 26.7 | 17.6 |
| 231757_PM_at | TAS2R5 | taste receptor, type 2, member 5 | 0.000869775 | −1.12 | 231757_PM_at | 9.3 | 10.4 |
| 231958_PM_at | C3orf31 | Chromosome 3 open reading frame 31 | 4.09E−05 | 1.22 | 231958_PM_at | 20.1 | 16.4 |
| 237290_PM_at | — | — | 0.000948318 | −1.22 | 237290_PM_at | 10.3 | 12.5 |
| 237806_PM_s_at | LOC729296 | hypothetical LOC729296 | 0.00092234 | −1.18 | 237806_PM_s_at | 10.2 | 12.0 |
| 238459_PM_x_at | SPATA6 | spermatogenesis associated 6 | 0.000116525 | −1.15 | 238459_PM_x_at | 9.2 | 10.5 |
| 241331_PM_at | SKAP2 | Src kinase associated phosphoprotein 2 | 0.000821476 | −1.39 | 241331_PM_at | 16.4 | 22.9 |
| 241368_PM_at | PLIN5 | perilipin 5 | 0.000406066 | −1.61 | 241368_PM_at | 84.5 | 136.3 |
| 241543_PM_at | — | — | 0.000478221 | −1.17 | 241543_PM_at | 9.4 | 11.0 |

TABLE 4

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1 | 238108_PM_at | — | — | 1.70E−10 | 8.27E−06 | 73.3 | 45.4 | 44.4 |
| 2 | 243524_PM_at | — | — | 3.98E−10 | 9.70E−06 | 72.3 | 41.3 | 37.7 |
| 3 | 1558831_PM_x_at | — | — | 5.11E−09 | 8.30E−05 | 48.1 | 30.8 | 31.4 |
| 4 | 229858_PM_at | — | — | 7.49E−09 | 8.31E−05 | 576.2 | 359.3 | 348.4 |
| 5 | 236685_PM_at | — | — | 8.53E−09 | 8.31E−05 | 409.1 | 213.3 | 211.0 |
| 6 | 213546_PM_at | DKFZP586I1420 | hypothetical protein DKFZp586I1420 | 3.52E−08 | 2.60E−04 | 619.2 | 453.7 | 446.0 |
| 7 | 231958_PM_at | C3orf31 | Chromosome 3 open reading frame 31 | 4.35E−08 | 2.60E−04 | 22.8 | 20.1 | 16.4 |
| 8 | 210275_PM_s_at | ZFAND5 | zinc finger, AN1-type domain 5 | 4.96E−08 | 2.60E−04 | 1045.9 | 1513.6 | 1553.8 |
| 9 | 244341_PM_at | — | — | 5.75E−08 | 2.60E−04 | 398.3 | 270.7 | 262.8 |
| 10 | 1558822_PM_at | — | — | 5.84E−08 | 2.60E−04 | 108.6 | 62.9 | 56.8 |
| 11 | 242175_PM_at | — | — | 5.87E−08 | 2.60E−04 | 69.1 | 37.2 | 40.0 |
| 12 | 222357_PM_at | ZBTB20 | zinc finger and BTB domain containing 20 | 6.97E−08 | 2.83E−04 | 237.4 | 127.4 | 109.8 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 13 | 206288_PM_at | PGGT1B | protein geranylgeranyltransferase type I, beta subunit | 9.42E−08 | 3.53E−04 | 20.8 | 34.7 | 34.2 |
| 14 | 222306_PM_at | — | — | 1.03E−07 | 3.59E−04 | 23.3 | 15.8 | 16.0 |
| 15 | 1569601_PM_at | — | — | 1.67E−07 | 4.80E−04 | 49.5 | 34.1 | 29.7 |
| 16 | 235138_PM_at | — | — | 1.69E−07 | 4.80E−04 | 1169.9 | 780.0 | 829.7 |
| 17 | 240452_PM_at | GSPT1 | G1 to S phase transition 1 | 1.74E−07 | 4.80E−04 | 97.7 | 54.4 | 48.6 |
| 18 | 243003_PM_at | — | — | 1.77E−07 | 4.80E−04 | 92.8 | 52.5 | 51.3 |
| 19 | 218109_PM_s_at | MFSD1 | major facilitator superfamily domain containing 1 | 1.90E−07 | 4.87E−04 | 1464.0 | 1881.0 | 1886.4 |
| 20 | 241681_PM_at | — | — | 2.00E−07 | 4.87E−04 | 1565.7 | 845.7 | 794.6 |
| 21 | 243878_PM_at | — | — | 2.19E−07 | 5.08E−04 | 76.1 | 39.7 | 39.5 |
| 22 | 233296_PM_x_at | — | — | 2.33E−07 | 5.17E−04 | 347.7 | 251.5 | 244.7 |
| 23 | 243318_PM_at | DCAF8 | DDB1 and CUL4 associated factor 8 | 2.52E−07 | 5.34E−04 | 326.2 | 229.5 | 230.2 |
| 24 | 236354_PM_at | — | — | 3.23E−07 | 6.39E−04 | 47.1 | 31.2 | 27.8 |
| 25 | 243768_PM_at | — | — | 3.35E−07 | 6.39E−04 | 1142.0 | 730.6 | 768.5 |
| 26 | 238558_PM_at | — | — | 3.65E−07 | 6.39E−04 | 728.5 | 409.4 | 358.4 |
| 27 | 237825_PM_x_at | — | — | 3.66E−07 | 6.39E−04 | 34.2 | 20.9 | 19.9 |
| 28 | 244414_PM_at | — | — | 3.67E−07 | 6.39E−04 | 548.7 | 275.2 | 284.0 |
| 29 | 215221_PM_at | — | — | 4.06E−07 | 6.83E−04 | 327.2 | 176.7 | 171.9 |
| 30 | 235912_PM_at | — | — | 4.46E−07 | 7.25E−04 | 114.1 | 71.4 | 59.5 |
| 31 | 239348_PM_at | — | — | 4.87E−07 | 7.54E−04 | 20.1 | 14.5 | 13.4 |
| 32 | 240499_PM_at | — | — | 5.06E−07 | 7.54E−04 | 271.4 | 180.1 | 150.2 |
| 33 | 208054_PM_at | HERC4 | hect domain and RLD 4 | 5.11E−07 | 7.54E−04 | 114.9 | 57.6 | 60.0 |
| 34 | 240263_PM_at | — | — | 5.46E−07 | 7.81E−04 | 120.9 | 78.7 | 71.6 |
| 35 | 241303_PM_x_at | — | — | 5.78E−07 | 7.81E−04 | 334.5 | 250.3 | 261.5 |
| 36 | 233692_PM_at | — | — | 5.92E−07 | 7.81E−04 | 22.4 | 15.5 | 15.0 |
| 37 | 243561_PM_at | — | — | 5.93E−07 | 7.81E−04 | 341.1 | 215.1 | 207.3 |
| 38 | 232778_PM_at | — | — | 6.91E−07 | 8.86E−04 | 46.5 | 31.0 | 28.5 |
| 39 | 237632_PM_at | — | — | 7.09E−07 | 8.86E−04 | 108.8 | 61.0 | 57.6 |
| 40 | 233690_PM_at | — | — | 7.30E−07 | 8.89E−04 | 351.1 | 222.7 | 178.1 |
| 41 | 220221_PM_at | VPS13D | vacuolar protein sorting 13 homolog D (S. cerevisiae) | 7.50E−07 | 8.89E−04 | 93.5 | 60.0 | 59.9 |
| 42 | 242877_PM_at | — | — | 7.72E−07 | 8.89E−04 | 173.8 | 108.1 | 104.0 |
| 43 | 218155_PM_x_at | TSR1 | TSR1, 20S rRNA accumulation, homolog (S. cerevisiae) | 7.86E−07 | 8.89E−04 | 217.2 | 165.6 | 164.7 |
| 44 | 239603_PM_x_at | — | — | 8.24E−07 | 8.89E−04 | 120.9 | 75.5 | 81.1 |
| 45 | 242859_PM_at | — | — | 8.48E−07 | 8.89E−04 | 221.1 | 135.4 | 138.3 |
| 46 | 240866_PM_at | — | — | 8.54E−07 | 8.89E−04 | 65.7 | 33.8 | 35.2 |
| 47 | 239661_PM_at | — | — | 8.72E−07 | 8.89E−04 | 100.5 | 48.3 | 45.2 |
| 48 | 224493_PM_x_at | C18orf45 | chromosome 18 open reading frame 45 | 8.77E−07 | 8.89E−04 | 101.8 | 78.0 | 89.7 |
| 49 | 1569202_PM_x_at | — | — | 8.98E−07 | 8.89E−04 | 23.3 | 18.5 | 16.6 |
| 50 | 1560474_PM_at | — | — | 9.12E−07 | 8.89E−04 | 25.2 | 17.8 | 18.5 |
| 51 | 232511_PM_at | — | — | 9.48E−07 | 9.06E−04 | 77.2 | 46.1 | 49.9 |
| 52 | 228119_PM_at | LRCH3 | leucine-rich repeats and calponin homology (CH) domain containing 3 | 1.01E−06 | 9.51E−04 | 117.2 | 84.2 | 76.1 |
| 53 | 228545_PM_at | ZNF148 | zinc finger protein 148 | 1.17E−06 | 9.99E−04 | 789.9 | 571.1 | 579.7 |
| 54 | 232779_PM_at | — | — | 1.17E−06 | 9.99E−04 | 36.7 | 26.0 | 20.7 |
| 55 | 239005_PM_at | FLJ39739 | Hypothetical FLJ39739 | 1.18E−06 | 9.99E−04 | 339.1 | 203.7 | 177.7 |
| 56 | 244478_PM_at | LRRC37A3 | leucine rich repeat containing 37, member A3 | 1.20E−06 | 9.99E−04 | 15.7 | 12.6 | 12.7 |
| 57 | 244535_PM_at | — | — | 1.28E−06 | 9.99E−04 | 261.5 | 139.5 | 137.8 |
| 58 | 1562673_PM_at | — | — | 1.28E−06 | 9.99E−04 | 77.4 | 46.5 | 51.8 |
| 59 | 240601_PM_at | — | — | 1.29E−06 | 9.99E−04 | 212.6 | 107.7 | 97.7 |
| 60 | 239533_PM_at | GPR155 | G protein-coupled receptor 155 | 1.30E−06 | 9.99E−04 | 656.3 | 396.7 | 500.1 |
| 61 | 222358_PM_x_at | — | — | 1.32E−06 | 9.99E−04 | 355.2 | 263.1 | 273.7 |
| 62 | 214707_PM_x_at | ALMS1 | Alstrom syndrome 1 | 1.32E−06 | 9.99E−04 | 340.2 | 255.9 | 266.0 |
| 63 | 236435_PM_at | — | — | 1.32E−06 | 9.99E−04 | 144.0 | 92.6 | 91.1 |
| 64 | 232333_PM_at | — | — | 1.33E−06 | 9.99E−04 | 487.7 | 243.7 | 244.3 |
| 65 | 222366_PM_at | — | — | 1.33E−06 | 9.99E−04 | 289.1 | 186.1 | 192.8 |
| 66 | 215611_PM_at | TCF12 | transcription factor 12 | 1.38E−06 | 9.99E−04 | 45.5 | 32.4 | 30.8 |
| 67 | 1558002_PM_at | STRAP | Serine/threonine kinase receptor associated protein | 1.40E−06 | 1.02E−03 | 199.6 | 146.7 | 139.7 |
| 68 | 239716_PM_at | — | — | 1.43E−06 | 1.02E−03 | 77.6 | 49.5 | 45.5 |
| 69 | 239091_PM_at | — | — | 1.45E−06 | 1.02E−03 | 76.9 | 44.0 | 45.0 |
| 70 | 238883_PM_at | — | — | 1.68E−06 | 1.15E−03 | 857.1 | 475.5 | 495.1 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 71 | 235615_PM_at | PGGT1B | protein geranylgeranyltransferase type 1, beta subunit | 1.72E-06 | 1.15E-03 | 127.0 | 235.0 | 245.6 |
| 72 | 204055_PM_s_at | CTAGE5 | CTAGE family, member 5 | 1.77E-06 | 1.15E-03 | 178.8 | 115.2 | 105.9 |
| 73 | 239757_PM_at | ZFAND6 | Zinc finger, AN1-type domain 6 | 1.81E-06 | 1.15E-03 | 769.6 | 483.3 | 481.9 |
| 74 | 1558409_PM_at | — | — | 1.82E-06 | 1.15E-03 | 14.8 | 10.9 | 11.8 |
| 75 | 242688_PM_at | — | — | 1.85E-06 | 1.15E-03 | 610.5 | 338.4 | 363.4 |
| 76 | 242377_PM_x_at | THUMPD3 | THUMP domain containing 3 | 1.87E-06 | 1.15E-03 | 95.5 | 79.0 | 81.3 |
| 77 | 242650_PM_at | — | — | 1.88E-06 | 1.15E-03 | 86.0 | 55.5 | 47.4 |
| 78 | 243589_PM_at | KIAA1267 /// LOC100294337 | KIAA1267 /// hypothetical LOC100294337 | 1.89E-06 | 1.15E-03 | 377.8 | 220.3 | 210.4 |
| 79 | 227384_PM_s_at | — | — | 1.90E-06 | 1.15E-03 | 3257.0 | 2255.5 | 2139.7 |
| 80 | 237854_PM_at | — | — | 1.91E-06 | 1.15E-03 | 121.0 | 69.2 | 73.4 |
| 81 | 243490_PM_at | — | — | 1.92E-06 | 1.15E-03 | 24.6 | 17.5 | 16.5 |
| 82 | 244383_PM_at | — | — | 1.96E-06 | 1.17E-03 | 141.7 | 93.0 | 77.5 |
| 83 | 215908_PM_at | — | — | 2.06E-06 | 1.19E-03 | 98.5 | 67.9 | 67.5 |
| 84 | 230651_PM_at | — | — | 2.09E-06 | 1.19E-03 | 125.9 | 74.3 | 71.5 |
| 85 | 1561195_PM_at | — | — | 2.14E-06 | 1.19E-03 | 86.6 | 45.1 | 43.9 |
| 86 | 239268_PM_at | NDUFS1 | NADH dehydrogenase (ubiquinone) Fe—S protein 1, 75 kDa (NADH-coenzyme Q reductase) | 2.14E-06 | 1.19E-03 | 14.0 | 12.0 | 11.3 |
| 87 | 236431_PM_at | SR140 | U2-associated SR140 protein | 2.16E-06 | 1.19E-03 | 69.4 | 47.9 | 43.9 |
| 88 | 236978_PM_at | — | — | 2.19E-06 | 1.19E-03 | 142.4 | 88.6 | 88.1 |
| 89 | 1562957_PM_at | — | — | 2.21E-06 | 1.19E-03 | 268.3 | 181.8 | 165.4 |
| 90 | 238913_PM_at | — | — | 2.21E-06 | 1.19E-03 | 30.9 | 20.2 | 20.1 |
| 91 | 239646_PM_at | — | — | 2.23E-06 | 1.19E-03 | 100.3 | 63.1 | 60.8 |
| 92 | 235701_PM_at | — | — | 2.34E-06 | 1.24E-03 | 133.2 | 66.1 | 60.0 |
| 93 | 235601_PM_at | — | — | 2.37E-06 | 1.24E-03 | 121.9 | 75.5 | 79.0 |
| 94 | 230918_PM_at | — | — | 2.42E-06 | 1.25E-03 | 170.4 | 114.5 | 94.4 |
| 95 | 219112_PM_at | FNIP1 /// RAPGEF6 | folliculin interacting protein 1 /// Rap guanine nucleotide exchange factor (GEF) 6 | 2.49E-06 | 1.28E-03 | 568.2 | 400.2 | 393.4 |
| 96 | 202228_PM_s_at | NPTN | neuroplastin | 2.52E-06 | 1.28E-03 | 1017.7 | 1331.5 | 1366.4 |
| 97 | 242839_PM_at | — | — | 2.78E-06 | 1.39E-03 | 17.9 | 14.0 | 13.6 |
| 98 | 244778_PM_x_at | — | — | 2.85E-06 | 1.42E-03 | 205.1 | 68.0 | 65.9 |
| 99 | 237388_PM_at | — | — | 2.91E-06 | 1.42E-03 | 59.3 | 38.0 | 33.0 |
| 100 | 202770_PM_s_at | CCNG2 | cyclin G2 | 2.92E-06 | 1.42E-03 | 142.2 | 269.0 | 270.0 |
| 101 | 240008_PM_at | — | — | 2.96E-06 | 1.42E-03 | 96.2 | 65.6 | 56.2 |
| 102 | 1557718_PM_at | PPP2R5C | protein phosphatase 2, regulatory subunit B', gamma | 2.97E-06 | 1.42E-03 | 615.2 | 399.8 | 399.7 |
| 103 | 215528_PM_at | — | — | 3.01E-06 | 1.42E-03 | 126.8 | 62.6 | 69.0 |
| 104 | 204689_PM_at | HHEX | hematopoietically expressed homeobox | 3.08E-05 | 1.44E-03 | 381.0 | 499.9 | 567.9 |
| 105 | 213718_PM_at | RBM4 | RNA binding motif protein 4 | 3.21E-06 | 1.46E-03 | 199.3 | 140.6 | 132.2 |
| 106 | 243233_PM_at | — | — | 3.22E-06 | 1.46E-03 | 582.3 | 343.0 | 337.1 |
| 107 | 239597_PM_at | — | — | 3.23E-06 | 1.46E-03 | 1142.9 | 706.6 | 720.8 |
| 108 | 232890_PM_at | — | — | 3.24E-06 | 1.46E-03 | 218.0 | 148.7 | 139.9 |
| 109 | 232883_PM_at | — | — | 3.42E-06 | 1.53E-03 | 127.5 | 79.0 | 73.1 |
| 110 | 241391_PM_at | — | — | 3.67E-06 | 1.62E-03 | 103.8 | 51.9 | 48.3 |
| 111 | 244197_PM_x_at | — | — | 3.71E-06 | 1.62E-03 | 558.0 | 397.3 | 418.8 |
| 112 | 205434_PM_s_at | AAK1 | AP2 associated kinase 1 | 3.75E-06 | 1.62E-03 | 495.2 | 339.9 | 301.2 |
| 113 | 235725_PM_at | SMAD4 | SMAD family member 4 | 3.75E-06 | 1.62E-03 | 147.1 | 102.1 | 112.0 |
| 114 | 203137_PM_at | WTAP | Wilms tumor 1 associated protein | 3.89E-06 | 1.66E-03 | 424.1 | 609.4 | 555.8 |
| 115 | 231075_PM_x_at | RAPH1 | Ras association (RalGDS/AF-6) and pleckstrin homology domains 1 | 3.91E-06 | 1.66E-03 | 30.4 | 193 | 18.2 |
| 116 | 236043_PM_at | LOC100130175 | hypothetical protein LOC100130175 | 3.98E-06 | 1.67E-03 | 220.6 | 146.2 | 146.5 |
| 117 | 238299_PM_at | — | — | 4.09E-06 | 1.70E-03 | 217.1 | 130.4 | 130.3 |
| 118 | 243667_PM_at | — | — | 4.12E-06 | 1.70E-03 | 314.5 | 225.3 | 232.8 |
| 119 | 223937_PM_at | FOXP1 | forkhead box P1 | 4.20E-06 | 1.72E-03 | 147.7 | 85.5 | 90.9 |
| 120 | 238666_PM_at | — | — | 4.25E-06 | 1.72E-03 | 219.1 | 1483 | 145.5 |
| 121 | 1554771_PM_at | — | — | 4.28E-06 | 1.72E-03 | 67.2 | 41.5 | 40.8 |
| 122 | 202379_PM_s_at | NKTR | natural killer-tumor recognition sequence | 4.34E-06 | 1.73E-03 | 1498.2 | 1170.6 | 1042.6 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 123 | 244695_PM_at | GHRLOS | ghrelin opposite strand (non-protein coding) | 4.56E−06 | 1.79E−03 | 78.0 | 53.0 | 52.5 |
| 124 | 239393_PM_at | — | — | 4.58E−06 | 1.79E−03 | 852.0 | 554.2 | 591.7 |
| 125 | 242920_PM_at | — | — | 4.60E−06 | 1.79E−03 | 392.8 | 220.9 | 251.8 |
| 126 | 242405_PM_at | — | — | 4.66E−06 | 1.80E−03 | 415.8 | 193.8 | 207.4 |
| 127 | 1556432_PM_at | — | — | 4.69E−06 | 1.80E−03 | 61.5 | 43.1 | 38.1 |
| 128 | 1570299_PM_at | — | — | 4.77E−06 | 1.81E−03 | 27.0 | 18.0 | 19.8 |
| 129 | 225198_PM_at | VAPA | VAMP (vesicle-associated membrane protein)-associated protein A, 33 kDa | 4.85E−06 | 1.83E−03 | 192.0 | 258.3 | 273.9 |
| 130 | 230702_PM_at | — | — | 4.94E−06 | 1.85E−03 | 28.2 | 18.4 | 17.5 |
| 131 | 240262_PM_at | — | — | 5.07E−06 | 1.88E−03 | 46.9 | 22.8 | 28.0 |
| 132 | 232216_PM_at | YME1L1 | YME1-like 1 (*S. cerevisiae*) | 5.14E−06 | 1.89E−03 | 208.6 | 146.6 | 130.1 |
| 133 | 225171_PM_at | ARHGAP18 | Rho GTPase activating protein 18 | 5.16E−06 | 1.89E−03 | 65.9 | 109.1 | 121.5 |
| 134 | 243992_PM_at | — | — | 5.28E−06 | 1.92E−03 | 187.1 | 115.0 | 125.6 |
| 135 | 227082_PM_at | — | — | 5.45E−06 | 1.96E−03 | 203.8 | 140.4 | 123.0 |
| 136 | 239948_PM_at | NUP153 | nucleoporin 153 kDa | 5.50E−06 | 1.96E−03 | 39.6 | 26.5 | 27.8 |
| 137 | 221905_PM_at | CYLD | cylindromatosis (turban tumor syndrome) | 5.51E−06 | 1.96E−03 | 433.0 | 316.8 | 315.1 |
| 138 | 242578_PM_x_at | SLC22A3 | Solute carrier family 22 (extraneuronal monoamine transporter), member 3 | 5.56E−06 | 1.96E−03 | 148.4 | 109.2 | 120.1 |
| 139 | 1569238_PM_a_at | — | — | 5.73E−06 | 1.99E−03 | 71.0 | 33.0 | 36.1 |
| 140 | 201453_PM_x_at | RHEB | Ras homolog enriched in brain | 5.76E−06 | 1.99E−03 | 453.3 | 600.0 | 599.0 |
| 141 | 236802_PM_at | — | — | 5.76E−06 | 1.99E−03 | 47.9 | 29.1 | 29.6 |
| 142 | 232615_PM_at | — | — | 5.82E−06 | 1.99E−03 | 4068.5 | 3073.4 | 2907.4 |
| 143 | 237179_PM_at | PCMTD2 | protein-L-isoaspartate (D-aspartate) O-methyltransferase domain containing 2 | 5.84E−06 | 1.99E−03 | 48.7 | 30.2 | 26.8 |
| 144 | 203255_PM_at | FBXO11 | F-box protein 11 | 5.98E−06 | 2.02E−03 | 748.3 | 529.4 | 539.6 |
| 145 | 212989_PM_at | SGMS1 | sphingomyelin synthase 1 | 6.04E−06 | 2.03E−03 | 57.2 | 93.1 | 107.9 |
| 146 | 236754_PM_at | PPP1R2 | protein phosphatase 1, regulatory (inhibitor) subunit 2 | 6.17E−06 | 2.05E−03 | 505.3 | 380.7 | 370.1 |
| 147 | 1559456_PM_at | PPA2 | pyrophosphatase (inorganic) 2 | 6.24E−06 | 2.05E−03 | 68.8 | 39.7 | 39.3 |
| 148 | 236494_PM_x_at | — | — | 6.26E−06 | 2.05E−03 | 135.0 | 91.1 | 82.9 |
| 149 | 237554_PM_at | — | — | 6.30E−06 | 2.05E−03 | 53.4 | 31.5 | 30.1 |
| 150 | 243469_PM_at | — | — | 6.37E−06 | 2.05E−03 | 635.2 | 308.1 | 341.5 |
| 151 | 240155_PM_x_at | ZNF493 /// ZNF738 | zinc finger protein 493 /// zinc finger protein 738 | 6.45E−06 | 2.05E−03 | 483.9 | 299.9 | 316.6 |
| 152 | 222442_PM_s_at | ARL8B | ADP-ribosylation factor-like 8B | 6.47E−06 | 2.05E−03 | 201.5 | 292.6 | 268.3 |
| 153 | 240307_PM_at | — | — | 6.48E−06 | 2.05E−03 | 55.4 | 36.8 | 33.1 |
| 154 | 200864_PM_s_at | RAB11A | RAB11A, member RAS oncogene family | 6.50E−06 | 2.05E−03 | 142.1 | 210.9 | 233.0 |
| 155 | 235757_PM_at | — | — | 6.53E−06 | 2.05E−03 | 261.4 | 185.2 | 158.9 |
| 156 | 222351_PM_at | PPP2R1B | protein phosphatase 2, regulatory subunit A, beta | 6.58E−06 | 2.06E−03 | 75.8 | 51.1 | 45.4 |
| 157 | 222788_PM_s_at | RSBN1 | round spermatid basic protein 1 | 6.63E−06 | 2.06E−03 | 389.9 | 302.7 | 288.2 |
| 158 | 239815_PM_at | — | — | 6.70E−06 | 2.06E−03 | 216.9 | 171.4 | 159.5 |
| 159 | 219392_PM_x_at | PRR11 | proline rich 11 | 6.77E−06 | 2.07E−03 | 1065.3 | 827.5 | 913.2 |
| 160 | 240458_PM_at | — | — | 6.80E−06 | 2.07E−03 | 414.3 | 244.6 | 242.0 |
| 161 | 235879_PM_at | MBNL1 | Muscleblind-like (*Drosophila*) | 6.88E−06 | 2.08E−03 | 1709.2 | 1165.5 | 1098.0 |
| 162 | 230529_PM_at | HECA | headcase homolog (*Drosophila*) | 7.08E−06 | 2.13E−03 | 585.1 | 364.3 | 418.4 |
| 163 | 1562063_PM_x_at | KIAA1245 /// NBPF1 /// NBPF10 /// NBPF11 /// NBPF12 /// NBPF24 /// NBPF8 /// NBPF9 | KIAA1245 /// neuroblastoma breakpoint family, member 1 /// neuroblastoma breakpoint fam | 7.35E−06 | 2.20E−03 | 350.4 | 238.8 | 260.8 |
| 164 | 202769_PM_at | CCNG2 | cyclin G2 | 7.42E−06 | 2.20E−03 | 697.1 | 1164.0 | 1264.6 |
| 165 | 1556493_PM_a_at | KDM4C | lysine (K)-specific demethylase 4C | 7.64E−06 | 2.24E−03 | 81.4 | 49.0 | 44.5 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 166 | 216509_PM_x_at | MLLT10 | myeloid/lymphoid or mixed-lineage leukemia (trithorax homolog, *Drosophila*); translocate | 7.64E−06 | 2.24E−03 | 22.4 | 17.9 | 19.3 |
| 167 | 223697_PM_x_at | C9orf64 | chromosome 9 open reading frame 64 | 7.70E−06 | 2.25E−03 | 1013.6 | 771.2 | 836.8 |
| 168 | 235999_PM_at | — | — | 7.77E−06 | 2.25E−03 | 227.6 | 174.1 | 182.1 |
| 169 | 244766_PM_at | LOC100271836 /// LOC440354 /// LOC595101 /// LOC541298 /// SMG1 | SMG1 homolog, phosphatIdylinositol 3-kinase-related kinase pseudogene /// PI-3-kinase-r | 8.03E−06 | 2.31E−03 | 133.4 | 99.4 | 87.5 |
| 170 | 230332_PM_at | ZCCHC7 | Zinc finger, CCHC domain containing 7 | 8.07E−06 | 2.31E−03 | 467.4 | 265.1 | 263.2 |
| 171 | 235308_PM_at | ZBTB20 | zinc finger and BTB domain containing 20 | 8.17E−06 | 2.32E−03 | 256.7 | 184.2 | 167.3 |
| 172 | 242492_PM_at | CLNS1A | Chloride channel, nucleotide-sensitive, 1A | 8.19E−06 | 2.32E−03 | 128.5 | 82.8 | 79.2 |
| 173 | 215898_PM_at | TTLL5 | tubulin tyrosine ligase-like family, member 5 | 8.24E−05 | 2.32E−03 | 20.9 | 14.0 | 13.8 |
| 174 | 244840_PM_x_at | DOCK4 | dedicator of cytokinesis 4 | 8.65E−06 | 2.42E−03 | 43.1 | 16.5 | 21.5 |
| 175 | 220235_PM_s_at | C1orf103 | chromosome 1 open reading frame 103 | 8.72E−06 | 2.43E−03 | 88.4 | 130.5 | 143.3 |
| 176 | 229467_PM_at | PCBP2 | Poly(rC) binding protein 2 | 8.80E−06 | 2.44E−03 | 186.5 | 125.4 | 135.8 |
| 177 | 232527_PM_at | — | — | 8.99E−06 | 2.48E−03 | 667.4 | 453.9 | 461.3 |
| 178 | 243286_PM_at | — | — | 9.24E−06 | 2.53E−03 | 142.6 | 98.2 | 87.2 |
| 179 | 215628_PM_x_at | — | — | 9.28E−06 | 2.53E−03 | 49.6 | 36.3 | 39.4 |
| 180 | 1556412_PM_at | — | — | 9.45E−06 | 2.56E−03 | 34.9 | 24.7 | 23.8 |
| 181 | 204786_PM_s_at | IFNAR2 | Interferon (alpha, beta and omega) receptor 2 | 9.64E−06 | 2.59E−03 | 795.6 | 573.0 | 639.2 |
| 182 | 234258_PM_at | — | — | 9.73E−06 | 2.60E−03 | 27.4 | 17.8 | 20.3 |
| 183 | 233274_PM_at | — | — | 9.76E−06 | 2.60E−03 | 109.9 | 77.5 | 79.4 |
| 184 | 239784_PM_at | — | — | 9.82E−05 | 2.60E−03 | 137.0 | 80.1 | 70.1 |
| 185 | 242498_PM_x_at | — | — | 1.01E−05 | 2.65E−03 | 59.2 | 40.4 | 38.9 |
| 186 | 231351_PM_at | — | — | 1.02E−05 | 2.67E−03 | 124.8 | 70.8 | 60.6 |
| 187 | 222368_PM_at | — | — | 1.03E−05 | 2.67E−03 | 89.9 | 54.5 | 44.3 |
| 188 | 236524_PM_at | — | — | 1.03E−05 | 2.67E−03 | 313.2 | 234.7 | 214.2 |
| 189 | 243834_PM_at | TNRC6A | trinucleotide repeat containing 6A | 1.04E−05 | 2.67E−03 | 211.8 | 145.1 | 146.9 |
| 190 | 239167_PM_at | — | — | 1.04E−05 | 2.67E−03 | 287.4 | 150.2 | 160.3 |
| 191 | 239238_PM_at | — | — | 1.05E−05 | 2.67E−03 | 136.0 | 81.6 | 92.0 |
| 192 | 237194_PM_at | — | — | 1.05E−05 | 2.67E−03 | 57.2 | 34.4 | 27.9 |
| 193 | 242772_PM_x_at | — | — | 1.06E−05 | 2.67E−03 | 299.2 | 185.2 | 189.4 |
| 194 | 243827_PM_at | — | — | 1.06E−05 | 2.67E−03 | 115.9 | 50.1 | 56.4 |
| 195 | 1552536_PM_at | VTI1A | vesicle transport through interaction with t-SNAREs homolog 1A (yeast) | 1.10E−05 | 2.75E−03 | 61.7 | 35.1 | 34.6 |
| 196 | 243696_PM_at | KIAA0562 | KIAA0562 | 1.12E−05 | 2.77E−03 | 19.0 | 14.8 | 15.0 |
| 197 | 233648_PM_at | — | — | 1.12E−05 | 2.77E−03 | 33.9 | 21.0 | 24.1 |
| 198 | 225858_PM_s_at | XIAP | X-linked inhibitor of apoptosis | 1.16E−05 | 2.85E−03 | 1020.7 | 760.3 | 772.6 |
| 199 | 238736_PM_at | REV3L | REV3-like, catalytic subunit of DNA polymerase zeta (yeast) | 1.19E−05 | 2.91E−03 | 214.2 | 135.8 | 151.6 |
| 200 | 221192_PM_x_at | MFSD11 | major facilitator superfamily domain containing 11 | 1.20E−05 | 2.92E−03 | 100.4 | 74.5 | 81.2 |
| 201 | 238549_PM_at | CBFA2T2 | core-binding factor, runt domain, alpha subunit 2; translocated to, 2 | 1.22E−05 | 2.95E−03 | 277.5 | 222.0 | 206.6 |
| 202 | 213015_PM_at | BBX | bobby sox homolog (*Drosophila*) | 1.23E−05 | 2.96E−03 | 567.2 | 446.8 | 419.6 |
| 203 | 60528_PM_at | JMJD7-PLA2G4B /// PLA2G4B | JMJD7-PLA2G4B readthrough /// phospholipase A2, group IVB (cytosolic) | 1.28E−05 | 3.07E−03 | 37.3 | 29.2 | 28.7 |
| 204 | 242014_PM_at | — | — | 1.30E−05 | 3.09E−03 | 121.9 | 75.6 | 86.1 |
| 205 | 238277_PM_at | — | — | 1.30E−05 | 3.09E−03 | 30.9 | 20.4 | 20.9 |
| 206 | 243527_PM_at | — | — | 1.32E−05 | 3.11E−03 | 869.5 | 517.7 | 530.8 |
| 207 | 237383_PM_at | — | — | 1.33E−05 | 3.11E−03 | 167.0 | 86.8 | 93.6 |
| 208 | 218854_PM_at | DSE | dermatan sulfate epimerase | 1.33E−05 | 3.11E−03 | 223.0 | 318.1 | 360.7 |
| 209 | 239331_PM_at | — | — | 1.35E−05 | 3.14E−03 | 556.5 | 296.9 | 302.5 |
| 210 | 228105_PM_at | — | — | 1.35E−05 | 3.14E−03 | 387.4 | 274.0 | 270.3 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
| --- | --- | --- | --- | --- | --- | --- | --- | --- |
| 211 | 237006_PM_at | — | — | 1.37E-05 | 3.15E-03 | 316.4 | 177.8 | 185.3 |
| 212 | 244822_PM_at | — | — | 1.40E-05 | 3.21E-03 | 45.3 | 32.6 | 27.3 |
| 213 | 241965_PM_at | — | — | 1.43E-05 | 3.27E-03 | 194.7 | 121.1 | 130.9 |
| 214 | 230389_PM_at | FNBP1 | formin binding protein 1 | 1.45E-05 | 3.30E-03 | 760.9 | 567.6 | 527.1 |
| 215 | 239171_PM_at | — | — | 1.45E-05 | 3.30E-03 | 112.1 | 67.6 | 65.2 |
| 216 | 236450_PM_at | — | — | 1.46E-05 | 3.30E-03 | 28.3 | 20.2 | 18.5 |
| 217 | 204236_PM_at | FLI1 | Friend leukemia virus integration 1 | 1.48E-05 | 3.33E-03 | 862.0 | 1066.1 | 1074.7 |
| 218 | 235925_PM_at | — | — | 1.49E-05 | 3.33E-03 | 61.2 | 41.7 | 35.3 |
| 219 | 243736_PM_at | — | — | 1.50E-05 | 3.33E-03 | 131.8 | 76.7 | 70.0 |
| 220 | 236293_PM_at | PDSS1 | Prenyl (decaprenyl) diphosphate synthase, subunit 1 | 1.51E-05 | 3.33E-03 | 79.7 | 59.5 | 60.9 |
| 221 | 1558410_PM_s_at | — | — | 1.51E-05 | 3.33E-03 | 40.1 | 24.8 | 22.6 |
| 222 | 1570621_PM_at | — | — | 1.52E-05 | 3.33E-03 | 24.1 | 16.1 | 18.0 |
| 223 | 233228_PM_at | — | — | 1.54E-05 | 3.35E-03 | 256.6 | 149.9 | 137.1 |
| 224 | 244801_PM_at | PSMB7 | Proteasome (prosome, macropain) subunit, beta type, 7 | 1.54E-05 | 3.35E-03 | 71.6 | 53.7 | 48.7 |
| 225 | 236779_PM_at | MRPS5 | Mitochondrial ribosomal protein S5 | 1.55E-05 | 3.35E-03 | 25.4 | 20.5 | 17.1 |
| 226 | 241063_PM_at | — | — | 1.55E-05 | 3.35E-03 | 16.8 | 13.4 | 12.4 |
| 227 | 239166_PM_at | — | — | 1.56E-05 | 3.35E-03 | 151.4 | 84.6 | 79.8 |
| 228 | 222371_PM_at | — | — | 1.59E-05 | 3.38E-03 | 1038.5 | 638.6 | 629.2 |
| 229 | 1553349_PM_at | ARID2 | AT rich interactive domain 2 (ARID, RFX-like) | 1.59E-05 | 3.38E-03 | 98.2 | 66.1 | 65.9 |
| 230 | 238894_PM_at | — | — | 1.60E-05 | 3.38E-03 | 95.0 | 58.9 | 56.8 |
| 231 | 236621_PM_at | RPS27 | ribosomal protein S27 | 1.61E-05 | 3.40E-03 | 74.6 | 38.2 | 41.4 |
| 232 | 222310_PM_at | SFRS15 | splicing factor, arginine/serine-rich 15 | 1.62E-05 | 3.41E-03 | 154.5 | 95.5 | 106.7 |
| 233 | 1569180_PM_at | — | — | 1.65E-05 | 3.44E-03 | 232.8 | 126.6 | 126.8 |
| 234 | 240544_PM_at | — | — | 1.67E-05 | 3.48E-03 | 45.3 | 24.9 | 25.8 |
| 235 | 226062_PM_x_at | FAM63A | family with sequence similarity 63, member A | 1.74E-05 | 3.61E-03 | 532.9 | 375.1 | 412.3 |
| 236 | 210679_PM_x_at | — | — | 1.75E-05 | 3.62E-03 | 167.5 | 119.6 | 123.6 |
| 237 | 203482_PM_at | FAM178A | family with sequence similarity 178, member A | 1.76E-05 | 3.62E-03 | 88.2 | 69.3 | 66.3 |
| 238 | 203318_PM_s_at | ZNF148 | zinc finger protein 148 | 1.86E-05 | 3.80E-03 | 812.1 | 633.8 | 647.6 |
| 239 | 233027_PM_at | — | — | 1.87E-05 | 3.80E-03 | 167.2 | 107.4 | 119.2 |
| 240 | 236966_PM_at | ARMC8 | armadillo repeat containing 8 | 1.87E-05 | 3.80E-03 | 373.4 | 272.2 | 240.4 |
| 241 | 217446_PM_x_at | — | — | 1.89E-05 | 3.82E-03 | 204.7 | 158.6 | 170.8 |
| 242 | 241508_PM_at | — | — | 1.91E-05 | 3.85E-03 | 106.6 | 62.3 | 69.3 |
| 243 | 213940_PM_s_at | FNBP1 | formin binding protein 1 | 1.94E-05 | 3.87E-03 | 911.3 | 766.0 | 710.7 |
| 244 | 215373_PM_x_at | — | — | 1.94E-05 | 3.87E-03 | 77.9 | 54.4 | 65.9 |
| 245 | 242480_PM_at | — | — | 1.95E-05 | 3.89E-03 | 605.9 | 358.6 | 393.2 |
| 246 | 228271_PM_at | — | — | 1.97E-05 | 3.90E-03 | 109.8 | 81.3 | 64.9 |
| 247 | 216211_PM_at | — | — | 1.98E-05 | 3.90E-03 | 182.9 | 132.4 | 111.1 |
| 248 | 1557632_PM_at | — | — | 1.99E-05 | 3.90E-03 | 576.5 | 426.5 | 400.0 |
| 249 | 244826_PM_at | — | — | 2.00E-05 | 3.90E-03 | 363.7 | 257.1 | 267.9 |
| 250 | 239264_PM_at | — | — | 2.01E-05 | 3.90E-03 | 162.6 | 98.9 | 89.0 |
| 251 | 227931_PM_at | INO80D | INO80 complex subunit D | 2.01E-05 | 3.90E-03 | 841.6 | 635.5 | 661.8 |
| 252 | 242563_PM_at | — | — | 2.03E-05 | 3.93E-03 | 246.4 | 126.9 | 135.0 |
| 253 | 238172_PM_at | — | — | 2.05E-05 | 3.95E-03 | 88.6 | 56.1 | 51.4 |
| 254 | 241893_PM_at | — | — | 2.06E-05 | 3.96E-03 | 123.1 | 59.6 | 59.3 |
| 255 | 233323_PM_at | — | — | 2.08E-05 | 3.96E-03 | 223.8 | 136.7 | 135.2 |
| 256 | 242865_PM_at | — | — | 2.08E-05 | 3.96E-03 | 382.4 | 247.8 | 273.3 |
| 257 | 226252_PM_at | — | — | 2.09E-05 | 3.97E-03 | 124.6 | 91.1 | 84.0 |
| 258 | 225490_PM_at | ARID2 | AT rich interactive domain 2 (ARID, RFX-like) | 2.11E-05 | 3.97E-03 | 240.9 | 185.3 | 169.2 |
| 259 | 208654_PM_s_at | CD164 | CD164 molecule, sialomucin | 2.12E-05 | 3.97E-03 | 676.3 | 1044.0 | 939.9 |
| 260 | 215338_PM_s_at | NKTR | natural killer-tumor recognition sequence | 2.13E-05 | 3.97E-03 | 457.1 | 352.4 | 328.2 |
| 261 | 242110_PM_at | — | — | 2.13E-05 | 3.97E-03 | 54.2 | 31.6 | 29.8 |
| 262 | 218360_PM_at | RAB22A | RAB22A, member RAS oncogene family | 2.15E-05 | 4.00E-03 | 78.8 | 122.7 | 118.7 |
| 263 | 1570166_PM_a_at | — | — | 2.16E-05 | 4.00E-03 | 38.7 | 26.0 | 27.1 |
| 264 | 208724_PM_s_at | RAB1A | RAB1A, member RAS oncogene family | 2.17E-05 | 4.00E-03 | 1357.9 | 1688.2 | 1672.7 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 265 | 239901_PM_at | — | — | 2.19E−05 | 4.03E−03 | 455.7 | 255.1 | 273.1 |
| 266 | 238988_PM_at | — | — | 2.21E−05 | 4.05E−03 | 315.4 | 194.7 | 209.8 |
| 267 | 235023_PM_at | VPS13C | Vacuolar protein sorting 13 homolog C (S. cerevisiae) | 2.23E−05 | 4.08E−03 | 649.4 | 471.9 | 435.1 |
| 268 | 217619_PM_x_at | — | — | 2.24E−05 | 4.08E−03 | 48.0 | 39.5 | 43.3 |
| 269 | 215618_PM_at | RSU1 | Ras suppressor protein 1 | 2.27E−05 | 4.10E−03 | 34.5 | 24.9 | 25.4 |
| 270 | 230779_PM_at | TNRC68 | trinucleotide repeat containing 68 | 2.27E−05 | 4.10E−03 | 767.7 | 495.5 | 508.6 |
| 271 | 243981_PM_at | STK4 | serine/threonine kinase 4 | 2.31E−05 | 4.16E−03 | 490.0 | 312.1 | 335.1 |
| 272 | 1569181_PM_x_at | — | — | 2.33E−05 | 4.17E−03 | 233.9 | 127.7 | 121.5 |
| 273 | 203321_PM_s_at | ADNP2 | ADNP homeobox 2 | 2.34E−05 | 4.17E−03 | 150.5 | 117.4 | 113.4 |
| 274 | 204373_PM_s_at | CEP350 | centrosomal protein 350 kDa | 2.36E−05 | 4.19E−03 | 439.2 | 350.3 | 352.4 |
| 275 | 239071_PM_at | RBBP4 | Retinoblastoma binding protein 4 | 2.37E−05 | 4.20E−03 | 173.1 | 131.7 | 122.9 |
| 276 | 224437_PM_s_at | VTA1 | Vps20-associated 1 homolog (S. cerevisiae) | 2.38E−05 | 4.21E−03 | 229.2 | 335.9 | 330.0 |
| 277 | 243522_PM_at | — | — | 2.41E−05 | 4.24E−03 | 14.9 | 12.5 | 11.7 |
| 278 | 237803_PM_x_at | — | — | 2.42E−05 | 4.24E−03 | 89.4 | 65.8 | 54.7 |
| 279 | 229036_PM_at | TNRC6B | trinucleotide repeat containing 6B | 2.45E−05 | 4.28E−03 | 575.8 | 426.5 | 436.5 |
| 280 | 222282_PM_at | — | — | 2.47E−05 | 4.29E−03 | 340.4 | 214.0 | 230.4 |
| 281 | 227074_PM_at | LOC100131564 | hypothetical LOC100131564 | 2.49E−05 | 4.32E−03 | 389.3 | 291.8 | 239.7 |
| 282 | 242343_PM_x_at | — | — | 2.55E−05 | 4.38E−03 | 595.3 | 403.5 | 403.1 |
| 283 | 213086_PM_s_at | CSNK1A1 | casein kinase 1, alpha 1 | 2.55E−05 | 4.38E−03 | 565.0 | 667.9 | 660.5 |
| 284 | 205383_PM_s_at | ZBTB20 | zinc finger and BTB domain containing 20 | 2.56E−05 | 4.38E−03 | 151.5 | 104.9 | 92.1 |
| 285 | 233919_PM_s_at | HASP4 | hyaluronan binding protein 4 | 2.57E−05 | 4.38E−03 | 33.3 | 22.3 | 20.4 |
| 286 | 231552_PM_at | — | — | 2.57E−05 | 4.38E−03 | 258.2 | 173.1 | 182.0 |
| 287 | 239017_PM_at | LOC100507273 | collagen alpha-4(VI) chain-like | 2.58E−05 | 4.39E−03 | 75.4 | 40.3 | 39.1 |
| 288 | 240072_PM_at | ASXL2 | Additional sex combs like 2 (Drosophila) | 2.61E−05 | 4.42E−03 | 81.5 | 50.0 | 56.0 |
| 289 | 242362_PM_at | — | — | 2.65E−05 | 4.47E−03 | 414.8 | 279.8 | 307.1 |
| 290 | 238317_PM_x_at | — | — | 2.67E−05 | 4.49E−03 | 386.3 | 284.6 | 287.8 |
| 291 | 242471_PM_at | — | — | 2.71E−05 | 4.53E−03 | 741.8 | 426.8 | 386.9 |
| 292 | 209308_PM_s_at | BNIP2 | BCL2/adenovirus E1B 19 kDa interacting protein 2 | 2.73E−05 | 4.55E−03 | 306.3 | 444.4 | 450.1 |
| 293 | 240254_PM_at | — | — | 2.75E−05 | 4.57E−03 | 41.2 | 27.6 | 21.5 |
| 294 | 233313_PM_at | — | — | 2.80E−05 | 4.61E−03 | 46.3 | 33.3 | 30.5 |
| 295 | 1559401_PM_a_at | — | — | 2.80E−05 | 4.61E−03 | 20.0 | 14.2 | 13.3 |
| 296 | 217158_PM_at | LOC442421 /// LOC728297 | hypothetical LOC442421 /// prostaglandin E2 receptor EP4 subtype-like | 2.82E−05 | 4.61E−03 | 12.6 | 14.2 | 12.0 |
| 297 | 239758_PM_at | — | — | 2.82E−05 | 4.61E−03 | 133.3 | 79.2 | 78.9 |
| 298 | 232882_PM_at | — | — | 2.82E−05 | 4.61E−03 | 203.8 | 95.0 | 85.1 |
| 299 | 226250_PM_at | — | — | 2.83E−05 | 4.61E−03 | 151.7 | 105.8 | 97.6 |
| 300 | 201619_PM_at | PRDX3 | peroxiredoxin 3 | 2.84E−05 | 4.62E−03 | 605.8 | 852.3 | 804.1 |
| 301 | 213229_PM_at | DICER1 | dicer 1, ribonuclease type III | 2.87E−05 | 4.62E−03 | 971.6 | 652.0 | 668.8 |
| 302 | 242068_PM_at | — | — | 2.87E−05 | 4.62E−03 | 281.2 | 157.5 | 152.9 |
| 303 | 243470_PM_at | — | — | 2.87E−05 | 4.62E−03 | 60.0 | 43.1 | 44.4 |
| 304 | 218519_PM_at | SLC35A5 | solute carrier family 35, member A5 | 2.88E−05 | 4.62E−03 | 173.2 | 228.3 | 234.9 |
| 305 | 240399_PM_at | — | — | 2.92E−05 | 4.64E−03 | 15.6 | 11.2 | 12.6 |
| 306 | 241501_PM_at | — | — | 2.92E−05 | 4.64E−03 | 265.7 | 175.6 | 164.5 |
| 307 | 228623_PM_at | — | — | 2.93E−05 | 4.64E−03 | 369.6 | 223.4 | 226.0 |
| 308 | 225007_PM_at | G3BP1 | GTPase activating protein (SH3 domain) binding protein 1 | 2.99E−05 | 4.72E−03 | 549.8 | 423.9 | 371.4 |
| 309 | 244239_PM_at | — | — | 3.04E−05 | 4.78E−03 | 13.6 | 9.8 | 9.9 |
| 310 | 243054_PM_at | — | — | 3.04E−05 | 4.78E−03 | 73.9 | 53.0 | 50.8 |
| 311 | 219724_PM_s_at | KIAA0748 | KIAA0748 | 3.07E−05 | 4.81E−03 | 16.6 | 12.4 | 12.0 |
| 312 | 240594_PM_at | — | — | 3.09E−05 | 4.82E−03 | 44.0 | 27.7 | 28.2 |
| 313 | 208003_PM_s_at | NFAT5 | nuclear factor of activated T-cells 5, tonicity-responsive | 3.13E−05 | 4.88E−03 | 763.2 | 510.3 | 539.6 |
| 314 | 243147_PM_x_at | — | — | 3.16E−05 | 4.91E−03 | 420.2 | 325.4 | 351.8 |
| 315 | 236742_PM_at | — | — | 3.18E−05 | 4.92E−03 | 102.3 | 61.7 | 60.2 |
| 316 | 209964_PM_s_at | ATXN7 | ataxin 7 | 3.20E−05 | 4.92E−03 | 361.1 | 250.7 | 229.7 |
| 317 | 202106_PM_at | GOLGA3 | golgin A3 | 3.20E−05 | 4.92E−03 | 136.8 | 110.1 | 96.0 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 318 | 237001_PM_at | — | — | 3.22E−05 | 4.93E−03 | 64.6 | 39.1 | 38.5 |
| 319 | 202539_PM_s_at | HMGCR | 3-hydroxy-3-methylglutaryl-CoA reductase | 3.25E−05 | 4.93E−03 | 128.3 | 175.3 | 192.0 |
| 320 | 244474_PM_at | — | — | 3.26E−05 | 4.93E−03 | 86.2 | 62.4 | 52.5 |
| 321 | 41512_PM_at | BRAP | BRCA1 associated protein | 3.26E−05 | 4.93E−03 | 287.1 | 234.9 | 234.3 |
| 322 | 215707_PM_s_at | PRNP | prion protein | 3.27E−05 | 4.93E−03 | 25.5 | 42.5 | 34.2 |
| 323 | 243088_PM_at | — | — | 3.27E−05 | 4.93E−03 | 201.5 | 119.7 | 132.3 |
| 324 | 244733_PM_at | — | — | 3.29E−05 | 4.95E−03 | 38.9 | 27.1 | 26.4 |
| 325 | 223215_PM_s_at | JKAMP | JNK1/MAPK8-associated membrane protein | 3.31E−05 | 4.96E−03 | 327.6 | 455.8 | 450.7 |
| 326 | 1559410_PM_at | — | — | 3.34E−05 | 4.96E−03 | 31.4 | 20.7 | 16.7 |
| 327 | 222311_PM_s_at | SFRS15 | splicing factor, arginine/serine-rich 15 | 3.34E−05 | 4.96E−03 | 121.9 | 92.5 | 89.7 |
| 328 | 242696_PM_at | — | — | 3.34E−05 | 4.96E−03 | 138.7 | 100.5 | 88.5 |
| 329 | 223021_PM_x_at | VTA1 | Vps20-associated 1 homolog (S. cerevisiae) | 3.35E−05 | 4.96E−03 | 140.1 | 205.9 | 194.5 |
| 330 | 241472_PM_at | — | — | 3.36E−05 | 4.97E−03 | 172.1 | 122.6 | 120.7 |
| 331 | 238000_PM_at | — | — | 3.37E−05 | 4.97E−03 | 131.5 | 83.1 | 82.0 |
| 332 | 236492_PM_at | PPP2R2A | protein phosphatase 2, regulatory subunit B, alpha | 3.41E−05 | 5.01E−03 | 307.2 | 195.9 | 205.4 |
| 333 | 220939_PM_s_at | DPP8 | dipeptidyl-peptidase 8 | 3.44E−05 | 5.02E−03 | 1061.4 | 845.7 | 839.7 |
| 334 | 200733_PM_s_at | PTP4A1 | protein tyrosine phosphatase type IVA, member 1 | 3.44E−05 | 5.02E−03 | 198.9 | 272.5 | 268.8 |
| 335 | 233440_PM_at | — | — | 3.50E−05 | 5.06E−03 | 58.5 | 35.2 | 36.5 |
| 336 | 205435_PM_s_at | AAK1 | AP2 associated kinase 1 | 3.51E−05 | 5.06E−03 | 71.1 | 51.7 | 42.0 |
| 337 | 233893_PM_s_at | KIAA1530 | KIAA1530 | 3.51E−05 | 5.06E−03 | 470.7 | 303.9 | 368.9 |
| 338 | 232180_PM_at | UGP2 | UDP-glucose pyrophosphorylase 2 | 3.52E−05 | 5.06E−03 | 276.2 | 182.6 | 185.7 |
| 339 | 244450_PM_at | — | — | 3.52E−05 | 5.06E−03 | 88.9 | 59.8 | 59.7 |
| 340 | 238619_PM_at | — | — | 3.53E−05 | 5.06E−03 | 906.1 | 477.0 | 493.4 |
| 341 | 1555372_PM_at | BCL2L11 | BCL2-like 11 (apoptosis facilitator) | 3.56E−05 | 5.08E−03 | 254.9 | 161.0 | 194.6 |
| 342 | 210742_PM_at | CDC14A | CDC14 cell division cycle 14 homolog A (S. cerevisiae) | 3.59E−05 | 5.09E−03 | 214.1 | 160.8 | 113.2 |
| 343 | 225351_PM_at | FAM45A | family with sequence similarity 45, member A | 3.59E−05 | 5.09E−03 | 421.1 | 568.4 | 623.5 |
| 344 | 231716_PM_at | RC3H2 | ring finger and CCCH-type domains 2 | 3.61E−05 | 5.11E−03 | 334.5 | 272.9 | 279.1 |
| 345 | 239673_PM_at | — | — | 3.63E−05 | 5.13E−03 | 71.8 | 29.9 | 21.2 |
| 346 | 232509_PM_at | PDE4DIP | phosphodiesterase 4D interacting protein | 3.66E−05 | 5.15E−03 | 19.8 | 15.3 | 15.2 |
| 347 | 202749_PM_at | WRB | tryptophan rich basic protein | 3.77E−05 | 5.30E−03 | 240.9 | 333.2 | 316.9 |
| 348 | 231199_PM_at | — | — | 3.79E−05 | 5.30E−03 | 415.2 | 293.5 | 303.8 |
| 349 | 215513_PM_at | HYMAI | hydatidiform mole associated and imprinted (non-protein coding) | 3.80E−05 | 5.30E−03 | 66.4 | 35.9 | 42.9 |
| 350 | 232323_PM_s_at | TTC17 | tetratricopeptide repeat domain 17 | 3.81E−05 | 5.30E−03 | 354.0 | 286.9 | 265.6 |
| 351 | 240824_PM_at | — | — | 3.85E−05 | 5.34E−03 | 300.3 | 202.7 | 216.3 |
| 352 | 243640_PM_x_at | — | — | 3.86E−05 | 5.34E−03 | 36.3 | 26.9 | 25.6 |
| 353 | 239902_PM_at | — | — | 3.96E−05 | 5.47E−03 | 40.7 | 32.0 | 25.5 |
| 354 | 244495_PM_x_at | C18orf45 | chromosome 18 open reading frame 45 | 4.00E−05 | 5.48E−03 | 111.4 | 89.9 | 100.0 |
| 355 | 221176_PM_x_at | — | — | 4.02E−05 | 5.48E−03 | 135.2 | 107.7 | 114.4 |
| 356 | 236243_PM_at | ZCCHC6 | Zinc finger, CCHC domain containing 6 | 4.03E−05 | 5.48E−03 | 868.0 | 534.2 | 530.6 |
| 357 | 243964_PM_at | — | — | 4.03E−05 | 5.48E−03 | 114.0 | 75.3 | 69.3 |
| 358 | 226970_PM_at | FBXO33 | F-box protein 33 | 4.03E−05 | 5.48E−03 | 460.9 | 359.9 | 344.0 |
| 359 | 206169_PM_x_at | ZC3H7B | zinc finger CCCH-type containing 7B | 4.04E−05 | 5.48E−03 | 439.3 | 319.9 | 341.9 |
| 360 | 227969_PM_at | LOC400960 | hypothetical LOC400960 | 4.05E−05 | 5.48E−03 | 65.4 | 50.7 | 46.7 |
| 361 | 207186_PM_s_at | BPTF | bromodomain PHD finger transcription factor | 4.09E−05 | 5.52E−03 | 1217.2 | 958.4 | 894.3 |
| 362 | 242918_PM_at | NASP | Nuclear autoantigenic sperm protein (histone-binding) | 4.13E−05 | 5.56E−03 | 212.8 | 127.0 | 158.1 |
| 363 | 241226_PM_at | — | — | 4.14E−05 | 5.56E−03 | 32.6 | 22.4 | 21.0 |
| 364 | 1556382_PM_a_at | NAA15 | N(alpha)-acetyltransferase 15, NatA auxiliary subunit | 4.15E−05 | 5.56E−03 | 15.9 | 12.2 | 12.3 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 365 | 237018_PM_at | — | — | 4.19E−05 | 5.58E−03 | 460.1 | 322.7 | 305.5 |
| 366 | 225367_PM_at | PGM2 | phosphoglucomutase 2 | 4.20E−05 | 5.58E−03 | 550.7 | 709.4 | 778.0 |
| 367 | 236134_PM_at | DCAF7 | DDB1 and CUL4 associated factor 7 | 4.20E−05 | 5.58E−03 | 120.0 | 78.1 | 74.3 |
| 368 | 242143_PM_at | — | — | 4.24E−05 | 5.62E−03 | 295.6 | 177.4 | 179.6 |
| 369 | 237881_PM_at | — | — | 4.31E−05 | 5.69E−03 | 128.5 | 56.6 | 52.1 |
| 370 | 203100_PM_s_at | CDYL | chromodomain protein, Y-like | 4.32E−05 | 5.69E−03 | 85.5 | 116.1 | 121.1 |
| 371 | 244236_PM_at | — | — | 4.34E−05 | 5.70E−03 | 22.7 | 18.1 | 16.0 |
| 372 | 236561_PM_at | — | — | 4.36E−05 | 5.71E−03 | 577.8 | 412.5 | 389.2 |
| 373 | 236149_PM_at | — | — | 4.38E−05 | 5.71E−03 | 52.7 | 31.8 | 29.7 |
| 374 | 214715_PM_x_at | ZNF160 | zinc finger protein 160 | 4.38E−05 | 5.71E−03 | 860.0 | 646.3 | 690.2 |
| 375 | 219326_PM_s_at | B3GNT2 | UDP-GlcNAc:betaGal beta-1,3-N-acetylglucosaminyltransferase 2 | 4.40E−05 | 5.72E−03 | 18.1 | 26.8 | 28.6 |
| 376 | 201959_PM_s_at | MYCBP2 | MYC binding protein 2 | 4.44E−05 | 5.75E−03 | 1010.4 | 762.0 | 722.2 |
| 377 | 236404_PM_at | — | — | 4.47E−05 | 5.77E−03 | 310.1 | 182.7 | 185.3 |
| 378 | 233037_PM_at | — | — | 4.52E−05 | 5.83E−03 | 19.4 | 14.3 | 14.8 |
| 379 | 237768_PM_x_at | — | — | 4.55E−05 | 5.85E−03 | 531.4 | 367.3 | 361.5 |
| 380 | 202549_PM_at | VAPB | VAMP (vesicle-associated membrane protein)-associated protein B and C | 4.57E−05 | 5.86E−03 | 21.9 | 15.6 | 18.9 |
| 381 | 237264_PM_at | — | — | 4.61E−05 | 5.89E−03 | 192.5 | 114.0 | 115.6 |
| 382 | 226465_PM_s_at | SON | SON DNA binding protein | 4.64E−05 | 5.89E−03 | 1664.7 | 1345.0 | 1359.5 |
| 383 | 226412_PM_at | SFRS18 | splicing factor, arginine/serine-rich 18 | 4.65E−05 | 5.89E−03 | 619.8 | 443.1 | 467.6 |
| 384 | 244860_PM_at | — | — | 4.66E−05 | 5.89E−03 | 37.8 | 22.5 | 21.1 |
| 385 | 240139_PM_at | — | — | 4.67E−05 | 5.89E−03 | 162.8 | 110.0 | 101.9 |
| 386 | 238807_PM_at | GAPDHP62 | glyceraldehyde 3 phosphate dehydrogenase pseudogene 62 | 4.67E−05 | 5.89E−03 | 126.7 | 88.3 | 78.4 |
| 387 | 230866_PM_at | CYSLTR1 | cysteinyl leukotriene receptor 1 | 4.72E−05 | 5.93E−03 | 171.2 | 267.5 | 284.1 |
| 388 | 236000_PM_s_at | — | — | 4.72E−05 | 5.93E−03 | 326.9 | 240.3 | 242.0 |
| 389 | 237895_PM_at | — | — | 4.74E−05 | 5.94E−03 | 469.8 | 258.1 | 223.9 |
| 390 | 243966_PM_at | — | — | 4.79E−05 | 5.97E−03 | 227.7 | 174.9 | 165.4 |
| 391 | 1556060_PM_a_at | ZNF451 | zinc finger protein 451 | 4.80E−05 | 5.97E−03 | 550.1 | 418.5 | 416.6 |
| 392 | 242598_PM_at | — | — | 4.81E−05 | 5.97E−03 | 465.2 | 250.1 | 308.0 |
| 393 | 1569237_PM_at | — | — | 4.83E−05 | 5.97E−03 | 52.8 | 35.4 | 37.1 |
| 394 | 232791_PM_at | — | — | 4.83E−05 | 5.97E−03 | 25.2 | 17.7 | 16.8 |
| 395 | 1565567_PM_at | — | — | 4.85E−05 | 5.97E−03 | 1032.1 | 665.2 | 779.1 |
| 396 | 222252_PM_x_at | UBQLN4 | ubiquilin 4 | 4.85E−05 | 5.97E−03 | 73.1 | 59.3 | 61.8 |
| 397 | 229765_PM_at | ZNF207 | zinc finger protein 207 | 4.90E−05 | 6.01E−03 | 722.8 | 581.6 | 540.4 |
| 398 | 201302_PM_at | ANXA4 | annexin A4 | 4.92E−05 | 6.01E−03 | 303.7 | 429.1 | 454.7 |
| 399 | 1556783_PM_a_at | — | — | 4.92E−05 | 6.01E−03 | 15.2 | 11.7 | 11.7 |
| 400 | 215200_PM_x_at | — | — | 4.94E−05 | 6.02E−03 | 97.7 | 79.4 | 80.4 |
| 401 | 231005_PM_at | — | — | 4.98E−05 | 6.04E−03 | 243.5 | 155.8 | 167.8 |
| 402 | 243249_PM_at | — | — | 4.99E−05 | 6.04E−03 | 832.1 | 598.5 | 633.0 |
| 403 | 233702_PM_x_at | — | — | 5.00E−05 | 6.04E−03 | 381.5 | 289.0 | 318.0 |
| 404 | 1564077_PM_at | — | — | 5.01E−05 | 6.04E−03 | 99.8 | 65.3 | 47.8 |
| 405 | 232613_PM_at | PBRM1 | polybromo 1 | 5.04E−05 | 6.06E−03 | 152.3 | 108.9 | 117.0 |
| 406 | 225859_PM_at | XIAP | X-linked inhibitor of apoptosis | 5.11E−05 | 6.13E−03 | 716.1 | 535.6 | 524.7 |
| 407 | 240302_PM_at | — | — | 5.20E−05 | 6.23E−03 | 70.6 | 46.5 | 42.3 |
| 408 | 244791_PM_at | — | — | 5.22E−05 | 6.24E−03 | 72.4 | 41.7 | 43.0 |
| 409 | 244508_PM_at | 7-Sep | Septin 7 | 5.26E−05 | 6.26E−03 | 80.0 | 50.2 | 46.2 |
| 410 | 1554251_PM_at | HP1BP3 | heterochromatin protein 1, binding protein 3 | 5.28E−05 | 6.26E−03 | 192.1 | 150.9 | 123.2 |
| 411 | 242862_PM_x_at | — | — | 5.28E−05 | 6.26E−03 | 114.4 | 82.9 | 88.5 |
| 412 | 243381_PM_at | — | — | 5.29E−05 | 6.26E−03 | 35.7 | 24.3 | 23.6 |
| 413 | 1561763_PM_at | — | — | 5.38E−05 | 6.35E−03 | 92.4 | 56.7 | 59.8 |
| 414 | 239102_PM_s_at | — | — | 5.41E−05 | 6.35E−03 | 1585.7 | 933.9 | 1087.2 |
| 415 | 215179_PM_x_at | PGF | Placental growth factor | 5.41E−05 | 6.35E−03 | 820.1 | 625.4 | 683.9 |
| 416 | 200730_PM_s_at | PTP4A1 | protein tyrosine phosphatase type IVA, member 1 | 5.42E−05 | 6.35E−03 | 76.9 | 120.8 | 125.1 |
| 417 | 233309_PM_at | — | — | 5.44E−05 | 6.35E−03 | 142.7 | 89.0 | 102.0 |
| 418 | 210282_PM_at | ZMYM2 | zinc finger, MYM-type 2 | 5.48E−05 | 6.39E−03 | 246.4 | 166.5 | 163.2 |
| 419 | 243025_PM_at | — | — | 5.62E−05 | 6.53E−03 | 74.0 | 52.0 | 54.7 |
| 420 | 237475_PM_x_at | CCDC152 | coiled-coil domain containing 152 | 5.72E−05 | 6.63E−03 | 830.9 | 624.3 | 684.3 |
| 421 | 212526_PM_at | SPG20 | spastic paraplegia 20 (Troyer syndrome) | 5.73E−05 | 6.63E−03 | 150.6 | 197.3 | 204.9 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 422 | 210146_PM_x_at | ULRB2 | leukocyte immunoglobulin-like receptor, subfamily B (with TM and ITIM domains), member | 5.75E−05 | 6.64E−03 | 992.0 | 1158.5 | 1393.3 |
| 423 | 236274_PM_at | EIF3B | eukaryotic translation initiation factor 3, subunit B | 5.76E−05 | 6.64E−03 | 30.4 | 24.7 | 22.7 |
| 424 | 232383_PM_at | TFEC | transcription factor EC | 5.79E−05 | 6.66E−03 | 49.6 | 132.2 | 94.3 |
| 425 | 235803_PM_at | — | — | 5.84E−05 | 6.70E−03 | 116.0 | 73.4 | 66.2 |
| 426 | 208238_PM_x_at | — | — | 5.86E−05 | 6.70E−03 | 589.1 | 460.7 | 496.6 |
| 427 | 1555057_PM_at | NDUFS4 | NADH dehydrogenase (ubiquinone) Fe—S protein 4, 18 kDa (NADH-coenzyme Q reductase) | 5.87E−05 | 6.70E−03 | 27.7 | 20.0 | 19.1 |
| 428 | 209188_PM_x_at | DR1 | down-regulator of transcription 1, TBP-binding (negative cofactor 2) | 5.88E−05 | 6.70E−03 | 157.9 | 207.6 | 214.8 |
| 429 | 1559020_PM_a_at | — | — | 5.92E−05 | 6.73E−03 | 60.4 | 39.6 | 38.3 |
| 430 | 212872_PM_s_at | MED20 | mediator complex subunit 20 | 5.95E−05 | 6.75E−03 | 65.5 | 89.8 | 88.9 |
| 431 | 234032_PM_at | — | — | 5.98E−05 | 6.76E−03 | 245.4 | 134.1 | 120.3 |
| 432 | 232516_PM_x_at | YY1AP1 | YY1 associated protein 1 | 6.02E−05 | 6.76E−03 | 277.0 | 206.7 | 227.8 |
| 433 | 218611_PM_at | IER5 | Immediate early response 5 | 6.02E−05 | 6.76E−03 | 384.0 | 516.5 | 548.6 |
| 434 | 242712_PM_x_at | RANBP2 /// RGPD1 /// RGPD2 /// RGPD3 /// RGPD4 /// RGPD5 /// RGPD6 /// RGPD8 | RAN binding protein 2 /// RANBP2-like and GRIP domain containing 1 /// RANBP2-like and | 6.02E−05 | 6.76E−03 | 92.4 | 52.4 | 61.2 |
| 435 | 229434_PM_at | — | — | 6.10E−05 | 6.81E−03 | 1281.8 | 990.5 | 982.0 |
| 436 | 236379_PM_at | — | — | 6.11E−05 | 6.81E−03 | 489.0 | 318.7 | 299.6 |
| 437 | 231495_PM_at | — | — | 6.12E−05 | 6.81E−03 | 261.0 | 163.0 | 135.0 |
| 438 | 232012_PM_at | CAPN1 | calpain 1, (mu/l) large subunit | 6.13E−05 | 6.81E−03 | 179.2 | 143.7 | 133.3 |
| 439 | 1558740_PM_s_at | — | — | 6.15E−05 | 6.81E−03 | 246.8 | 179.6 | 171.8 |
| 440 | 235837_PM_at | — | — | 6.17E−05 | 6.81E−03 | 97.7 | 76.6 | 73.6 |
| 441 | 201737_PM_s_at | 6-Mar | membrane-associated ring finger (C3HC4) 6 | 6.18E−05 | 6.81E−03 | 558.7 | 409.2 | 370.6 |
| 442 | 239561_PM_at | — | — | 6.20E−05 | 6.81E−03 | 143.1 | 75.4 | 80.9 |
| 443 | 243473_PM_at | — | — | 6.23E−05 | 6.81E−03 | 20.0 | 15.1 | 15.1 |
| 444 | 215887_PM_at | ZNF277 | zinc finger protein 277 | 6.24E−05 | 6.81E−03 | 144.3 | 101.2 | 106.6 |
| 445 | 241155_PM_at | — | — | 6.25E−05 | 6.81E−03 | 308.3 | 207.2 | 204.8 |
| 446 | 1563455_PM_at | SIK3 | SIK family kinase 3 | 6.27E−05 | 6.81E−03 | 133.1 | 86.6 | 90.7 |
| 447 | 243089_PM_at | — | — | 6.27E−05 | 6.81E−03 | 49.4 | 28.7 | 24.7 |
| 448 | 232726_PM_at | — | — | 6.27E−05 | 6.81E−03 | 185.5 | 77.8 | 84.3 |
| 449 | 238880_PM_at | GTF3A | general transcription factor IIIA | 6.28E−05 | 6.81E−03 | 471.0 | 322.6 | 305.2 |
| 450 | 216652_PM_s_at | DR1 | down-regulator of transcription 1, TBP-binding (negative cofactor 2) | 6.30E−05 | 6.82E−03 | 110.6 | 152.5 | 153.6 |
| 451 | 215605_PM_at | NCOA2 | Nuclear receptor coactivator 2 | 6.41E−05 | 6.92E−03 | 302.5 | 184.3 | 220.5 |
| 452 | 239383_PM_at | — | — | 6.47E−05 | 6.98E−03 | 95.2 | 62.9 | 54.6 |
| 453 | 230713_PM_at | — | — | 6.50E−05 | 6.99E−03 | 179.2 | 116.7 | 108.1 |
| 454 | 201300_PM_s_at | PRNP | prion protein | 6.53E−05 | 7.01E−03 | 327.7 | 516.1 | 538.4 |
| 455 | 232264_PM_at | — | — | 6.59E−05 | 7.06E−03 | 124.7 | 63.8 | 62.6 |
| 456 | 243759_PM_at | SFRS15 | Splicing factor, arginine/serine-rich 15 | 6.65E−05 | 7.11E−03 | 103.6 | 67.4 | 71.4 |
| 457 | 235493_PM_at | — | — | 6.72E−05 | 7.16E−03 | 97.5 | 67.3 | 66.6 |
| 458 | 1561346_PM_at | — | — | 6.73E−05 | 7.16E−03 | 126.0 | 89.3 | 97.7 |
| 459 | 234989_PM_at | — | — | 6.78E−05 | 7.19E−03 | 560.8 | 300.7 | 287.5 |
| 460 | 221616_PM_s_at | TAF9B | TAF9B RNA polymerase II, TATA box binding protein (TBP)-associated factor, 31 kDa | 6.87E−05 | 7.27E−03 | 241.5 | 162.4 | 168.8 |
| 461 | 1562062_PM_at | KIAA1245 /// N8PF1 /// NBPF10 /// NBPF11 /// | KIAA1245 /// neuroblastoma breakpoint family, member 1 /// neuroblastoma breakpoint | 6.93E−05 | 7.31E−03 | 345.4 | 232.4 | 266.6 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| | | NBPF12 /// NBPF24 /// NBPF8 /// NBPF9 | fam | | | | | |
| 462 | 202829_PM_s_at | VAMP7 | vesicle-associated membrane protein 7 | 6.93E−05 | 7.31E−03 | 563.9 | 752.2 | 674.2 |
| 463 | 1557830_PM_at | — | — | 7.06E−05 | 7.42E−03 | 48.1 | 33.4 | 29.9 |
| 464 | 200667_PM_at | UBE2D3 | ubiquitin-conjugating enzyme E2D 3 (UBC4/5 homolog, yeast) | 7.06E−05 | 7.42E−03 | 1057.4 | 1367.1 | 1384.4 |
| 465 | 221899_PM_at | N4BP2L2 | NEDD4 binding protein 2-like 2 | 7.10E−05 | 7.44E−03 | 4054.4 | 3196.6 | 3171.5 |
| 466 | 236934_PM_at | — | — | 7.13E−05 | 7.45E−03 | 143.5 | 63.2 | 56.1 |
| 467 | 1565762_PM_at | — | — | 7.21E−05 | 7.50E−03 | 59.0 | 40.2 | 33.8 |
| 468 | 222316_PM_at | — | — | 7.21E−05 | 7.50E−03 | 247.1 | 154.8 | 164.9 |
| 469 | 239811_PM_at | — | — | 7.26E−05 | 7.53E−03 | 1050.3 | 645.8 | 708.3 |
| 470 | 212326_PM_at | VPS13D | vacuolar protein sorting 13 homolog D (S. cerevisiae) | 7.26E−05 | 7.53E−03 | 30.4 | 23.0 | 23.6 |
| 471 | 228070_PM_at | PPP2R5E | protein phosphatase 2, regulatory subunit B', epsilon isoform | 7.29E−05 | 7.54E−03 | 365.2 | 286.1 | 275.0 |
| 472 | 1563080_PM_at | — | — | 7.33E−05 | 7.56E−03 | 21.3 | 16.7 | 15.5 |
| 473 | 1560082_PM_at | — | — | 7.41E−05 | 7.63E−03 | 39.8 | 29.5 | 27.4 |
| 474 | 224778_PM_s_at | — | — | 7.44E−05 | 7.65E−03 | 1054.6 | 845.9 | 906.9 |
| 475 | 240174_PM_at | — | — | 7.48E−05 | 7.66E−03 | 249.8 | 144.1 | 143.7 |
| 476 | 1566887_PM_x_at | — | — | 7.48E−05 | 7.66E−03 | 320.8 | 247.9 | 284.8 |
| 477 | 222104_PM_x_at | GTF2H3 | general transcription factor IIH, polypeptide 3, 34 kDa | 7.54E−05 | 7.70E−03 | 468.3 | 361.7 | 374.9 |
| 478 | 233427_PM_x_at | — | — | 7.58E−05 | 7.73E−03 | 278.5 | 218.3 | 236.5 |
| 479 | 241917_PM_at | — | — | 7.60E−05 | 7.74E−03 | 115.7 | 62.5 | 64.7 |
| 480 | 230392_PM_at | — | — | 7.63E−05 | 7.74E−03 | 119.3 | 80.5 | 83.5 |
| 481 | 242876_PM_at | AKT3 | V-akt murine thymoma viral oncogene homolog 3 (protein kinase B, gamma) | 7.74E−05 | 7.83E−03 | 29.6 | 19.3 | 18.5 |
| 482 | 217482_PM_at | — | — | 7.74E−05 | 7.83E−03 | 53.7 | 33.0 | 30.6 |
| 483 | 205647_PM_at | RAD52 | RAD52 homolog (S. cerevisiae) | 7.76E−05 | 7.83E−03 | 17.6 | 15.1 | 13.8 |
| 484 | 1570007_PM_at | LRRC8C | leucine rich repeat containing 8 family, member C | 7.80E−05 | 7.85E−03 | 21.6 | 15.4 | 16.5 |
| 485 | 230505_PM_at | LOC145474 | hypothetical LOC145474 | 7.81E−05 | 7.85E−03 | 302.3 | 137.3 | 148.1 |
| 486 | 232929_PM_at | — | — | 7.87E−05 | 7.89E−03 | 51.2 | 28.8 | 28.1 |
| 487 | 239868_PM_at | — | — | 7.91E−05 | 7.92E−03 | 21.5 | 14.5 | 14.5 |
| 488 | 236974_PM_at | — | — | 8.05E−05 | 8.04E−03 | 245.7 | 165.1 | 165.5 |
| 489 | 204342_PM_at | SLC25A24 | solute carrier family 25 (mitochondrial carrier; phosphate carrier), member 24 | 8.09E−05 | 8.06E−03 | 281.9 | 464.1 | 438.3 |
| 490 | 229574_PM_at | TRA2A | transformer 2 alpha homolog (Drosophila) | 8.10E−05 | 8.06E−03 | 850.9 | 620.8 | 645.7 |
| 491 | 228694_PM_at | — | — | 8.13E−05 | 8.07E−03 | 167.1 | 125.4 | 121.9 |
| 492 | 208082_PM_x_at | — | — | 8.15E−05 | 8.07E−03 | 716.5 | 587.4 | 601.3 |
| 493 | 235983_PM_at | — | — | 8.28E−05 | 8.18E−03 | 121.1 | 88.8 | 72.2 |
| 494 | 232169_PM_x_at | NDUFS8 | NADH dehydrogenase (ubiquinone) Fe—S protein 8, 23 kDa (NADH-coenzyme Q reductase) | 8.39E−05 | 8.28E−03 | 466.1 | 349.6 | 373.1 |
| 495 | 237290_PM_at | — | — | 8.52E−05 | 8.38E−03 | 10.1 | 10.3 | 12.5 |
| 496 | 244599_PM_at | — | — | 8.54E−05 | 8.39E−03 | 257.4 | 185.5 | 169.4 |
| 497 | 1557433_PM_at | — | — | 8.56E−05 | 8.39E−03 | 23.1 | 17.8 | 16.7 |
| 498 | 244433_PM_at | — | — | 8.59E−05 | 8.39E−03 | 752.7 | 478.2 | 540.7 |
| 499 | 242748_PM_at | SREBF2 | sterol regulatory element binding transcription factor 2 | 8.59E−05 | 8.39E−03 | 87.0 | 61.1 | 61.9 |
| 500 | 1563505_PM_at | DUSP16 | Dual specificity phosphatase 16 | 8.73E−05 | 8.51E−03 | 14.0 | 11.0 | 11.7 |
| 501 | 237987_PM_x_at | — | — | 8.76E−05 | 8.51E−03 | 8.4 | 8.8 | 9.8 |
| 502 | 239808_PM_at | — | — | 8.77E−05 | 8.51E−03 | 210.2 | 163.0 | 137.8 |
| 503 | 232584_PM_at | — | — | 8.82E−05 | 8.53E−03 | 21.4 | 13.1 | 11.9 |
| 504 | 243993_PM_at | — | — | 8.82E−05 | 8.53E−03 | 194.6 | 118.3 | 117.0 |
| 505 | 54051_PM_at | PKNOX1 | PBX/knotted 1 homeobox 1 | 8.84E−05 | 8.53E−03 | 39.4 | 30.4 | 30.7 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 506 | 225522_PM_at | AAK1 | AP2 associated kinase 1 | 8.97E−05 | 8.64E−03 | 223.6 | 176.1 | 151.7 |
| 507 | 222667_PM_s_at | ASH1L | ash1 (absent, small, or homeotic)-like (*Drosophila*) | 9.02E−05 | 8.67E−03 | 1637.7 | 1288.3 | 1282.8 |
| 508 | 202822_PM_at | LPP | LIM domain containing preferred translocation partner in lipoma | 9.05E−05 | 8.69E−03 | 371.8 | 281.4 | 299.5 |
| 509 | 242995_PM_at | — | — | 9.10E−05 | 8.70E−03 | 59.4 | 38.9 | 36.7 |
| 510 | 243512_PM_x_at | — | — | 9.11E−05 | 8.70E−03 | 36.0 | 22.1 | 22.0 |
| 511 | 243826_PM_at | — | — | 9.12E−05 | 8.70E−03 | 317.0 | 181.4 | 215.2 |
| 512 | 201443_PM_s_at | ATP6AP2 | ATPase, H+ transporting, lysosomal accessory protein 2 | 9.16E−05 | 8.72E−03 | 1784.1 | 2195.2 | 2170.5 |
| 513 | 243578_PM_at | — | — | 9.20E−05 | 8.73E−03 | 26.9 | 18.2 | 17.5 |
| 514 | 240971_PM_x_at | — | — | 9.21E−05 | 8.73E−03 | 215.1 | 144.4 | 139.0 |
| 515 | 238853_PM_at | RAB3IP | RAB3A interacting protein (rabin3) | 9.23E−05 | 8.73E−03 | 35.1 | 22.9 | 23.6 |
| 516 | 221829_PM_s_at | TNPO1 | transportin 1 | 9.28E−05 | 8.76E−03 | 1035.0 | 803.0 | 842.0 |
| 517 | 242529_PM_x_at | — | — | 9.30E−05 | 8.77E−03 | 34.6 | 23.5 | 22.3 |
| 518 | 239301_PM_at | — | — | 9.34E−05 | 8.78E−03 | 226.9 | 128.8 | 139.8 |
| 519 | 1570194_PM_x_at | — | — | 9.38E−05 | 8.81E−03 | 196.3 | 91.9 | 121.4 |
| 520 | 233867_PM_at | — | — | 9.49E−05 | 8.89E−03 | 863.1 | 555.6 | 564.0 |
| 521 | 242479_PM_s_at | — | — | 9.52E−05 | 8.90E−03 | 9.5 | 10.4 | 11.4 |
| 522 | 217679_PM_x_at | — | — | 9.54E−05 | 8.90E−03 | 680.8 | 483.9 | 513.8 |
| 523 | 1559142_PM_at | MYST3 | MYST histone acetyltransferase (monocytic leukemia) 3 | 9.60E−05 | 8.94E−03 | 25.5 | 19.8 | 21.0 |
| 524 | 209089_PM_at | RAB5A | RAB5A, member RAS oncogene family | 9.75E−05 | 9.06E−03 | 740.4 | 904.4 | 950.5 |
| 525 | 232372_PM_at | — | — | 9.84E−05 | 9.13E−03 | 23.3 | 17.3 | 17.1 |
| 526 | 218534_PM_s_at | AGGF1 | angiogenic factor with G patch and FHA domains 1 | 9.91E−05 | 9.18E−03 | 82.0 | 118.9 | 114.9 |
| 527 | 1559723_PM_s_at | — | — | 9.99E−05 | 9.20E−03 | 20.1 | 14.8 | 14.3 |
| 528 | 232784_PM_at | — | — | 0.000100001 | 0.00919631 | 68.2 | 51.7 | 46.1 |
| 529 | 242233_PM_at | — | — | 0.000100081 | 0.00919631 | 614.1 | 453.5 | 466.0 |
| 530 | 223662_PM_x_at | DDX59 | DEAD (Asp-Glu-Ala-Asp) box polypeptide 59 | 0.000100162 | 0.00919631 | 129.3 | 106.9 | 114.9 |
| 531 | 244865_PM_at | — | — | 0.000100377 | 0.00919631 | 24.8 | 19.1 | 19.7 |
| 532 | 242121_PM_at | NCRNA00182 | non-protein coding RNA 182 | 0.000100405 | 0.00919631 | 1332.1 | 853.7 | 927.4 |
| 533 | 202946_PM_s_at | BTBD3 | BTB (POZ) domain containing 3 | 0.000100622 | 0.00919889 | 26.6 | 42.1 | 44.6 |
| 534 | 244611_PM_at | MED13 | Mediator complex subunit 13 | 0.000102003 | 0.00928958 | 65.6 | 43.8 | 38.7 |
| 535 | 205992_PM_s_at | IL15 | Interleukin 15 | 0.000102174 | 0.00928958 | 177.2 | 292.0 | 335.6 |
| 536 | 242889_PM_x_at | LOC645431 | hypothetical LOC645431 | 0.000102186 | 0.00928958 | 170.7 | 141.4 | 145.9 |
| 537 | 243030_PM_at | — | — | 0.000102974 | 0.00933895 | 384.8 | 242.9 | 256.3 |
| 538 | 242482_PM_at | PRKAR1A | protein kinase, cAMP-dependent, regulatory, type 1, alpha (tissue specific extinguisher | 0.000103274 | 0.00933895 | 131.2 | 79.8 | 90.5 |
| 539 | 220085_PM_at | HELLS | helicase, lymphoid-specific | 0.000103304 | 0.00933895 | 18.5 | 15.4 | 12.7 |
| 540 | 219017_PM_at | ETNK1 | ethanolamine kinase 1 | 0.000103707 | 0.00935802 | 52.2 | 83.1 | 91.3 |
| 541 | 240665_PM_at | — | — | 0.000104299 | 0.0093768 | 1121.4 | 732.2 | 726.7 |
| 542 | 230097_PM_at | — | — | 0.0001043 | 0.0093768 | 96.4 | 68.6 | 58.9 |
| 543 | 237868_PM_x_at | — | — | 0.000104648 | 0.00939076 | 167.5 | 123.1 | 138.3 |
| 544 | 201298_PM_s_at | MOBKL1B | MOB1, Mps One Binder kinase activator-like 1B (yeast) | 0.000105824 | 0.00947713 | 1271.1 | 1594.6 | 1649.3 |
| 545 | 236931_PM_at | — | — | 0.000106187 | 0.00947713 | 145.2 | 76.8 | 65.6 |
| 546 | 222230_PM_s_at | ACTR10 | actin-related protein 10 homolog (*S. cerevisiae*) | 0.000106194 | 0.00947713 | 641.3 | 778.2 | 745.3 |
| 547 | 217662_PM_x_at | — | — | 0.000106587 | 0.00947997 | 49.5 | 41.1 | 43.3 |
| 548 | 224787_PM_s_at | RAB18 | RAB18, member RAS oncogene family | 0.000106745 | 0.00947997 | 233.3 | 359.4 | 359.2 |
| 549 | 240019_PM_at | — | — | 0.000106882 | 0.00947997 | 653.3 | 366.6 | 385.3 |
| 550 | 204771_PM_s_at | TTF1 | transcription termination factor, RNA polymerase I | 0.000107004 | 0.00947997 | 468.3 | 364.4 | 376.0 |
| 551 | 238875_PM_at | — | — | 0.000109875 | 0.00971666 | 159.5 | 114.3 | 108.4 |
| 552 | 213574_PM_s_at | — | — | 0.000110256 | 0.00973269 | 1540.5 | 1142.7 | 1168.0 |
| 553 | 1558237_PM_x_at | — | — | 0.000112606 | 0.00990882 | 275.2 | 205.9 | 217.7 |
| 554 | 244771_PM_at | KBTBD12 | kelch repeat and BTB (POZ) domain containing 12 | 0.000112658 | 0.00990882 | 11.0 | 9.1 | 10.2 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 555 | 239049_PM_at | — | — | 0.000113136 | 0.00992062 | 357.9 | 233.0 | 253.1 |
| 556 | 215191_PM_at | — | — | 0.000113298 | 0.00992062 | 300.6 | 196.1 | 185.8 |
| 557 | 226651_PM_at | HOMER1 | homer homolog 1 (Drosophila) | 0.000113403 | 0.00992062 | 63.4 | 42.8 | 43.1 |
| 558 | 215383_PM_x_at | SPG21 | spastic paraplegia 21 (autosomal recessive, Mast syndrome) | 0.000114806 | 0.0100254 | 666.6 | 540.4 | 568.6 |
| 559 | 227435_PM_at | KIAA2018 | KIAA2018 | 0.000115657 | 0.0100816 | 501.0 | 352.7 | 394.7 |
| 560 | 205104_PM_at | SNPH | syntaphilin | 0.000117244 | 0.0102017 | 21.9 | 17.7 | 17.0 |
| 561 | 1558569_PM_at | LOC100131541 | Hypothetical LOC100131541 | 0.00011856 | 0.0102806 | 104.4 | 51.7 | 55.9 |
| 562 | 243404_PM_at | — | — | 0.00011868 | 0.0102806 | 198.4 | 140.6 | 145.0 |
| 563 | 220467_PM_at | — | — | 0.000118879 | 0.0102806 | 205.4 | 130.1 | 107.4 |
| 564 | 211509_PM_s_at | RTN4 | reticulon 4 | 0.000119113 | 0.0102806 | 1430.3 | 1755.3 | 1868.7 |
| 565 | 204715_PM_at | PANX1 | pannexin 1 | 0.000119206 | 0.0102806 | 16.5 | 22.6 | 21.9 |
| 566 | 235847_PM_at | — | — | 0.000120325 | 0.0103588 | 329.6 | 175.4 | 160.4 |
| 567 | 239600_PM_at | — | — | 0.000120761 | 0.010378 | 281.8 | 144.6 | 145.5 |
| 568 | 244457_PM_at | — | — | 0.000121998 | 0.0104658 | 241.3 | 153.0 | 150.3 |
| 569 | 226140_PM_s_at | OTUD1 | OTU domain containing 1 | 0.00012251 | 0.0104913 | 407.3 | 538.5 | 585.7 |
| 570 | 227576_PM_at | — | — | 0.000123208 | 0.0105326 | 377.0 | 214.1 | 192.3 |
| 571 | 242739_PM_at | — | — | 0.000123432 | 0.0105332 | 41.3 | 28.0 | 24.7 |
| 572 | 244625_PM_at | — | — | 0.000123749 | 0.0105418 | 39.7 | 22.7 | 23.5 |
| 573 | 228415_PM_at | AP1S2 | adaptor-related protein complex 1, sigma 2 subunit | 0.000125275 | 0.0106532 | 141.1 | 213.5 | 223.3 |
| 574 | 214902_PM_x_at | — | — | 0.000126202 | 0.0106943 | 470.2 | 356.8 | 390.5 |
| 575 | 241460_PM_at | — | — | 0.000126341 | 0.0106943 | 423.2 | 274.7 | 295.1 |
| 576 | 1564733_PM_at | — | — | 0.000126417 | 0.0106943 | 137.6 | 93.8 | 92.7 |
| 577 | 235959_PM_at | — | — | 0.000126652 | 0.0106956 | 309.3 | 200.7 | 227.3 |
| 578 | 1556420_PM_s_at | YPEL2 | yippee-like 2 (Drosophila) | 0.000127836 | 0.0107739 | 110.9 | 77.0 | 79.7 |
| 579 | 243450_PM_at | — | — | 0.000128021 | 0.0107739 | 51.7 | 31.2 | 30.3 |
| 580 | 234048_PM_s_at | KIAA1632 | KIAA1632 | 0.000128316 | 0.0107801 | 12.9 | 10.6 | 11.7 |
| 581 | 201057_PM_s_at | GOLGB1 | golgin B1 | 0.000129333 | 0.0108468 | 196.9 | 149.2 | 148.0 |
| 582 | 242827_PM_x_at | — | — | 0.000130436 | 0.0109205 | 345.7 | 226.7 | 192.8 |
| 583 | 230607_PM_at | — | — | 0.000131409 | 0.0109798 | 29.9 | 22.3 | 18.8 |
| 584 | 218379_PM_at | RBM7 | RNA binding motif protein 7 | 0.000131656 | 0.0109798 | 249.9 | 336.2 | 329.5 |
| 585 | 241930_PM_x_at | — | — | 0.00013191 | 0.0109798 | 27.0 | 20.7 | 20.0 |
| 586 | 235804_PM_at | — | — | 0.000132077 | 0.0109798 | 42.3 | 33.0 | 28.3 |
| 587 | 241688_PM_at | — | — | 0.000132271 | 0.0109798 | 32.0 | 21.7 | 22.8 |
| 588 | 230970_PM_at | — | — | 0.000133316 | 0.0110392 | 1228.2 | 700.6 | 742.7 |
| 589 | 235613_PM_at | — | — | 0.000133562 | 0.0110392 | 113.6 | 77.4 | 73.3 |
| 590 | 214990_PM_at | PIGO | phosphatidylinositol glycan anchor biosynthesis, class O | 0.000133666 | 0.0110392 | 11.9 | 9.6 | 10.3 |
| 591 | 242349_PM_at | HECTD1 | HECT domain containing 1 | 0.000134359 | 0.0110777 | 95.2 | 68.2 | 67.4 |
| 592 | 225204_PM_at | PPTC7 | PTC7 protein phosphatase homolog (S. cerevisiae) | 0.000134942 | 0.011107 | 790.6 | 552.0 | 605.7 |
| 593 | 235660_PM_at | — | — | 0.000136056 | 0.0111798 | 130.3 | 89.4 | 97.7 |
| 594 | 216682_PM_s_at | FAM48A | Family with sequence similarity 48, member A | 0.000136461 | 0.0111942 | 232.3 | 149.8 | 165.4 |
| 595 | 1556373_PM_a_at | — | — | 0.000136827 | 0.0112053 | 321.3 | 172.5 | 180.8 |
| 596 | 1556352_PM_at | — | — | 0.000137503 | 0.0112418 | 256.9 | 139.8 | 138.1 |
| 597 | 239655_PM_at | — | — | 0.00013785 | 0.0112513 | 110.5 | 74.2 | 73.5 |
| 598 | 240600_PM_at | — | — | 0.000138859 | 0.0113048 | 324.9 | 212.7 | 211.5 |
| 599 | 1556462_PM_a_at | — | — | 0.00013897 | 0.0113048 | 99.4 | 61.8 | 42.5 |
| 600 | 1556323_PM_at | CELF2 | CUGBP, Elav-like family member 2 | 0.000139628 | 0.0113223 | 1100.4 | 748.0 | 757.0 |
| 601 | 225207_PM_at | PDK4 | pyruvate dehydrogenase kinase, isozyme 4 | 0.00013965 | 0.0113223 | 85.6 | 214.9 | 192.3 |
| 602 | 235811_PM_at | — | — | 0.000140131 | 0.0113425 | 802.0 | 498.5 | 381.6 |
| 603 | 226952_PM_at | EAF1 | ELL associated factor 1 | 0.000141842 | 0.0114619 | 129.3 | 158.6 | 157.6 |
| 604 | 202484_PM_s_at | MBD2 | methyl-CpG binding domain protein 2 | 0.000144855 | 0.011686 | 799.5 | 984.4 | 1005.3 |
| 605 | 217803_PM_at | GOLPH3 | golgi phosphoprotein 3 (coat-protein) | 0.000146215 | 0.0117762 | 690.0 | 818.8 | 813.0 |
| 606 | 213624_PM_at | SMPDL3A | sphingomyelin phosphodiesterase, acid-like 3A | 0.000147195 | 0.0118356 | 113.5 | 213.6 | 238.0 |
| 607 | 229528_PM_at | SBNO1 | strawberry notch homolog 1 (Drosophila) | 0.000148186 | 0.0118956 | 177.6 | 129.9 | 124.2 |
| 603 | 230669_PM_at | RASA2 | RAS p21 protein activator 2 | 0.00014871 | 0.0119178 | 1010.8 | 776.3 | 762.2 |
| 609 | 242369_PM_x_at | — | — | 0.000148951 | 0.0119173 | 234.7 | 155.9 | 163.8 |
| 610 | 239978_PM_at | — | — | 0.000149912 | 0.011975 | 185.5 | 145.0 | 134.1 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 611 | 235841_PM_at | — | — | 0.000150894 | 0.0119968 | 182.1 | 93.8 | 106.3 |
| 612 | 229457_PM_at | ANKHD1 | ankyrin repeat and KH domain containing 1 | 0.000150905 | 0.0119968 | 94.5 | 65.6 | 61.7 |
| 613 | 240997_PM_at | — | — | 0.000150923 | 0.0119968 | 25.9 | 20.3 | 22.3 |
| 614 | 1554595_PM_at | SYMPK | symplekin | 0.000151416 | 0.0120164 | 157.9 | 108.3 | 107.0 |
| 615 | 201097_PM_s_at | ARF4 | ADP-ribosylation factor 4 | 0.000151957 | 0.0120262 | 1063.5 | 1248.9 | 1279.6 |
| 616 | 233319_PM_x_at | — | — | 0.000152034 | 0.0120262 | 23.2 | 18.3 | 19.5 |
| 617 | 232834_PM_at | — | — | 0.000153247 | 0.0121025 | 84.1 | 52.9 | 40.6 |
| 618 | 225236_PM_at | RDM18 | RNA binding motif protein 18 | 0.000153692 | 0.0121151 | 104.6 | 142.4 | 140.8 |
| 619 | 239285_PM_at | — | — | 0.000154204 | 0.0121151 | 260.6 | 184.2 | 159.7 |
| 620 | 239409_PM_at | — | — | 0.000154229 | 0.0121151 | 694.8 | 433.8 | 443.4 |
| 621 | 213860_PM_x_at | CSNK1A1 | casein kinase 1, alpha 1 | 0.000154641 | 0.0121151 | 679.8 | 796.3 | 765.4 |
| 622 | 215600_PM_x_at | FBXW12 | F-box and WD repeat domain containing 12 | 0.000154649 | 0.0121151 | 449.4 | 342.1 | 375.4 |
| 623 | 234043_PM_at | — | — | 0.000155523 | 0.012164 | 16.1 | 11.7 | 11.8 |
| 624 | 238214_PM_at | LRRC69 | leucine rich repeat containing 69 | 0.000157072 | 0.0122546 | 85.9 | 62.5 | 59.4 |
| 625 | 243170_PM_at | — | — | 0.000157184 | 0.0122546 | 869.6 | 505.9 | 573.4 |
| 626 | 241906_PM_at | — | — | 0.000158212 | 0.012315 | 315.8 | 182.8 | 218.3 |
| 627 | 217713_PM_x_at | — | — | 0.000159055 | 0.0123617 | 132.7 | 106.6 | 120.4 |
| 628 | 213404_PM_s_at | RHEB | Ras homolog enriched in brain | 0.000159625 | 0.0123757 | 216.5 | 277.0 | 267.3 |
| 629 | 1563130_PM_a_at | — | — | 0.000159754 | 0.0123757 | 129.8 | 89.9 | 95.1 |
| 630 | 213936_PM_x_at | SFTPB | surfactant protein B | 0.00016064 | 0.0124057 | 69.3 | 56.9 | 57.5 |
| 631 | 222380_PM_s_at | PDCD6 | Programmed cell death 6 | 0.00016065 | 0.0124057 | 244.5 | 160.8 | 166.0 |
| 632 | 222313_PM_at | — | — | 0.00016161 | 0.0124269 | 284.8 | 214.1 | 218.2 |
| 633 | 232420_PM_x_at | LOC100289341 | Similar to hCG2022304 | 0.000162106 | 0.012472 | 86.6 | 68.9 | 77.8 |
| 634 | 225041_PM_at | MPHOSPH8 | M-phase phosphoprotein 8 | 0.000162277 | 0.012472 | 826.1 | 647.9 | 621.4 |
| 635 | 243559_PM_at | — | — | 0.000163991 | 0.0125745 | 23.6 | 16.6 | 16.1 |
| 636 | 201218_PM_at | CTBP2 | C-terminal binding protein 2 | 0.000164126 | 0.0125745 | 475.6 | 589.0 | 644.6 |
| 637 | 244292_PM_at | — | — | 0.000164428 | 0.0125778 | 107.0 | 69.3 | 60.4 |
| 638 | 232874_PM_at | DOCK9 | dedicator of cytokinesis 9 | 0.00016535 | 0.0126285 | 31.3 | 19.1 | 15.3 |
| 639 | 1565886_PM_at | — | — | 0.000165997 | 0.0126581 | 151.6 | 99.6 | 94.8 |
| 640 | 208873_PM_s_at | REEP5 | receptor accessory protein 5 | 0.000166895 | 0.0127067 | 449.8 | 656.5 | 674.1 |
| 641 | 242077_PM_x_at | C6orf150 | chromosome 6 open reading frame 150 | 0.000167363 | 0.0127225 | 1009.1 | 819.5 | 869.4 |
| 642 | 214722_PM_at | NOTCH2NL | notch 2 N-terminal like | 0.000168102 | 0.0127587 | 1850.6 | 1351.5 | 1425.5 |
| 643 | 1558014_PM_s_at | FAR1 | fatty acyl CoA reductase 1 | 0.000169744 | 0.0128455 | 41.8 | 79.3 | 73.2 |
| 644 | 1563204_PM_at | ZNF627 | Zinc finger protein 627 | 0.000169773 | 0.0128455 | 10.5 | 10.6 | 12.2 |
| 645 | 204181_PM_s_at | ZBTB43 | zinc finger and BTB domain containing 43 | 0.000170738 | 0.0128985 | 146.3 | 112.8 | 105.2 |
| 646 | 241491_PM_at | — | — | 0.000171717 | 0.0129524 | 25.9 | 18.5 | 18.7 |
| 647 | 206965_PM_at | KLF12 | Kruppel-like factor 12 | 0.000173042 | 0.0130322 | 72.3 | 46.6 | 37.1 |
| 648 | 1562364_PM_at | GVIN1 | GTPase, very large interferon inducible 1 | 0.000174604 | 0.0131295 | 43.6 | 29.8 | 27.8 |
| 649 | 217810_PM_x_at | LARS | leucyl-tRNA synthetase | 0.000175517 | 0.013168 | 324.3 | 259.5 | 248.2 |
| 650 | 225890_PM_at | C20orf72 | chromosome 20 open reading frame 72 | 0.000175656 | 0.013168 | 191.3 | 269.4 | 253.2 |
| 651 | 241041_PM_at | — | — | 0.000176027 | 0.0131755 | 168.1 | 70.3 | 79.7 |
| 652 | 226261_PM_at | ZNRF2 | zinc and ring finger 2 | 0.000176915 | 0.0132217 | 34.7 | 48.9 | 49.9 |
| 653 | 240134_PM_at | — | — | 0.000177936 | 0.0132776 | 145.1 | 82.6 | 89.0 |
| 654 | 213593_PM_s_at | TRA2A | transformer 2 alpha homolog (Drosophila) | 0.000178805 | 0.0133221 | 1349.1 | 958.0 | 977.3 |
| 655 | 244845_PM_at | — | — | 0.000179762 | 0.0133567 | 283.3 | 150.4 | 159.3 |
| 656 | 236558_PM_at | — | — | 0.000179818 | 0.0133567 | 168.5 | 97.3 | 92.2 |
| 657 | 239387_PM_at | — | — | 0.000180312 | 0.013373 | 89.7 | 59.2 | 68.7 |
| 658 | 215378_PM_at | — | — | 0.000181169 | 0.0134161 | 79.3 | 46.5 | 53.2 |
| 659 | 204516_PM_at | ATXN7 | ataxin 7 | 0.000181726 | 0.013437 | 948.0 | 736.1 | 700.4 |
| 660 | 242037_PM_at | — | — | 0.000183073 | 0.0135161 | 153.1 | 102.2 | 105.5 |
| 661 | 1557707_PM_at | — | — | 0.00018375 | 0.0135455 | 71.2 | 54.3 | 543 |
| 662 | 241065_PM_x_at | CMAS | Cytidine monophosphate N-acetylneuraminic acid synthetase | 0.000187162 | 0.0137205 | 146.0 | 117.7 | 124.7 |
| 663 | 1557814_PM_a_at | — | — | 0.00018742 | 0.0137205 | 153.0 | 95.7 | 119.2 |
| 664 | 1559249_PM_at | ATXN1 | ataxin 1 | 0.000187463 | 0.0137205 | 135.3 | 79.7 | 78.1 |
| 665 | 236474_PM_at | — | — | 0.000187832 | 0.0137205 | 39.1 | 26.0 | 26.2 |
| 666 | 234762_PM_x_at | NLN | neurolysin (metallopeptidase M3 family) | 0.000187929 | 0.0137205 | 416.0 | 322.3 | 333.7 |
| 667 | 215529_PM_x_at | DIP2A | DIP2 disco-interacting protein 2 homolog A (Drosophila) | 0.00018854 | 0.0137205 | 359.6 | 290.1 | 291.0 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 668 | 208648_PM_at | VCP | valosin-containing protein | 0.000188635 | 0.0137205 | 264.7 | 194.0 | 192.4 |
| 669 | 225612_PM_s_at | B3GNT5 | UDP-GlcNAc:betaGal beta-1,3-N-acetylglucosaminyltransferase 5 | 0.00018864 | 0.0137205 | 155.2 | 206.5 | 290.7 |
| 670 | 234758_PM_at | — | — | 0.000188803 | 0.0137205 | 15.8 | 12.4 | 12.3 |
| 671 | 208857_PM_s_at | PCMT1 | protein-L-isoaspartate (D-aspartate) O-methyltransferase | 0.000188939 | 0.0137205 | 532.7 | 785.1 | 766.5 |
| 672 | 241438_PM_at | — | — | 0.000189877 | 0.0137681 | 43.6 | 28.5 | 27.2 |
| 673 | 1558233_PM_s_at | ATF1 | activating transcription factor 1 | 0.000192141 | 0.0139007 | 47.1 | 78.5 | 73.9 |
| 674 | 240168_PM_at | XPO7 | exportin 7 | 0.000192277 | 0.0139007 | 27.1 | 19.5 | 19.1 |
| 675 | 208662_PM_s_at | TTC3 | tetratricopeptide repeat domain 3 | 0.000192568 | 0.0139011 | 470.2 | 354.0 | 311.1 |
| 676 | 230629_PM_s_at | EP400 | E1A binding protein p400 | 0.000192856 | 0.0139013 | 77.5 | 54.0 | 43.4 |
| 677 | 244610_PM_x_at | — | — | 0.000194955 | 0.013997 | 26.9 | 18.4 | 18.8 |
| 678 | 229429_PM_x_at | LOC728855 | hypothetical LOC728855 | 0.000195003 | 0.013997 | 1167.6 | 986.3 | 930.5 |
| 679 | 236829_PM_at | — | — | 0.000195045 | 0.013997 | 199.0 | 138.3 | 143.6 |
| 680 | 222326_PM_at | — | — | 0.000196028 | 0.0140277 | 706.2 | 438.5 | 470.9 |
| 681 | 1556442_PM_x_at | — | — | 0.000196049 | 0.0140277 | 333.7 | 272.2 | 283.4 |
| 682 | 1569477_PM_at | — | — | 0.000197297 | 0.0140963 | 120.8 | 59.0 | 58.9 |
| 683 | 244046_PM_at | URGCP | upregulator of cell proliferation | 0.000198236 | 0.0141427 | 108.0 | 76.3 | 66.7 |
| 684 | 1567044_PM_s_at | — | — | 0.000198703 | 0.0141553 | 209.9 | 146.6 | 159.4 |
| 685 | 1566491_PM_at | — | — | 0.000199875 | 0.014191 | 11.5 | 9.4 | 9.6 |
| 686 | 1559097_PM_at | C14orf64 | chromosome 14 open reading frame 64 | 0.000199963 | 0.014191 | 61.3 | 42.7 | 25.5 |
| 687 | 1565079_PM_at | RPS16P5 | ribosomal protein S16 pseudogene 5 | 0.000200078 | 0.014191 | 705.1 | 416.1 | 477.2 |
| 688 | 202710_PM_at | BET1 | blocked early in transport 1 homolog (S. cerevisiae) | 0.000201418 | 0.0142653 | 91.6 | 140.3 | 137.2 |
| 689 | 220071_PM_x_at | HAUS2 | HAUS augmin-like complex, subunit 2 | 0.000201879 | 0.0142772 | 262.4 | 219.6 | 221.5 |
| 690 | 239274_PM_at | — | — | 0.000203017 | 0.0143368 | 600.6 | 310.5 | 341.3 |
| 691 | 231927_PM_at | ATF6 | activating transcription factor 6 | 0.000205596 | 0.0144979 | 192.0 | 140.0 | 146.2 |
| 692 | 242361_PM_at | IMMT | Inner membrane protein, mitochondrial (mitofilin) | 0.000209917 | 0.0147813 | 29.0 | 23.7 | 21.6 |
| 693 | 236368_PM_at | KIAA0368 | KIAA0368 | 0.000210329 | 0.0147889 | 93.7 | 59.9 | 62.1 |
| 694 | 241737_PM_x_at | — | — | 0.000211224 | 0.0148304 | 50.3 | 35.9 | 33.5 |
| 695 | 235213_PM_at | ITPKB | Inositol 1,4,5-trisphosphate 3-kinase B | 0.000212538 | 0.0149012 | 224.7 | 157.1 | 139.1 |
| 696 | 1562280_PM_at | — | — | 0.000213758 | 0.0149652 | 43.1 | 26.7 | 27.3 |
| 697 | 236715_PM_x_at | UACA | uveal autoantigen with coiled-coil domains and ankyrin repeats | 0.000214698 | 0.0150095 | 311.8 | 251.4 | 282.5 |
| 698 | 242558_PM_at | — | — | 0.000215749 | 0.0150613 | 620.4 | 465.6 | 453.1 |
| 699 | 225957_PM_at | C5orf41 | chromosome 5 open reading frame 41 | 0.000216336 | 0.0150799 | 2095.9 | 1538.8 | 1569.1 |
| 700 | 242494_PM_at | — | — | 0.000216773 | 0.0150799 | 28.0 | 18.8 | 19.4 |
| 701 | 1557238_PM_s_at | — | — | 0.000216944 | 0.0150799 | 59.0 | 41.6 | 41.6 |
| 702 | 200969_PM_at | SERP1 | stress-associated endoplasmic reticulum protein 1 | 0.000217306 | 0.0150836 | 236.0 | 362.5 | 361.3 |
| 703 | 234033_PM_at | — | — | 0.000218357 | 0.015135 | 201.4 | 97.1 | 111.1 |
| 704 | 1556567_PM_at | NAP1L4 | nucleosome assembly protein 1-like 4 | 0.000218709 | 0.0151378 | 137.9 | 111.7 | 109.3 |
| 705 | 244332_PM_at | — | — | 0.000219503 | 0.0151712 | 21.9 | 15.0 | 17.2 |
| 706 | 201297_PM_s_at | MOBKL1B | MOB1, Mps One Binder kinase activator-like 1B (yeast) | 0.000220874 | 0.0152444 | 361.7 | 467.5 | 482.8 |
| 707 | 202511_PM_s_at | ATG5 | ATG5 autophagy related 5 homolog (S. cerevisiae) | 0.000221384 | 0.015258 | 92.5 | 138.8 | 132.5 |
| 708 | 240759_PM_at | — | — | 0.000223975 | 0.0154147 | 245.6 | 150.7 | 144.4 |
| 709 | 200970_PM_s_at | SERP1 | stress-associated endoplasmic reticulum protein 1 | 0.000225987 | 0.0155094 | 473.6 | 677.3 | 597.2 |
| 710 | 1559687_PM_at | TMEM221 | transmembrane protein 221 | 0.000225987 | 0.0155094 | 14.4 | 13.0 | 15.1 |
| 711 | 210124_PM_x_at | SEMA4F | sema domain, immunoglobulin domain (Ig), transmembrane domain (TM) and short cytoplasmi | 0.000227139 | 0.0155665 | 18.3 | 14.7 | 15.1 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 712 | 202838_PM_at | FUCA1 | fucosidase, alpha-L-1, tissue | 0.000227972 | 0.0156017 | 335.3 | 478.9 | 509.8 |
| 713 | 222697_PM_s_at | ABHD10 | abhydrolase domain containing 10 | 0.000228563 | 0.0156202 | 33.7 | 51.1 | 50.2 |
| 714 | 215067_PM_x_at | PRDX2 | peroxiredoxin 2 | 0.000229843 | 0.0156857 | 222.6 | 180.4 | 172.9 |
| 715 | 232030_PM_at | KIAA1632 | KIAA1632 | 0.000231505 | 0.0157696 | 146.0 | 87.0 | 88.2 |
| 716 | 1556818_PM_at | — | — | 0.000231721 | 0.0157696 | 256.0 | 175.5 | 169.8 |
| 717 | 213684_PM_s_at | PDLIM5 | PDZ and LIM domain 5 | 0.000233554 | 0.0158667 | 45.4 | 33.0 | 33.3 |
| 718 | 229268_PM_at | FAM105B | family with sequence similarity 105, member B | 0.000233799 | 0.0158667 | 109.1 | 80.0 | 85.0 |
| 719 | 241223_PM_x_at | — | — | 0.000239453 | 0.0162279 | 97.7 | 75.5 | 83.4 |
| 720 | 1560259_PM_at | — | — | 0.000240266 | 0.0162603 | 82.2 | 53.8 | 40.2 |
| 721 | 213473_PM_at | BRAP | BRCA1 associated protein | 0.000241741 | 0.0163375 | 474.0 | 404.6 | 393.7 |
| 722 | 221626_PM_at | ZNF506 | zinc finger protein 506 | 0.000242376 | 0.0163577 | 65.0 | 46.8 | 47.9 |
| 723 | 233834_PM_at | — | — | 0.000243203 | 0.0164403 | 126.5 | 70.0 | 73.5 |
| 724 | 206792_PM_x_at | PDE4C | phosphodiesterase 4C, cAMP-specific | 0.000245343 | 0.0165122 | 484.6 | 390.8 | 415.9 |
| 725 | 241751_PM_at | OFD1 | oral-facial-digital syndrome 1 | 0.000246523 | 0.0165687 | 213.3 | 134.2 | 138.4 |
| 726 | 219695_PM_at | SMPD3 | sphingomyelin phosphodiesterase 3, neutral membrane (neutral sphingomyelinase II) | 0.000249284 | 0.0167312 | 13.0 | 12.0 | 17.6 |
| 727 | 232215_PM_x_at | PRR11 | proline rich 11 | 0.00025089 | 0.0167955 | 560.9 | 438.6 | 461.7 |
| 728 | 1569484_PM_S_at | MDN1 | MDN1, midasin homolog (yeast) | 0.000250931 | 0.0167955 | 19.2 | 12.8 | 12.9 |
| 729 | 243303_PM_at | — | — | 0.000253404 | 0.0169377 | 255.0 | 170.9 | 182.6 |
| 730 | 225697_PM_at | CDK12 | cyclin-dependent kinase 12 | 0.000253787 | 0.0169401 | 256.4 | 204.5 | 211.2 |
| 731 | 1568702_PM_a_at | PAAF1 | proteasomal ATPase-associated factor 1 | 0.00025533 | 0.0170198 | 20.3 | 15.9 | 15.6 |
| 732 | 225435_PM_at | SSR1 | signal sequence receptor, alpha | 0.000255878 | 0.017033 | 234.7 | 159.6 | 143.3 |
| 733 | 220969_PM_s_at | — | — | 0.00025792 | 0.0171455 | 84.5 | 55.9 | 53.7 |
| 734 | 232909_PM_s_at | BPTF | bromodomain PHD finger transcription factor | 0.000260807 | 0.0173036 | 394.0 | 315.2 | 313.4 |
| 735 | 230415_PM_at | — | — | 0.000261008 | 0.0173036 | 227.1 | 144.1 | 134.3 |
| 736 | 241724_PM_x_at | — | — | 0.000264391 | 0.017504 | 30.4 | 25.9 | 27.5 |
| 737 | 244061_PM_at | — | — | 0.000265286 | 0.0175395 | 1448.2 | 941.9 | 1025.5 |
| 738 | 239496_PM_at | — | — | 0.000268384 | 0.0177203 | 66.1 | 49.8 | 47.6 |
| 739 | 240367_PM_at | — | — | 0.000271372 | 0.0178933 | 18.6 | 15.2 | 14.7 |
| 740 | 240969_PM_at | — | — | 0.000272419 | 0.0179381 | 22.1 | 16.6 | 16.0 |
| 741 | 244539_PM_at | — | — | 0.000278311 | 0.0183013 | 256.0 | 173.7 | 154.7 |
| 742 | 1565913_PM_at | — | — | 0.00028053 | 0.0184224 | 116.1 | 60.3 | 69.1 |
| 743 | 239545_PM_at | — | — | 0.000281028 | 0.0184302 | 157.3 | 109.5 | 102.4 |
| 744 | 228590_PM_at | PTCD3 | Pentatricopeptide repeat domain 3 | 0.000281682 | 0.0184332 | 167.3 | 129.6 | 109.1 |
| 745 | 204038_PM_s_at | LPAR1 | lysophosphatidic acid receptor 1 | 0.000282319 | 0.0184332 | 11.6 | 13.0 | 16.0 |
| 746 | 242146_PM_at | SNRPA1 | Small nuclear ribonucleoprotein polypeptide A' | 0.000282356 | 0.0184332 | 134.4 | 91.6 | 84.9 |
| 747 | 207654_PM_x_at | DR1 | down-regulator of transcription 1, TBP-binding (negative cofactor 2) | 0.000282587 | 0.0184332 | 153.3 | 207.5 | 204.0 |
| 748 | 213254_PM_at | TNRC6B | trinucleotide repeat containing 6B | 0.000285688 | 0.0185887 | 278.5 | 214.6 | 213.3 |
| 749 | 1568867_PM_x_at | — | — | 0.000286168 | 0.0185887 | 11.3 | 9.4 | 9.1 |
| 750 | 240315_PM_at | — | — | 0.000286463 | 0.0185887 | 67.1 | 48.5 | 44.3 |
| 751 | 224740_PM_at | C5orf43 | chromosome 5 open reading frame 43 | 0.000286497 | 0.0185687 | 114.1 | 197.5 | 163.1 |
| 752 | 235340_PM_at | GANC | glucosidase, alpha; neutral C | 0.00028733 | 0.0185987 | 9.4 | 8.1 | 9.3 |
| 753 | 226432_PM_at | ETNK1 | ethanolamine kinase 1 | 0.000287446 | 0.0185987 | 58.4 | 111.9 | 97.8 |
| 754 | 236462_PM_at | — | — | 0.000287796 | 0.0185987 | 45.8 | 32.3 | 31.5 |
| 755 | 232396_PM_at | — | — | 0.000288551 | 0.0186228 | 611.0 | 404.4 | 427.0 |
| 756 | 208185_PM_x_at | — | — | 0.000288946 | 0.0186236 | 24.9 | 19.3 | 20.3 |
| 757 | 241786_PM_at | — | — | 0.000290529 | 0.0187009 | 332.1 | 222.1 | 256.0 |
| 758 | 208286_PM_x_at | POU5F1 /// POU5F1B /// POU5F1P3 /// POU5F1P4 | POU class 5 homeobox 1 /// POU class 5 homeobox 1B /// POU class 5 homeobox 1 pseudogen | 0.000294645 | 0.0188949 | 34.0 | 27.1 | 27.8 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 759 | 238350_PM_at | UBN2 | ubinuclein 2 | 0.000294683 | 0.0188949 | 159.5 | 129.5 | 127.9 |
| 760 | 239451_PM_at | — | — | 0.000294888 | 0.0188949 | 63.5 | 46.9 | 48.3 |
| 761 | 236930_PM_at | NUMB | Numb homolog (*Drosophila*) | 0.000295483 | 0.0188949 | 387.5 | 234.0 | 261.8 |
| 762 | 242268_PM_at | CELF2 | CUGBP, Elav-like family member 2 | 0.000295958 | 0.0188949 | 1646.3 | 1171.9 | 1088.1 |
| 763 | 1556461_PM_at | — | — | 0.000296154 | 0.0188949 | 27.6 | 17.7 | 15.6 |
| 764 | 1560492_PM_at | — | — | 0.000296256 | 0.0188949 | 27.0 | 19.7 | 20.2 |
| 765 | 227277_PM_at | MTDH | metadherin | 0.000296841 | 0.0189074 | 167.6 | 134.6 | 123.8 |
| 766 | 225674_PM_at | BCAP29 | B-cell receptor-associated protein 29 | 0.000297445 | 0.0189212 | 155.2 | 231.0 | 231.6 |
| 767 | 242024_PM_at | — | — | 0.000299844 | 0.0190371 | 27.4 | 19.6 | 19.0 |
| 768 | 222661_PM_at | AGGF1 | angiogenic factor with G patch and FHA domains 1 | 0.000300049 | 0.0190371 | 104.8 | 158.7 | 143.0 |
| 769 | 214595_PM_at | KCNG1 | potassium voltage-gated channel, subfamily G, member 1 | 0.000301269 | 0.0190896 | 12.9 | 9.4 | 8.6 |
| 770 | 242431_PM_at | — | — | 0.000302138 | 0.0191198 | 291.4 | 220.9 | 238.4 |
| 771 | 1555485_PM_s_at | FAM153B | family with sequence similarity 153, member B | 0.000304641 | 0.0192296 | 12.9 | 11.0 | 10.5 |
| 772 | 1556658_PM_a_at | — | — | 0.000304832 | 0.0192296 | 234.0 | 134.6 | 122.0 |
| 773 | 243997_PM_x_at | — | — | 0.000305056 | 0.0192296 | 71.2 | 45.7 | 42.8 |
| 774 | 216782_PM_at | — | — | 0.000306202 | 0.0192769 | 1179.9 | 554.5 | 652.8 |
| 775 | 232670_PM_at | — | — | 0.000306719 | 0.0192845 | 40.6 | 24.4 | 27.2 |
| 776 | 203457_PM_at | STX7 | syntaxin 7 | 0.000309226 | 0.0194171 | 160.3 | 198.1 | 203.8 |
| 777 | 241494_PM_at | — | — | 0.000311987 | 0.0195652 | 15.7 | 11.3 | 12.3 |
| 778 | 231281_PM_at | — | — | 0.000312819 | 0.0195832 | 167.7 | 103.7 | 108.9 |
| 779 | 218423_PM_x_at | VPS54 | vacuolar protein sorting 54 homoog (*S. cerevisiae*) | 0.000313078 | 0.0195832 | 71.0 | 118.1 | 105.6 |
| 780 | 215587_PM_x_at | — | — | 0.000314098 | 0.0196219 | 185.0 | 134.1 | 154.6 |
| 781 | 244642_PM_at | — | — | 0.000315442 | 0.0196806 | 162.3 | 88.4 | 116.2 |
| 782 | 200731_PM_s_at | PTP4A1 | protein tyrosine phosphatase type IVA, member 1 | 0.000317118 | 0.0197599 | 111.8 | 158.4 | 154.4 |
| 783 | 243006_PM_at | — | — | 0.000317737 | 0.0197731 | 231.8 | 154.1 | 127.3 |
| 784 | 233241_PM_at | PLK1S1 | polo-like kinase 1 substrate 1 | 0.000318798 | 0.0198139 | 101.6 | 66.1 | 73.3 |
| 785 | 239876_PM_at | — | — | 0.00031958 | 0.0198189 | 200.3 | 127.8 | 137.7 |
| 786 | 243509_PM_at | — | — | 0.000319692 | 0.0198189 | 187.1 | 130.6 | 118.2 |
| 787 | 207657_PM_x_at | TNPO1 | transportin 1 | 0.000322118 | 0.0198746 | 481.0 | 406.6 | 389.3 |
| 788 | 208731_PM_at | RAB2A | RAB2A, member RAS oncogene family | 0.000321406 | 0.0198746 | 499.3 | 642.0 | 675.0 |
| 789 | 235482_PM_at | LOC400960 | hypothetical LOC400960 | 0.000322138 | 0.0198946 | 166.6 | 126.8 | 113.8 |
| 790 | 1570021_PM_at | — | — | 0.000322901 | 0.0199165 | 105.0 | 61.6 | 56.1 |
| 791 | 227012_PM_at | SLC25A40 | solute carrier family 25, member 40 | 0.000324196 | 0.0199607 | 205.9 | 347.0 | 346.6 |
| 792 | 1564236_PM_at | — | — | 0.00032473 | 0.0199607 | 13.3 | 10.5 | 9.5 |
| 793 | 237594_PM_at | — | — | 0.000325682 | 0.0199607 | 69.8 | 45.4 | 40.3 |
| 794 | 205370_PM_x_at | DBT | dihydrolipoamide branched chain transacylase E2 | 0.000326157 | 0.0199607 | 643.8 | 520.2 | 544.4 |
| 795 | 222590_PM_s_at | NLK | nemo-like kinase | 0.000326287 | 0.0199607 | 29.2 | 39.3 | 37.3 |
| 796 | 227080_PM_at | ZNF697 | zinc finger protein 697 | 0.000326712 | 0.0199607 | 25.9 | 33.0 | 42.6 |
| 797 | 222984_PM_at | PAIP2 | poly(A) binding protein interacting protein 2 | 0.000326816 | 0.0199607 | 1189.8 | 1490.1 | 1482.1 |
| 798 | 215385_PM_at | — | — | 0.000326896 | 0.0199607 | 89.5 | 67.0 | 62.9 |
| 799 | 234788_PM_x_at | — | — | 0.000330026 | 0.0201266 | 642.7 | 487.1 | 540.2 |
| 800 | 213156_PM_at | — | — | 0.000332799 | 0.020247 | 207.5 | 134.8 | 138.0 |
| 801 | 238771_PM_at | — | — | 0.000333234 | 0.020247 | 68.1 | 48.8 | 55.2 |
| 802 | 243954_PM_at | LOC285286 | hypothetical LOC285286 | 0.000333247 | 0.020247 | 86.4 | 42.3 | 50.3 |
| 803 | 217371_PM_s_at | IL15 | interleukin 15 | 0.000333774 | 0.0202538 | 69.5 | 102.3 | 107.6 |
| 804 | 207966_PM_s_at | GLG1 | golgi glycoprotein 1 | 0.000334197 | 0.0202543 | 565.4 | 431.9 | 393.5 |
| 805 | 228812_PM_at | — | — | 0.000335281 | 0.0202947 | 194.9 | 296.3 | 301.7 |
| 806 | 214055_PM_x_at | BAT2L2 | HLA-B associated transcript 2-like 2 | 0.000336279 | 0.0203299 | 1235.4 | 935.3 | 857.5 |
| 807 | 212461_PM_at | AZIN1 | antizyme inhibitor 1 | 0.000337965 | 0.0204065 | 311.7 | 433.9 | 363.5 |
| 808 | 232939_PM_at | — | — | 0.000338564 | 0.0204173 | 57.3 | 32.0 | 30.7 |
| 809 | 243874_PM_at | LPP | LIM domain containing preferred translocation partner in lipoma | 0.000339708 | 0.0204554 | 89.8 | 51.9 | 52.2 |
| 810 | 244871_PM_s_at | USP32 | ubiquitin specific peptidase 32 | 0.000340034 | 0.0204554 | 821.3 | 495.7 | 564.1 |
| 811 | 241769_PM_at | — | — | 0.000341157 | 0.0204976 | 124.4 | 93.3 | 91.4 |
| 812 | 1559425_PM_at | — | — | 0.000341643 | 0.0205015 | 368.8 | 248.7 | 153.5 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 813 | 219117_PM_s_at | FKBP11 | FK506 binding protein 11, 19 kDa | 0.000342451 | 0.0205247 | 272.8 | 206.2 | 157.7 |
| 814 | 243454_PM_at | — | — | 0.000346485 | 0.0207013 | 64.2 | 41.7 | 45.5 |
| 815 | 224726_PM_at | MIB1 | mindbomb homolog 1 (*Drosophila*) | 0.000346636 | 0.0207013 | 814.7 | 655.9 | 693.6 |
| 816 | 208097_PM_s_at | TMX1 | thioredoxin-related transmembrane protein 1 | 0.000346672 | 0.0207013 | 63.6 | 127.7 | 102.5 |
| 817 | 215268_PM_at | KIAA0754 | KIAA0754 | 0.000353336 | 0.0210734 | 71.5 | 52.3 | 50.4 |
| 818 | 217703_PM_x_at | — | — | 0.000360795 | 0.021492 | 55.9 | 48.0 | 49.6 |
| 819 | 238076_PM_at | GATAD2B | GATA zinc finger domain containing 2B | 0.000362252 | 0.0215506 | 296.9 | 221.6 | 231.6 |
| 820 | 223168_PM_at | RHOU | ras homolog gene family, member U | 0.000362992 | 0.0215506 | 128.2 | 217.8 | 211.7 |
| 821 | 232814_PM_x_at | C14orf153 | Chromosome 14 open reading frame 153 | 0.000363106 | 0.0215506 | 353.7 | 278.7 | 295.3 |
| 822 | 244185_PM_at | — | — | 0.000366343 | 0.0217163 | 120.6 | 86.2 | 81.3 |
| 823 | 222489_PM_s_at | WRNIP1 | Werner helicase interacting protein 1 | 0.000368949 | 0.0218442 | 119.2 | 158.8 | 143.9 |
| 824 | 231825_PM_x_at | ATF7IP | activating transcription factor 7 interacting protein | 0.000370872 | 0.0219314 | 735.8 | 556.6 | 565.4 |
| 825 | 1556277_PM_a_at | — | — | 0.000371726 | 0.0219553 | 332.1 | 197.4 | 223.8 |
| 826 | 211040_PM_x_at | GTSE1 | G-2 and S-phase expressed 1 | 0.00037274 | 0.021962 | 279.4 | 225.3 | 246.5 |
| 827 | 242225_PM_at | — | — | 0.000373261 | 0.021962 | 167.4 | 110.8 | 114.7 |
| 828 | 211559_PM_s_at | CCNG2 | cyclin G2 | 0.000373375 | 0.021962 | 72.3 | 152.3 | 134.6 |
| 829 | 217331_PM_at | — | — | 0.000373643 | 0.021962 | 16.7 | 14.5 | 14.0 |
| 830 | 239234_PM_at | — | — | 0.000378038 | 0.0221936 | 233.6 | 147.9 | 150.2 |
| 831 | 235926_PM_at | — | — | 0.000378499 | 0.0221939 | 165.9 | 112.1 | 104.9 |
| 832 | 230868_PM_at | — | — | 0.000382228 | 0.0223843 | 117.2 | 83.3 | 82.9 |
| 833 | 244878_PM_at | — | — | 0.000382665 | 0.0223843 | 46.5 | 29.9 | 28.0 |
| 834 | 233940_PM_at | — | — | 0.000383892 | 0.0224291 | 39.0 | 30.5 | 26.9 |
| 835 | 236002_PM_at | — | — | 0.000387199 | 0.0225953 | 155.0 | 104.4 | 96.6 |
| 836 | 237330_PM_at | — | — | 0.000388717 | 0.0226567 | 404.4 | 224.4 | 219.3 |
| 837 | 225793_PM_at | LIX1L | Lix1 homolog (mouse)-like | 0.000392446 | 0.0228467 | 485.3 | 425.6 | 383.2 |
| 838 | 240216_PM_at | — | — | 0.000395157 | 0.022961 | 46.6 | 32.5 | 30.2 |
| 839 | 23187_PM_at | C16orf53 | chromosome 16 open reading frame 53 | 0.00039576 | 0.022961 | 181.8 | 144.8 | 146.6 |
| 840 | 234649_PM_at | — | — | 0.000395823 | 0.022961 | 78.5 | 51.7 | 49.3 |
| 841 | 242074_PM_at | — | — | 0.000397651 | 0.0230396 | 145.7 | 113.1 | 99.5 |
| 842 | 231109_PM_at | — | — | 0.000399417 | 0.0231145 | 778.5 | 455.6 | 469.9 |
| 843 | 239923_PM_at | — | — | 0.000400186 | 0.0231315 | 615.5 | 352.9 | 368.1 |
| 844 | 201180_PM_s_at | GNAI3 | guanine nucleotide binding protein (G protein), alpha inhibiting activity polypeptide 3 | 0.000404234 | 0.0233378 | 830.7 | 1001.7 | 978.1 |
| 845 | 202040_PM_s_at | KDM5A | lysine (K)-specific demethylase 5A | 0.000405437 | 0.0233796 | 824.0 | 646.3 | 703.7 |
| 846 | 239969_PM_at | — | — | 0.000406037 | 0.0233865 | 89.6 | 62.7 | 62.6 |
| 847 | 228180_PM_at | — | — | 0.000408895 | 0.0235042 | 202.3 | 158.5 | 146.2 |
| 848 | 232134_PM_at | — | — | 0.000409046 | 0.0235042 | 121.3 | 96.1 | 88.1 |
| 849 | 1570192_PM_at | — | — | 0.000410178 | 0.0235174 | 222.3 | 110.7 | 140.9 |
| 850 | 223547_PM_at | JKAMP | JNK1/MAPK8-associated membrane protein | 0.00041024 | 0.0235174 | 57.3 | 84.1 | 82.3 |
| 851 | 228456_PM_s_at | CDS2 /// LOC149832 | CDP-diacylglycerol synthase (phosphatidate cytidylyltransferase) 2 /// hypothetical pro | 0.000412023 | 0.0235756 | 473.4 | 361.8 | 388.5 |
| 852 | 1561167_PM_at | — | — | 0.000412223 | 0.0235756 | 318.7 | 174.6 | 180.3 |
| 853 | 237456_PM_at | — | — | 0.000413833 | 0.0236399 | 197.6 | 102.4 | 107.6 |
| 854 | 215203_PM_at | GOLGA4 | golgin A4 | 0.000415851 | 0.0237274 | 33.5 | 26.6 | 27.5 |
| 855 | 244473_PM_at | — | — | 0.000417637 | 0.023785 | 24.6 | 19.7 | 17.8 |
| 856 | 217745_PM_s_at | NAA50 | N(alpha)-acetyltransferase 50, NatE catalytic subunit | 0.000417837 | 0.023785 | 342.9 | 454.8 | 420.4 |
| 857 | 232096_PM_x_at | — | — | 0.000423244 | 0.0240647 | 132.7 | 93.5 | 97.3 |
| 858 | 236367_PM_at | SMG7 | Smg-7 homolog, nonsense mediated mRNA decay factor (*C. elegans*) | 0.000426413 | 0.0242038 | 60.3 | 43.6 | 39.9 |
| 859 | 219099_PM_at | C12orf5 | chromosome 12 open reading frame 5 | 0.000426684 | 0.0242038 | 143.5 | 195.8 | 191.5 |
| 860 | 239614_PM_x_at | — | — | 0.000428523 | 0.0242599 | 83.0 | 63.3 | 57.2 |
| 861 | 1565598_PM_at | — | — | 0.000429465 | 0.0242599 | 219.4 | 108.9 | 116.5 |
| 862 | 244548_PM_at | — | — | 0.000429552 | 0.0242599 | 989.0 | 528.6 | 550.3 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 863 | 222133_PM_s_at | PHF20L1 | PHD finger protein 20-like 1 | 0.000429665 | 0.0242599 | 344.9 | 246.8 | 263.9 |
| 864 | 206095_PM_s_at | SRSF10 | serine/arginine-rich spiking factor 10 | 0.000430876 | 0.0243001 | 169.2 | 260.5 | 244.5 |
| 865 | 243325_PM_at | GSTK1 | Glutathione S-transferase kappa 1 | 0.000432321 | 0.0243534 | 48.8 | 34.7 | 36.0 |
| 866 | 32099_PM_at | SAFB2 | scaffold attachment factor B2 | 0.000433362 | 0.0243839 | 252.4 | 183.1 | 203.6 |
| 867 | 1570200_PM_at | HELB | helicase (DNA) B | 0.000434885 | 0.0244413 | 78.9 | 60.2 | 52.9 |
| 868 | 238651_PM_at | — | — | 0.000436948 | 0.024529 | 298.5 | 217.3 | 217.3 |
| 869 | 236617_PM_at | — | — | 0.00043989 | 0.0246657 | 18.3 | 12.2 | 13.4 |
| 870 | 240148_PM_at | MSH6 | MutS homolog 6 (*E. coli*) | 0.000440564 | 0.0246751 | 26.4 | 21.5 | 21.6 |
| 871 | 202874_PM_s_at | ATP6V1C1 | ATPase, H+ transporting, lysosomal 42 kDa, V1 subunit C1 | 0.000441569 | 0.024703 | 180.5 | 283.6 | 242.1 |
| 872 | 225313_PM_at | C20orf177 | chromosome 20 open reading frame 177 | 0.00044279 | 0.0247389 | 212.6 | 288.7 | 286.2 |
| 873 | 237189_PM_at | LOC100506360 | hypothetical LOC100506360 | 0.000443225 | 0.0247389 | 30.5 | 18.9 | 18.4 |
| 874 | 243691_PM_at | — | — | 0.000444048 | 0.0247564 | 30.8 | 21.6 | 24.6 |
| 875 | 209684_PM_at | RIN2 | Ras and Rab Interactor 2 | 0.000444718 | 0.0247648 | 136.4 | 227.4 | 238.7 |
| 876 | 244078_PM_at | — | — | 0.000445215 | 0.0247648 | 35.5 | 26.5 | 25.4 |
| 877 | 240939_PM_x_at | — | — | 0.000448669 | 0.0249274 | 29.4 | 21.3 | 21.6 |
| 878 | 239131_PM_at | — | — | 0.000449161 | 0.0249274 | 29.5 | 20.2 | 17.8 |
| 879 | 1560199_PM_x_at | LOC728153 | similar to FAM133B protein | 0.00044992 | 0.0249411 | 400.0 | 271.5 | 281.7 |
| 880 | 240108_PM_at | — | — | 0.000451383 | 0.0249938 | 167.6 | 119.5 | 119.7 |
| 881 | 239674_PM_at | — | — | 0.00045305 | 0.0250575 | 17.3 | 14.7 | 14.3 |
| 882 | 214948_PM_s_at | TMF1 | TATA element modulatory factor 1 | 0.000454991 | 0.0251364 | 517.2 | 389.8 | 389.4 |
| 883 | 234260_PM_at | — | — | 0.000455932 | 0.0251599 | 105.2 | 74.3 | 73.8 |
| 884 | 1556925_PM_at | SMC3 | Structural maintenance of chromosomes 3 | 0.000459008 | 0.025301 | 14.0 | 11.7 | 11.9 |
| 885 | 1558922_PM_at | — | — | 0.000460623 | 0.0253613 | 116.9 | 86.3 | 78.3 |
| 886 | 215504_PM_x_at | — | — | 0.000462655 | 0.0254445 | 705.6 | 581.4 | 607.1 |
| 887 | 224986_PM_s_at | PDPK1 | 3-phosphoinositide dependent protein kinase-1 | 0.000464555 | 0.0255201 | 313.0 | 372.9 | 393.7 |
| 888 | 214100_PM_x_at | NSUN5P1 | NOP2/Sun domain family, member 5 pseudogene 1 | 0.000466365 | 0.0255446 | 217.7 | 195.5 | 155.9 |
| 889 | 243458_PM_at | — | — | 0.000467592 | 0.0255446 | 44.9 | 31.2 | 31.0 |
| 890 | 1558135_PM_at | TAF11 | TAF11 RNA polymerase II, TATA box binding protein (TBP)-associated factor, 28 kDa | 0.000467741 | 0.0255446 | 105.9 | 72.9 | 80.8 |
| 891 | 211947_PM_s_at | BAT2L2 | HLA-B associated transcript 2-like 2 | 0.000467783 | 0.0255446 | 394.8 | 277.9 | 283.8 |
| 892 | 244622_PM_at | BRWD1 | Bromodomain and WD repeat domain containing 1 | 0.000468257 | 0.0255446 | 44.1 | 32.7 | 32.9 |
| 893 | 233836_PM_at | TNRC6A | trinucleotide repeat containing 6A | 0.00046938 | 0.0255446 | 19.5 | 15.2 | 15.5 |
| 894 | 1555303_PM_at | — | — | 0.000469387 | 0.0255446 | 141.3 | 79.5 | 85.0 |
| 895 | 227026_PM_at | MPHOSPH8 | M-phase phosphoprotein 8 | 0.000469724 | 0.0255446 | 318.7 | 234.3 | 248.6 |
| 896 | 244607_PM_at | — | — | 0.000469836 | 0.0255446 | 43.4 | 30.9 | 33.0 |
| 897 | 227905_PM_s_at | AZI2 | 5-azacytidine induced 2 | 0.000470243 | 0.0255446 | 24.6 | 37.2 | 30.8 |
| 898 | 243300_PM_at | — | — | 0.000472394 | 0.0256052 | 15.4 | 11.8 | 12.8 |
| 899 | 241891_PM_at | — | — | 0.000472887 | 0.0256052 | 1177.4 | 796.8 | 777.5 |
| 900 | 222514_PM_at | RRAGC | Ras-related GTP binding C | 0.000472935 | 0.0256052 | 607.8 | 722.1 | 691.1 |
| 901 | 219658_PM_at | PTCD2 | pentatricopeptide repeat domain 2 | 0.00047383 | 0.0256252 | 61.8 | 52.7 | 44.8 |
| 902 | 215092_PM_s_at | NFAT5 | nuclear factor of activated T-cells 5, tonicity-responsive | 0.000474541 | 0.0256352 | 205.3 | 133.5 | 151.1 |
| 903 | 207078_PM_at | MED6 | mediator complex subunit 6 | 0.000475119 | 0.0256558 | 58.5 | 41.8 | 39.4 |
| 904 | 230608_PM_at | C1orf182 | chromosome 1 open reading frame 182 | 0.000478577 | 0.025796 | 17.0 | 15.9 | 18.8 |
| 905 | 1559101_PM_at | FYN | FYN oncogene related to SRC, FGR, YES | 0.000480045 | 0.0258276 | 306.8 | 224.5 | 184.9 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 906 | 1562059_PM_at | — | — | 0.000480222 | 0.0258276 | 125.5 | 76.2 | 87.5 |
| 907 | 206233_PM_at | B4GALT6 | UDP-Gal:betaGlcNAc beta 1,4-galactosyltransferase, polypeptide 6 | 0.000482556 | 0.0259245 | 9.9 | 11.3 | 11.9 |
| 908 | 239571_PM_at | — | — | 0.000484875 | 0.0260053 | 352.5 | 248.8 | 249.2 |
| 909 | 1558469_PM_at | LPP | LIM domain containing preferred translocation partner in lipoma | 0.000485128 | 0.0260053 | 17.7 | 14.0 | 12.8 |
| 910 | 233308_PM_at | COPB1 | Coatomer protein complex, subunit beta 1 | 0.00048641 | 0.0260266 | 99.9 | 68.6 | 74.7 |
| 911 | 207499_PM_x_at | UNC45A | unc-45 homolog A (C. elegans) | 0.000486594 | 0.0260266 | 23.4 | 19.1 | 20.4 |
| 912 | 241240_PM_at | — | — | 0.000488335 | 0.0260911 | 245.3 | 151.5 | 178.6 |
| 913 | 215604_PM_x_at | — | — | 0.000491675 | 0.0262191 | 386.7 | 308.8 | 333.0 |
| 914 | 1568866_PM_at | — | — | 0.000491806 | 0.0262191 | 46.1 | 36.8 | 37.0 |
| 915 | 243801_PM_x_at | — | — | 0.000494418 | 0.0263295 | 38.4 | 31.2 | 31.7 |
| 916 | 224963_PM_at | SLC26A2 | solute carrier family 26 (sulfate transporter), member 2 | 0.000496442 | 0.0264084 | 88.6 | 94.3 | 64.0 |
| 917 | 223289_PM_s_at | USP38 | ubiquitin specific peptidase 38 | 0.000497818 | 0.0264325 | 88.8 | 121.2 | 112.3 |
| 918 | 226843_PM_s_at | PAPD5 | PAP associated domain containing 5 | 0.000498428 | 0.0264325 | 449.5 | 361.7 | 348.9 |
| 919 | 228471_PM_at | ANKRD44 | ankyrin repeat domain 44 | 0.000498876 | 0.0264325 | 2457.5 | 1972.3 | 2043.1 |
| 920 | 237588_PM_at | — | — | 0.000499064 | 0.0264325 | 198.7 | 112.0 | 101.2 |
| 921 | 237185_PM_at | — | — | 0.000501862 | 0.0265442 | 106.8 | 41.3 | 58.3 |
| 922 | 1556416_PM_s_at | — | — | 0.000502263 | 0.0265442 | 49.8 | 39.0 | 35.8 |
| 923 | 239926_PM_at | — | — | 0.000505191 | 0.0266645 | 82.1 | 45.7 | 55.2 |
| 924 | 231794_PM_at | CTLA4 | cytotoxic T-lymphocyte-associated protein 4 | 0.000505633 | 0.0266645 | 13.8 | 13.0 | 11.5 |
| 925 | 225366_PM_at | PGM2 | phosphoglucomutase 2 | 0.000506926 | 0.0266801 | 99.2 | 146.5 | 151.2 |
| 926 | 1557706_PM_at | ZHX2 | zinc fingers and homeoboxes 2 | 0.000507025 | 0.0266801 | 38.1 | 24.1 | 25.8 |
| 927 | 1557278_PM_s_at | TNPO1 | Transportin 1 | 0.00051016 | 0.0267982 | 50.6 | 37.7 | 35.2 |
| 928 | 212907_PM_at | SLC30A1 | solute carrier family 30 (zinc transporter), member 1 | 0.000510575 | 0.0267982 | 279.7 | 452.7 | 413.3 |
| 929 | 228866_PM_at | — | — | 0.00051121 | 0.0267982 | 123.7 | 79.6 | 76.7 |
| 930 | 200047_PM_s_at | YY1 | YY1 transcription factor | 0.000511468 | 0.0267982 | 947.2 | 1166.0 | 1192.6 |
| 931 | 214405_PM_at | — | — | 0.000512036 | 0.0267991 | 378.5 | 258.8 | 245.1 |
| 932 | 204344_PM_s_at | SEC23A | Sec23 homolog A (S. cerevisiae) | 0.000513855 | 0.0268655 | 18.8 | 25.8 | 22.9 |
| 933 | 215592_PM_at | — | — | 0.000518172 | 0.0270383 | 99.2 | 65.0 | 61.2 |
| 934 | 219947_PM_at | CLEC4A | C-type lectin domain family 4, member A | 0.000518808 | 0.0270383 | 908.1 | 1191.3 | 1202.9 |
| 935 | 209095_PM_at | DLD | dihydrolipoamide dehydrogenase | 0.000518826 | 0.0270383 | 318.4 | 443.1 | 400.3 |
| 936 | 215888_PM_at | PDS5B | PDS5, regulator of cohesion maintenance, homolog B (S. cerevisiae) | 0.000522684 | 0.0272103 | 137.4 | 96.3 | 92.6 |
| 937 | 206235_PM_at | LIG4 | ligase IV, DNA, ATP-dependent | 0.000525807 | 0.0273436 | 15.7 | 21.8 | 19.5 |
| 938 | 222235_PM_s_at | CSGALNACT2 | chondroitin sulfate r N-acetytgalatosaminyltransferase 2 | 0.000527308 | 0.0273925 | 309.6 | 499.7 | 460.3 |
| 939 | 226587_PM_at | SNRPN | small nuclear ribonucleoprotein polypeptide N | 0.000528757 | 0.0274201 | 74.2 | 41.9 | 36.9 |
| 940 | 1556033_PM_at | FLJ39739 | hypothetical FLJ39739 | 0.000528966 | 0.0274201 | 229.2 | 205.4 | 172.5 |
| 941 | 218669_PM_at | RAP2C | RAP2C, member of RAS oncogene family | 0.000532546 | 0.0275764 | 317.5 | 474.9 | 457.3 |
| 942 | 232190_PM_x_at | LOC100133445 /// LOC115110 | hypothetical LOC100133445 /// hypothetical LOC115110 | 0.000534373 | 0.0276416 | 33.7 | 28.3 | 30.4 |
| 943 | 212921_PM_at | SMYD2 | SET and MYND domain containing 2 | 0.000538535 | 0.0278274 | 54.8 | 41.5 | 34.4 |
| 944 | 232266_PM_x_at | CDK13 | Cyclin-dependent kinase 13 | 0.000539275 | 0.0278361 | 960.9 | 730.0 | 803.7 |
| 945 | 219027_PM_s_at | MYO9A | myosin IXA | 0.000544917 | 0.0280839 | 57.5 | 46.0 | 47.1 |
| 946 | 1560332_PM_at | — | — | 0.000545515 | 0.0280839 | 21.5 | 14.2 | 17.6 |
| 947 | 240165_PM_at | — | — | 0.000546311 | 0.0280839 | 231.0 | 148.7 | 172.7 |
| 948 | 231205_PM_at | — | — | 0.000546629 | 0.0280839 | 440.9 | 251.8 | 278.3 |
| 949 | 241060_PM_x_at | — | — | 0.000546958 | 0.0280839 | 29.1 | 20.6 | 17.6 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 950 | 226975_PM_at | RNPC3 | RNA-binding region (RNP1, RRM) containing 3 | 0.000548452 | 0.028131 | 660.2 | 526.7 | 538.6 |
| 951 | 226419_PM_s_at | FLJ44342 | hypothetical LOC645460 | 0.000552685 | 0.02829 | 291.7 | 195.4 | 218.9 |
| 952 | 203261_PM_at | DCTN6 | dynactin 6 | 0.000552713 | 0.02829 | 106.4 | 155.4 | 155.1 |
| 953 | 224990_PM_at | C4orf34 | chromosome 4 open reading frame 34 | 0.000553439 | 0.0282974 | 129.9 | 172.5 | 178.9 |
| 954 | 227393_PM_at | ANO9 | anoctamin 9 | 0.000554704 | 0.0283323 | 17.4 | 14.9 | 13.3 |
| 955 | 233099_PM_at | — | — | 0.000556499 | 0.0283496 | 13.0 | 10.3 | 10.7 |
| 956 | 1559663_PM_at | — | — | 0.000556916 | 0.0283496 | 36.6 | 21.5 | 23.0 |
| 957 | 203077_PM_s_at | SMAD2 | SMAD family member 2 | 0.000557342 | 0.0283496 | 109.8 | 133.3 | 139.1 |
| 958 | 232347_PM_x_at | — | — | 0.000557372 | 0.0283496 | 149.6 | 112.3 | 117.7 |
| 959 | 1559136_PM_s_at | LOC100272228 | hypothetical LOC100272228 | 0.000557951 | 0.0283496 | 10.9 | 10.5 | 9.5 |
| 960 | 239333_PM_x_at | GSTK1 | glutathione S-transferase kappa 1 | 0.000560501 | 0.0284495 | 225.0 | 175.7 | 187.6 |
| 961 | 244777_PM_at | DCP2 | DCP2 decapping enzyme homolog (S. cerevisiae) | 0.000561209 | 0.0284558 | 818.1 | 604.5 | 698.2 |
| 962 | 237953_PM_at | — | — | 0.000564728 | 0.0286045 | 24.5 | 16.1 | 13.3 |
| 963 | 211084_PM_x_at | PRKD3 | protein kinase D3 | 0.000565658 | 0.0286218 | 44.2 | 35.8 | 34.1 |
| 964 | 218012_PM_at | TSPYL2 | TSPY-like 2 | 0.000570721 | 0.0288481 | 19.3 | 16.4 | 14.8 |
| 965 | 243646_PM_at | — | — | 0.000572724 | 0.0289193 | 31.7 | 24.4 | 22.1 |
| 966 | 214594_PM_x_at | ATP8B1 | ATPase, aminophospholipid transporter, class I, type 8B, member 1 | 0.000577893 | 0.0291079 | 133.5 | 93.2 | 101.8 |
| 967 | 243216_PM_x_at | — | — | 0.000578007 | 0.0291079 | 125.1 | 103.4 | 101.7 |
| 968 | 221523_PM_s_at | RRAGD | Ras-related GTP binding D | 0.000578251 | 0.0291079 | 128.2 | 205.9 | 191.1 |
| 969 | 1558877_PM_at | — | — | 0.000579125 | 0.0291218 | 177.8 | 89.7 | 95.9 |
| 970 | 200071_PM_at | SMNDC1 | survival motor neuron domain containing 1 | 0.000582434 | 0.0292484 | 563.2 | 694.7 | 713.0 |
| 971 | 204681_PM_s_at | RAPGEF5 | Rap guanine nucleotide exchange factor (GEF) 5 | 0.000582843 | 0.0292484 | 9.3 | 9.6 | 11.3 |
| 972 | 239721_PM_at | — | — | 0.000584451 | 0.0292839 | 143.4 | 96.3 | 95.6 |
| 973 | 217102_PM_at | LOC100287076 | Similar to malignancy-associated protein | 0.000585345 | 0.0292839 | 10.7 | 9.3 | 9.9 |
| 974 | 215232_PM_at | ARHGAP44 | Rho GTPase activating protein 44 | 0.000585353 | 0.0292839 | 12.7 | 11.1 | 13.1 |
| 975 | 232340_PM_at | LOC388889 | hypothetical LOC388889 | 0.000589789 | 0.0294389 | 69.9 | 55.0 | 48.8 |
| 976 | 244358_PM_at | — | — | 0.000589852 | 0.0294389 | 304.7 | 149.5 | 155.6 |
| 977 | 226833_PM_at | CYB5D1 | cytochrome b5 domain containing 1 | 0.000590265 | 0.0294389 | 21.1 | 16.7 | 16.5 |
| 978 | 234731_PM_at | — | — | 0.000591523 | 0.0294715 | 801.1 | 622.0 | 673.2 |
| 979 | 239163_PM_at | UBE2B | ubiquitin-conjugating enzyme E2B (RAD6 homolog) | 0.000593286 | 0.0295292 | 442.8 | 263.6 | 337.4 |
| 980 | 242735_PM_x_at | ELF2 | E74-like factor 2 (ets domain transcription factor) | 0.000596326 | 0.0296502 | 207.9 | 156.9 | 168.0 |
| 981 | 234621_PM_at | — | — | 0.000599272 | 0.0297358 | 18.9 | 12.7 | 13.6 |
| 982 | 242031_PM_at | — | — | 0.000599401 | 0.0297358 | 55.6 | 42.0 | 32.3 |
| 983 | 235647_PM_at | AP4S1 | Adaptor-related protein complex 4, sigma 1 subunit | 0.000599879 | 0.0297358 | 66.0 | 49.9 | 48.6 |
| 984 | 222870_PM_s_at | B3GNT2 | UDP-GlcNAc:betaGal beta-1,3-N-acetylglucosaminyltransferase 2 | 0.000601513 | 0.0297865 | 115.6 | 176.2 | 194.0 |
| 985 | 220546_PM_at | MLL | myeloid/lymphoid or mixed-lineage leukemia (trithorax homolog, Drosophila) | 0.000602412 | 0.0298007 | 88.2 | 69.7 | 61.7 |
| 986 | 214052_PM_x_at | BAT2L2 | HLA-B associated transcript 2-like 2 | 0.000603516 | 0.0298251 | 78.2 | 55.7 | 57.5 |
| 987 | 230590_PM_at | — | — | 0.000604485 | 0.0298303 | 474.5 | 243.9 | 242.2 |
| 988 | 218404_PM_at | SNX10 | sorting nexin 10 | 0.000605146 | 0.0298303 | 975.9 | 1292.9 | 1317.3 |
| 989 | 236755_PM_at | — | — | 0.000605459 | 0.0298303 | 81.1 | 57.7 | 62.3 |
| 990 | 1560171_PM_at | — | — | 0.000607629 | 0.0299 | 78.4 | 64.9 | 50.2 |
| 991 | 242374_PM_at | — | — | 0.0006081 | 0.0299 | 105.3 | 74.4 | 69.9 |
| 992 | 201435_PM_s_at | EIF4E | eukaryotic translation initiation factor 4E | 0.000609565 | 0.029922 | 131.1 | 192.8 | 172.8 |
| 993 | 218627_PM_at | DRAM1 | DNA-damage regulated autophagy modulator 1 | 0.000609775 | 0.029922 | 117.1 | 152.4 | 184.4 |
| 994 | 1560552_PM_a_at | — | — | 0.000612413 | 0.0300212 | 23.0 | 16.5 | 15.4 |
| 995 | 216187_PM_x_at | — | — | 0.000613591 | 0.0300487 | 1334.9 | 1072.4 | 1127.7 |
| 996 | 234753_PM_x_at | — | — | 0.000617785 | 0.0302237 | 17.6 | 13.7 | 15.4 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
| --- | --- | --- | --- | --- | --- | --- | --- | --- |
| 997 | 232556_PM_at | — | — | 0.000623426 | 0.0304281 | 32.8 | 24.8 | 23.5 |
| 998 | 214705_PM_at | INADL | InaD-llke (*Drosophila*) | 0.000624089 | 0.0304281 | 27.6 | 18.1 | 16.2 |
| 999 | 207112_PM_s_at | GAB1 | GRB2-associated binding protein 1 | 0.000624139 | 0.0304281 | 11.9 | 13.5 | 14.0 |
| 1000 | 223886_PM_s_at | RNF146 | ring finger protein 146 | 0.000524461 | 0.0304281 | 469.8 | 581.7 | 633.1 |
| 1001 | 225117_PM_at | KIAA1267 | KIAA1267 | 0.000629473 | 0.0305965 | 708.1 | 567.5 | 592.4 |
| 1002 | 227268_PM_at | RNFT1 | ring finger protein, transmembrane 1 | 0.000530131 | 0.0305965 | 100.0 | 162.8 | 165.7 |
| 1003 | 235328_PM_at | PLXNC1 | Plexin C1 | 0.000630354 | 0.0305965 | 27.6 | 20.9 | 19.8 |
| 1004 | 222103_PM_at | ATF1 | activating transcription factor 1 | 0.000630428 | 0.0305965 | 121.6 | 203.3 | 197.1 |
| 1005 | 235084_PM_x_at | — | — | 0.000531188 | 0.0306029 | 680.3 | 521.1 | 548.9 |
| 1006 | 200056_PM_s_at | C1D | C1D nuclear receptor corepressor | 0.00063303 | 0.0306617 | 383.0 | 501.9 | 499.8 |
| 1007 | 218178_PM_s_at | CHMP1B | chromatin modifying protein 1B | 0.00063573 | 0.0307619 | 413.1 | 622.1 | 593.8 |
| 1008 | 201876_PM_at | PON2 | paraoxonase 2 | 0.000642018 | 0.0310353 | 64.4 | 83.3 | 103.8 |
| 1009 | 227412_PM_at | PPP1R3E | protein phosphatase 1, regulatory (inhibitor) subunit 3E | 0.000643748 | 0.0310881 | 42.0 | 31.4 | 27.0 |
| 1010 | 1560680_PM_at | — | — | 0.000647985 | 0.0312507 | 27.6 | 24.2 | 21.1 |
| 1011 | 226712_PM_at | SSR1 | signal sequence receptor, alpha | 0.000648398 | 0.0312507 | 146.7 | 108.2 | 101.4 |
| 1012 | 220843_PM_s_at | DCAF13 | DDB1 and CUL4 associated factor 13 | 0.000649108 | 0.031254 | 14.9 | 12.4 | 11.0 |
| 1013 | 243808_PM_at | — | — | 0.000652146 | 0.0313693 | 42.7 | 31.9 | 26.9 |
| 1014 | 218738_PM_s_at | RNF138 | ring finger protein 138 | 0.000655843 | 0.031516 | 346.9 | 514.4 | 498.2 |
| 1015 | 204185_PM_x_at | PPID | peptidylprolyl isomerase D | 0.000658305 | 0.0316032 | 235.6 | 290.5 | 285.7 |
| 1016 | 241081_PM_at | — | — | 0.000660309 | 0.0316682 | 19.2 | 14.2 | 13.5 |
| 1017 | 242851_PM_at | KIAA1919 | KIAA1919 | 0.000661733 | 0.0316927 | 43.6 | 31.9 | 32.3 |
| 1018 | 209066_PM_x_at | UQCRB | ubiquinol-cytochrome c reductase binding protein | 0.000662121 | 0.0316927 | 170.0 | 360.1 | 345.4 |
| 1019 | 238970_PM_at | — | — | 0.000664525 | 0.0317609 | 155.2 | 114.4 | 96.2 |
| 1020 | 216197_PM_at | ATF7IP | activating transcription factor 7 interacting protein | 0.000664849 | 0.0317609 | 143.4 | 109.2 | 98.8 |
| 1021 | 221834_PM_at | LONP2 | Lon peptidase 2, peroxisomal | 0.000666186 | 0.0317936 | 451.8 | 354.8 | 312.9 |
| 1022 | 219876_PM_s_at | GOLGA2B | golgin A2 family, member B | 0.000669547 | 0.0319227 | 12.9 | 10.7 | 11.9 |
| 1023 | 1556568_PM_a_at | — | — | 0.000671247 | 0.0319431 | 107.8 | 74.0 | 74.0 |
| 1024 | 215269_PM_at | TRAPPC10 | trafficking protein particle complex 10 | 0.000671285 | 0.0319431 | 259.6 | 180.1 | 180.4 |
| 1025 | 240568_PM_at | — | — | 0.000674356 | 0.0320579 | 23.8 | 17.8 | 13.6 |
| 1026 | 236437_PM_at | — | — | 0.000678439 | 0.0322206 | 154.6 | 89.5 | 113.1 |
| 1027 | 240690_PM_at | — | — | 0.00067947 | 0.0322269 | 102.0 | 59.2 | 58.4 |
| 1028 | 242505_PM_at | — | — | 0.000680031 | 0.0322269 | 30.2 | 22.9 | 22.5 |
| 1029 | 210711_PM_at | NCRNA00260 | non-protein coding RNA 260 | 0.000680577 | 0.0322269 | 89.5 | 63.5 | 51.5 |
| 1030 | 229491_PM_at | NHEDC2 | Na+/H+ exchanger domain containing 2 | 0.000681217 | 0.0322269 | 21.2 | 18.7 | 15.6 |
| 1031 | 241997_PM_at | — | — | 0.000687566 | 0.0324957 | 140.2 | 105.5 | 97.8 |
| 1032 | 1563509_PM_at | — | — | 0.000693415 | 0.0326067 | 1276.9 | 893.8 | 849.1 |
| 1033 | 203693_PM_s_at | E2F3 | E2F transcription factor 3 | 0.000694069 | 0.0326067 | 129.9 | 171.1 | 179.0 |
| 1034 | 203594_PM_at | RTCD1 | RNA terminal phosphate cyclase domain 1 | 0.000694477 | 0.0326067 | 149.6 | 205.7 | 170.5 |
| 1035 | 229398_PM_at | RAB18 | RAB18, member RAS oncogene family | 0.000694934 | 0.0326067 | 414.7 | 289.6 | 309.1 |
| 1036 | 218465_PM_at | TMEM33 | transmembrane protein 33 | 0.000695471 | 0.0326067 | 77.1 | 113.0 | 130.5 |
| 1037 | 236155_PM_at | ZCCHC6 | Zinc finger, CCHC domain containing 6 | 0.000695476 | 0.0326067 | 1242.2 | 877.5 | 826.6 |
| 1038 | 209510_PM_at | RNF139 | ring finger protein 139 | 0.000695929 | 0.0326067 | 387.4 | 514.6 | 481.4 |
| 1039 | 1564443_PM_at | DLEU2 | Deleted in lymphocytic leukemia 2 (non-protein coding) | 0.000696802 | 0.0326067 | 20.6 | 14.3 | 14.7 |
| 1040 | 208137_PM_x_at | ZNF611 | zinc finger protein 611 | 0.000697333 | 0.0326067 | 75.5 | 58.4 | 59.9 |
| 1041 | 234148_PM_at | — | — | 0.000697378 | 0.0326067 | 24.2 | 18.6 | 17.1 |
| 1042 | 243064_PM_at | — | — | 0.000697497 | 0.0326067 | 44.8 | 31.5 | 33.5 |
| 1043 | 201730_PM_s_at | TPR | translocated promoter region (to activated MET oncogene) | 0.000697945 | 0.0326067 | 759.5 | 569.8 | 580.7 |
| 1044 | 239629_PM_at | CFLAR | CASPB and FADD-like apoptosis regulator | 0.000699042 | 0.0326256 | 1603.5 | 1034.2 | 1151.0 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1045 | 242320_PM_at | — | — | 0.000701964 | 0.0327287 | 327.6 | 186.6 | 191.3 |
| 1046 | 230229_PM_at | DLG1 | Discs, large homolog 1 (Drosophila) | 0.000702654 | 0.0327287 | 162.6 | 134.8 | 110.5 |
| 1047 | 225997_PM_at | MOBKL1A | MOB1, Mps One Binder kinase activator-like 1A (yeast) | 0.000703244 | 0.0327287 | 86.8 | 151.6 | 150.0 |
| 1048 | 239724_PM_at | — | — | 0.000703974 | 0.0327314 | 42.3 | 28.3 | 30.1 |
| 1049 | 236160_PM_at | TRIP11 | thyroid hormone receptor interactor 11 | 0.000706422 | 0.0327917 | 67.5 | 49.3 | 45.3 |
| 1050 | 236386_PM_at | LOC100506501 | hypothetical LOC100506501 | 0.000706617 | 0.0327917 | 81.6 | 57.5 | 59.8 |
| 1051 | 231896_PM_s_at | DENR | density-regulated protein | 0.00070898 | 0.0328701 | 279.2 | 383.3 | 376.1 |
| 1052 | 203159_PM_at | GLS | glutaminase | 0.000712753 | 0.0329977 | 271.6 | 224.4 | 196.8 |
| 1053 | 225400_PM_at | TSEN15 | tRNA splicing endonuclease 15 homolog (S. cerevisiae) | 0.000713875 | 0.0329977 | 25.4 | 36.7 | 28.3 |
| 1054 | 212234_PM_at | ASXL1 | additional sex combs like 1 (Drosophila) | 0.00071392 | 0.0329977 | 55.3 | 47.0 | 41.6 |
| 1055 | 237337_PM_at | — | — | 0.000714441 | 0.0329977 | 59.0 | 43.2 | 42.0 |
| 1056 | 217534_PM_at | FAM49B | family with sequence similarity 49, member B | 0.000717444 | 0.0331009 | 138.0 | 82.9 | 86.4 |
| 1057 | 238544_PM_at | — | — | 0.00071842 | 0.0331009 | 72.4 | 39.7 | 35.5 |
| 1058 | 233430_PM_at | TBC1D22B | TBC1 domain family, member 22B | 0.000718714 | 0.0331009 | 28.4 | 22.4 | 19.9 |
| 1059 | 221155_PM_x_at | — | — | 0.000722005 | 0.0332211 | 62.0 | 46.7 | 52.0 |
| 1060 | 244233_PM_at | C18orf10 | chromosome 18 open reading frame 10 | 0.000723209 | 0.0332264 | 17.8 | 14.4 | 14.9 |
| 1061 | 1558711_PM_at | FAM13AOS | FAM13A opposite strand (non-protein coding) | 0.000723485 | 0.0332264 | 558.5 | 363.4 | 368.1 |
| 1062 | 202714_PM_s_at | KIAA0391 | KIAA0391 | 0.000730644 | 0.0335236 | 13.5 | 12.3 | 11.1 |
| 1063 | 1565703_PM_at | SMAD4 | SMAD family member 4 | 0.000733037 | 0.0335891 | 43.4 | 30.8 | 28.9 |
| 1064 | 216000_PM_at | — | — | 0.000733449 | 0.0335891 | 33.8 | 28.8 | 24.2 |
| 1065 | 225651_PM_at | UBE2E2 | ubiquitin-conjugating enzyme E2E 2 (UBC4/5 homolog, yeast) | 0.000735351 | 0.0336446 | 178.7 | 226.0 | 265.1 |
| 1066 | 209566_PM_at | INSIG2 | insulin induced gene 2 | 0.000737382 | 0.0336959 | 51.0 | 88.7 | 79.6 |
| 1067 | 234135_PM_x_at | — | — | 0.000737857 | 0.0336959 | 51.0 | 51.9 | 54.6 |
| 1068 | 212908_PM_at | DNAJC16 | DnaJ (Hsp40) homolog, subfamily C, member 16 | 0.000740783 | 0.0337979 | 225.1 | 188.2 | 173.3 |
| 1069 | 212158_PM_at | SDC2 | syndecan 2 | 0.000741594 | 0.0338032 | 20.7 | 20.5 | 34.6 |
| 1070 | 242652_PM_at | — | — | 0.00074305 | 0.0338277 | 13.5 | 11.6 | 11.6 |
| 1071 | 240478_PM_at | — | — | 0.00074352 | 0.0338277 | 176.2 | 129.2 | 132.6 |
| 1072 | 44790_PM_s_at | C13orf18 | chromosome 13 open reading frame 18 | 0.000744289 | 0.0338311 | 452.2 | 473.1 | 696.4 |
| 1073 | 233270_PM_x_at | — | — | 0.000746251 | 0.0338887 | 83.1 | 61.5 | 62.7 |
| 1074 | 239740_PM_at | ETV6 | ets variant 6 | 0.000753532 | 0.0341875 | 97.5 | 60.9 | 66.4 |
| 1075 | 215588_PM_x_at | RIOK3 | RIO kinase 3 (yeast) | 0.000754615 | 0.0342048 | 473.9 | 368.9 | 409.2 |
| 1076 | 202536_PM_at | CHMP2B | chromatin modifying protein 2B | 0.000755843 | 0.0342286 | 111.7 | 163.4 | 167.2 |
| 1077 | 243963_PM_at | SDCCAG8 | Serologically defined colon cancer antigen 8 | 0.000758246 | 0.034298 | 234.5 | 183.6 | 179.2 |
| 1078 | 222378_PM_at | — | — | 0.000758784 | 0.034298 | 39.0 | 22.5 | 24.9 |
| 1079 | 215553_PM_x_at | — | — | 0.000760604 | 0.0343484 | 21.9 | 17.8 | 18.8 |
| 1080 | 239651_PM_at | ANAPC5 | anaphase promoting complex subunit 5 | 0.000762903 | 0.0344203 | 27.5 | 20.7 | 21.2 |
| 1081 | 1562528_PM_at | — | — | 0.000764376 | 0.0344549 | 97.0 | 67.3 | 41.5 |
| 1082 | 239748_PM_x_at | OCIAD1 | OCIA domain containing 1 | 0.000766272 | 0.0345084 | 930.4 | 716.6 | 775.3 |
| 1083 | 238595_PM_at | — | — | 0.000771117 | 0.0346946 | 269.3 | 167.7 | 171.4 |
| 1084 | 240465_PM_at | C4orf32 | chromosome 4 open reading frame 32 | 0.0007729 | 0.0347427 | 20.0 | 15.6 | 15.2 |
| 1085 | 236327_PM_at | — | — | 0.000773651 | 0.0347444 | 157.1 | 119.1 | 121.3 |
| 1086 | 243410_PM_at | — | — | 0.000774723 | 0.0347605 | 70.9 | 55.2 | 50.7 |
| 1087 | 232588_PM_at | STAG1 | stromal antigen 1 | 0.000776932 | 0.0348276 | 55.5 | 40.0 | 36.5 |
| 1088 | 242457_PM_at | — | — | 0.000779275 | 0.0349005 | 137.5 | 64.9 | 58.7 |
| 1089 | 207953_PM_at | — | — | 0.000780244 | 0.0349118 | 18.6 | 14.9 | 14.7 |
| 1090 | 215287_PM_at | LOC100288939 | Similar to hCG1987955 | 0.000782993 | 0.0350027 | 238.6 | 180.7 | 179.6 |
| 1091 | 1560794_PM_at | — | — | 0.000787684 | 0.0351801 | 13.2 | 10.4 | 11.3 |
| 1092 | 232565_PM_at | — | — | 0.000790598 | 0.0352779 | 36.6 | 28.1 | 25.2 |
| 1093 | 222169_PM_x_at | SH2D3A | SH2 domain containing 3A | 0.000793064 | 0.0353556 | 14.2 | 12.6 | 11.8 |
| 1094 | 244868_PM_at | — | — | 0.000794252 | 0.0353762 | 33.5 | 22.8 | 22.1 |
| 1095 | 201311_PM_s_at | SH3BGRL | SH3 domain binding glutamic acid-rich protein like | 0.000797082 | 0.0354698 | 830.9 | 1084.3 | 1071.6 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
| --- | --- | --- | --- | --- | --- | --- | --- | --- |
| 1096 | 1568815_PM_a_at | DDX50 | DEAD (Asp-Glu-Ala-Asp) box polypeptide 50 | 0.00079804 | 0.03548 | 122.3 | 86.7 | 91.9 |
| 1097 | 227163_PM_at | GSTO2 | glutathione S-transferase omega 2 | 0.000814076 | 0.03616 | 14.7 | 12.5 | 13.5 |
| 1098 | 212460_PM_at | C14orf147 | chromosome 14 open reading frame 147 | 0.000820682 | 0.0364202 | 90.2 | 137.8 | 134.3 |
| 1099 | 1569053_PM_at | AP3M2 | adaptor-related protein complex 3, mu 2 subunit | 0.00082218 | 0.0364535 | 20.4 | 17.2 | 16.8 |
| 1100 | 242407_PM_at | — | — | 0.00082641 | 0.0365795 | 537.1 | 400.3 | 365.6 |
| 1101 | 239946_PM_at | — | — | 0.000826524 | 0.0365795 | 317.5 | 187.7 | 188.9 |
| 1102 | 215070_PM_x_at | RABGAP1 | RAB GTPase activating protein 1 | 0.000827856 | 0.0366052 | 11.5 | 9.7 | 10.3 |
| 1103 | 233884_PM_at | HIVEP3 | human immunodeficiency virus type I enhancer binding protein 3 | 0.000832504 | 0.0367699 | 31.8 | 25.8 | 18.1 |
| 1104 | 217843_PM_s_at | MED4 | mediator complex subunit 4 | 0.000833089 | 0.0367699 | 196.9 | 248.0 | 257.6 |
| 1105 | 238944_PM_at | ZNF404 | Zinc finger protein 404 | 0.000835718 | 0.0368525 | 34.7 | 24.3 | 23.2 |
| 1106 | 1557688_PM_at | — | — | 0.000837575 | 0.036901 | 546.6 | 314.2 | 328.6 |
| 1107 | 230885_PM_at | SPG7 | spastic paraplegia 7 (pure and complicated autosomal recessive) | 0.000838625 | 0.0369139 | 372.5 | 277.2 | 282.1 |
| 1108 | 221268_PM_s_at | SGPP1 | sphingosine-1-phosphate phosphatase 1 | 0.000839543 | 0.0369253 | 25.1 | 41.9 | 39.5 |
| 1109 | 244581_PM_at | — | — | 0.00084432 | 0.0370975 | 29.7 | 22.6 | 21.0 |
| 1110 | 215626_PM_at | — | — | 0.000846447 | 0.0371575 | 13.3 | 11.3 | 10.4 |
| 1111 | 218446_PM_s_at | FAM18B1 | family with sequence similarity 18, member B1 | 0.000848307 | 0.0371994 | 68.2 | 108.6 | 120.4 |
| 1112 | 203414_PM_at | MMD | monocyte to macrophage differentiation-associated | 0.000849571 | 0.0371994 | 452.7 | 712.2 | 689.2 |
| 1113 | 237218_PM_at | — | — | 0.000849691 | 0.0371994 | 82.8 | 53.8 | 54.7 |
| 1114 | 222553_PM_x_at | OXR1 | oxidation resistance 1 | 0.00085174 | 0.0372556 | 100.8 | 160.4 | 169.3 |
| 1115 | 242824_PM_at | — | — | 0.000854784 | 0.0373427 | 34.5 | 24.5 | 23.7 |
| 1116 | 206551_PM_x_at | KLHL24 | kelch-like 24 (Drosophila) | 0.000855873 | 0.0373427 | 211.6 | 156.3 | 174.8 |
| 1117 | 210260_PM_s_at | TNFAIP8 | tumor necrosis factor, alpha-induced protein 8 | 0.000856031 | 0.0373427 | 528.5 | 780.3 | 666.8 |
| 1118 | 242156_PM_at | — | — | 0.00086286 | 0.0375636 | 15.8 | 11.6 | 11.5 |
| 1119 | 244571_PM_s_at | TTC12 | Tetratricopeptide repeat domain 12 | 0.000863136 | 0.0375636 | 14.5 | 11.4 | 11.2 |
| 1120 | 233302_PM_at | — | — | 0.000863406 | 0.0375636 | 217.7 | 146.6 | 75.8 |
| 1121 | 1558236_PM_at | — | — | 0.000866834 | 0.0376791 | 287.5 | 220.0 | 226.6 |
| 1122 | 212887_PM_at | SEC23A | Sec23 homolog A (S. cerevisiae) | 0.00087007 | 0.0377662 | 162.7 | 225.6 | 212.1 |
| 1123 | 208694_PM_at | PRKDC | protein kinase, DNA-activated, catalytic polypeptide | 0.00087039 | 0.0377662 | 310.8 | 194.2 | 200.2 |
| 1124 | 239917_PM_at | VPS8 | Vacuolar protein sorting 8 homolog (S. cerevisiae) | 0.00087152 | 0.0377705 | 261.2 | 174.0 | 187.7 |
| 1125 | 228645_PM_at | SNHG9 | small nucleolar RNA host gene 9 (non-protein coding) | 0.000872038 | 0.0377705 | 23.9 | 21.1 | 17.5 |
| 1126 | 236007_PM_at | AKAP10 | A kinase (PRKA) anchor protein 10 | 0.000873781 | 0.0378124 | 759.7 | 582.0 | 627.1 |
| 1127 | 234604_PM_at | — | — | 0.000876504 | 0.0378965 | 76.3 | 38.0 | 39.8 |
| 1128 | 244290_PM_at | — | — | 0.000882117 | 0.0380845 | 21.3 | 15.0 | 15.4 |
| 1129 | 203983_PM_at | TSNAX | translin-associated factor X | 0.000882415 | 0.0380845 | 239.3 | 365.9 | 374.5 |
| 1130 | 225519_PM_at | PPP4R2 | protein phosphatase 4, regulatory subunit 2 | 0.000885487 | 0.0380901 | 258.8 | 370.4 | 427.5 |
| 1131 | 227766_PM_at | UG4 | ligase IV, DNA, ATP-dependent | 0.00088588 | 0.0380901 | 22.7 | 37.2 | 39.7 |
| 1132 | 242646_PM_at | — | — | 0.000885928 | 0.0380901 | 249.4 | 193.5 | 181.7 |
| 1133 | 215750_PM_at | KIAA1659 | KIAA1659 protein | 0.000886213 | 0.0380901 | 21.6 | 16.9 | 15.5 |
| 1134 | 225222_PM_at | HIAT1 | hippocampus abundant transcript 1 | 0.000886801 | 0.0380901 | 479.9 | 584.0 | 600.6 |
| 1135 | 240238_PM_at | — | — | 0.000887234 | 0.0380901 | 116.7 | 78.0 | 73.5 |
| 1136 | 243876_PM_at | — | — | 0.000889423 | 0.0381505 | 23.3 | 18.7 | 17.0 |
| 1137 | 216263_PM_s_at | NGDN | neuroguidin, EIF4E binding protein | 0.000890647 | 0.0381694 | 25.4 | 20.3 | 18.6 |
| 1138 | 215330_PM_at | — | — | 0.000895074 | 0.038306 | 43.2 | 27.1 | 23.7 |
| 1139 | 1561720_PM_at | RECQL5 | RecQ protein-like 5 | 0.000895407 | 0.038306 | 15.4 | 12.6 | 12.4 |
| 1140 | 232583_PM_at | — | — | 0.000897151 | 0.0383382 | 247.3 | 164.7 | 142.8 |
| 1141 | 1558996_PM_at | FOXP1 | forkhead box P1 | 0.000897734 | 0.0383382 | 243.0 | 177.1 | 166.9 |
| 1142 | 215615_PM_x_at | — | — | 0.000900021 | 0.0384022 | 14.7 | 12.6 | 13.6 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1143 | 238800_PM_s_at | ZCCHC6 | Zinc finger, CCHC domain containing 6 | 0.000901045 | 0.0384123 | 561.9 | 379.1 | 373.7 |
| 1144 | 217856_PM_at | RBM8A | RNA binding motif protein 8A | 0.000902061 | 0.038422 | 240.2 | 196.3 | 196.1 |
| 1145 | 208370_PM_s_at | RCAN1 | regulator of calcineurin 1 | 0.000904627 | 0.0384976 | 56.1 | 81.4 | 72.8 |
| 1146 | 222262_PM_s_at | ETNK1 | ethanolamine kinase 1 | 0.000905546 | 0.0385031 | 34.9 | 47.7 | 50.2 |
| 1147 | 224870_PM_at | KIAA0114 | KIAA0114 | 0.000910077 | 0.038662 | 132.2 | 114.3 | 77.9 |
| 1148 | 244490_PM_at | — | — | 0.000914068 | 0.0387977 | 17.0 | 15.1 | 12.5 |
| 1149 | 233223_PM_at | — | — | 0.000916204 | 0.0388545 | 229.8 | 126.8 | 132.5 |
| 1150 | 241294_PM_at | — | — | 0.000917347 | 0.0388566 | 78.9 | 57.4 | 53.2 |
| 1151 | 237119_PM_at | — | — | 0.000917848 | 0.0388566 | 275.7 | 172.7 | 157.4 |
| 1152 | 54632_PM_at | THADA | thyroid adenoma associated | 0.000918721 | 0.0388598 | 65.8 | 54.9 | 46.8 |
| 1153 | 215151_PM_at | DOCK10 | dedicator of cytokinesis 10 | 0.000919627 | 0.0388644 | 68.3 | 52.4 | 43.4 |
| 1154 | 222719_PM_s_at | PDGFC | platelet derived growth factor C | 0.000923078 | 0.0389764 | 10.0 | 11.9 | 12.8 |
| 1155 | 231890_PM_at | — | — | 0.000929908 | 0.0392308 | 91.0 | 61.5 | 63.0 |
| 1156 | 1560706_PM_at | — | — | 0.000934795 | 0.0394027 | 813.7 | 489.7 | 487.1 |
| 1157 | 1562236_PM_at | MYST4 | MYST histone acetyltransferase (monocytic leukemia) 4 | 0.000935599 | 0.0394027 | 16.7 | 14.7 | 13.4 |
| 1158 | 37079_PM_at | NUS1P3 | nuclear undecaprenyl pyrophosphate synthase 1 homolog (*S. cerevisiae*) pseudogene 3 | 0.000936954 | 0.0394257 | 9.2 | 10.9 | 10.2 |
| 1159 | 241331_PM_at | SKAP2 | Src kinase associated phosphoproteln 2 | 0.000937938 | 0.039433 | 24.9 | 16.4 | 22.9 |
| 1160 | 209187_PM_at | DR1 | down-regulator of transcription 1, TBP-binding (negative cofactor 2) | 0.030939306 | 0.0394565 | 334.6 | 522.1 | 505.2 |
| 1161 | 228181_PM_at | SLC30A1 | solute carrier family 30 (zinc transporter), member 1 | 0.000940396 | 0.0394683 | 27.7 | 39.3 | 38.1 |
| 1162 | 226901_PM_at | C17orf58 | chromosome 17 open reading frame 58 | 0.000942438 | 0.0395199 | 19.8 | 26.8 | 25.8 |
| 1163 | 39313_PM_at | WNK1 | WNK lysine deficient protein kinase 1 | 0.000944928 | 0.0395903 | 113.9 | 80.5 | 75.3 |
| 1164 | 242279_PM_at | — | — | 0.000947662 | 0.0396562 | 124.3 | 86.5 | 82.8 |
| 1165 | 223134_PM_at | BBX | bobby sox homolog (*Drosophila*) | 0.000948129 | 0.0396562 | 594.6 | 470.1 | 457.6 |
| 1166 | 204738_PM_s_at | KRIT1 | KRIT1, ankyrin repeat containing | 0.000950724 | 0.0397306 | 41.2 | 41.2 | 34.0 |
| 1167 | 233914_PM_s_at | SBF2 | SET binding factor 2 | 0.00095246 | 0.0397369 | 221.5 | 144.0 | 159.3 |
| 1168 | 239449_PM_at | — | — | 0.000952504 | 0.0397369 | 37.2 | 22.9 | 23.0 |
| 1169 | 1561166_PM_a_at | — | — | 0.000956757 | 0.0398802 | 30.6 | 21.5 | 21.2 |
| 1170 | 235786_PM_at | — | — | 0.000963166 | 0.040113 | 228.1 | 176.8 | 165.5 |
| 1171 | 1568986_PM_x_at | PIGT | phosphatidylinositol glycan anchor biosynthesis, class T | 0.000967031 | 0.0402396 | 22.7 | 18.0 | 19.7 |
| 1172 | 233800_PM_at | — | — | 0.000969773 | 0.0403192 | 207.8 | 148.8 | 142.8 |
| 1173 | 208663_PM_s_at | TTC3 | tetratricopeptide repeat domain 3 | 0.000977441 | 0.0405812 | 454.5 | 378.8 | 313.8 |
| 1174 | 1556646_PM_at | — | — | 0.00097774 | 0.0405812 | 104.7 | 78.1 | 73.0 |
| 1175 | 213852_PM_at | RBM8A | RNA binding motif protein 8A | 0.000978667 | 0.0405851 | 408.4 | 313.7 | 313.5 |
| 1176 | 210145_PM_at | PLA2G4A | phospholipase A2, group IVA (cytosolic, calcium-dependent) | 0.000984729 | 0.0408018 | 50.8 | 84.4 | 84.4 |
| 1177 | 225770_pM_at | RSPRY1 | ring finger and SPRY domain containing 1 | 0.000988575 | 0.0408945 | 233.6 | 203.8 | 193.3 |
| 1178 | 234981_PM_x_at | CMBL | carboxymethylenebutenolidase homolog (*Pseudomonas*) | 0.000988861 | 0.0408945 | 1572.4 | 1302.0 | 1387.2 |
| 1179 | 235444_PM_at | FOXP1 | forkhead box P1 | 0.000990226 | 0.0408945 | 426.6 | 299.7 | 316.1 |
| 1180 | 218595_PM_s_at | HEATR1 | HEAT repeat containing 1 | 0.000990634 | 0.0408945 | 131.9 | 97.8 | 101.0 |
| 1181 | 242874_PM_at | — | — | 0.000991162 | 0.0408945 | 32.6 | 23.7 | 18.1 |
| 1182 | 228315_PM_at | ZMAT3 | zinc finger, matrin-type 3 | 0.000992797 | 0.0409273 | 651.6 | 538.8 | 516.1 |
| 1183 | 215757_PM_at | PRKDC | Protein kinase, DNA-activated, catalytic polypeptide | 0.000998001 | 0.041107 | 29.5 | 15.8 | 17.5 |
| 1184 | 215597_PM_x_at | — | — | 0.00100129 | 0.0412077 | 13.8 | 11.9 | 12.2 |
| 1185 | 1555842_PM_at | CYTH2 | cytohesin 2 | 0.00100876 | 0.04148 | 15.2 | 12.0 | 12.1 |
| 1186 | 1556305_PM_at | — | — | 0.0010118 | 0.04157 | 400.4 | 248.7 | 281.5 |
| 1187 | 1569597_PM_at | — | — | 0.00101421 | 0.0416339 | 53.3 | 47.0 | 34.4 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1188 | 232614_PM_at | — | — | 0.00101542 | 0.0416485 | 134.2 | 69.5 | 48.3 |
| 1189 | 206821_PM_x_at | AGFG2 | ArfGAP with FG repeats 2 | 0.00101641 | 0.041654 | 11.0 | 11.1 | 12.4 |
| 1190 | 229078_PM_s_at | KIAA1704 /// LOC100507773 | KIAA1704 /// hypothetical LOC100507773 | 0.00102065 | 0.0417784 | 128.1 | 106.6 | 89.3 |
| 1191 | 1559822_PM_s_at | MTDH | metadherin | 0.00102116 | 0.0417784 | 135.0 | 117.7 | 99.5 |
| 1192 | 206567_PM_s_at | PHF20 | PHD finger protein 20 | 0.00102394 | 0.041857 | 379.0 | 287.3 | 287.7 |
| 1193 | 218496_PM_at | RNASEH1 | ribonuclease H1 | 0.00102602 | 0.0419069 | 100.7 | 86.0 | 68.6 |
| 1194 | 214917_PM_at | PRKAA1 | protein kinase, AMP-activated, alpha 1 catalytic subunit | 0.0010283 | 0.0419648 | 148.0 | 103.7 | 105.4 |
| 1195 | 215063_PM_x_at | LRRC40 | leucine rich repeat containing 40 | 0.00103399 | 0.0421379 | 415.2 | 351.3 | 361.9 |
| 1196 | 217982_PM_s_at | MORF4L1 | mortality factor 4 like 1 | 0.00103427 | 0.0421379 | 2083.6 | 2398.1 | 2340.4 |
| 1197 | 201769_PM_at | CLINT1 | clathrin interactor 1 | 0.00103627 | 0.0421841 | 427.8 | 569.7 | 594.9 |
| 1198 | 244687_PM_at | DBT | dihydrolipoamide branched chain transacylase E2 | 0.00103809 | 0.0422064 | 49.0 | 41.3 | 34.0 |
| 1199 | 221264_PM_s_at | TARDBP | TAR DNA binding protein | 0.00103855 | 0.0422064 | 406.9 | 328.6 | 302.5 |
| 1200 | 241242_PM_at | — | — | 0.00104186 | 0.0423056 | 198.4 | 130.9 | 143.4 |
| 1201 | 215310_PM_at | APC | adenomatous polyposis coli | 0.00104337 | 0.0423316 | 227.1 | 157.6 | 168.5 |
| 1202 | 238231_PM_at | NFYC | Nuclear transcription factor Y, gamma | 0.00104517 | 0.0423427 | 98.2 | 66.4 | 62.2 |
| 1203 | 238863_PM_x_at | — | — | 0.00104538 | 0.0423427 | 20.3 | 16.7 | 17.3 |
| 1204 | 1561310_PM_at | — | — | 0.0010478 | 0.0424054 | 10.7 | 9.4 | 10.1 |
| 1205 | 238560_PM_at | CALCOCO2 | calcium binding and coiled-coil domain 2 | 0.0010503 | 0.0424713 | 146.3 | 94.4 | 98.3 |
| 1206 | 243546_PM_at | — | — | 0.00105358 | 0.0425687 | 95.8 | 69.2 | 64.2 |
| 1207 | 244674_PM_at | — | — | 0.00105727 | 0.0426823 | 33.6 | 22.0 | 23.0 |
| 1208 | 236321_PM_at | FAM200B | family with sequence similarity 200, member B | 0.00105871 | 0.0427051 | 75.1 | 108.0 | 114.6 |
| 1209 | 203628_PM_at | IGF1R | insulin-like growth factor 1 receptor | 0.00106019 | 0.0427294 | 442.5 | 240.2 | 246.7 |
| 1210 | 244312_PM_at | — | — | 0.00106163 | 0.0427602 | 414.4 | 295.2 | 313.4 |
| 1211 | 215589_PM_at | — | — | 0.0010636 | 0.0427784 | 15.4 | 12.4 | 11.4 |
| 1212 | 203283_PM_s_at | HS2ST1 | heparan sulfate 2-O-sulfotransferase 1 | 0.00106404 | 0.0427784 | 46.3 | 55.0 | 61.5 |
| 1213 | 217873_PM_at | CAB39 | calcium binding protein 39 | 0.00106547 | 0.042788 | 901.3 | 1106.4 | 1107.1 |
| 1214 | 243423_PM_at | — | — | 0.00106721 | 0.042788 | 115.9 | 86.4 | 73.8 |
| 1215 | 218195_PM_at | C6orf211 | chromosome 6 open reading frame 211 | 0.00106818 | 0.042788 | 193.8 | 286.2 | 278.4 |
| 1216 | 216751_PM_at | — | — | 0.00106819 | 0.042788 | 19.1 | 15.7 | 15.7 |
| 1217 | 226119_PM_at | PCMTD1 | protein-L-isoaspartate (D-aspartate) O-methyltransferase domain containing 1 | 0.00106929 | 0.042788 | 363.2 | 622.9 | 612.1 |
| 1218 | 240621_PM_at | — | — | 0.0010696 | 0.042788 | 21.6 | 18.0 | 18.0 |
| 1219 | 236610_PM_at | — | — | 0.00107052 | 0.042788 | 43.8 | 30.3 | 26.5 |
| 1220 | 1555446_PM_s_at | TRAPPC10 | trafficking protein particle complex 10 | 0.00107184 | 0.042788 | 270.7 | 178.4 | 175.9 |
| 1221 | 238468_PM_at | TNRC6B | trinucleotide repeat containing 6B | 0.00107218 | 0.042788 | 494.2 | 355.2 | 363.6 |
| 1222 | 222699_PM_s_at | PLEKHF2 | pleckstrin homology domain containing, family F (with FYVE domain) member 2 | 0.00107435 | 0.0428128 | 69.9 | 110.8 | 101.8 |
| 1223 | 233193_PM_x_at | INTS4 | integrator complex subunit 4 | 0.00107456 | 0.0428128 | 13.9 | 11.9 | 12.5 |
| 1224 | 227270_PM_at | FAM200B | family with sequence similarity 200, member B | 0.00108465 | 0.0431514 | 64.3 | 91.5 | 106.1 |
| 1225 | 217653_PM_x_at | — | — | 0.00108483 | 0.0431514 | 47.2 | 37.5 | 39.9 |
| 1226 | 212126_PM_at | CBX5 | chromobox homolog 5 | 0.00108729 | 0.043214 | 156.4 | 112.9 | 124.7 |
| 1227 | 240326_PM_at | — | — | 0.00108962 | 0.0432385 | 182.3 | 103.5 | 119.0 |
| 1228 | 232307_PM_at | — | — | 0.00108968 | 0.0432385 | 113.5 | 64.6 | 59.1 |
| 1229 | 239232_PM_at | MSI2 | Musashi homolog 2 (*Drosophila*) | 0.00109848 | 0.0435522 | 39.6 | 28.7 | 28.2 |
| 1230 | 1552343_PM_s_at | PDE7A | phosphodiesterase 7A | 0.00109961 | 0.0435615 | 51.0 | 35.9 | 35.9 |
| 1231 | 1557553_PM_at | PPP1R12B | protein phosphatase 1, regulatory (inhibitor) subunit 12B | 0.00110324 | 0.0436698 | 182.7 | 94.7 | 102.2 |
| 1232 | 236814_PM_at | MDM4 | Mdm4 p53 binding protein homolog (mouse) | 0.00110559 | 0.0437273 | 1429.5 | 1127.2 | 1112.4 |
| 1233 | 234428_PM_at | — | — | 0.00110678 | 0.0437389 | 13.1 | 10.0 | 10.5 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1234 | 222640_PM_at | DNMT3A | DNA(cytosine-5-)-methyltransferase 3 alpha | 0.00110857 | 0.0437741 | 93.3 | 73.9 | 71.7 |
| 1235 | 212027_PM_at | RBM25 | RNA binding motif protein 25 | 0.0011165 | 0.0440516 | 702.5 | 556.5 | 540.7 |
| 1236 | 210561_PM_s_at | WSB1 | WD repeat and SOC5 box-containing 1 | 0.00111899 | 0.0441141 | 991.0 | 1310.4 | 1331.4 |
| 1237 | 1570089_PM_at | — | — | 0.0011224 | 0.0441774 | 24.2 | 20.6 | 18.8 |
| 1238 | 241913_PM_at | — | — | 0.00112241 | 0.0441774 | 56.1 | 35.6 | 34.1 |
| 1239 | 202194_PM_at | TMED5 | transmembrane emp24 protein transport domain containing 5 | 0.00112677 | 0.0442901 | 705.1 | 1045.9 | 972.3 |
| 1240 | 207630_PM_s_at | CREM | cAMP responsive element modulator | 0.00112709 | 0.0442901 | 28.1 | 37.5 | 39.2 |
| 1241 | 237839_PM_at | — | — | 0.00113444 | 0.044543 | 26.4 | 15.7 | 13.6 |
| 1242 | 226276_PM_at | TMEM167A | transmembrane protein 167A | 0.00113546 | 0.0445471 | 426.3 | 579.1 | 594.3 |
| 1243 | 234609_PM_at | — | — | 0.00114012 | 0.044682 | 23.3 | 16.4 | 16.3 |
| 1244 | 1570210_PM_x_at | PPP6R2 | protein phosphatase 6, regulatory subunit 2 | 0.00114073 | 0.044682 | 37.7 | 28.3 | 27.6 |
| 1245 | 232628_PM_at | — | — | 0.00114327 | 0.0447326 | 334.1 | 202.5 | 202.2 |
| 1246 | 203921_PM_at | CHST2 | carbohydrate (N-acetylglucosamine-6-O) sulfotransferase 2 | 0.00114386 | 0.0447326 | 235.8 | 301.3 | 363.2 |
| 1247 | 225700_PM_at | GLCCI1 | glucocorticoid induced transcript 1 | 0.00114929 | 0.0449089 | 39.4 | 29.6 | 27.0 |
| 1248 | 222589_PM_at | NLK | nemo-like kinase | 0.00115377 | 0.0449844 | 118.3 | 159.0 | 160.3 |
| 1249 | 235894_PM_at | — | — | 0.00115378 | 0.0449844 | 117.3 | 86.7 | 98.0 |
| 1250 | 241993_PM_x_at | — | — | 0.00115399 | 0.0449844 | 389.1 | 290.4 | 301.5 |
| 1251 | 233473_PM_x_at | — | — | 0.00115584 | 0.0450205 | 974.0 | 689.3 | 713.7 |
| 1252 | 224984_PM_at | NFAT5 | nuclear factor of activated T-cells 5, tonicity-responsive | 0.00116222 | 0.0452328 | 857.3 | 694.2 | 743.5 |
| 1253 | 1570531_PM_at | — | — | 0.00116466 | 0.0452916 | 12.4 | 10.5 | 12.0 |
| 1254 | 234326_PM_at | — | — | 0.0011656 | 0.045292 | 337.1 | 194.8 | 209.7 |
| 1255 | 222444_PM_at | ARMCX3 | armadillo repeat containing, X-linked 3 | 0.00116672 | 0.0452994 | 24.2 | 32.1 | 37.0 |
| 1256 | 243792_PM_x_at | PTPN13 | Protein tyrosine phosphatase, non-receptor type 13 (APO-1/CD95 (Fas)-associated phospha | 0.0011703 | 0.0454022 | 19.1 | 15.6 | 16.6 |
| 1257 | 205202_PM_at | PCMT1 | protein-L-isoaspartate (D-aspartate) O-methyltransferase | 0.00117229 | 0.0454433 | 509.3 | 727.1 | 742.4 |
| 1258 | 243739_PM_at | — | — | 0.00117713 | 0.0455946 | 62.6 | 40.9 | 40.3 |
| 1259 | 215000_PM_s_at | FEZ2 | fasciculation and elongation protein zeta 2 (zygin II) | 0.00118371 | 0.0458131 | 286.2 | 368.4 | 385.7 |
| 1250 | 1569815_PM_x_at | STRN | striatin, calmodulin binding protein | 0.00118601 | 0.0458656 | 28.4 | 19.4 | 20.0 |
| 1261 | 207365_PM_x_at | USP34 | ubiquitin specific peptidase 34 | 0.0011908 | 0.0460096 | 258.2 | 201.7 | 206.2 |
| 1262 | 205849_PM_s_at | UQCRB | ubiquinol-cytochrome c reductase binding protein | 0.00119162 | 0.0460096 | 151.4 | 304.8 | 294.7 |
| 1263 | 210743_PM_s_at | CDC14A | CDC14 cell division cycle 14 homolog A (*S. cerevisiae*) | 0.00119405 | 0.0460669 | 21.4 | 17.3 | 14.7 |
| 1264 | 237180_PM_at | PSME4 | Proteasome (prosome, macropain) activator subunit 4 | 0.00119818 | 0.0461896 | 133.8 | 95.9 | 109.5 |
| 1265 | 206056_PM_x_at | SPN | sialophorin | 0.00120053 | 0.0462437 | 422.4 | 352.8 | 366.3 |
| 1256 | 234159_PM_at | — | — | 0.00120174 | 0.0462537 | 82.6 | 57.7 | 55.6 |
| 1267 | 224104_PM_at | — | — | 0.00120531 | 0.0463545 | 9.8 | 9.7 | 11.1 |
| 1268 | 219694_PM_at | FAM105A | family with sequence similarity 105, member A | 0.00120711 | 0.0463871 | 123.2 | 175.8 | 167.3 |
| 1269 | 237184_PM_at | — | — | 0.001209 | 0.0464218 | 26.6 | 20.2 | 19.7 |
| 1270 | 204011_PM_at | SPRY2 | sprouty homolog 2 (*Drosophila*) | 0.00121023 | 0.0464218 | 11.0 | 14.5 | 13.6 |
| 1271 | 218303_PM_x_at | KRCC1 | lysine-rich coiled-coil 1 | 0.00121087 | 0.0464218 | 165.2 | 258.0 | 253.6 |
| 1272 | 1559391_PM_s_at | — | — | 0.00121924 | 0.0467059 | 740.8 | 414.6 | 457.1 |
| 1273 | 225837_PM_at | C12orf32 | chromosome 12 open reading frame 32 | 0.00122486 | 0.0468451 | 36.3 | 53.4 | 40.6 |
| 1274 | 232469_PM_x_at | C1orf191 | chromosome 1 open reading frame 191 | 0.0012259 | 0.0468451 | 92.0 | 77.4 | 71.0 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1275 | 237216_PM_at | — | — | 0.00122711 | 0.0468451 | 23.5 | 17.6 | 17.0 |
| 1276 | 1559282_PM_at | — | — | 0.00122737 | 0.0468451 | 28.0 | 21.0 | 21.3 |
| 1277 | 1554148_PM_a_at | SLC33A1 | solute carrier family 33 (acetyl-CoA transporter), member 1 | 0.00122768 | 0.0468451 | 14.7 | 20.1 | 16.8 |
| 1278 | 228793_PM_at | JMJD1C | jumonji domain containing 1C | 0.00122969 | 0.0468593 | 994.7 | 644.1 | 725.0 |
| 1279 | 242611_PM_at | — | — | 0.00123041 | 0.0468593 | 16.4 | 13.4 | 13.5 |
| 1280 | 230086_PM_at | FNBP1 | formin binding protein 1 | 0.00123107 | 0.0468593 | 18.6 | 15.0 | 14.5 |
| 1281 | 215212_PM_at | — | — | 0.0012319 | 0.0468593 | 122.8 | 79.5 | 79.0 |
| 1282 | 230099_PM_at | — | — | 0.00123347 | 0.0468824 | 370.8 | 275.0 | 251.1 |
| 1283 | 232555_PM_at | CREB5 | cAMP responsive element binding protein 5 | 0.00124092 | 0.0471288 | 1517.2 | 924.2 | 1042.4 |
| 1284 | 241036_PM_at | — | — | 0.00124392 | 0.047206 | 224.0 | 169.5 | 158.1 |
| 1285 | 230270_PM_at | PRPF38B | PRP38 pre-mRNA processing factor 38 (yeast) domain containing B | 0.00124844 | 0.0473407 | 806.4 | 593.9 | 635.5 |
| 1286 | 235730_PM_at | — | — | 0.00125167 | 0.0474262 | 239.8 | 174.3 | 192.8 |
| 1287 | 234423_PM_x_at | — | — | 0.00125281 | 0.0474325 | 280.4 | 230.9 | 229.0 |
| 1288 | 224751_PM_at | PL-5283 | PL-5283 protein | 0.00125969 | 0.047656 | 617.3 | 876.2 | 848.8 |
| 1289 | 241368_PM_at | PLIN5 | perilipin 5 | 0.00126593 | 0.0478549 | 123.5 | 84.5 | 136.3 |
| 1290 | 232284_PM_at | PSMD6 | Proteasome (prosome, macropain) 26S subunit, non-ATPase, 6 | 0.0012684 | 0.0479111 | 198.2 | 124.3 | 123.6 |
| 1291 | 233909_PM_at | — | — | 0.00127099 | 0.0479718 | 12.7 | 10.8 | 10.8 |
| 1292 | 213164_PM_at | SLC5A3 | solute carrier family 5 (sodium/myo-inositol cotransporter), member 3 | 0.00127396 | 0.0480466 | 613.0 | 462.3 | 491.5 |
| 1293 | 1553644_PM_at | C14orf49 | chromosome 14 open reading frame 49 | 0.00127584 | 0.0480603 | 10.5 | 10.1 | 11.7 |
| 1294 | 241750_PM_x_at | — | — | 0.00127776 | 0.0481155 | 109.8 | 72.7 | 81.1 |
| 1295 | 1560926_PM_at | — | — | 0.00127908 | 0.048128 | 249.4 | 159.7 | 191.7 |
| 1296 | 1559589_PM_a_at | — | — | 0.00128515 | 0.0483151 | 28.9 | 21.7 | 22.7 |
| 1297 | 237626_PM_at | — | — | 0.00129452 | 0.0486338 | 295.5 | 211.0 | 216.1 |
| 1298 | 226353_PM_at | SPPL2A | signal peptide peptidase-like 2A | 0.00130512 | 0.0489943 | 789.5 | 991.8 | 943.1 |
| 1299 | 211277_PM_x_at | APP | amyloid beta (A4) precursor protein | 0.00130823 | 0.0490732 | 24.3 | 21.9 | 21.7 |
| 1300 | 1569450_PM_at | CAP2A2 | capping protein (actin filament) muscle Z-line, alpha 2 | 0.00131042 | 0.0491176 | 30.2 | 21.4 | 23.8 |
| 1301 | 225600_PM_at | C8orf83 | chromosome 8 open reading frame 83 | 0.00131519 | 0.0492585 | 59.8 | 94.1 | 96.0 |
| 1302 | 206154_PM_at | RLBP1 | retinaldehyde binding protein 1 | 0.00131658 | 0.0492727 | 12.5 | 11.0 | 12.4 |
| 1303 | 1561633_PM_at | HMGA2 | high mobility group AT-hook 2 | 0.00132318 | 0.0494817 | 12.7 | 11.4 | 10.8 |
| 1304 | 207436_PM_x_at | KIAA0894 | KIAA0894 protein | 0.00132539 | 0.0495263 | 354.6 | 306.9 | 318.7 |
| 1305 | 1557350_PM_at | G3BP1 | GTPase activating protein (SH3 domain) binding protein 1 | 0.00132688 | 0.049544 | 44.8 | 32.4 | 29.4 |
| 1306 | 202169_PM_s_at | AASDHPPT | aminoadipate-semialdehyde dehydrogenase-phosphopantetheinyl transferase | 0.00132799 | 0.0495474 | 178.6 | 260.1 | 242.2 |
| 1307 | 232210_PM_at | — | — | 0.00132904 | 0.0495487 | 391.2 | 221.5 | 144.3 |
| 1308 | 1558691_PM_a_at | DOCK4 | dedicator of cytokinesis 4 | 0.00133158 | 0.0496054 | 13.8 | 12.1 | 11.3 |
| 1309 | 209833_PM_at | CRADD | CASP2 and RIPK1 domain containing adaptor with death domain | 0.00133577 | 0.04967 | 35.8 | 45.8 | 42.0 |
| 1310 | 1554963_PM_at | — | — | 0.00133636 | 0.04967 | 13.8 | 11.1 | 11.8 |
| 1311 | 234131_PM_at | — | — | 0.00133696 | 0.04967 | 106.2 | 76.1 | 76.5 |
| 1312 | 1559054_PM_a_at | — | — | 0.00133739 | 0.04967 | 68.0 | 47.8 | 50.7 |
| 1313 | 242467_PM_at | — | — | 0.00134002 | 0.0496908 | 280.3 | 218.5 | 215.2 |
| 1314 | 238733_PM_at | — | — | 0.00134142 | 0.0496908 | 143.7 | 88.7 | 105.1 |
| 1315 | 221808_PM_at | RAB9A | RAB9A, member RAS oncogene family | 0.00134149 | 0.0496908 | 307.4 | 375.4 | 369.8 |
| 1316 | 201830_PM_s_at | NET1 | neuroepithelial cell transforming 1 | 0.00134203 | 0.0496908 | 18.7 | 24.9 | 18.2 |
| 1317 | 217016_PM_x_at | TMEM212 | transmembrane protein 212 | 0.00134421 | 0.0497337 | 18.0 | 14.8 | 17.0 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1318 | 212721_PM_at | SREK1 | splicing regulatory glutamine/lysine-rich protein 1 | 0.00134616 | 0.0497681 | 105.3 | 175.8 | 182.7 |
| 1319 | 224105_PM_x_at | — | — | 0.00134808 | 0.0498013 | 56.2 | 47.9 | 51.4 |
| 1320 | 232978_PM_at | — | — | 0.00135736 | 0.0501061 | 27.9 | 24.4 | 19.4 |
| 1321 | 236370_PM_at | — | — | 0.00136023 | 0.0501741 | 40.7 | 30.8 | 28.3 |
| 1322 | 208246_PM_x_at | — | — | 0.00136454 | 0.050295 | 1858.8 | 1458.0 | 1576.1 |
| 1323 | 239701_PM_at | — | — | 0.00136972 | 0.0504477 | 202.0 | 111.2 | 112.8 |
| 1324 | 224644_PM_at | — | — | 0.0013769 | 0.0506184 | 521.7 | 670.3 | 638.6 |
| 1325 | 212408_PM_at | TOR1AIP1 | torsin A interacting protein 1 | 0.00137762 | 0.0506184 | 1217.4 | 1446.6 | 1448.5 |
| 1326 | 205998_PM_x_at | CYP3A4 | cytochrome P450, family 3, subfamily A, polypeptide 4 | 0.00137763 | 0.0506184 | 21.6 | 18.8 | 20.6 |
| 1327 | 224416_PM_s_at | MED28 | mediator complex subunit 28 | 0.00137851 | 0.0506184 | 66.6 | 85.5 | 90.3 |
| 1328 | 220694_PM_at | ASAP1-IT | ASAP1 intronic transcript (non-protein coding) | 0.00137967 | 0.0506229 | 314.9 | 161.1 | 189.3 |
| 1329 | 1556728_PM_at | — | — | 0.00138078 | 0.0506255 | 75.9 | 54.2 | 47.9 |
| 1330 | 236417_PM_at | — | — | 0.00138772 | 0.0508134 | 188.3 | 124.2 | 115.5 |
| 1331 | 205401_PM_at | AGPS | alkylglycerone phosphate synthase | 0.00138799 | 0.0508134 | 26.7 | 36.6 | 28.6 |
| 1332 | 1561130_PM_at | C12orf51 | chromosome 12 open reading frame 51 | 0.00139089 | 0.0508306 | 29.8 | 22.8 | 23.3 |
| 1333 | 220410_PM_s_at | CAMSAP1 | calmodulin regulated spectrin-associated protein 1 | 0.00139091 | 0.0508306 | 21.8 | 16.6 | 16.2 |
| 1334 | 219095_PM_at | JMJD7-PLA264B /// PLA2G4B | JMJD7-PLA2G4B readthrough /// phospholipase A2, group IVB (cytosolic) | 0.00139159 | 0.0508305 | 25.6 | 20.9 | 20.2 |
| 1335 | 209096_PM_at | UBE2V2 | ubiquitin-conjugating enzyme E2 variant 2 | 0.00139729 | 0.0510006 | 89.4 | 132.0 | 126.3 |
| 1336 | 218559_PM_s_at | MAFB | v-maf musculoaponeurotic fibrosarcoma oncogene homolog B (avian) | 0.00140241 | 0.0511491 | 592.3 | 883.7 | 939.1 |
| 1337 | 242793_PM_at | — | — | 0.00140523 | 0.0512136 | 50.0 | 32.8 | 31.7 |
| 1338 | 242008_PM_at | — | — | 0.00140833 | 0.0512516 | 1505.6 | 1047.9 | 1116.4 |
| 1339 | 228913_PM_at | LOC100190939 | hypothetical LOC100190939 | 0.00140855 | 0.0512516 | 42.8 | 29.7 | 29.3 |
| 1340 | 223336_PM_s_at | RAB18 | RAB18, member RAS oncogene family | 0.00140948 | 0.0512516 | 229.6 | 362.7 | 345.9 |
| 1341 | 225147_PM_at | CYTH3 | cytohesin 3 | 0.00141048 | 0.0512516 | 32.7 | 36.9 | 45.9 |
| 1342 | 208278_PM_s_at | — | — | 0.00141367 | 0.0513293 | 53.2 | 31.8 | 33.6 |
| 1343 | 233678_PM_at | — | — | 0.00141576 | 0.0513669 | 14.5 | 12.9 | 12.1 |
| 1344 | 244357_PM_at | — | — | 0.00141804 | 0.0514113 | 621.3 | 320.1 | 324.5 |
| 1345 | 240205_PM_x_at | — | — | 0.00141966 | 0.0514318 | 115.2 | 85.3 | 88.1 |
| 1346 | 226493_PM_at | KCTD18 | potassium channel tetramerisation domain containing 18 | 0.00142551 | 0.0516054 | 121.5 | 161.6 | 157.9 |
| 1347 | 216745_PM_x_at | — | — | 0.00142692 | 0.0516181 | 39.0 | 32.0 | 34.4 |
| 1348 | 233007_PM_at | — | — | 0.00142903 | 0.05162 | 60.1 | 43.8 | 43.0 |
| 1349 | 1568594_PM_s_at | TRIM52 | tripartite motif-containing 52 | 0.00143095 | 0.05162 | 92.5 | 86.8 | 71.2 |
| 1350 | 1554564_PM_a_at | SPPL3 | signal peptide peptidase 3 | 0.00143162 | 0.05162 | 29.5 | 23.7 | 24.3 |
| 1351 | 225210_PM_s_at | FAM103A1 | family with sequence similarity 103, member A1 | 0.00143168 | 0.05162 | 444.6 | 500.7 | 522.9 |
| 1352 | 243587_PM_x_at | — | — | 0.00143227 | 0.05162 | 85.5 | 61.0 | 59.5 |
| 1353 | 1563075_PM_s_at | — | — | 0.00143366 | 0.0516319 | 678.1 | 437.5 | 494.0 |
| 1354 | 236703_PM_at | NT5C2 | 5'-nucteotidase, cytosolic II | 0.00143781 | 0.0517431 | 425.1 | 268.3 | 297.8 |
| 1355 | 239227_PM_at | — | — | 0.00144381 | 0.0519158 | 65.8 | 36.7 | 38.9 |
| 1356 | 244165_PM_at | C10orf18 | chromosome 10 open reading frame 18 | 0.00144474 | 0.0519158 | 161.6 | 97.3 | 90.3 |
| 1357 | 231087_PM_at | — | — | 0.00144663 | 0.0519454 | 35.7 | 30.6 | 25.4 |
| 1358 | 1560928_PM_at | LOC151657 | hypothetical protein LOC151657 | 0.00144829 | 0.0519667 | 42.0 | 32.2 | 31.3 |
| 1359 | 232031_PM_s_at | KIAA1632 | KIAA1632 | 0.00145151 | 0.0520286 | 33.8 | 24.3 | 24.0 |
| 1360 | 1570108_PM_at | — | — | 0.00145234 | 0.0520286 | 33.3 | 24.4 | 24.3 |
| 1361 | 203883_PM_s_at | RAB11FIP2 | RAB11 family Interacting protein 2 (class I) | 0.00145364 | 0.0520286 | 433.2 | 330.8 | 343.2 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1362 | 230489_PM_at | CD5 | CD5 molecule | 0.00145462 | 0.0520286 | 41.7 | 37.5 | 23.5 |
| 1363 | 242136_PM_x_at | MGC70870 | C-terminal binding protein 2 pseudogene | 0.00145553 | 0.0520286 | 35.7 | 42.5 | 47.0 |
| 1364 | 235288_PM_at | — | — | 0.00145642 | 0.0520286 | 209.1 | 145.5 | 158.8 |
| 1365 | 243016_PM_at | — | — | 0.00145891 | 0.052078 | 26.2 | 19.4 | 17.0 |
| 1366 | 222720_PM_x_at | C1orf27 | chromosome 1 open reading frame 27 | 0.00145994 | 0.052078 | 12.3 | 15.7 | 15.0 |
| 1367 | 236607_PM_at | — | — | 0.00146319 | 0.052145 | 86.5 | 64.5 | 64.7 |
| 1368 | 213056_PM_at | FRMD4B | FERM domain containing 4B | 0.00146422 | 0.052145 | 75.3 | 96.5 | 128.6 |
| 1369 | 1557895_PM_at | FLJ35934 | FLJ35934 | 0.00146503 | 0.052145 | 25.2 | 18.1 | 18.2 |
| 1370 | 218059_PM_at | ZNF706 | zinc finger protein 706 | 0.00147057 | 0.052304 | 824.7 | 1059.4 | 921.0 |
| 1371 | 238303_PM_at | STT3B | STT3, subunit of the oligosaccharyltransferase complex, homolog B (S. cerevisiae) | 0.00147382 | 0.0523813 | 57.8 | 43.7 | 37.9 |
| 1372 | 205140_PM_at | FPGT | fucose-1-phosphate guanylyltransferase | 0.00147672 | 0.0524307 | 29.9 | 47.3 | 47.5 |
| 1373 | 227916_PM_x_at | EXOSC3 | exosome component 3 | 0.00147736 | 0.0524307 | 219.2 | 275.0 | 268.7 |
| 1374 | 201973_PM_s_at | C7orf28B /// CCZ1 | chromosome 7 open reading frame 28B /// CC21 vacuolar protein trafficking and biogenesi | 0.00148545 | 0.0526794 | 809.5 | 979.5 | 901.4 |
| 1375 | 209455_PM_at | FBXW11 | F-box and WD repeat domain containing 11 | 0.00149798 | 0.0530851 | 129.5 | 150.0 | 146.2 |
| 1376 | 201865_PM_x_at | NR3C1 | nuclear receptor subfamily 3, group C, member 1 (glucocorticoid receptor) | 0.00150008 | 0.0531209 | 2013.9 | 1715.9 | 1694.7 |
| 1377 | 209228_PM_x_at | TUSC3 | tumor suppressor candidate 3 | 0.00150159 | 0.0531358 | 9.4 | 8.9 | 10.1 |
| 1378 | 240498_PM_at | — | — | 0.0015055 | 0.0532708 | 54.8 | 29.9 | 31.3 |
| 1379 | 230987_PM_at | — | — | 0.00150865 | 0.0533082 | 264.9 | 153.4 | 172.8 |
| 1380 | 240626_PM_at | — | — | 0.00150978 | 0.0533095 | 15.1 | 12.7 | 12.6 |
| 1381 | 231069_PM_at | — | — | 0.0015111 | 0.0533135 | 36.6 | 28.9 | 29.9 |
| 1382 | 214553_PM_s_at | ARPP19 | cAMP-regulated phosphoprotein, 19 kDa | 0.0015131 | 0.0533135 | 24.5 | 36.0 | 33.9 |
| 1383 | 1561060_PM_at | — | — | 0.00151345 | 0.0533135 | 11.6 | 9.9 | 10.9 |
| 1384 | 242256_PM_X_at | — | — | 0.00151427 | 0.0533135 | 34.1 | 26.5 | 31.1 |
| 1385 | 233017_PM_x_at | — | — | 0.00151651 | 0.0533487 | 141.5 | 120.1 | 130.7 |
| 1386 | 208073_PM_x_at | TTC3 | tetratricopeptide repeat domain 3 | 0.00151746 | 0.0533487 | 378.1 | 300.5 | 254.2 |
| 1387 | 223809_PM_at | RGS18 | regulator of G-protein signaling 18 | 0.00152081 | 0.0534279 | 1124.9 | 1686.1 | 1664.1 |
| 1388 | 236546_PM_at | — | — | 0.00152367 | 0.0534898 | 15.1 | 12.3 | 13.2 |
| 1389 | 1557300_PM_s_at | — | — | 0.00152525 | 0.0534991 | 45.8 | 33.1 | 31.9 |
| 1390 | 232744_PM_x_at | — | — | 0.00152613 | 0.0534991 | 147.6 | 89.9 | 84.2 |
| 1391 | 238783_PM_at | TMEM161B | transmembrane protein 161B | 0.0015277 | 0.0535156 | 158.6 | 125.3 | 119.1 |
| 1392 | 218107_PM_at | WDR26 | WD repeat domain 26 | 0.00153315 | 0.0536511 | 826.4 | 974.5 | 1036.8 |
| 1393 | 1558732_PM_at | MAP4K4 | mitogen-activated protein kinase kinase kinase kinase 4 | 0.00153377 | 0.0536511 | 244.7 | 154.4 | 174.4 |
| 1394 | 229360_PM_at | ZNF280B | zinc finger protein 280B | 0.00153761 | 0.0537469 | 15.3 | 12.5 | 12.1 |
| 1395 | 225324_PM_at | CRLS1 | cardiolipin synthase 1 | 0.00154301 | 0.053897 | 61.9 | 108.9 | 91.7 |
| 1396 | 209893_PM_s_at | FUT4 | fucosyltransferase 4 (alpha (1,3) fucosyltransferase, myeloid-specific) | 0.00154586 | 0.0539405 | 54.5 | 81.2 | 64.4 |
| 1397 | 1567045_PM_at | — | — | 0.00154647 | 0.0539405 | 33.2 | 24.5 | 25.5 |
| 1398 | 227986_PM_at | ZNF343 | zinc finger protein 343 | 0.0015482 | 0.0539622 | 17.5 | 14.0 | 14.8 |
| 1399 | 239788_PM_at | — | — | 0.00154927 | 0.05397 | 34.9 | 25.6 | 25.0 |
| 1400 | 241851_PM_x_at | LOC100130429 | hypothetical LOC100130429 | 0.00155064 | 0.05397 | 29.1 | 20.7 | 22.3 |
| 1401 | 232375_PM_at | — | — | 0.0015584 | 0.0541008 | 468.2 | 294.9 | 276.6 |
| 1402 | 217346_PM_at | LOC100293160 /// PPIA | peptlidyl-prolyl cis-trans isomerase A-like /// peptidylprolyl isomerase A (cyclophilin | 0.00155947 | 0.0541008 | 55.0 | 46.5 | 47.8 |
| 1403 | 226941_PM_at | ATF6 | activating transcription factor 6 | 0.00155955 | 0.0541008 | 622.1 | 497.8 | 535.6 |
| 1404 | 212749_PM_s_at | RCHY1 | ring finger and CHY zinc finger domain containing 1 | 0.00155965 | 0.0541008 | 197.3 | 276.9 | 253.5 |
| 1405 | 201944_PM_at | HEXB | hexosaminidase B (beta polypeptide) | 0.00155995 | 0.0541008 | 847.7 | 1061.3 | 1043.5 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1406 | 1570227_PM_at | — | — | 0.00156173 | 0.0541241 | 27.0 | 22.6 | 22.1 |
| 1407 | 217152_PM_at | — | — | 0.00156614 | 0.0542135 | 158.2 | 111.0 | 105.3 |
| 1408 | 211374_PM_x_at | — | — | 0.00156833 | 0.0542135 | 26.8 | 21.7 | 22.9 |
| 1409 | 210438_PM_x_at | TROVE2 | TROVE domain family, member 2 | 0.00156842 | 0.0542135 | 693.6 | 597.4 | 559.3 |
| 1410 | 222942_PM_s_at | TIAM2 | T-cell lymphoma invasion and metastasis 2 | 0.00156876 | 0.0542135 | 90.6 | 50.1 | 51.0 |
| 1411 | 236883_PM_at | — | — | 0.00157206 | 0.0542719 | 205.7 | 153.4 | 149.9 |
| 1412 | 216006_PM_at | — | — | 0.00157268 | 0.0542719 | 108.6 | 68.0 | 73.3 |
| 1413 | 1556359_PM_at | C6orf89 | Chromosome 6 open reading frame 89 | 0.00157408 | 0.0542724 | 54.2 | 40.5 | 41.7 |
| 1414 | 242171_PM_at | — | — | 0.00157492 | 0.0542724 | 15.5 | 12.6 | 13.4 |
| 1415 | 236941_PM_at | C22orf30 | chromosome 22 open reading frame 30 | 0.00157693 | 0.0543003 | 110.5 | 74.9 | 75.2 |
| 1416 | 232769_PM_at | — | — | 0.00157796 | 0.0543003 | 44.4 | 27.0 | 34.9 |
| 1417 | 212132_PM_at | LSM14A | LSM14A, SCD6 homolog A (S. cerevisiae) | 0.00158011 | 0.0543067 | 314.5 | 358.5 | 375.3 |
| 1418 | 224642_PM_at | FYTTD1 | forty-two-three domain containing 1 | 0.00158105 | 0.0543067 | 44.2 | 63.9 | 56.4 |
| 1419 | 201312_PM_s_at | SH3BGRL | SH3 domain binding glutamic acid-rich protein like | 0.00158149 | 0.0543057 | 2316.5 | 2827.1 | 2855.1 |
| 1420 | 228654_PM_at | SPIN4 | spindlin family, member 4 | 0.00159134 | 0.0545691 | 24.3 | 41.3 | 45.5 |
| 1421 | 232580_PM_x_at | — | — | 0.0015921 | 0.0545691 | 129.6 | 96.6 | 94.3 |
| 1422 | 205175_PM_x_at | ZNF222 | zinc finger protein 222 | 0.00159338 | 0.0545691 | 19.6 | 24.1 | 25.3 |
| 1423 | 208866_PM_at | CSNK1A1 | casein kinase 1, alpha 1 | 0.00159405 | 0.0545691 | 401.6 | 342.0 | 314.0 |
| 1424 | 218365_PM_s_at | DARS2 | aspartyl-tRNA synthetase 2, mitochondrial | 0.00159473 | 0.0545691 | 16.4 | 17.2 | 14.5 |
| 1425 | 236254_PM_at | VPS13B | vacuolar protein sorting 13 homolog B (yeast) | 0.00160153 | 0.0547633 | 1169.4 | 933.1 | 958.7 |
| 1426 | 244691_PM_at | SETD5 | SET domain containing 5 | 0.00160515 | 0.0548486 | 22.0 | 17.4 | 15.7 |
| 1427 | 1557529_PM_at | C12orf51 | chromosome 12 open reading frame 51 | 0.0016064 | 0.0548529 | 58.8 | 46.9 | 44.1 |
| 1428 | 228454_PM_at | LCOR | ligand dependent nuclear receptor compressor | 0.00161199 | 0.0550052 | 703.4 | 514.4 | 559.2 |
| 1429 | 243554_PM_at | — | — | 0.00161638 | 0.0551164 | 77.7 | 53.9 | 54.3 |
| 1430 | 221509_PM_at | DENR | density-regulated protein | 0.00162004 | 0.0551499 | 219.1 | 296.9 | 302.8 |
| 1431 | 237703_PM_at | — | — | 0.0016203 | 0.0551499 | 40.8 | 29.4 | 30.2 |
| 1432 | 205994_PM_at | ELK4 | ELK4, ETS-domain protein (SRF accessory protein 1) | 0.00162089 | 0.0551499 | 10.3 | 11.5 | 10.7 |
| 1433 | 227046_PM_at | SLC39A11 | solute carrier family 39 (metal ion transporter), member 11 | 0.00162189 | 0.0551499 | 62.4 | 87.0 | 77.7 |
| 1434 | 240527_PM_at | — | — | 0.00162319 | 0.0551556 | 71.1 | 52.2 | 54.9 |
| 1435 | 240154_PM_at | — | — | 0.00163371 | 0.0554633 | 1222.2 | 811.2 | 806.3 |
| 1436 | 1564773_PM_x_at | — | — | 0.00163452 | 0.0554633 | 20.0 | 17.0 | 16.3 |
| 1437 | 232341_PM_x_at | HABP4 | hyaluronan binding protein 4 | 0.00163784 | 0.0555373 | 28.7 | 20.8 | 19.4 |
| 1438 | 215595_PM_x_at | — | — | 0.00163972 | 0.0555623 | 29.2 | 23.4 | 25.2 |
| 1439 | 224452_PM_s_at | C7orf70 | chromosome 7 open reading frame 70 | 0.00164229 | 0.0555725 | 244.0 | 320.1 | 298.0 |
| 1440 | 243709_PM_at | SLC38A9 | solute carrier family 38, member 9 | 0.0016423 | 0.0555725 | 76.1 | 54.1 | 57.5 |
| 1441 | 236592_PM_at | — | — | 0.00164591 | 0.0556184 | 119.9 | 56.1 | 57.6 |
| 1442 | 236453_PM_at | — | — | 0.00164594 | 0.0556184 | 10.7 | 11.7 | 14.4 |
| 1443 | 242111_PM_at | METTL3 | methyltransferase like 3 | 0.00166042 | 0.0560644 | 33.3 | 25.6 | 23.6 |
| 1444 | 1560445_PM_x_at | ARHGEF1 | Rho guanine nucleotide exchange factor (GEF) 1 | 0.0016618 | 0.0560644 | 93.5 | 71.0 | 75.4 |
| 1445 | 239175_PM_at | — | — | 0.00166259 | 0.0560644 | 533.1 | 407.2 | 435.4 |
| 1446 | 243414_PM_at | PPIL2 | Peptidylprolyl isomerase (cyclophilin)-like 2 | 0.0016666 | 0.0561576 | 36.8 | 31.1 | 27.5 |
| 1447 | 232659_PM_at | — | — | 0.00166766 | 0.0561576 | 41.8 | 27.6 | 27.2 |
| 1448 | 201816_PM_s_at | GBAS | glioblastoma amplified sequence | 0.00167064 | 0.0562191 | 322.9 | 439.5 | 389.3 |
| 1449 | 225332_PM_at | LOC729082 | Hypothetical protein LOC729032 | 0.0016728 | 0.056253 | 684.2 | 569.3 | 532.4 |
| 1450 | 242106_PM_at | — | — | 0.00167411 | 0.0562582 | 52.7 | 30.1 | 31.5 |
| 1451 | 239173_PM_at | INADL | InaD-like (Drosophila) | 0.00167659 | 0.0563027 | 22.4 | 16.8 | 14.6 |
| 1452 | 1562194_PM_at | — | — | 0.00168148 | 0.0564239 | 389.6 | 240.5 | 242.9 |
| 1453 | 205931_PM_s_at | CREB5 | cAMP responsive element binding protein 5 | 0.0016834 | 0.0564239 | 1458.6 | 949.7 | 1263.1 |
| 1454 | 203347_PM_s_at | MTF2 | metal response element binding transcription factor 2 | 0.00168467 | 0.0564239 | 34.7 | 52.0 | 50.7 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1455 | 244181_PM_at | — | — | 0.0016858 | 0.0564239 | 82.8 | 61.8 | 58.4 |
| 1456 | 217586_PM_x_at | — | — | 0.00168599 | 0.0564239 | 23.3 | 18.5 | 19.1 |
| 1457 | 233369_PM_at | — | — | 0.00168731 | 0.0564293 | 589.3 | 362.9 | 442.4 |
| 1458 | 223169_PM_s_at | RHOU | ras homolog gene family, member U | 0.00169034 | 0.0565086 | 11.3 | 14.8 | 15.3 |
| 1459 | 232796_PM_at | — | — | 0.00169555 | 0.0566272 | 15.9 | 12.8 | 12.3 |
| 1460 | 212250_PM_at | MTDH | metadherin | 0.00169897 | 0.0566921 | 268.8 | 395.3 | 343.4 |
| 1461 | 227017_PM_at | ERICH1 | glutamate-rich 1 | 0.00169982 | 0.0566921 | 183.7 | 214.7 | 242.6 |
| 1462 | 1569730_PM_at | HEATR7B2 | HEAT repeat family member 7B2 | 0.00170215 | 0.056731 | 11.5 | 10.0 | 10.8 |
| 1463 | 240446_PM_at | — | — | 0.00170444 | 0.0567551 | 33.7 | 25.2 | 26.0 |
| 1464 | 239892_PM_at | — | — | 0.0017053 | 0.0567551 | 48.7 | 38.8 | 35.8 |
| 1465 | 240052_PM_at | ITPR1 | Inositol 1,4,5-triphosphate receptor, type 1 | 0.00170637 | 0.0567551 | 105.7 | 71.7 | 73.7 |
| 1466 | 244100_PM_at | — | — | 0.00171135 | 0.056882 | 29.4 | 22.5 | 23.2 |
| 1467 | 242608_PM_x_at | FAM161B | Family with sequence similarity 161, member B | 0.00171743 | 0.0569937 | 603.0 | 486.0 | 517.6 |
| 1468 | 216022_PM_at | — | — | 0.00171835 | 0.0569937 | 16.0 | 13.4 | 12.6 |
| 1469 | 238436_PM_s_at | ZNF805 | zinc finger protein 805 | 0.00171856 | 0.0569937 | 143.2 | 124.8 | 102.8 |
| 1470 | 200753_PM_x_at | SRSF2 | serine/arginine-rich spiking factor 2 | 0.00171939 | 0.0569937 | 162.5 | 218.7 | 197.1 |
| 1471 | 213922_PM_at | TTBK2 | tau tubulin kinase 2 | 0.00172865 | 0.0572617 | 164.7 | 119.5 | 127.7 |
| 1472 | 226729_PM_at | USP37 | ubiquitin specific peptidase 37 | 0.00173056 | 0.0572706 | 35.0 | 32.9 | 26.6 |
| 1473 | 204483_PM_at | ENO3 | enolase 3 (beta, muscle) | 0.00173146 | 0.0572706 | 15.3 | 13.5 | 12.9 |
| 1474 | 240260_PM_at | — | — | 0.00173258 | 0.0572706 | 45.6 | 34.2 | 31.8 |
| 1475 | 220720_PM_x_at | MZT2B | mitotic spindle organizing protein 2B | 0.00173362 | 0.0572706 | 150.8 | 118.6 | 118.7 |
| 1476 | 1562529_PM_s_at | — | — | 0.00173646 | 0.0573255 | 508.3 | 342.7 | 224.4 |
| 1477 | 1564736_PM_a_at | CASP12 | caspase 12 (gene/pseudogene) | 0.00173894 | 0.0573685 | 10.3 | 10.3 | 12.0 |
| 1478 | 228516_PM_at | CDAN1 | congenital dyserythropoietic anemia, type I | 0.00174063 | 0.0573854 | 51.1 | 44.5 | 38.4 |
| 1479 | 241995_PM_at | DGUOK | deoxyguanosine kinase | 0.00174243 | 0.0574059 | 37.8 | 28.6 | 28.5 |
| 1480 | 244594_PM_x_at | — | — | 0.00175136 | 0.0576159 | 78.1 | 59.4 | 61.6 |
| 1481 | 212190_PM_at | SERPINE2 | serpin peptidase inhibitor, clade E (nexin, plasminogen activator inhibitor type 1), me | 0.00175198 | 0.0576159 | 25.8 | 26.4 | 36.5 |
| 1482 | 243474_PM_at | — | — | 0.00175235 | 0.0576159 | 147.6 | 84.9 | 88.8 |
| 1483 | 216278_PM_at | — | — | 0.00175491 | 0.0576612 | 38.8 | 34.0 | 28.3 |
| 1484 | 234118_PM_at | — | — | 0.00175682 | 0.0576836 | 12.4 | 9.6 | 10.0 |
| 1485 | 242983_PM_at | — | — | 0.00175796 | 0.0576836 | 37.0 | 31.1 | 27.2 |
| 1486 | 213956_PM_at | CEP350 | centrosomal protein 350 kDa | 0.00176171 | 0.0577677 | 154.0 | 117.9 | 111.9 |
| 1487 | 232626_PM_at | — | — | 0.00176762 | 0.0578856 | 24.1 | 17.2 | 20.6 |
| 1488 | 236005_PM_at | — | — | 0.00176768 | 0.0578856 | 23.9 | 18.0 | 16.5 |
| 1489 | 222336_PM_at | C4orf34 | chromosome 4 open reading frame 34 | 0.00177041 | 0.0579315 | 22.6 | 15.2 | 17.7 |
| 1490 | 213317_PM_at | CLIC5 | chloride intracellular channel 5 | 0.00177146 | 0.0579315 | 14.6 | 12.5 | 11.7 |
| 1491 | 231377_PM_at | CXorf65 | chromosome X open reading frame 65 | 0.00177794 | 0.0580906 | 87.7 | 64.8 | 56.2 |
| 1492 | 215852_PM_x_at | C20orf117 | chromosome 20 open reading frame 117 | 0.00177871 | 0.0580906 | 13.9 | 12.2 | 12.5 |
| 1493 | 239778_PM_x_at | — | — | 0.0017819 | 0.0581223 | 67.7 | 45.2 | 46.6 |
| 1494 | 242732_PM_at | — | — | 0.00178484 | 0.0581223 | 38.6 | 24.2 | 25.0 |
| 1495 | 227523_PM_s_at | PHF20L1 | PHD finger protein 20-like 1 | 0.00178487 | 0.0581223 | 1104.7 | 904.2 | 905.0 |
| 1496 | 232344_PM_at | — | — | 0.00178515 | 0.0581223 | 112.5 | 76.2 | 76.8 |
| 1497 | 205438_PM_at | PTPN21 | protein tyrosine phosphatase, non-receptor type 21 | 0.00178672 | 0.0581223 | 9.7 | 9.7 | 11.6 |
| 1498 | 244208_PM_at | — | — | 0.00178756 | 0.0581223 | 26.7 | 18.7 | 19.4 |
| 1499 | 243860_PM_at | — | — | 0.00178803 | 0.0581223 | 157.5 | 104.9 | 113.1 |
| 1500 | 1561139_PM_at | — | — | 0.00179722 | 0.0583549 | 31.0 | 24.3 | 24.3 |
| 1501 | 231304_PM_at | PPP3R2 | protein phosphatase 3, regulatory subunit B, beta | 0.00179758 | 0.0583549 | 9.5 | 9.1 | 10.6 |
| 1502 | 230777_PM_s_at | PRDM15 | PR domain containing 15 | 0.0017995 | 0.0583783 | 43.9 | 35.9 | 33.0 |
| 1503 | 242664_PM_at | — | — | 0.00180506 | 0.0584844 | 11.6 | 9.9 | 9.6 |
| 1504 | 233399_PM_x_at | ZNF252 | Zinc finger protein 252 | 0.00180517 | 0.0584844 | 73.9 | 59.8 | 63.5 |
| 1505 | 1566166_PM_at | — | — | 0.00181697 | 0.0588276 | 27.6 | 21.2 | 20.1 |
| 1506 | 238548_PM_at | — | — | 0.00181899 | 0.0588287 | 20.6 | 15.4 | 16.4 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1507 | 225016_PM_at | APCDD1 | adenomatosis polyposis coil down-regulated 1 | 0.00182182 | 0.0588287 | 15.8 | 18.2 | 22.0 |
| 1508 | 244032_PM_at | — | — | 0.00182239 | 0.0588287 | 17.7 | 14.9 | 14.6 |
| 1509 | 202026_PM_at | SDHD | succinate dehydrogenase complex, subunit D, integral membrane protein | 0.00182256 | 0.0588287 | 403.6 | 505.0 | 510.6 |
| 1510 | 232466_PM_at | CUL4A | Cullin 4A | 0.00182304 | 0.0588287 | 16.7 | 16.3 | 13.3 |
| 1511 | 221566_PM_s_at | NOL3 | nucleolar protein 3 (apoptosis repressor with CARD domain) | 0.00182839 | 0.0589481 | 10.0 | 10.4 | 11.8 |
| 1512 | 1560342_PM_at | — | — | 0.00182916 | 0.0589481 | 51.7 | 32.7 | 34.1 |
| 1513 | 240593_PM_x_at | — | — | 0.00183593 | 0.0591167 | 21.4 | 14.8 | 15.7 |
| 1514 | 242968_PM_at | — | — | 0.00183682 | 0.0591167 | 354.7 | 260.4 | 265.7 |
| 1515 | 219892_PM_at | TM6SF1 | trans membrane 6 superfamily member 1 | 0.00184024 | 0.0591877 | 295.4 | 402.3 | 432.6 |
| 1516 | 230747_PM_s_at | TTC39C | tetratricopeptide repeat domain 39C | 0.0018479 | 0.0593924 | 72.8 | 57.6 | 45.9 |
| 1517 | 239223_PM_S_at | FBXL20 | F-box and leucine-rich repeat protein 20 | 0.00184921 | 0.0593924 | 124.3 | 87.3 | 81.9 |
| 1518 | 243819_PM_at | — | — | 0.00185026 | 0.0593924 | 593.4 | 471.6 | 404.2 |
| 1519 | 227133_PM_at | FAM199X | family with sequence similarity 199, X-linked | 0.0018569 | 0.0594225 | 120.2 | 146.3 | 158.7 |
| 1520 | 1557239_PM_at | BBX | bobby sox homolog (Drosophila) | 0.00185785 | 0.0594225 | 55.9 | 38.2 | 37.6 |
| 1521 | 230350_PM_at | — | — | 0.00185917 | 0.0594225 | 255.5 | 195.1 | 184.9 |
| 1522 | 221547_PM_at | PRPF18 | PRP18 pre-mRNA processing factor 18 homolog (S. cerevisiae) | 0.00185948 | 0.0594225 | 65.0 | 88.7 | 82.7 |
| 1523 | 214101_PM_s_at | NPEPPS | Aminopeptidase puromycin sensitive | 0.0018602 | 0.0594225 | 120.2 | 81.0 | 81.3 |
| 1524 | 221613_PM_s_at | ZFAND6 | zinc finger, AN1-type domain 6 | 0.00186232 | 0.0594225 | 479.2 | 578.4 | 589.9 |
| 1525 | 223288_PM_at | USP38 | ubiquitin specific peptidase 38 | 0.00186358 | 0.0594225 | 179.4 | 221.9 | 237.0 |
| 1526 | 239258_PM_at | — | — | 0.00186474 | 0.0594225 | 176.4 | 111.1 | 121.8 |
| 1527 | 239096_PM_at | — | — | 0.00186551 | 0.0594225 | 215.0 | 167.5 | 187.3 |
| 1528 | 81811_PM_at | — | — | 0.00186608 | 0.0594225 | 55.3 | 41.5 | 40.7 |
| 1529 | 231149_PM_s_at | ULK4 | unc-51-like kinase 4 (C. elegans) | 0.0018674 | 0.0594225 | 17.7 | 13.3 | 13.1 |
| 1530 | 236664_PM_at | AKT2 | v-akt murine thymoma viral oncogene homolog 2 | 0.00186813 | 0.0594225 | 28.9 | 24.1 | 22.8 |
| 1531 | 226322_PM_at | TMTC1 | transmembrane and tetratricopeptide repeat containing 1 | 0.00186893 | 0.0594225 | 46.2 | 92.9 | 143.5 |
| 1532 | 207923_PM_x_at | PAX8 | paired box 8 | 0.00186921 | 0.0594225 | 10.9 | 9.3 | 10.3 |
| 1533 | 244682_PM_at | CAMSAP1 | calmodulin regulated spectrin-associated protein 1 | 0.00186949 | 0.0594225 | 13.5 | 10.9 | 11.9 |
| 1534 | 243612_PM_at | NSD1 | nuclear receptor binding SET domain protein 1 | 0.00187215 | 0.0594609 | 148.1 | 110.2 | 117.1 |
| 1535 | 232205_PM_at | — | — | 0.00187314 | 0.0594609 | 53.3 | 39.8 | 39.2 |
| 1536 | 239186_PM_at | MGC39372 | serpin peptidase inhibitor, clade B (ovalbumin), member 9 pseudogene | 0.0018809 | 0.0596684 | 32.5 | 21.0 | 20.9 |
| 1537 | 240351_PM_at | — | — | 0.00188672 | 0.0598141 | 18.5 | 14.8 | 15.3 |
| 1538 | 209363_PM_s_at | MED21 | mediator complex subunit 21 | 0.00189018 | 0.059861 | 22.3 | 31.2 | 25.3 |
| 1539 | 236216_PM_at | — | — | 0.00189247 | 0.059861 | 76.6 | 42.3 | 45.1 |
| 1540 | 207730_PM_x_at | — | — | 0.0018927 | 0.059861 | 528.9 | 425.8 | 475.0 |
| 1541 | 210942_PM_s_at | ST3GAL6 | ST3 beta-galactoside alpha-2,3-sialyltransferase 6 | 0.00189461 | 0.059861 | 77.6 | 113.7 | 124.9 |
| 1542 | 203102_PM_s_at | MGAT2 | mannosyl (alpha-1,6-)-glycoprotein beta-1,2-N-acetylglucosaminyltransferase | 0.00189569 | 0.059861 | 302.8 | 410.8 | 387.0 |
| 1543 | 215057_PM_at | LOC100272228 | hypothetical LOC100272228 | 0.00189599 | 0.059861 | 49.5 | 34.6 | 35.9 |
| 1544 | 1569871_PM_at | LMF1 | lipase maturation factor 1 | 0.0018968 | 0.059861 | 29.9 | 23.1 | 24.2 |
| 1545 | 235990_PM_at | LOC100130987 | similar to hCG1815675 | 0.00190152 | 0.0599711 | 24.4 | 19.1 | 19.4 |
| 1546 | 222752_PM_s_at | TMEM206 | transmembrane protein 206 | 0.00190406 | 0.0600124 | 69.6 | 103.3 | 105.9 |
| 1547 | 242311_PM_x_at | — | — | 0.00190812 | 0.0600907 | 46.6 | 38.8 | 40.4 |
| 1548 | 232150_PM_at | — | — | 0.00190901 | 0.0600907 | 688.6 | 493.5 | 539.7 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1549 | 231247_PM_s_at | LOC727820 | Hypothetical protein LOC727820 | 0.00191175 | 0.0601381 | 87.0 | 61.5 | 68.7 |
| 1550 | 227626_PM_at | PAQR8 | progestin and adipoQ receptor family member VIII | 0.00191435 | 0.0601495 | 171.2 | 132.9 | 117.8 |
| 1551 | 212449_PM_s_at | LYPLA1 | lysophospholipase 1 | 0.00191734 | 0.0601495 | 730.3 | 1021.2 | 965.0 |
| 1552 | 235616_PM_at | TSHZ2 | teashirt zinc finger homeobox 2 | 0.00191751 | 0.0601495 | 16.9 | 12.5 | 12.9 |
| 1553 | 225445_PM_at | UBN2 | ubinuclein 2 | 0.00191834 | 0.0601495 | 220.9 | 171.9 | 186.6 |
| 1554 | 234151_PM_at | — | — | 0.00191915 | 0.0601495 | 1955.4 | 1313.1 | 1262.3 |
| 1555 | 208661_PM_s_at | TTC3 | tetratricopeptide repeat domain 3 | 0.00191952 | 0.0601495 | 329.1 | 269.7 | 222.6 |
| 1556 | 242195_PM_x_at | NUMBL | numb homolog (Drosophila)-like | 0.00192097 | 0.0601562 | 610.5 | 523.6 | 550.5 |
| 1557 | 229483_PM_at | — | — | 0.00192503 | 0.060238 | 251.4 | 176.0 | 178.2 |
| 1558 | 241268_PM_x_at | — | — | 0.00192669 | 0.060238 | 54.4 | 45.1 | 46.7 |
| 1559 | 243153_PM_at | CDK5RAP2 | CDK5 regulatory subunit associated protein 2 | 0.00192729 | 0.060238 | 19.2 | 16.9 | 15.0 |
| 1560 | 208610_PM_s_at | SRRM2 | serine/arginine repetitive matrix 2 | 0.00193003 | 0.060285 | 1239.8 | 918.2 | 933.7 |
| 1561 | 238159_PM_at | — | — | 0.00193206 | 0.0602852 | 48.9 | 31.9 | 34.6 |
| 1562 | 204028_PM_s_at | RABGAP1 | RAB GTPase activating protein 1 | 0.00193251 | 0.0602852 | 268.4 | 228.4 | 239.8 |
| 1563 | 219463_PM_at | C20orf103 | chromosome 20 open reading frame 103 | 0.0019351 | 0.0603273 | 18.6 | 20.4 | 26.0 |
| 1564 | 230998_PM_at | — | — | 0.00193805 | 0.0603503 | 176.2 | 124.6 | 145.8 |
| 1565 | 219471_PM_at | C13orf18 | chromosome 13 open reading frame 18 | 0.00193993 | 0.0603503 | 336.4 | 358.0 | 496.3 |
| 1566 | 244434_PM_at | GPR82 | 6 protein-coupled receptor 82 | 0.00194032 | 0.0603503 | 15.5 | 18.4 | 28.1 |
| 1567 | 1564424_PM_at | — | — | 0.00194079 | 0.0603503 | 18.0 | 14.4 | 14.5 |
| 1568 | 201100_PM_s_at | USP9X | ubiquitin specific peptidase 9, X-linked | 0.00194416 | 0.0603603 | 1396.1 | 1129.4 | 1179.0 |
| 1569 | 1569409_PM_x_at | — | — | 0.00194437 | 0.0603603 | 111.5 | 87.2 | 89.8 |
| 1570 | 244726_PM_at | — | — | 0.00194483 | 0.0603603 | 253.6 | 152.8 | 152.8 |
| 1571 | 1552370_PM_at | C4orf33 | chromosome 4 open reading frame 33 | 0.0019501 | 0.0604854 | 27.3 | 40.9 | 41.9 |
| 1572 | 220113_PM_x_at | POLR1B | polymerase (RNA) I polypeptide 8, 128 kDa | 0.00195433 | 0.0605705 | 74.9 | 59.3 | 62.8 |
| 1573 | 226035_PM_at | USP31 | ubiquitin specific peptidase 31 | 0.00195533 | 0.0605705 | 38.0 | 29.3 | 27.7 |
| 1574 | 244019_PM_at | — | — | 0.00196076 | 0.0606229 | 50.9 | 34.0 | 34.4 |
| 1575 | 241686_PM_x_at | — | — | 0.0019612 | 0.0606229 | 33.2 | 27.5 | 29.5 |
| 1576 | 220768_PM_s_at | CSNK1G3 | casein kinase 1, gamma 3 | 0.00196126 | 0.0606229 | 51.2 | 73.4 | 78.2 |
| 1577 | 214241_PM_at | NDUFB8 | NADH dehydrogenase (ubiquinone) 1 beta subcomplex, 8, 19 kDa | 0.001962 | 0.0606229 | 102.2 | 85.3 | 72.9 |
| 1578 | 216524_PM_x_at | — | — | 0.00196509 | 0.0606799 | 222.8 | 180.3 | 198.3 |
| 1579 | 215110_PM_at | MBL1P | mannose-binding lectin (protein A) 1, pseudogene | 0.00196859 | 0.0607495 | 9.7 | 9.2 | 10.4 |
| 1580 | 222983_PM_s_at | PAIP2 | poly(A) binding protein interacting protein 2 | 0.00197803 | 0.0610022 | 946.3 | 1132.8 | 1164.7 |
| 1581 | 224584_PM_at | C20orf30 | chromosome 20 open reading frame 30 | 0.00198083 | 0.0610514 | 1214.2 | 1518.9 | 1382.1 |
| 1582 | 1555392_PM_at | LOC100128868 | Testin-related protein TRG | 0.00198345 | 0.061092 | 196.5 | 140.7 | 141.3 |
| 1583 | 1562736_PM_at | LHX9 | LIM homeobox 9 | 0.00199467 | 0.0613988 | 8.3 | 8.3 | 93 |
| 1584 | 217743_PM_s_at | TMEM30A | transmembrane protein 30A | 0.00199593 | 0.0613988 | 434.6 | 564.3 | 616.8 |
| 1585 | 217985_PM_s_at | BAZ1A | bromodomain adjacent to zinc finger domain, 1A | 0.00199906 | 0.0614563 | 1612.3 | 1280.7 | 1389.1 |
| 1586 | 210539_PM_at | TTLL5 | tubulin tyrosine ligase-like family, member 5 | 0.00200268 | 0.0615287 | 16.5 | 12.6 | 13.6 |
| 1587 | 229364_PM_at | — | — | 0.00200899 | 0.0616837 | 68.1 | 48.3 | 42.9 |
| 1588 | 225507_PM_at | SFRS1B | splicing factor, arginine/serine-rich 18 | 0.00201916 | 0.0619569 | 1153.7 | 931.0 | 862.7 |
| 1589 | 211893_PM_x_at | CD6 | CD6 molecule | 0.00202531 | 0.0620482 | 17.9 | 17.1 | 12.7 |
| 1590 | 1566959_PM_at | — | — | 0.00202547 | 0.0620482 | 193.6 | 105.4 | 107.9 |
| 1591 | 241920_PM_x_at | SPG11 | spastic paraplegia 11 (autosomal recessive) | 0.00202662 | 0.0620482 | 28.0 | 22.0 | 22.2 |
| 1592 | 221071_PM_at | — | — | 0.00202821 | 0.0620482 | 38.7 | 29.4 | 29.0 |
| 1593 | 233411_PM_at | — | — | 0.0020285 | 0.0620482 | 193.0 | 137.8 | 99.2 |
| 1594 | 1557684_PM_at | ZNF286A | zinc finger protein 286A | 0.00203037 | 0.0620664 | 28.6 | 25.6 | 20.5 |
| 1595 | 240775_PM_at | — | — | 0.00203278 | 0.0620778 | 21.6 | 15.4 | 15.8 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1596 | 231288_PM_at | CCDC88C | coiled-coil domain containing 88C | 0.00203329 | 0.0620778 | 97.8 | 81.1 | 68.8 |
| 1597 | 224933_PM_s_at | JMJD1C | jumonji domain containing 1C | 0.00203726 | 0.06216 | 2710.7 | 1952.4 | 2061.8 |
| 1598 | 235927_PM_at | XPO1 | exportin 1 (CRM1 homolog, yeast) | 0.00204212 | 0.0622693 | 169.3 | 129.5 | 108.4 |
| 1599 | 200829_PM_x_at | ZNF207 | zinc finger protein 207 | 0.00204523 | 0.0623252 | 492.3 | 600.0 | 596.9 |
| 1600 | 225239_PM_at | — | | 0.00204808 | 0.0623651 | 1535.8 | 882.2 | 876.0 |
| 1601 | 224838_PM_at | FOXP1 | forkhead box P1 | 0.0020491 | 0.0623651 | 1161.4 | 888.0 | 915.3 |
| 1602 | 202540_PM_s_at | HMGCR | 3-hydroxy-3-methylglutaryl-CoA reductase | 0.00205127 | 0.0623922 | 117.9 | 144.8 | 163.6 |
| 1603 | 210905_PM_x_at | POU5F1P4 | POU class 5 homeobox 1 pseudogene 4 | 0.00205558 | 0.0624842 | 12.7 | 10.5 | 11.1 |
| 1604 | 226566_PM_at | FAM102B | family with sequence similarity 102, member B | 0.00205805 | 0.0625203 | 155.4 | 219.4 | 221.5 |
| 1605 | 221756_PM_at | PIK3IP1 | phosphoinositide-3-kinase interacting protein 1 | 0.00206058 | 0.0625582 | 315.4 | 242.7 | 187.0 |
| 1606 | 241988_PM_x_at | — | | 0.0020683 | 0.0627535 | 30.5 | 22.7 | 21.8 |
| 1607 | 200777_PM_s_at | BZW1 | basic leucine zipper and W2 domains 1 | 0.00207506 | 0.0628699 | 590.6 | 782.6 | 676.4 |
| 1608 | 214402_PM_s_at | SFI1 | Sfi1 homolog, spindle assembly associated (yeast) | 0.00207518 | 0.0628699 | 30.9 | 25.5 | 22.7 |
| 1609 | 1556203_PM_a_at | SRGAP2 | SLIT-ROBO Rho GTPase activating protein 2 | 0.00207655 | 0.0628699 | 246.0 | 183.7 | 157.1 |
| 1610 | 232184_PM_at | ALS2 | amyotrophic lateral sclerosis 2 (juvenile) | 0.0020773 | 0.0628699 | 9.5 | 10.3 | 11.4 |
| 1611 | 218659_PM_at | ASXL2 | additional sex combs like 2 (*Drosophila*) | 0.00207993 | 0.0629105 | 485.2 | 373.5 | 403.3 |
| 1612 | 233289_PM_at | — | | 0.00208249 | 0.0629488 | 66.7 | 49.3 | 45.9 |
| 1613 | 204137_PM_at | GPR137B | G protein-coupled receptor 137B | 0.00208751 | 0.0630614 | 106.7 | 150.6 | 169.9 |
| 1614 | 226050_PM_at | TMCO3 | transmembrane and coiled-coil domains 3 | 0.00209242 | 0.0631705 | 253.6 | 311.0 | 353.6 |
| 1615 | 224377_PM_s_at | RAB18 | RAB18, member RAS oncogene family | 0.0020964 | 0.0632399 | 367.1 | 499.6 | 515.7 |
| 1616 | 216695_PM_s_at | TNKS | tankyrase, TRF1-interacting ankyrin-related ADP-ribose polymerase | 0.00209731 | 0.0632399 | 13.0 | 11.1 | 11.9 |
| 1617 | 205586_PM_x_at | VGF | VGF nerve growth factor inducible | 0.00210124 | 0.0632482 | 11.1 | 9.6 | 9.6 |
| 1618 | 1556657_PM_at | — | | 0.00210147 | 0.0632482 | 221.5 | 133.9 | 124.3 |
| 1619 | 202147_PM_s_at | IFRD1 | Interferon-related developmental regulator 1 | 0.00210148 | 0.0632482 | 283.9 | 372.9 | 436.2 |
| 1620 | 200098_PM_s_at | ANAPC5 | anaphase promoting complex subunit 5 | 0.00211129 | 0.0635042 | 688.6 | 614.3 | 556.9 |
| 1621 | 204403_PM_x_at | FAM115A | family with sequence similarity 115, member A | 0.00212582 | 0.0538777 | 28.1 | 24.0 | 25.7 |
| 1622 | 1561263_PM_at | C1QTNF3 | C1q and tumor necrosis factor related protein 3 | 0.00212633 | 0.0638777 | 14.6 | 12.3 | 11.9 |
| 1623 | 209442_PM_x_at | ANK3 | ankyrin 3, node of Ranvier (ankyrin G) | 0.00212886 | 0.0639143 | 29.8 | 18.7 | 16.4 |
| 1624 | 232646_PM_at | TTC17 | Tetratricopeptide repeat domain 17 | 0.00213201 | 0.0639695 | 37.5 | 27.3 | 26.4 |
| 1625 | 213615_PM_at | LPCAT3 | Lysophosphatidylcholine acyltransferase 3 | 0.00213472 | 0.0640114 | 21.7 | 19.8 | 16.8 |
| 1626 | 212642_PM_s_at | HIVEP2 | human immunodeficiency virus type 1 enhancer binding protein 2 | 0.00213796 | 0.064059 | 75.5 | 55.7 | 55.2 |
| 1627 | 235740_PM_at | MCTP1 | multiple C2 domains, transmembrane 1 | 0.00213967 | 0.064059 | 109.0 | 168.0 | 163.5 |
| 1628 | 221145_PM_at | — | | 0.00214126 | 0.064059 | 10.9 | 10.3 | 12.1 |
| 1629 | 236924_PM_at | — | | 0.00214209 | 0.064059 | 45.1 | 30.4 | 28.4 |
| 1630 | 1560443_PM_at | — | | 0.00214288 | 0.064059 | 246.7 | 150.8 | 169.6 |
| 1631 | 244301_PM_at | — | | 0.0021528 | 0.0643161 | 8.9 | 10.0 | 10.1 |
| 1632 | 225992_PM_at | MLLT10 | myeloid/lymphoid or mixed-lineage leukemia (trithorax homolog, *Drosophila*); translocate | 0.00215843 | 0.0643965 | 51.9 | 74.9 | 64.5 |
| 1633 | 221786_PM_at | C6orf120 | chromosome 6 open reading frame 120 | 0.00215863 | 0.0643965 | 162.4 | 223.2 | 214.2 |
| 1634 | 1552711_PM_a_at | CYB5D1 | cytochrome b5 domain containing 1 | 0.00216069 | 0.0643965 | 36.4 | 28.8 | 28.9 |
| 1635 | 242844_PM_at | — | | 0.00216078 | 0.0643965 | 14.6 | 17.7 | 20.8 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1636 | 207892_PM_at | CD40LG | CD40 ligand | 0.00216866 | 0.0645919 | 20.0 | 16.4 | 14.5 |
| 1637 | 237442_PM_at | — | — | 0.00217083 | 0.064617 | 671.6 | 502.7 | 522.2 |
| 1638 | 242428_PM_at | DCUN1D1 | DCN1, defective in cullin neddylation 1, domain containing 1 (*S. cerevisiae*) | 0.00217479 | 0.0646954 | 184.1 | 113.6 | 122.7 |
| 1639 | 1561927_PM_at | C3orf16 | chromosome 3 open reading frame 16 | 0.00218042 | 0.0648233 | 14.2 | 12.1 | 12.0 |
| 1640 | 215435_PM_at | — | — | 0.00218988 | 0.0650184 | 213.7 | 131.6 | 158.6 |
| 1641 | 235798_PM_at | TMEM170B | transmembrane protein 170B | 0.00219052 | 0.0650184 | 362.9 | 561.8 | 538.5 |
| 1642 | 222654_PM_at | IMPAD1 | inositol monophosphatase domain containing 1 | 0.00219198 | 0.0650184 | 25.7 | 37.4 | 38.8 |
| 1643 | 235984_PM_at | — | — | 0.00219232 | 0.0650184 | 296.8 | 235.1 | 242.2 |
| 1644 | 240156_PM_at | — | — | 0.00220135 | 0.0652465 | 131.5 | 63.9 | 72.5 |
| 1645 | 232991_PM_at | — | — | 0.00220964 | 0.0654524 | 85.9 | 59.2 | 56.7 |
| 1646 | 1569759_PM_at | — | — | 0.00221902 | 0.0656903 | 14.9 | 12.1 | 12.9 |
| 1647 | 221617_PM_at | TAF9B | TAF9B RNA polymerase II, TATA box binding protein (TBP)-associated factor, 31 kDa | 0.00222895 | 0.0659442 | 204.2 | 144.2 | 146.6 |
| 1648 | 229872_PM_s_at | LOC100132999 | hypothetical LOC100132999 | 0.00223246 | 0.0659972 | 943.4 | 778.9 | 743.2 |
| 1649 | 218718_PM_at | PDGFC | platelet derived growth factor C | 0.00223345 | 0.0659972 | 71.4 | 106.8 | 129.1 |
| 1650 | 1570439_PM_at | — | — | 0.00223614 | 0.066031 | 13.2 | 11.6 | 11.5 |
| 1651 | 203139_PM_at | DAPK1 | death-associated protein kinase 1 | 0.00223852 | 0.066031 | 276.5 | 370.6 | 396.6 |
| 1652 | 204177_PM_s_at | KLHL20 | kelch-like 20 (*Drosophila*) | 0.00223866 | 0.066031 | 66.4 | 66.5 | 54.7 |
| 1653 | 216245_PM_at | IL1RN | interleukin 1 receptor antagonist | 0.00224247 | 0.0661033 | 10.3 | 10.2 | 11.7 |
| 1654 | 202381_PM_at | ADAM9 | ADAM metallopeptidase domain 9 | 0.00224445 | 0.0661217 | 95.2 | 129.1 | 153.8 |
| 1655 | 226976_PM_at | KPNA6 | karyopherin alpha 6 (importin alpha 7) | 0.00224819 | 0.0661919 | 295.4 | 248.6 | 243.4 |
| 1656 | 205540_PM_s_at | RRAGB | Ras-related GTP binding B | 0.00224968 | 0.0661957 | 14.5 | 18.0 | 16.1 |
| 1657 | 215349_PM_at | BT8D18 | BTB (POZ) domain containing 18 | 0.00225601 | 0.0663004 | 25.3 | 19.4 | 20.4 |
| 1658 | 210281_PM_s_at | ZMYM2 | zinc finger, MYM-type 2 | 0.00225691 | 0.0663004 | 268.8 | 199.4 | 179.7 |
| 1659 | 242645_PM_at | — | — | 0.00225732 | 0.0663004 | 57.4 | 45.6 | 41.4 |
| 1660 | 234044_PM_at | — | — | 0.00226424 | 0.0664636 | 163.7 | 91.1 | 94.7 |
| 1661 | 226829_PM_at | AFAP1L2 | actin filament associated protein 1-like 2 | 0.00226642 | 0.0664876 | 10.5 | 12.2 | 11.2 |
| 1662 | 203165_PM_s_at | SLC33A1 | solute carrier family 33 (acetyl-CoA transporter), member 1 | 0.0022697 | 0.0665403 | 13.4 | 19.3 | 17.2 |
| 1663 | 233816_PM_at | — | — | 0.00227095 | 0.0665403 | 282.3 | 144.3 | 154.1 |
| 1664 | 226556_PM_at | MAP3K13 | mitogen-activated protein kinase kinase kinase 13 | 0.00227425 | 0.0665672 | 34.7 | 51.5 | 48.3 |
| 1665 | 242390_PM_at | — | — | 0.0022746 | 0.0665672 | 113.8 | 82.3 | 74.1 |
| 1666 | 214295_PM_at | KIAA0485 | hypothetical LOC57235 | 0.00227737 | 0.0665968 | 20.7 | 15.3 | 16.3 |
| 1667 | 1557436_PM_at | XKR6 | XK, Kell blood group complex subunit-related family, member 6 | 0.00227948 | 0.0665968 | 12.9 | 11.0 | 11.1 |
| 1668 | 226858_PM_at | CSNK1E | casein kinase 1, epsilon | 0.00228161 | 0.0665968 | 24.3 | 23.7 | 19.4 |
| 1669 | 239404_PM_at | — | — | 0.00228336 | 0.0665968 | 371.8 | 250.2 | 266.3 |
| 1670 | 202713_PM_s_at | KIAA0391 | KIAA0391 | 0.00228465 | 0.0665968 | 177.0 | 149.8 | 131.3 |
| 1671 | 244772_PM_at | — | — | 0.00228494 | 0.0665968 | 49.5 | 39.5 | 37.8 |
| 1672 | 203123_PM_s_at | SLC11A2 | solute carrier family 11 (proton-coupled divalent metal ion transporters), member 2 | 0.00228665 | 0.0665968 | 72.9 | 56.7 | 49.0 |
| 1673 | 203007_PM_x_at | LYPLA1 | lysophospholipase I | 0.00228733 | 0.0665958 | 556.2 | 723.5 | 626.0 |
| 1674 | 217671_PM_at | — | — | 0.00228791 | 0.0665958 | 88.4 | 62.1 | 55.2 |
| 1675 | 236119_PM_s_at | SPRR2G | small proline-rich protein 2G | 0.00229039 | 0.066609 | 12.0 | 10.8 | 10.4 |
| 1676 | 225876_PM_at | NIPAL3 | NIPA-like domain containing 3 | 0.00229168 | 0.066609 | 168.8 | 142.1 | 113.1 |
| 1677 | 222432_PM_s_at | CCDC47 | coiled-coil domain containing 47 | 0.00229243 | 0.066609 | 149.3 | 169.9 | 192.9 |
| 1678 | 228738_PM_at | D2HGDH | D-2-hydroxyglutarate dehydrogenase | 0.00229436 | 0.0666253 | 28.1 | 25.3 | 20.3 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1679 | 230712_PM_at | NBPF1 | neuroblastoma breakpoint family, member 1 | 0.0022965 | 0.0666477 | 157.3 | 107.3 | 103.5 |
| 1680 | 242780_PM_at | VAPA | VAMP (vesicle-associated membrane protein)-associated protein A, 33 kDa | 0.00229898 | 0.0666526 | 60.8 | 41.4 | 47.4 |
| 1681 | 1553107_PM_s_at | C5orf24 | chromosome 5 open reading frame 24 | 0.00230072 | 0.0666525 | 130.7 | 108.4 | 108.2 |
| 1682 | 203885_PM_at | RAB21 | RAB21, member RAS oncogene family | 0.00230077 | 0.0566526 | 184.2 | 236.8 | 240.0 |
| 1683 | 243005_PM_at | — | — | 0.0023065 | 0.0667789 | 43.4 | 32.7 | 30.0 |
| 1684 | 222307_PM_at | LOC282997 | hypothetical LOC282997 | 0.00231381 | 0.0659231 | 100.3 | 68.8 | 65.1 |
| 1685 | 243182_PM_at | — | — | 0.00231423 | 0.0669231 | 135.3 | 83.7 | 81.2 |
| 1686 | 228249_PM_at | C11orf74 | chromosome 11 open reading frame 74 | 0.00231604 | 0.0669358 | 13.3 | 15.3 | 17.3 |
| 1687 | 225228_PM_at | DRAM2 | DNA-damage regulated autophagy modulator 2 | 0.0023257 | 0.0671751 | 111.9 | 158.2 | 147.6 |
| 1688 | 204594_PM_s_at | SMCR7L | Smith-Magenis syndrome chromosome region, candidate 7-like | 0.0023287 | 0.0672219 | 90.8 | 78.2 | 67.1 |
| 1689 | 238393_PM_at | — | — | 0.00233582 | 0.0673875 | 10.2 | 8.6 | 9.2 |
| 1690 | 217945_PM_at | BTBD1 | BTB (POZ) domain containing 1 | 0.00233926 | 0.0674236 | 226.9 | 290.8 | 294.2 |
| 1691 | 226939_PM_at | CPEB2 | cytoplasmic polyadenylation element binding protein 2 | 0.00233984 | 0.0674236 | 263.3 | 395.7 | 474.0 |
| 1692 | 227116_PM_at | MON1B | MON1 homolog B (yeast) | 0.00234772 | 0.0675747 | 296.8 | 367.9 | 364.0 |
| 1693 | 242759_PM_at | — | — | 0.00234837 | 0.0675747 | 31.3 | 25.3 | 24.0 |
| 1694 | 1553352_PM_x_at | ERVWE1 | endogenous retroviral family W, env(C7), member 1 | 0.00234941 | 0.0675747 | 18.5 | 15.5 | 19.6 |
| 1695 | 1566889_PM_at | THADA | Thyroid adenoma associated | 0.00235063 | 0.0675747 | 21.6 | 17.7 | 16.3 |
| 1696 | 226426_PM_at | ADNP | activity-dependent neuroprotector homeobox | 0.00235345 | 0.0676159 | 173.2 | 140.4 | 137.5 |
| 1697 | 243296_PM_at | NAMPT | Nicotinamide phosphoribosyltransferase | 0.00235557 | 0.0676369 | 6234.7 | 4363.4 | 5001.5 |
| 1698 | 232330_PM_at | — | — | 0.00235802 | 0.0676674 | 353.4 | 276.0 | 237.6 |
| 1699 | 230147_PM_at | F2RL2 | coagulation factor II (thrombin) receptor-like 2 | 0.00236341 | 0.0677822 | 8.9 | 9.8 | 10.3 |
| 1700 | 227752_PM_at | SPTLC3 | serine palmitoyltransferase, long chain base subunit 3 | 0.00236684 | 0.0678239 | 9.6 | 9.4 | 10.7 |
| 1701 | 242297_PM_at | RREB1 | ras responsive element binding protein 1 | 0.00236765 | 0.0678239 | 263.6 | 209.9 | 203.7 |
| 1702 | 223391_PM_at | SGPP1 | sphingosine-1-phosphate phosphatase 1 | 0.0023695 | 0.067837 | 98.1 | 146.7 | 144.4 |
| 1703 | 215612_PM_at | — | — | 0.00238305 | 0.068164 | 39.4 | 30.1 | 28.8 |
| 1704 | 1570078_PM_a_at | DOCK5 | dedicator of cytokinesis 5 | 0.00238372 | 0.068164 | 238.5 | 134.7 | 130.1 |
| 1705 | 226085_PM_at | CBX5 | chromobox homolog 5 | 0.00238525 | 0.0681678 | 45.1 | 32.5 | 29.3 |
| 1706 | 237943_PM_at | — | — | 0.00238947 | 0.0682484 | 206.3 | 121.3 | 134.9 |
| 1707 | 241159_PM_x_at | — | — | 0.00239578 | 0.0683885 | 34.0 | 28.0 | 27.2 |
| 1708 | 1555561_PM_a_at | UGGT2 | UDP-glucose glycoprotein glucosyltransferase 2 | 0.00240013 | 0.0684726 | 8.8 | 10.5 | 9.9 |
| 1709 | 225040_PM_s_at | RPE | ribulose-5-phosphate-3-epimerase | 0.0024137 | 0.0687956 | 66.9 | 108.6 | 104.9 |
| 1710 | 1570335_PM_at | — | — | 0.00241512 | 0.0687956 | 15.0 | 12.2 | 12.1 |
| 1711 | 201534_PM_s_at | UBL3 | ubiquitin-like 3 | 0.00241611 | 0.0687956 | 333.0 | 456.3 | 410.9 |
| 1712 | 1557283_PM_a_at | ZNF519 | zinc finger protein 519 | 0.0024171 | 0.0687956 | 15.0 | 12.1 | 11.7 |
| 1713 | 237544_PM_at | — | — | 0.00242071 | 0.0688581 | 256.5 | 186.1 | 171.6 |
| 1714 | 238888_PM_at | — | — | 0.00242768 | 0.0690161 | 126.5 | 88.2 | 90.5 |
| 1715 | 232763_PM_at | TLN1 | Talin 1 | 0.00243337 | 0.069137 | 68.8 | 42.3 | 52.9 |
| 1716 | 236645_PM_at | LOC100506312 | hypothetical LOC100506312 | 0.00243477 | 0.069137 | 176.0 | 119.5 | 113.9 |
| 1717 | 218482_PM_at | ENY2 | enhancer of yellow 2 homolog (*Drosophila*) | 0.00244156 | 0.0692326 | 279.5 | 381.1 | 398.2 |
| 1718 | 237176_PM_at | — | — | 0.00244236 | 0.0692326 | 755.4 | 544.8 | 580.0 |
| 1719 | 226176_PM_s_at | USP42 | ubiquitin specific peptidase 42 | 0.0024424 | 0.0692326 | 250.5 | 200.0 | 196.3 |
| 1720 | 211139_PM_s_at | NAB1 | NGFI-A binding protein 1 (EGR1 binding protein 1) | 0.00244949 | 0.0693932 | 122.4 | 87.3 | 88.4 |
| 1721 | 202647_PM_s_at | NRAS | neuroblastoma RAS viral (v-ras) oncogene homolog | 0.00245174 | 0.0694166 | 50.4 | 71.1 | 64.3 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1722 | 201653_PM_at | CNIH | cornichon homolog (Drosophila) | 0.00245348 | 0.0694255 | 395.5 | 542.0 | 471.3 |
| 1723 | 201800_PM_s_at | OSBP | oxysterol binding protein | 0.00245706 | 0.0694865 | 145.1 | 130.5 | 123.8 |
| 1724 | 234565_PM_x_at | — | — | 0.00246042 | 0.0695411 | 23.7 | 20.0 | 20.8 |
| 1725 | 242235_PM_x_at | — | — | 0.0024639 | 0.069563 | 514.7 | 396.2 | 447.4 |
| 1726 | 239063_PM_at | — | — | 0.00246405 | 0.069563 | 23.6 | 21.9 | 15.8 |
| 1727 | 228660_PM_x_at | SEMA4F | sema domain, immunoglobulin domain (Ig), transmembrane domain (TM) and short cytoplasmi | 0.00246807 | 0.0696004 | 17.0 | 14.8 | 14.1 |
| 1728 | 1569041_PM_at | — | — | 0.00246823 | 0.0696004 | 15.9 | 12.4 | 13.4 |
| 1729 | 229773_PM_at | SNAP23 | Synaptosomal-associated protein, 23 kDa | 0.0024732 | 0.0697002 | 176.6 | 119.6 | 128.5 |
| 1730 | 221735_PM_at | WDR43 | WD repeat domain 48 | 0.00247658 | 0.0697551 | 383.4 | 349.4 | 325.4 |
| 1731 | 228902_PM_at | NUP214 | nucleoporin 214 kDa | 0.00248086 | 0.0698353 | 74.2 | 97.1 | 99.1 |
| 1732 | 200833_PM_s_at | RAP1B | RAP1B, member of RAS oncogene family | 0.00248892 | 0.0700217 | 2219.0 | 3042.4 | 2647.5 |
| 1733 | 228512_PM_at | PTCD3 | Pentatricopeptide repeat domain 3 | 0.00249085 | 0.0700356 | 85.7 | 69.5 | 61.6 |
| 1734 | 232653_PM_at | — | — | 0.00249628 | 0.0701385 | 200.2 | 122.6 | 134.9 |
| 1735 | 1556151_PM_at | ITFG1 | Integrin alpha FG-GAP repeat containing 1 | 0.00249739 | 0.0701385 | 311.4 | 371.2 | 395.4 |
| 1736 | 224098_PM_at | — | — | 0.00250148 | 0.0702129 | 78.9 | 55.1 | 46.8 |
| 1737 | 202079_PM_s_at | TRAK1 | trafficking protein, kinesin binding 1 | 0.00251159 | 0.0704561 | 52.9 | 72.4 | 70.4 |
| 1738 | 241642_PM_x_at | TLK1 | tousled-like kinase 1 | 0.00251368 | 0.0704742 | 113.5 | 94.7 | 97.3 |
| 1739 | 219292_PM_at | THAP1 | THAP domain containing, apoptosis associated protein 1 | 0.00251533 | 0.0704799 | 44.0 | 65.0 | 61.5 |
| 1740 | 206862_PM_at | ZNF254 | zinc finger protein 254 | 0.00251742 | 0.0704979 | 11.5 | 12.9 | 14.8 |
| 1741 | 223511_PM_at | C1orf124 | chromosome 1 open reading frame 124 | 0.0025221 | 0.0705884 | 17.1 | 23.8 | 23.8 |
| 1742 | 242728_PM_at | — | — | 0.00252386 | 0.0705971 | 44.3 | 36.2 | 34.5 |
| 1743 | 232560_PM_at | UROS | uroporphyrinogen III synthase | 0.00252897 | 0.0706265 | 9.4 | 10.4 | 10.5 |
| 1744 | 241435_PM_at | — | — | 0.00252939 | 0.0706265 | 1042.7 | 727.8 | 585.8 |
| 1745 | 243280_PM_at | — | — | 0.00253007 | 0.0706265 | 106.8 | 75.9 | 76.7 |
| 1746 | 219157_PM_at | KLHL2 | kelch-like 2, Mayven (Drosophila) | 0.00253071 | 0.0706265 | 479.7 | 694.1 | 769.2 |
| 1747 | 1569512_PM_at | — | — | 0.00253461 | 0.0706949 | 253.0 | 138.5 | 149.2 |
| 1748 | 244425_PM_at | — | — | 0.00253824 | 0.0707556 | 202.7 | 139.5 | 142.0 |
| 1749 | 226217_PM_at | SLC30A7 | solute carrier family 30 (zinc transporter), member 7 | 0.00254144 | 0.0708043 | 549.2 | 467.6 | 440.6 |
| 1750 | 224985_PM_at | NRAS | neuroblastoma RAS viral (v-ras) oncogene homolog | 0.00254497 | 0.0708515 | 260.7 | 368.1 | 329.9 |
| 1751 | 215270_PM_at | LFNG | LFNG O-fucosylpeptide 3-beta-N-acetylglucosaminyltransferase | 0.00254604 | 0.0708515 | 23.6 | 33.9 | 32.4 |
| 1752 | 237750_PM_at | XPNPEP3 | X-prolyl aminopeptidase (aminopeptidase P) 3, putative | 0.00255399 | 0.0709593 | 29.5 | 22.7 | 21.5 |
| 1753 | 227744_PM_s_at | HNRNPD | Heterogeneous nuclear ribonucleoprotein D (AU-rich element RNA binding protein 1, 37 kDa | 0.00255406 | 0.0709593 | 10.4 | 10.5 | 11.9 |
| 1754 | 218196_PM_at | OSTM1 | osteopetrosis associated transmembrane protein 1 | 0.00255465 | 0.0709593 | 257.5 | 381.6 | 339.6 |
| 1755 | 204634_PM_at | NEK4 | NIMA (never in mitosis gene a)-related kinase 4 | 0.00255574 | 0.0709593 | 48.5 | 71.9 | 73.7 |
| 1756 | 1568834_PM_s_at | CCDC90B | coiled-coil domain containing 90B | 0.00255881 | 0.0710041 | 119.1 | 88.9 | 86.5 |
| 1757 | 212660_PM_at | PHF15 | PHD finger protein 15 | 0.00256264 | 0.0710677 | 172.7 | 144.7 | 116.6 |
| 1758 | 233976_PM_at | — | — | 0.00256539 | 0.0710677 | 198.4 | 152.6 | 158.3 |
| 1759 | 237239_PM_at | — | — | 0.00256548 | 0.0710677 | 369.0 | 258.8 | 281.9 |
| 1760 | 234883_PM_x_at | TRBV7-3 | T cell receptor beta variable 7-3 | 0.00257058 | 0.0711686 | 23.7 | 21.9 | 15.7 |
| 1761 | 237412_PM_at | — | — | 0.00257386 | 0.0711823 | 21.6 | 18.3 | 17.0 |
| 1762 | 223065_PM_s_at | STARD3NL | STARD3 N-terminal like | 0.002574 | 0.0711823 | 370.9 | 489.3 | 516.4 |
| 1763 | 233300_PM_at | — | — | 0.00258302 | 0.0713305 | 145.5 | 99.1 | 99.1 |
| 1764 | 241219_PM_at | — | — | 0.00258359 | 0.0713305 | 43.4 | 32.8 | 31.5 |
| 1765 | 238473_PM_at | LOC100216545 | hypothetical LOC100216545 | 0.00258375 | 0.0713305 | 17.1 | 13.9 | 14.2 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1766 | 218754_PM_at | NOL9 | nucleolar protein 9 | 0.00258597 | 0.0713514 | 136.3 | 122.6 | 96.6 |
| 1767 | 212833_PM_at | SLC25A46 | solute carrier family 25, member 46 | 0.00259083 | 0.0714078 | 259.1 | 361.0 | 335.9 |
| 1768 | 216994_PM_s_at | RUNX2 | runt-related transcription factor 2 | 0.00259224 | 0.0714078 | 10.7 | 9.4 | 9.4 |
| 1769 | 1556672_PM_a_at | RBM6 | RNA binding motif protein 6 | 0.00259241 | 0.0714078 | 24.7 | 17.4 | 17.9 |
| 1770 | 231212_PM_x_at | — | — | 0.00259651 | 0.0714803 | 17.2 | 14.5 | 16.7 |
| 1771 | 231035_PM_s_at | — | — | 0.00260088 | 0.0715432 | 42.1 | 59.5 | 67.4 |
| 1772 | 230756_PM_at | ZNF683 | zinc finger protein 683 | 0.00260173 | 0.0715432 | 21.2 | 26.7 | 17.6 |
| 1773 | 241448_PM_at | — | — | 0.00260385 | 0.0715611 | 29.1 | 23.2 | 22.8 |
| 1774 | 233693_PM_at | C1orf201 | chromosome 1 open reading frame 201 | 0.00260717 | 0.0716119 | 17.0 | 14.0 | 15.6 |
| 1775 | 1557505_PM_a_at | — | — | 0.0026167 | 0.0718332 | 85.3 | 58.4 | 61.0 |
| 1776 | 234657_PM_at | — | — | 0.0026244 | 0.072004 | 22.8 | 17.7 | 19.2 |
| 1777 | 225383_PM_at | ZNF275 | zinc finger protein 275 | 0.00263161 | 0.0721612 | 158.4 | 133.1 | 96.6 |
| 1778 | 213292_PM_s_at | SNX13 | sorting nexin 13 | 0.00263732 | 0.0722771 | 101.7 | 141.5 | 138.5 |
| 1779 | 218265_PM_at | SECISBP2 | SECIS binding protein 2 | 0.00264018 | 0.0723148 | 167.1 | 135.1 | 136.3 |
| 1780 | 238459_PM_x_at | SPATA5 | spermatogenesis associated 6 | 0.0026484 | 0.0724992 | 9.8 | 9.2 | 10.5 |
| 1781 | 212852_PM_5_at | TROVE2 | TROVE domain family, member 2 | 0.00265056 | 0.0725176 | 1001.7 | 839.5 | 867.1 |
| 1782 | 236963_PM_at | — | — | 0.00265207 | 0.0725182 | 22.9 | 15.9 | 15.2 |
| 1783 | 1560771_PM_at | — | — | 0.00265437 | 0.0725404 | 10.6 | 9.6 | 11.4 |
| 1784 | 232500_PM_at | RALGAPA2 | Ral GTPase activating protein, alpha subunit 2 (catalytic) | 0.00265586 | 0.0725404 | 844.3 | 552.7 | 563.1 |
| 1785 | 214188_PM_at | HEXIM1 | Hexamethylene bis-acetamide inducible 1 | 0.00267308 | 0.0729698 | 92.1 | 62.0 | 69.8 |
| 1786 | 225225_PM_at | LOC729082 | Hypothetical protein LOC729082 | 0.00268123 | 0.0731513 | 816.1 | 728.6 | 684.3 |
| 1787 | 214925_PM_s_at | SPTAN1 | spectrin, alpha, non-erythrocytic 1 (alpha-fodrin) | 0.00268359 | 0.0731748 | 18.5 | 14.9 | 13.7 |
| 1788 | 210619_PM_s_at | HYAL1 | hyaluronoglucosaminidase 1 | 0.00268625 | 0.0732063 | 123 | 12.5 | 14.6 |
| 1789 | 225785_PM_at | REEP3 | receptor accessory protein 3 | 0.00269026 | 0.0732746 | 155.5 | 216.8 | 220.9 |
| 1790 | 203248_PM_at | ZNF24 | zinc finger protein 24 | 0.00269663 | 0.0734071 | 25.1 | 32.1 | 31.7 |
| 1791 | 236946_PM_at | — | — | 0.00270089 | 0.0734562 | 35.5 | 25.9 | 29.2 |
| 1792 | 224667_PM_X_at | ANAPC16 | anaphase promoting complex subunit 16 | 0.00270145 | 0.0734562 | 965.2 | 789.1 | 852.8 |
| 1793 | 202538_PM_s_at | CHMP2B | chromatin modifying protein 2B | 0.00271151 | 0.0736886 | 261.4 | 335.9 | 311.5 |
| 1794 | 225774_PM_at | RSPRY1 | ring finger and SPRY domain containing 1 | 0.00271833 | 0.0738328 | 79.8 | 108.0 | 94.2 |
| 1795 | 219482_PM_at | SETD4 | SET domain containing 4 | 0.00272531 | 0.0739812 | 48.4 | 43.1 | 36.7 |
| 1796 | 216107_PM_at | LOC100129503 | hypothetical LOC100129503 | 0.00272787 | 0.0740094 | 11.0 | 10.6 | 12.2 |
| 1797 | 243931_PM_at | — | — | 0.00273033 | 0.0740349 | 1040.1 | 794.8 | 804.1 |
| 1798 | 220603_PM_s_at | MCTP2 | multiple C2 domains, transmembrane 2 | 0.00273533 | 0.0741293 | 330.0 | 339.5 | 465.8 |
| 1799 | 243361_PM_at | SREK1 | splicing regulatory glutamine/lysine-rich protein 1 | 0.00274347 | 0.0742805 | 44.4 | 35.3 | 35.6 |
| 1800 | 225484_PM_at | TSGA14 | testis specific, 14 | 0.00274396 | 0.0742805 | 39.7 | 33.5 | 29.7 |
| 1801 | 244249_PM_at | — | — | 0.00274878 | 0.0743697 | 31.1 | 22.7 | 25.8 |
| 1802 | 218474_PM_s_at | KCTD5 | potassium channel tetramerisation domain containing 5 | 0.00275283 | 0.0744379 | 141.9 | 210.2 | 182.5 |
| 1803 | 205277_PM_at | PRDM2 | PR domain containing 2, with ZNF domain | 0.00275856 | 0.0744924 | 102.5 | 78.6 | 66.3 |
| 1804 | 221013_PM_s_at | APOL2 | apolipoprotein L, 2 | 0.00276054 | 0.0744924 | 25.7 | 21.7 | 20.9 |
| 1805 | 220863_PM_at | MIP | major intrinsic protein of lens fiber | 0.00276109 | 0.0744924 | 10.7 | 11.0 | 12.3 |
| 1806 | 216555_PM_at | C22orf30 | chromosome 22 open reading frame 30 | 0.00276119 | 0.0744924 | 334.7 | 263.2 | 302.6 |
| 1807 | 203132_PM_at | RB1 | retinoblastoma 1 | 0.00276249 | 0.0744924 | 123.5 | 169.0 | 178.7 |
| 1808 | 228613_PM_at | RAB11FIP3 | RAB11 family interacting protein 3 (class II) | 0.00277251 | 0.0747213 | 88.9 | 60.0 | 52.1 |
| 1809 | 241588_PM_at | — | — | 0.00277507 | 0.0747489 | 18.3 | 15.8 | 14.4 |
| 1810 | 242216_PM_at | — | — | 0.00279169 | 0.0751551 | 41.1 | 31.4 | 28.1 |
| 1811 | 243442_PM_x_at | — | — | 0.00279361 | 0.0751652 | 35.2 | 29.8 | 31.8 |
| 1812 | 238860_PM_at | C6orf130 | chromosome 6 open reading frame 130 | 0.00280565 | 0.0754475 | 145.8 | 120.8 | 112.2 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1813 | 217164_PM_at | — | — | 0.00281545 | 0.0756693 | 309.4 | 245.1 | 197.5 |
| 1814 | 225501_PM_at | XPNPEP3 | X-prolyl aminopeptidase (aminopeptidase P) 3, putative | 0.00281717 | 0.0756738 | 133.0 | 96.7 | 98.4 |
| 1815 | 230324_PM_at | — | — | 0.00282409 | 0.0757882 | 123.6 | 91.1 | 88.4 |
| 1816 | 210266_PM_s_at | TRIM33 | tripartite motif-containing 33 | 0.00282454 | 0.0757882 | 891.0 | 758.8 | 761.0 |
| 1817 | 231302_PM_at | — | — | 0.00282886 | 0.0758491 | 137.7 | 86.0 | 97.4 |
| 1818 | 1557733_PM_a_at | — | — | 0.00283039 | 0.0758491 | 55.2 | 30.3 | 27.6 |
| 1819 | 204325_PM_s_at | NF1 | neurofibromin 1 | 0.00283195 | 0.0758491 | 11.3 | 9.6 | 9.6 |
| 1820 | 204226_PM_at | STAU2 | staufen, RNA binding protein, homolog 2 (Drosophila) | 0.00283353 | 0.0758491 | 41.7 | 62.6 | 57.3 |
| 1821 | 1556053_PM_at | DNAJC7 | DnaJ (Hsp40) homolog, subfamily C, member 7 | 0.00283528 | 0.0758491 | 263.2 | 211.4 | 219.2 |
| 1822 | 204165_PM_at | WASF1 | WAS protein family, member 1 | 0.00283615 | 0.0758491 | 20.1 | 23.2 | 32.0 |
| 1823 | 232304_PM_at | PELI1 | Pellino homolog 1 (Drosophila) | 0.00283972 | 0.0759029 | 1637.9 | 1045.8 | 1096.8 |
| 1824 | 221841_PM_s_at | KLF4 | Kruppel-like factor 4 (gut) | 0.00284676 | 0.0760384 | 365.1 | 487.7 | 528.4 |
| 1825 | 242440_PM_at | — | — | 0.00284916 | 0.0760384 | 30.0 | 19.9 | 20.9 |
| 1826 | 239726_PM_at | — | — | 0.00284947 | 0.0760384 | 40.2 | 26.5 | 21.4 |
| 1827 | 1563320_PM_at | — | — | 0.00285747 | 0.0761441 | 26.6 | 21.5 | 21.1 |
| 1828 | 242854_PM_x_at | DLEU2 | deleted in lymphocytic leukemia 2 (non-protein coding) | 0.00285768 | 0.0761441 | 161.6 | 125.0 | 112.2 |
| 1829 | 224645_PM_at | EIF4EBP2 | eukaryotic translation initiation factor 4E binding protein 2 | 0.00285812 | 0.0761441 | 210.2 | 174.5 | 159.1 |
| 1830 | 203496_PM_s_at | MED1 | mediator complex subunit 1 | 0.0028614 | 0.0761498 | 171.9 | 145.5 | 134.9 |
| 1831 | 1553282_PM_at | C21orf128 | chromosome 21 open reading frame 128 | 0.00286146 | 0.0761498 | 9.6 | 9.2 | 8.6 |
| 1832 | 242070_PM_at | LOC728485 | hypothetical LOC728485 | 0.00286444 | 0.0761872 | 10.9 | 11.4 | 12.7 |
| 1833 | 227208_PM_at | CCDC84 | coiled-coil domain containing 84 | 0.00286599 | 0.0761872 | 216.6 | 174.9 | 168.8 |
| 1834 | 1557797_PM_a_at | — | — | 0.00286808 | 0.0762012 | 309.0 | 220.5 | 223.1 |
| 1835 | 210820_PM_x_at | COQ7 | coenzyme Q7 homolog, ubiquinone (yeast) | 0.00287385 | 0.0762795 | 13.0 | 16.6 | 17.4 |
| 1836 | 231775_PM_at | TNFRSF10A | tumor necrosis factor receptor superfamlly, member 10a | 0.00287422 | 0.0762795 | 180.6 | 145.4 | 125.6 |
| 1837 | 219520_PM_s_at | WWC3 | WWC family member 3 | 0.00287674 | 0.0762795 | 756.0 | 570.8 | 589.3 |
| 1838 | 228983_PM_at | — | — | 0.00287729 | 0.0762795 | 33.4 | 25.1 | 27.5 |
| 1839 | 207761_PM_s_at | METTL7A | methyltransferase like 7A | 0.00287972 | 0.0763024 | 1051.5 | 1303.3 | 1344.0 |
| 1840 | 218873_PM_at | GON4L | gon-4-like (C. elegans) | 0.0028832 | 0.0763331 | 142.0 | 122.9 | 109.0 |
| 1841 | 242357_PM_x_at | — | — | 0.00288474 | 0.0763331 | 19.9 | 16.4 | 16.2 |
| 1842 | 236493_PM_at | NKAPP1 | NFKB activating protein pseudogene 1 | 0.00288558 | 0.0763331 | 17.0 | 14.8 | 13.7 |
| 1843 | 233775_PM_x_at | LOC100289333 | Hypothetical protein LOC100289333 | 0.00289763 | 0.0766103 | 769.1 | 631.0 | 679.7 |
| 1844 | 222930_PM_s_at | AGMAT | agmatine ureohydrolase (agmatinase) | 0.00290397 | 0.0767363 | 14.1 | 13.0 | 11.6 |
| 1845 | 217885_PM_at | IPO9 | importin 9 | 0.00290642 | 0.0767594 | 227.8 | 183.0 | 171.3 |
| 1846 | 244354_PM_at | LOC100288939 | Similar to hCG1987955 | 0.00291439 | 0.0768645 | 262.1 | 211.6 | 206.8 |
| 1847 | 240410_PM_at | — | — | 0.00291445 | 0.0768645 | 252.9 | 193.0 | 189.1 |
| 1848 | 230018_PM_at | DPP9 | dipeptidyl-peptidase 9 | 0.00291513 | 0.0768645 | 49.0 | 42.2 | 46.2 |
| 1849 | 217579_PM_x_at | — | — | 0.00291775 | 0.0768919 | 217.6 | 178.8 | 186.1 |
| 1850 | 218337_PM_at | FAM160B2 | family with sequence similarity 160, member B2 | 0.00292068 | 0.0769276 | 53.1 | 50.8 | 43.0 |
| 1851 | 225232_PM_at | MTMR12 | myotubularin related protein 12 | 0.00292317 | 0.0769515 | 305.0 | 361.8 | 389.4 |
| 1852 | 243677_PM_at | GORASP1 | Golgi reassembly stacking protein 1, 65 kDa | 0.00293066 | 0.0771071 | 9.7 | 10.1 | 10.9 |
| 1853 | 225446_PM_at | BRWD1 | bromodomain and WD repeat domain containing 1 | 0.00293424 | 0.0771219 | 47.9 | 62.2 | 47.6 |
| 1854 | 241727_PM_x_at | DHFRL1 | dihydrofolate reductase-like 1 | 0.00293439 | 0.0771219 | 82.0 | 68.9 | 70.9 |
| 1855 | 210285_PM_x_at | WTAP | Wilms tumor 1 associated protein | 0.00294086 | 0.0772503 | 94.4 | 149.5 | 115.1 |
| 1856 | 232432_PM_s_at | SLC30A5 | solute carrier family 30 (zinc transporter), member 5 | 0.00294546 | 0.0773294 | 79.1 | 113.1 | 86.3 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1857 | 238694_PM_at | DGKE | diacylglycerol kinase, epsilon 64 kDa | 0.00294979 | 0.0774014 | 27.3 | 22.0 | 18.3 |
| 1858 | 1558142_PM_at | TNRC6B | trinucleotide repeat containing 6B | 0.00295374 | 0.0774477 | 435.3 | 330.1 | 377.1 |
| 1859 | 1569296_PM_a_at | LOC493754 | RAB guanine nucleotide exchange factor (GEF) 1 pseudogene | 0.00295656 | 0.0774477 | 28.2 | 22.8 | 22.7 |
| 1860 | 217970_PM_s_at | CNOT6 | CCR4-NOT transcription complex, subunit 6 | 0.00295761 | 0.0774477 | 69.0 | 101.6 | 83.5 |
| 1861 | 1558289_PM_at | RFT1 | RFT1 homolog (*S. cerevisiae*) | 0.00295791 | 0.0774477 | 22.6 | 19.9 | 18.4 |
| 1862 | 1570496_PM_at | — | — | 0.00295955 | 0.077449 | 14.2 | 12.3 | 12.4 |
| 1863 | 1552652_PM_at | HPS4 | Hermansky-Pudlak syndrome 4 | 0.00296203 | 0.0774723 | 16.6 | 14.0 | 14.6 |
| 1864 | 1553466_PM_at | CXorf59 | chromosome X open reading frame 59 | 0.00297091 | 0.0776165 | 10.4 | 9.4 | 9.3 |
| 1865 | 1557486_PM_at | — | — | 0.00297149 | 0.0776165 | 13.7 | 10.8 | 11.7 |
| 1866 | 201417_PM_at | SOX4 | SRY (sex determining region Y)-box 4 | 0.00297303 | 0.0776165 | 122.3 | 169.0 | 185.8 |
| 1867 | 208772_PM_at | ANKHD1 /// ANKHD1-EIF4EBP3 | ankyrin repeat and KH domain containing 1 /// ANKHD1-EIF4EBP3 readthrough | 0.00297453 | 0.0776165 | 546.6 | 459.2 | 414.6 |
| 1868 | 207133_PM_x_at | ALPK1 | alpha-kinase 1 | 0.00297551 | 0.0776165 | 217.3 | 173.6 | 181.1 |
| 1869 | 1560512_PM_at | — | — | 0.0029797 | 0.0776842 | 18.8 | 13.9 | 12.4 |
| 1870 | 238064_PM_at | — | — | 0.00298875 | 0.0778785 | 669.2 | 441.3 | 512.2 |
| 1871 | 1559949_PM_at | — | — | 0.002993 | 0.0779476 | 38.0 | 26.2 | 30.0 |
| 1872 | 236116_PM_at | — | — | 0.00300046 | 0.0781001 | 26.7 | 21.8 | 20.0 |
| 1873 | 223871_PM_x_at | ING5 | Inhibitor of growth family, member 5 | 0.00300704 | 0.0782296 | 22.2 | 18.5 | 20.9 |
| 1874 | 1561606_PM_at | — | — | 0.00302995 | 0.0787613 | 11.8 | 11.5 | 13.3 |
| 1875 | 222345_PM_at | — | — | 0.00303071 | 0.0787613 | 11.6 | 10.7 | 9.9 |
| 1876 | 212079_PM_s_at | MLL | myeloid/lymphoid or mixed-lineage leukemia (trithorax homolog, *Drosophila*) | 0.00303461 | 0.0787729 | 155.0 | 119.7 | 104.9 |
| 1877 | 244579_PM_at | — | — | 0.00303534 | 0.0787729 | 397.7 | 260.5 | 288.6 |
| 1878 | 244168_PM_s_at | ULK4 | unc-51-like kinase 4 (*C. elegans*) | 0.003037 | 0.0787729 | 20.5 | 16.5 | 16.7 |
| 1879 | 204842_PM_x_at | PRKAR2A | protein kinase, cAMP-dependent, regulatory, type II, alpha | 0.00303806 | 0.0787729 | 535.4 | 456.5 | 466.2 |
| 1880 | 209704_PM_at | MTF2 | metal response element binding transcription factor 2 | 0.00303924 | 0.0787729 | 37.4 | 53.0 | 48.2 |
| 1881 | 1555908_PM_at | FAM120A | family with sequence similarity 120A | 0.00304219 | 0.0788074 | 14.4 | 15.8 | 17.8 |
| 1882 | 243178_PM_at | — | — | 0.00304966 | 0.0789333 | 1388.5 | 913.1 | 948.5 |
| 1883 | 206308_PM_at | TRDMT1 | tRNA aspartic acid methyltransferase 1 | 0.00305143 | 0.0789333 | 16.4 | 21.0 | 20.6 |
| 1884 | 217971_PM_at | MAPKSP1 | MAPK scaffold protein 1 | 0.00305191 | 0.0789333 | 366.5 | 504.9 | 497.5 |
| 1885 | 226808_PM_at | ZNF862 | zinc finger protein 862 | 0.00305746 | 0.0790349 | 392.1 | 308.8 | 321.6 |
| 1886 | 243988_PM_at | — | — | 0.00306374 | 0.0791106 | 13.0 | 10.8 | 11.0 |
| 1887 | 232232_PM_s_at | SLC22A16 | solute carrier family 22 (organic cation/carnitine transporter), member 16 | 0.00306384 | 0.0791106 | 30.7 | 45.8 | 53.9 |
| 1888 | 232532_PM_at | QRICH2 | glutamine rich 2 | 0.00306539 | 0.0791106 | 11.5 | 11.3 | 10.3 |
| 1889 | 215854_PM_at | — | — | 0.00306688 | 0.0791106 | 18.7 | 14.7 | 15.3 |
| 1890 | 236919_PM_at | — | — | 0.00306986 | 0.0791455 | 24.1 | 18.3 | 18.2 |
| 1891 | 202069_PM_s_at | IDH3A | isocitrate dehydrogenase 3 (NAD+) alpha | 0.00307338 | 0.0791944 | 63.0 | 85.5 | 79.3 |
| 1892 | 212818_PM_s_at | ASB1 | ankyrin repeat and SOCS box-containing 1 | 0.00308003 | 0.0793069 | 52.1 | 47.2 | 41.4 |
| 1893 | 203440_PM_at | CDH2 | cadherin 2, type 1, N-cadherin (neuronal) | 0.003081 | 0.0793069 | 11.9 | 11.5 | 16.0 |
| 1894 | 233326_PM_at | CCDC39 | coiled-coil domain containing 39 | 0.00309364 | 0.0795902 | 9.0 | 8.8 | 10.4 |
| 1895 | 225956_PM_at | C5orf41 | chromosome 5 open reading frame 41 | 0.00309558 | 0.0795981 | 1312.0 | 1010.4 | 1112.8 |
| 1896 | 242875_PM_at | — | — | 0.00310427 | 0.0797794 | 207.1 | 137.4 | 142.5 |
| 1897 | 215208_PM_x_at | RPL35A | Ribosomal protein L35a | 0.00311137 | 0.0799079 | 77.7 | 61.4 | 64.7 |
| 1898 | 244035_PM_at | — | — | 0.00311297 | 0.0799079 | 66.4 | 42.0 | 31.3 |
| 1899 | 226379_PM_s_at | C19orf25 | chromosome 19 open reading frame 25 | 0.00311564 | 0.0799079 | 16.9 | 14.6 | 14.8 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1900 | 219345_PM_at | BOLA1 | bolA homolog 1 (*E. coli*) | 0.00311784 | 0.0799079 | 35.6 | 37.0 | 29.7 |
| 1901 | 202195_PM_s_at | TMED5 | transmembrane emp24 protein transport domain containing 5 | 0.00311821 | 0.0799079 | 81.8 | 107.9 | 107.9 |
| 1902 | 1560861_PM_at | — | — | 0.00311953 | 0.0799079 | 12.6 | 11.0 | 10.5 |
| 1903 | 240528_PM_s_at | EXOC4 | exocyst complex component 4 | 0.00312075 | 0.0799079 | 47.4 | 42.9 | 33.2 |
| 1904 | 243295_PM_at | RBM27 | RNA binding motif protein 27 | 0.00312686 | 0.0800223 | 342.8 | 282.8 | 288.6 |
| 1905 | 1557235_PM_at | LOC100128002 | Hypothetical LOC100128002 | 0.00312941 | 0.080026 | 9.2 | 9.5 | 10.5 |
| 1906 | 1557246_PM_at | KIDINS220 | kinase D-interacting substrate, 220 kDa | 0.00313029 | 0.080026 | 347.0 | 245.0 | 265.2 |
| 1907 | 220349_PM_s_at | ENGASE | endo-beta-N-acetylglucosaminidase | 0.00314235 | 0.0802887 | 63.2 | 48.8 | 42.8 |
| 1908 | 200732_PM_s_at | PTP4A1 | protein tyrosine phosphatase type IVA, member 1 | 0.00314386 | 0.0802887 | 310.1 | 384.3 | 363.2 |
| 1909 | 240016_PM_at | — | — | 0.00314629 | 0.0803087 | 117.2 | 79.4 | 76.8 |
| 1910 | 222393_PM_s_at | NAA50 | N(alpha)-acetyltransferase 50, NatE catalytic subunit | 0.00315072 | 0.0803577 | 118.2 | 157.8 | 139.5 |
| 1911 | 232586_PM_x_at | OR7E126P | olfactory receptor, family 7, subfamily E, member 126 pseudogene | 0.00315151 | 0.0803577 | 25.8 | 24.5 | 20.0 |
| 1912 | 212500_PM_at | ADO | 2-aminoethanethiol (cysteamine) dioxygenase | 0.00315656 | 0.0804444 | 63.4 | 94.0 | 88.7 |
| 1913 | 240613_PM_at | JAK1 | Janus kinase 1 | 0.00316752 | 0.0806815 | 18.1 | 13.9 | 15.0 |
| 1914 | 215577_PM_at | — | — | 0.00317601 | 0.0808555 | 22.3 | 17.0 | 16.7 |
| 1915 | 231235_PM_at | NKTR | natural killer-tumor recognition sequence | 0.00317914 | 0.0808929 | 120.6 | 88.6 | 75.7 |
| 1916 | 213566_PM_at | 6-Sep | septin 6 | 0.00318269 | 0.0809166 | 261.2 | 200.3 | 180.0 |
| 1917 | 237317_PM_at | — | — | 0.00318339 | 0.0809166 | 26.6 | 24.2 | 19.8 |
| 1918 | 220925_PM_at | NAA35 | N(alpha)-acetyltransferase 35, NatC auxiliary subunit | 0.00319274 | 0.0811119 | 111.8 | 106.3 | 90.3 |
| 1919 | 214016_PM_s_at | LOC100506168 /// SFPQ | hypothetical LOC100506168 /// splicing factor proline/glutamine-rich | 0.00319481 | 0.0811222 | 873.4 | 726.2 | 724.4 |
| 1920 | 232371_PM_at | 7-Mar | Membrane-associated ring finger (C3HC4) 7 | 0.00319954 | 0.0812 | 148.4 | 101.0 | 98.8 |
| 1921 | 1557504_PM_at | — | — | 0.00320409 | 0.0812322 | 26.5 | 19.4 | 20.2 |
| 1922 | 223328_PM_at | ARMC10 | armadillo repeat containing 10 | 0.00320626 | 0.0312322 | 131.8 | 172.1 | 139.9 |
| 1923 | 218516_PM_s_at | IMPAD1 | inositol monophosphatase domain containing 1 | 0.0032072 | 0.0312322 | 18.5 | 25.3 | 24.2 |
| 1924 | 233674_PM_at | — | — | 0.00320811 | 0.0812322 | 170.7 | 95.5 | 91.3 |
| 1925 | 219485_PM_s_at | P5MD10 | proteasome (prosome, macropain) 26S subunit, non-ATPase, 10 | 0.00321022 | 0.0812322 | 213.8 | 289.3 | 263.0 |
| 1926 | 231316_PM_at | — | — | 0.00321081 | 0.0812322 | 78.9 | 65.9 | 58.9 |
| 1927 | 233333_PM_x_at | AVIL | advillin | 0.00321804 | 0.0812981 | 32.2 | 24.6 | 26.4 |
| 1928 | 1563502_PM_at | ZDHHC2 | Zinc finger, DHHC-type containing 2 | 0.00321858 | 0.0812981 | 29.9 | 23.3 | 20.9 |
| 1929 | 212098_PM_at | LOC151162 /// MGAT5 | hypothetical LOC151162 /// mannosyl (alpha-1,6-)-glycoprotein beta-1,6-N-acetyl-glucosa | 0.00321918 | 0.0812981 | 284.9 | 209.3 | 215.4 |
| 1930 | 1551652_PM_at | BECN1 | Beclin 1, autophagy related | 0.00322009 | 0.0812981 | 15.0 | 12.6 | 13.4 |
| 1931 | 201339_PM_s_at | SCP2 | sterol carrier protein 2 | 0.00322271 | 0.0813062 | 379.6 | 504.0 | 439.2 |
| 1932 | 236066_PM_at | — | — | 0.00322375 | 0.0813062 | 30.3 | 27.6 | 24.5 |
| 1933 | 220127_PM_s_at | FBXL12 | F-box and leucine-rich repeat protein 12 | 0.00322582 | 0.0813164 | 97.4 | 121.1 | 111.0 |
| 1934 | 206748_PM_s_at | SPAG9 | sperm associated antigen 9 | 0.00323155 | 0.0814013 | 23.2 | 17.0 | 18.7 |
| 1935 | 211795_PM_s_at | FYB | FYN binding protein | 0.00323253 | 0.0814013 | 4480.5 | 3726.3 | 3726.9 |
| 1936 | 218313_PM_s_at | GALNT7 | UDP-N-acetyl-alpha-D-galactosamine: polypeptide N-acetylgalactosaminyltransferase 7 (Gal | 0.00324116 | 0.0815764 | 213.4 | 276.0 | 290.7 |
| 1937 | 1564753_PM_at | — | — | 0.00324528 | 0.081591 | 12.9 | 10.7 | 11.8 |
| 1938 | 226544_PM_x_at | MUTED | muted homolog (mouse) | 0.00324648 | 0.081591 | 343.5 | 298.8 | 310.5 |
| 1939 | 228097_PM_at | MYLIP | myosin regulatory light chain interacting protein | 0.00324676 | 0.081591 | 129.4 | 87.6 | 80.9 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1940 | 224047_PM_at | — | — | 0.00325581 | 0.081766 | 8.6 | 8.4 | 9.5 |
| 1941 | 242352_PM_at | NIPBL | Nipped-B homolog (Drosophila) | 0.00325708 | 0.081766 | 1020.9 | 808.3 | 835.7 |
| 1942 | 227121_PM_at | — | — | 0.00326653 | 0.081961 | 67.1 | 48.7 | 47.0 |
| 1943 | 232174_PM_at | — | — | 0.00327857 | 0.0821646 | 369.3 | 203.0 | 212.0 |
| 1944 | 230526_PM_at | LOC100131096 | hypothetical LOC100131096 | 0.0032788 | 0.0821646 | 85.3 | 79.7 | 62.4 |
| 1945 | 244347_PM_at | — | — | 0.00328111 | 0.0821646 | 37.1 | 25.3 | 24.0 |
| 1946 | 1562591_PM_a_at | OFCC1 | orofacial cleft 1 candidate 1 | 0.00328139 | 0.0821646 | 10.8 | 9.9 | 11.4 |
| 1947 | 243608_PM_at | COG2 | component of oligomeric golgi complex 2 | 0.00328364 | 0.0821787 | 33.9 | 27.7 | 25.7 |
| 1948 | 207027_PM_at | HGFAC | HGF activator | 0.00330422 | 0.0826513 | 10.0 | 9.8 | 10.9 |
| 1949 | 235513_PM_at | — | — | 0.00330961 | 0.0827436 | 296.4 | 212.1 | 239.3 |
| 1950 | 230821_PM_at | ZNF148 | zinc finger protein 148 | 0.00331765 | 0.0829024 | 90.4 | 79.7 | 67.9 |
| 1951 | 237591_PM_at | NCRNA00173 | non-protein coding RNA 173 | 0.0033227 | 0.0829809 | 623.6 | 365.2 | 524.8 |
| 1952 | 215207_PM_x_at | NUS1 /// NUS1P3 | nuclear undecaprenyl pyrophosphate synthase 1 homolog (S. cerevisiae) /// nuclear undec | 0.00332421 | 0.0829809 | 26.0 | 34.8 | 32.8 |
| 1953 | 1560395_PM_at | — | — | 0.00333835 | 0.0832578 | 11.3 | 9.8 | 9.4 |
| 1954 | 232587_PM_at | EML4 | echinoderm microtubule associated protein like 4 | 0.00333872 | 0.0832578 | 42.6 | 32.3 | 28.3 |
| 1955 | 234059_PM_at | — | — | 0.00334076 | 0.0832661 | 10.7 | 9.3 | 10.4 |
| 1956 | 220618_PM_s_at | ZCWPW1 | zinc finger, CW type with PWWP domain 1 | 0.00334668 | 0.083371 | 15.6 | 12.7 | 14.0 |
| 1957 | 238735_PM_at | — | — | 0.00336694 | 0.0838328 | 34.3 | 26.7 | 23.4 |
| 1958 | 1562028_PM_at | CCND3 | Cyclin D3 | 0.00337137 | 0.0839003 | 15.6 | 11.7 | 11.9 |
| 1959 | 1565689_PM_at | — | — | 0.00337532 | 0.0839557 | 46.8 | 35.6 | 37.0 |
| 1960 | 217344_PM_at | FDPS | farnesyl diphosphate synthase | 0.00338219 | 0.0840837 | 9.4 | 9.9 | 10.7 |
| 1961 | 214719_PM_at | SLC46A3 | solute carrier family 46, member 3 | 0.00338423 | 0.0840915 | 419.8 | 342.3 | 348.5 |
| 1962 | 233439_PM_at | LETM1 | leucine zipper-EF-hand containing transmembrane protein 1 | 0.00338723 | 0.0840983 | 13.4 | 12.3 | 11.6 |
| 1963 | 203803_PM_at | PCYOX1 | prenylcysteine oxidase 1 | 0.0033906 | 0.0840983 | 20.7 | 18.8 | 15.6 |
| 1964 | 239296_PM_at | — | — | 0.00339104 | 0.0840983 | 104.3 | 66.0 | 80.3 |
| 1965 | 213351_PM_s_at | TMCC1 | transmembrane and coiled-coil domain family 1 | 0.00339141 | 0.0840983 | 446.1 | 281.1 | 311.4 |
| 1966 | 237181_PM_at | — | — | 0.00339341 | 0.0841051 | 27.0 | 19.7 | 17.2 |
| 1967 | 231016_PM_s_at | ARNT | Aryl hydrocarbon receptor nuclear translator | 0.00339928 | 0.0842078 | 21.4 | 21.6 | 26.7 |
| 1968 | 233713_PM_at | — | — | 0.00340118 | 0.084212 | 65.9 | 51.2 | 43.3 |
| 1969 | 220735_PM_s_at | SENP7 | SUMO1/sentrin specific peptidase 7 | 0.00341419 | 0.0844912 | 12.4 | 17.4 | 16.1 |
| 1970 | 221904_PM_at | FAM131A | family with sequence similarity 131, member A | 0.00341688 | 0.0845149 | 125.6 | 152.3 | 169.4 |
| 1971 | 218292_PM_s_at | PRKAG2 | protein kinase, AMP-activated, gamma 2 non-catalytic subunit | 0.00342353 | 0.0846231 | 78.7 | 107.9 | 100.2 |
| 1972 | 210810_PM_s_at | SLC6A5 | solute carrier family 6 (neurotransmitter transporter, glycine), member 5 | 0.00342473 | 0.0846231 | 10.4 | 9.2 | 9.9 |
| 1973 | 240865_PM_at | — | — | 0.00343655 | 0.0848722 | 29.3 | 22.0 | 17.9 |
| 1974 | 233656_PM_s_at | VPS54 | vacuolar protein sorting 54 homolog (S. cerevisiae) | 0.00344076 | 0.0849061 | 72.2 | 119.2 | 100.9 |
| 1975 | 244813_PM_at | — | — | 0.00344188 | 0.0349061 | 19.5 | 15.2 | 15.1 |
| 1976 | 211565_PM_at | SH3GL3 | SH3-domain GRB2-like 3 | 0.00344315 | 0.0849061 | 10.8 | 11.8 | 12.9 |
| 1977 | 214321_PM_at | NOV | nephroblastoma overexpressed gene | 0.00345461 | 0.0851456 | 77.2 | 88.5 | 163.6 |
| 1978 | 222266_PM_at | C19orf2 | Chromosome 19 open reading frame 2 | 0.00345958 | 0.0851917 | 321.2 | 256.1 | 206.0 |
| 1979 | 239307_PM_at | LOC100509703 | hypothetical LOC100509703 | 0.00345998 | 0.0851917 | 255.5 | 155.4 | 188.5 |
| 1980 | 200624_PM_s_at | MATR3 | matrin 3 | 0.00347416 | 0.0854977 | 255.1 | 378.0 | 322.4 |
| 1981 | 222048_PM_at | CRYBB2P1 | crystallin, beta B2 pseudogene 1 | 0.0034836 | 0.0856867 | 30.4 | 25.6 | 23.7 |
| 1982 | 226756_PM_at | — | — | 0.00348639 | 0.0857087 | 53.5 | 77.9 | 91.0 |
| 1983 | 239391_PM_at | FAM120AOS | Family with sequence similarity 120A opposite strand | 0.00348801 | 0.0857087 | 53.8 | 43.6 | 50.8 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 1984 | 211764_PM_s_at | UBE2D1 | ubiquitin-conjugating enzyme E2D 1 (UBC4/5 homolog, yeast) | 0.00349414 | 0.0857522 | 1682.5 | 2015.0 | 2192.3 |
| 1985 | 222835_PM_at | THSD4 | thrombospondin, type I, domain containing 4 | 0.00349443 | 0.0857522 | 10.6 | 9.8 | 11.2 |
| 1986 | 232313_PM_at | TMEM132C | transmembrane protein 132C | 0.00349506 | 0.0857522 | 11.7 | 11.0 | 12.5 |
| 1987 | 230735_PM_at | — | — | 0.00350442 | 0.0859385 | 921.5 | 683.6 | 628.9 |
| 1988 | 1555536_PM_at | ANTXR2 | anthrax toxin receptor 2 | 0.00350943 | 0.0860181 | 65.7 | 55.0 | 53.3 |
| 1989 | 241905_PM_at | PIK3C2A | Phosphoinositide-3-kinase, class 2, alpha polypeptide | 0.00351172 | 0.085031 | 127.2 | 95.1 | 96.4 |
| 1990 | 201784_PM_s_at | C11orf58 | chromosome 11 open reading frame 58 | 0.00351433 | 0.0860516 | 484.3 | 641.2 | 610.2 |
| 1991 | 203224_PM_at | RFK | riboflavin kinase | 0.0035255 | 0.0862084 | 127.7 | 179.7 | 175.5 |
| 1992 | 1566897_PM_at | — | — | 0.00352577 | 0.0862084 | 40.5 | 30.3 | 28.5 |
| 1993 | 233598_PM_at | C20orf187 | chromosome 20 open reading frame 187 | 0.00352604 | 0.0862084 | 9.3 | 9.4 | 10.3 |
| 1994 | 212519_PM_at | UBE2E1 | ubiquitin-conjugating enzyme E2E 1 (UBC4/5 homolog, yeast) | 0.00353349 | 0.0863142 | 694.7 | 905.4 | 845.0 |
| 1995 | 210119_PM_at | KCNJ15 | potassium inwardly-rectifying channel, subfamily J, member 15 | 0.00353391 | 0.0863142 | 2213.3 | 1462.5 | 1794.1 |
| 1996 | 241932_PM_at | — | — | 0.00353801 | 0.0863346 | 27.5 | 20.4 | 20.2 |
| 1997 | 230261_PM_at | ST8SIA4 | ST8 alpha-N-acetyl-neuraminide alpha-2,8-sialyltransferase 4 | 0.00353829 | 0.0863346 | 223.7 | 281.2 | 329.5 |
| 1998 | 204725_PM_s_at | NCK1 | NCK adaptor protein 1 | 0.00354863 | 0.0865436 | 62.3 | 93.1 | 83.9 |
| 1999 | 235965_PM_at | — | — | 0.00355144 | 0.0865688 | 8.7 | 9.1 | 10.5 |
| 2000 | 210368_PM_at | PCDHGA8 | protocadherin gamma subfamily A, 8 | 0.0035662 | 0.0868851 | 12.4 | 10.6 | 11.6 |
| 2001 | 231107_PM_at | — | — | 0.00357367 | 0.0870236 | 47.2 | 37.3 | 35.4 |
| 2002 | 234439_PM_at | — | — | 0.0035897 | 0.0873703 | 11.5 | 10.0 | 10.0 |
| 2003 | 243869_PM_at | — | — | 0.0035929 | 0.0874045 | 214.0 | 183.6 | 147.6 |
| 2004 | 235766_PM_x_at | RAB27A | RAB27A, member RAS oncogene family | 0.00359922 | 0.0875146 | 1165.1 | 1438.5 | 1374.9 |
| 2005 | 242853_PM_at | — | — | 0.00360722 | 0.0876653 | 52.3 | 38.3 | 41.2 |
| 2006 | 40446_PM_at | PHF1 | PHD finger protein 1 | 0.0036114 | 0.0876843 | 263.3 | 227.3 | 227.3 |
| 2007 | 244646_PM_at | — | — | 0.0036116 | 0.0876843 | 113.5 | 85.0 | 87.2 |
| 2008 | 232097_PM_at | TOX4 | TOX high mobility group box family member 4 | 0.00361452 | 0.0877115 | 159.7 | 112.9 | 128.3 |
| 2009 | 217877_PM_s_at | GPBP1L1 | GC-rich promoter binding protein 1-like 1 | 0.00351929 | 0.0877835 | 327.8 | 387.8 | 381.1 |
| 2010 | 1557452_PM_at | — | — | 0.00362626 | 0.0879088 | 46.4 | 33.4 | 36.8 |
| 2011 | 222214_PM_at | — | — | 0.00364195 | 0.0882453 | 40.0 | 27.0 | 26.2 |
| 2012 | 220918_PM_at | C21orf96 | chromosome 21 open reading frame 96 | 0.00364716 | 0.0883276 | 364.2 | 294.9 | 224.1 |
| 2013 | 1552563_PM_a_at | — | — | 0.00365851 | 0.0885585 | 14.2 | 12.3 | 11.9 |
| 2014 | 1568857_PM_a_at | NBR1 | Neighbor of BRCA1 gene 1 | 0.00366507 | 0.0886732 | 134.8 | 97.1 | 98.6 |
| 2015 | 1557501_PM_a_at | — | — | 0.00366836 | 0.0887088 | 38.9 | 31.1 | 30.6 |
| 2016 | 222182_PM_s_at | CNOT2 | CCR4-NOT transcription complex, subunit 2 | 0.00367216 | 0.0887566 | 466.6 | 388.5 | 402.9 |
| 2017 | 1560144_PM_at | — | — | 0.00367869 | 0.0888704 | 9.5 | 9.1 | 10.2 |
| 2018 | 202704_PM_at | TOB1 | transducer of ERBB2, 1 | 0.00368242 | 0.0889164 | 337.2 | 449.9 | 455.5 |
| 2019 | 223490_PM_s_at | EXOSC3 | exosome component 3 | 0.00368908 | 0.0890331 | 60.7 | 88.7 | 71.7 |
| 2020 | 228027_PM_at | GPRASP2 | G protein-coupled receptor associated sorting protein 2 | 0.00369478 | 0.0891265 | 11.1 | 10.3 | 9.4 |
| 2021 | 225805_PM_at | HNRNPU | heterogeneous nuclear ribonucleoprotein U (scaffold attachment factor A) | 0.00369714 | 0.0891393 | 22.1 | 31.7 | 25.1 |
| 2022 | 228628_PM_at | SRGAP2P1 | SLIT-ROBO Rho GTPase activating protein 2 pseudogene 1 | 0.00371487 | 0.0894886 | 461.9 | 362.6 | 338.6 |
| 2023 | 225023___PM_at | GOPC | golgi-associated PDZ and coiled-coil motif containing | 0.0037153 | 0.0894886 | 33.6 | 42.6 | 42.5 |
| 2024 | 215169_PM_at | SLC35E2 | solute carrier family 35, member E2 | 0.00372164 | 0.089597 | 157.6 | 108.2 | 117.3 |
| 2025 | 230856_PM_at | — | — | 0.00372727 | 0.0896882 | 113.2 | 84.2 | 84.6 |
| 2026 | 208669_PM_s_at | EID1 | EP300 interacting inhibitor of differentiation 1 | 0.00373918 | 0.0899183 | 553.2 | 801.6 | 679.5 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 2027 | 203226_PM_s_at | TSPAN31 | tetraspanin 31 | 0.00374052 | 0.0899183 | 64.9 | 90.1 | 76.5 |
| 2028 | 243765_PM_at | — | — | 0.00375004 | 0.0901027 | 19.5 | 17.2 | 16.2 |
| 2029 | 1562468_PM_at | — | — | 0.00376362 | 0.0903403 | 24.4 | 17.4 | 17.0 |
| 2030 | 209076_PM_s_at | WDR45L | WDR45-like | 0.00376364 | 0.0903403 | 142.3 | 162.8 | 167.8 |
| 2031 | 241543_PM_at | — | — | 0.00376716 | 0.0903803 | 10.4 | 9.4 | 11.0 |
| 2032 | 1559201_PM_a_at | — | — | 0.00378405 | 0.0906794 | 613.6 | 450.2 | 499.4 |
| 2033 | 224796_PM_at | ASAP1 | ArfGAP with SH3 domain, ankyrin repeat and PH domain 1 | 0.00378442 | 0.0906794 | 1795.7 | 1328.9 | 1478.4 |
| 2034 | 233041_PM_x_at | — | — | 0.00378521 | 0.0906794 | 855.4 | 706.6 | 739.4 |
| 2035 | 232597_PM_x_at | SRSF2IP | serine/arginine-rich splicing factor 2, interacting protein | 0.00378854 | 0.090698 | 766.8 | 615.4 | 621.3 |
| 2036 | 217550_PM_at | ATF6 | activating transcription factor 6 | 0.00378971 | 0.090698 | 220.4 | 149.4 | 200.6 |
| 2037 | 233476_PM_at | — | — | 0.00379655 | 0.0908171 | 420.4 | 284.9 | 293.1 |
| 2038 | 1554559_PM_at | GPR62 | G protein-coupled receptor 62 | 0.00382185 | 0.0913775 | 13.4 | 11.6 | 12.1 |
| 2039 | 217654_PM_at | CFLAR | CASP8 and FADD-like apoptosis regulator | 0.00382481 | 0.0914006 | 42.1 | 26.0 | 26.3 |
| 2040 | 224674_PM_at | TTYH3 | tweety homolog 3 (Drosophila) | 0.00382657 | 0.0914006 | 31.7 | 40.5 | 41.7 |
| 2041 | 232773_PM_at | — | — | 0.00383209 | 0.091467 | 107.9 | 81.8 | 78.2 |
| 2042 | 242232_PM_at | — | — | 0.00383319 | 0.091467 | 27.9 | 19.9 | 20.0 |
| 2043 | 239224_PM_at | FBXL20 | F-box and leucine-rich repeat protein 20 | 0.00383498 | 0.091467 | 38.6 | 31.3 | 31.1 |
| 2044 | 1552714_PM_at | CREG2 | cellular repressor of E1A-stimulated genes 2 | 0.00385834 | 0.0919468 | 10.2 | 9.7 | 11.5 |
| 2045 | 225677_PM_at | BCAP29 | B-cell receptor-associated protein 29 | 0.00386012 | 0.0919468 | 49.1 | 69.2 | 74.5 |
| 2046 | 238886_PM_at | TMED10 | transmembrane emp24-like trafficking protein 10 (yeast) | 0.00386076 | 0.0919468 | 45.5 | 32.9 | 33.1 |
| 2047 | 237426_PM_at | SP100 | SP100 nuclear antigen | 0.00386538 | 0.0919651 | 344.2 | 223.2 | 258.5 |
| 2048 | 239431_PM_at | TICAM2 /// TMED7-TICAM2 | toll-like receptor adaptor molecule 2 /// TMED7-TICAM2 readthrough | 0.00386718 | 0.0919651 | 42.0 | 59.7 | 60.8 |
| 2049 | 243013_PM_at | — | — | 0.00386719 | 0.0919651 | 68.1 | 53.2 | 48.5 |
| 2050 | 236612_PM_at | — | — | 0.00387911 | 0.092128 | 14.2 | 12.0 | 13.1 |
| 2051 | 222582_PM_at | PRKAG2 | protein kinase, AMP-activated, gamma 2 non-catalytic subunit | 0.00387911 | 0.092128 | 158.1 | 194.8 | 206.7 |
| 2052 | 227205_PM_at | TAF1 | TAF1 RNA polymerase II, TATA box binding protein (TBP)-associated factor, 250 kDa | 0.00387971 | 0.092128 | 45.6 | 60.0 | 51.5 |
| 2053 | 236836_PM_at | — | — | 0.00388617 | 0.0922081 | 85.6 | 72.4 | 60.0 |
| 2054 | 201375_PM_s_at | PPP2CB | protein phosphatase 2, catalytic subunit, beta isozyme | 0.00388709 | 0.0922081 | 410.6 | 507.3 | 496.6 |
| 2055 | 209130_PM_at | SNAP23 | synaptosomal-associated protein, 23 kDa | 0.00389024 | 0.0922081 | 1604.7 | 1776.5 | 1930.4 |
| 2056 | 224177_PM_s_at | CXorf26 | chromosome X open reading frame 26 | 0.00389364 | 0.0922081 | 51.1 | 76.8 | 57.5 |
| 2057 | 202505_PM_at | SNRPB2 | small nuclear ribonucleoprotein polypeptide B | 0.00389463 | 0.0922081 | 392.0 | 508.0 | 467.4 |
| 2058 | 1570124_PM_at | — | — | 0.00389516 | 0.0922081 | 11.6 | 10.6 | 12.2 |
| 2059 | 231968_PM_at | UGGT1 | UDP-glucose glycoprotein glucosyltransferase 1 | 0.00389633 | 0.0922081 | 302.7 | 247.7 | 259.2 |
| 2060 | 222631_PM_at | PI4K2B | phosphatidylinositol 4-kinase type 2 beta | 0.00390047 | 0.0922427 | 42.2 | 64.7 | 62.0 |
| 2061 | 235805_PM_at | — | — | 0.00390158 | 0.0922427 | 48.0 | 30.8 | 32.9 |
| 2062 | 230582_PM_at | HECA | Headcase homolog (Drosophila) | 0.00390887 | 0.0923703 | 15.5 | 13.2 | 13.6 |
| 2063 | 223011_PM_s_at | OCIAD1 | OCIA domain containing 1 | 0.00391975 | 0.0925825 | 608.3 | 727.8 | 657.3 |
| 2064 | 232135_PM_at | SAP30L | SAP30-like | 0.00392804 | 0.0927333 | 309.6 | 233.1 | 252.6 |
| 2065 | 206366_PM_X_at | XCL1 | chemokine (C motif) ligand 1 | 0.00393296 | 0.0928045 | 205.2 | 302.0 | 368.0 |
| 2066 | 226368_PM_at | CHST11 | carbohydrate (chondroitin 4) sulfotransferase 11 | 0.00395067 | 0.0931773 | 1079.8 | 818.7 | 836.0 |
| 2067 | 205068_PM_s_at | ARHGAP26 | Rho GTPase activating protein 26 | 0.00396416 | 0.0933895 | 1314.3 | 888.3 | 1031.9 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 2068 | 204037_PM_at | LPAR1 | lysophosphatidic acid receptor 1 | 0.00396514 | 0.0933895 | 20.3 | 23.4 | 27.6 |
| 2069 | 206499_PM_s_at | RCC1 | regulator of chromosome condensation 1 | 0.00395759 | 0.0933895 | 24.4 | 32.1 | 25.4 |
| 2070 | 239955_PM_at | — | — | 0.00396859 | 0.0933895 | 166.5 | 121.4 | 113.9 |
| 2071 | 222728_PM_s_at | TAF1D | TATA box binding protein (TBP)-associated factor, RNA polymerase I, D, 41 kDa | 0.00397247 | 0.0933895 | 591.6 | 472.2 | 470.7 |
| 2072 | 228787_PM_s_at | BCAS4 | breast carcinoma amplified sequence 4 | 0.00397319 | 0.0933895 | 24.3 | 22.9 | 19.6 |
| 2073 | 212802_PM_s_at | GAPVD1 | GTPase activating protein and VP59 domains 1 | 0.00397442 | 0.0933895 | 482.4 | 412.6 | 428.7 |
| 2074 | 223501_PM_at | TNFSF13B | tumor necrosis factor (ligand)superfamily, member 13b | 0.00397788 | 0.0933895 | 2123.6 | 2619.4 | 2925.4 |
| 2075 | 241425_PM_at | NUPL1 | nucleoporin like 1 | 0.00397867 | 0.0933895 | 506.9 | 376.8 | 406.3 |
| 2076 | 208853_PM_s_at | CANX | calnexin | 0.00398028 | 0.0933895 | 142.7 | 193.8 | 170.5 |
| 2077 | 1557813_PM_at | — | — | 0.00398075 | 0.0933895 | 161.6 | 103.7 | 117.7 |
| 2078 | 225626_PM_at | PAG1 | phosphoprotein associated with glycosphingolipid microdomains 1 | 0.00398708 | 0.0934504 | 1834.4 | 1353.6 | 1349.3 |
| 2079 | AFFX-r2-P1-cre-5_at | — | — | 0.00398718 | 0.0934504 | 10155.6 | 9861.1 | 10591.3 |
| 2080 | 225091_PM_at | ZCCHC3 | zinc finger, CCHC domain containing 3 | 0.00400655 | 0.0938592 | 106.6 | 132.3 | 117.4 |
| 2081 | 233669_PM_s_at | TRIM54 | tripartite motif-containing 54 | 0.00401166 | 0.0939338 | 12.0 | 10.7 | 11.8 |
| 2082 | 218325_PM_s_at | DIDO1 | death inducer-obliterator 1 | 0.00401405 | 0.0939446 | 122.7 | 106.7 | 98.9 |
| 2083 | 1558486_PM_at | ZNF493 | zinc finger protein 493 | 0.00402068 | 0.0940546 | 404.2 | 284.3 | 271.1 |
| 2084 | 219715_PM_s_at | TDP1 | tyrosyl-DNA phosphodiesterase 1 | 0.00402559 | 0.0941242 | 51.5 | 46.8 | 39.4 |
| 2085 | 1554806_PM_a_at | FBXO8 | F-box protein 8 | 0.00402917 | 0.0941438 | 64.3 | 91.0 | 72.2 |
| 2086 | 215545_PM_at | — | — | 0.00403029 | 0.0941438 | 69.3 | 56.4 | 55.5 |
| 2087 | 232835_PM_at | — | — | 0.004036 | 0.0941915 | 361.6 | 219.4 | 215.7 |
| 2088 | 229556_PM_at | LOC100288893 | hypothetical LOC100288893 | 0.0040362 | 0.0941915 | 12.6 | 14.9 | 16.1 |
| 2089 | 221883_PM_at | PKNOX1 | PBX/knotted 1 homeobox 1 | 0.00404237 | 0.0942721 | 67.9 | 51.4 | 46.6 |
| 2090 | 241018_PM_at | TMEM59 | transmembrane protein 59 | 0.00404702 | 0.0942721 | 52.1 | 39.9 | 37.4 |
| 2091 | 224673_PM_at | LENG8 | leukocyte receptor cluster (LRC) member 8 | 0.00404728 | 0.0942721 | 30.1 | 22.9 | 22.0 |
| 2092 | 211406_PM_at | IER3IP1 | immediate early response 3 interacting protein 1 | 0.00404739 | 0.0942721 | 15.9 | 18.5 | 19.5 |
| 2093 | 201056_PM_at | GOLGB1 | golgin B1 | 0.00405091 | 0.094309 | 89.6 | 70.1 | 71.1 |
| 2094 | 217911_PM_s_at | BAG3 | BCL2-associated athanogene 3 | 0.00405374 | 0.0943298 | 43.6 | 31.9 | 25.2 |
| 2095 | 237107_PM_at | PRKRA | protein kinase, interferon-inducible double stranded RNA dependent activator | 0.00407199 | 0.0946579 | 56.7 | 37.6 | 39.8 |
| 2096 | 202442_PM_at | AP3S1 | adaptor-related protein complex 3, sigma 1 subunit | 0.00407287 | 0.0946579 | 783.8 | 948.8 | 953.9 |
| 2097 | 203410_PM_at | AP3M2 | adaptor-related protein complex 3, mu 2 subunit | 0.00407367 | 0.0946579 | 58.6 | 45.9 | 40.2 |
| 2098 | 235985_PM_at | — | — | 0.00407823 | 0.0947187 | 110.9 | 84.1 | 75.6 |
| 2099 | 242371_PM_x_at | — | — | 0.00408809 | 0.094856 | 16.5 | 13.9 | 14.0 |
| 2100 | 228190_PM_at | ATG4C /// CTR9 | ATG4 autophagy related 4 homolog C (S. cerevisiae) /// Ctr9, Paf1/RNA polymerase II com | 0.00408993 | 0.094856 | 51.6 | 70.4 | 78.4 |
| 2101 | 203024_PM_s_at | C5orf15 | chromosome 5 open reading frame 15 | 0.00409089 | 0.094856 | 418.3 | 545.0 | 531.4 |
| 2102 | 202872_PM_at | ATP6V1C1 | ATPase, H+ transporting, lysosomal 42 kDa, V1 subunit C1 | 0.00409559 | 0.094855 | 81.6 | 115.8 | 118.9 |
| 2103 | 233496_PM_s_at | CFL2 | cofilin 2 (muscle) | 0.0040962 | 0.094856 | 9.5 | 9.6 | 10.8 |
| 2104 | 202080_PM_s_at | TRAK1 | trafficking protein, kinesin binding 1 | 0.00409747 | 0.094856 | 135.4 | 162.1 | 171.8 |
| 2105 | 243262_PM_at | — | — | 0.00409802 | 0.094856 | 19.5 | 15.0 | 15.8 |
| 2106 | 228087_PM_at | CCDC126 | coiled-coil domain containing 126 | 0.00410037 | 0.094856 | 80.0 | 119.2 | 136.9 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 2107 | 230630_PM_at | AK4 | adenylate kinase 4 | 0.00410166 | 0.094856 | 14.0 | 12.2 | 13.2 |
| 2108 | 218494_PM_s_at | SLC2A4RG | SLC2A4 regulator | 0.00410524 | 0.0948938 | 69.3 | 73.8 | 48.0 |
| 2109 | 211387_PM_x_at | RNGTT | RNA guanylyltransferase and 5'-phosphatase | 0.00411271 | 0.0950213 | 24.5 | 19.9 | 22.1 |
| 2110 | 230980_PM_x_at | — | — | 0.00412014 | 0.0951479 | 27.7 | 22.3 | 22.1 |
| 2111 | 236562_PM_at | ZNF439 | zinc finger protein 439 | 0.00413239 | 0.0953856 | 25.7 | 36.6 | 43.4 |
| 2112 | 239848_PM_at | — | — | 0.00413966 | 0.0955082 | 24.9 | 18.6 | 18.5 |
| 2113 | 226459_PM_at | PIK3AP1 | phosphoinositide-3-kinase adaptor protein 1 | 0.00415318 | 0.0957598 | 2062.2 | 2494.4 | 2596.3 |
| 2114 | 224837_PM_at | FOXP1 | forkhead box P1 | 0.00415683 | 0.0957598 | 688.1 | 567.3 | 535.8 |
| 2115 | 213500_PM_at | — | — | 0.00415703 | 0.0957598 | 75.5 | 61.9 | 62.1 |
| 2116 | 1556178_PM_x_at | TAF8 | TAF8 RNA polymerase II, TATA box binding protein (TBP)-associated factor, 43 kDa | 0.00416035 | 0.0957598 | 33.1 | 39.2 | 31.7 |
| 2117 | 204837_PM_at | MTMR9 | myotubularin related protein 9 | 0.00416123 | 0.0957598 | 315.8 | 269.5 | 270.1 |
| 2118 | 238812_PM_at | — | — | 0.00416236 | 0.0957598 | 153.0 | 105.4 | 101.1 |
| 2119 | 215127_PM_s_at | RBMS1 | RNA binding motif, single stranded interacting protein 1 | 0.00416626 | 0.0957867 | 2167.2 | 1825.2 | 2003.6 |
| 2120 | 222202_PM_at | — | — | 0.00416849 | 0.0957867 | 11.0 | 9.9 | 11.2 |
| 2121 | 226438_PM_at | SNTB1 | syntrophin, beta 1 (dystrophin-associated protein A1, 59 kDa, basic component 1) | 0.0041701 | 0.0957867 | 83.2 | 129.3 | 116.4 |
| 2122 | 222032_PM_s_at | USP7 | ubiquitin specific peptidase 7 (herpes virus-associated) | 0.00417139 | 0.0957867 | 22.9 | 18.3 | 20.0 |
| 2123 | 238631_PM_at | ZNF140 | Zinc finger protein 140 | 0.0041831 | 0.0960103 | 15.9 | 13.6 | 12.3 |
| 2124 | 218514_PM_at | C17orf71 | chromosome 17 open reading frame 71 | 0.00419327 | 0.0961984 | 94.3 | 118.2 | 111.3 |
| 2125 | 213369_PM_at | CDHR1 | cadherin-related family member 1 | 0.00419612 | 0.0962185 | 11.9 | 10.8 | 12.3 |
| 2126 | 240737_PM_at | — | — | 0.00420555 | 0.0963894 | 143.2 | 116.6 | 115.7 |
| 2127 | 216626_PM_at | — | — | 0.00423185 | 0.0969466 | 11.9 | 10.1 | 10.2 |
| 2128 | 241351_PM_at | — | — | 0.00423575 | 0.0969903 | 48.6 | 39.4 | 37.1 |
| 2129 | 1554964_PM_x_at | — | — | 0.00423798 | 0.0969958 | 13.8 | 11.0 | 11.9 |
| 2130 | 231601_PM_at | LOC100507224 | hypothetical LOC100507224 | 0.0042559 | 0.0973602 | 10.4 | 10.1 | 11.3 |
| 2131 | 200776_PM_s_at | BZW1 | basic leucine zipper and W2 domains 1 | 0.00426985 | 0.0975934 | 196.4 | 240.6 | 239.9 |
| 2132 | 239861_PM_at | — | — | 0.0042701 | 0.0975934 | 360.5 | 261.9 | 284.1 |
| 2133 | 1561006_PM_at | — | — | 0.00427945 | 0.0977613 | 13.5 | 12.8 | 11.9 |
| 2134 | 242443_PM_at | EML5 | Echinoderm microtubule associated protein like 5 | 0.00428213 | 0.0977766 | 25.4 | 18.7 | 18.7 |
| 2135 | 212078_PM_s_at | MLL | myeloid/lymphoid or mixed-lineage leukemia (trithorax homolog, *Drosophila*) | 0.0042932 | 0.0979835 | 186.7 | 143.2 | 117.3 |
| 2136 | 215470_PM_at | GTF2H2B | general transcription factor IIH, polypeptide 2B | 0.00429999 | 0.0980854 | 246.2 | 184.6 | 138.8 |
| 2137 | 224641_PM_at | FYTTD1 | forty-two-three domain containing 1 | 0.00430169 | 0.0980854 | 330.1 | 444.5 | 371.2 |
| 2138 | 209027_PM_s_at | ABI2 | abl-interactor 1 | 0.00430504 | 0.0981158 | 537.3 | 673.6 | 648.2 |
| 2139 | 224698_PM_at | ESYT2 | extended synaptotagmin-like protein 2 | 0.00431319 | 0.0982556 | 437.9 | 373.9 | 323.4 |
| 2140 | 225783_PM_at | UBE2F | ubiquitin-conjugating enzyme E2F (putative) | 0.00431806 | 0.0983206 | 262.9 | 338.1 | 367.5 |
| 2141 | 230742_PM_at | — | — | 0.00432039 | 0.098321 | 161.8 | 115.4 | 106.3 |
| 2142 | 232148_PM_at | NSMAF | Neutral sphingomyelinase (N-SMase) activation associated factor | 0.00432334 | 0.098321 | 144.0 | 94.9 | 94.9 |
| 2143 | 244636_PM_at | — | — | 0.00432413 | 0.098321 | 31.1 | 22.7 | 20.7 |
| 2144 | 244686_PM_at | TCOF1 | Treacher Collins-Franceschetti syndrome 1 | 0.00433005 | 0.0984099 | 14.2 | 12.6 | 14.4 |
| 2145 | 1569806_PM_at | — | — | 0.00435008 | 0.0987818 | 13.3 | 11.7 | 13.1 |
| 2146 | 235623_PM_at | ELP2 | Elongation protein 2 homolog (*S. cerevisiae*) | 0.00435048 | 0.0987818 | 148.9 | 119.0 | 117.2 |
| 2147 | 222207_PM_x_at | — | — | 0.00435892 | 0.0989274 | 752.8 | 633.6 | 673.2 |
| 2148 | 202544_PM_at | GMFB | glia maturation factor, beta | 0.00436196 | 0.0989503 | 350.5 | 476.6 | 471.2 |

TABLE 4-continued

List of 2156 differentially expressed probesets between AR, SCAR and TX from a 3-way ANOVA

| # | Probeset ID | Gene Symbol | Gene Title | p-value (Phenotype) | stepup p-value (Phenotype) | AR - Mean Signal | SCAR - Mean Signal | TX - Mean Signal |
|---|---|---|---|---|---|---|---|---|
| 2149 | 1553176_PM_at | SH2D1B | SH2 domain containing 1B | 0.00436721 | 0.0990233 | 11.4 | 12.7 | 13.5 |
| 2150 | 243492_PM_at | THEM4 | thioesterase superfamily member 4 | 0.00437206 | 0.0990871 | 28.2 | 20.9 | 17.9 |
| 2151 | 244154_PM_at | DDHD1 | DDHD domain containing 1 | 0.00437947 | 0.0992089 | 110.5 | 83.5 | 83.9 |
| 2152 | 242946_PM_at | — | — | 0.00438297 | 0.0992421 | 2226.9 | 1788.3 | 1732.9 |
| 2153 | 232665_PM_x_at | — | — | 0.00438865 | 0.0993245 | 17.4 | 14.9 | 16.1 |
| 2154 | 222035_PM_s_at | PAPOLA | poly(A) polymerase alpha | 0.00440072 | 0.0994865 | 299.9 | 376.9 | 346.1 |
| 2155 | 1566958_PM_at | — | — | 0.00440104 | 0.0994865 | 15.9 | 12.8 | 13.8 |
| 2156 | 215978_PM_x_at | ZNF721 | zinc finger protein 721 | 0.00440193 | 0.0994865 | 1251.4 | 972.1 | 1042.4 |

TABLE 5

Time to biopsy (days post transplant).

| | SCAR | CAR | TX |
|---|---|---|---|
| Mean | 287.6 | 921.2 | 267.8 |
| Range | 8-748 | 15-2876 | 84-2228 |

TABLE 6

3-Way 1-Step Microarray Analysis (AR v. subAR v. TX) using biopsy samples - Results

| Real | Predicted | | |
|---|---|---|---|
| | AR Bx | TX Bx | SCAR Bx |
| AR Bx | 16 | 0 | 4 |
| TX Bx | 0 | 21 | 4 |
| SCAR Bx | 5 | 5 | 12 |

| Method | Classifies | % Predictive Accuracy | Sensitivity (%) | Specificity (%) | Positive Predictive Value (%) | Negative Predicitve Value (%) | AUC |
|---|---|---|---|---|---|---|---|
| Nearest Centroid (1 Step Prediction) | TX vs. AR | 100% | 100% | 100% | 100% | 100% | 1.000 |
| | TX vs. SCAR | 78% | 81% | 75% | 84% | 71% | 0.785 |
| | AR vs. SCAR | 76% | 76% | 75% | 80% | 71% | 0.768 |

TABLE 7

Biopsy Microarray Signatures for subAR using a 2-way 2-Step approach - first step (AR + subAR vs .TX)

| Probeset ID | Gene Symbol | Gene Title | p-value (subAR + cAR Bx vs. TX Bx) |
|---|---|---|---|
| 211796_PM_s_at | TRBC1 /// TRBC2 | T cell receptor beta constant 1 /// T cell receptor beta constant 2 | 4.15E−12 |
| 213193_PM_x_at | TRBC1 | T cell receptor beta constant 1 | 3.16E−11 |
| 207238_PM_s_at | PTPRC | protein tyrosine phosphatase, receptor type, C | 3.47E−11 |
| 204118_PM_at | CD48 | CD48 molecule | 4.03E−11 |
| 212587_PM_s_at | PTPRC | protein tyrosine phosphatase, receptor type, C | 4.49E−11 |
| 204655_PM_at | CCL5 | chemokine (C-C motif) ligand 5 | 4.82E−11 |
| 34210_PM_at | CD52 | CD52 molecule | 5.80E−11 |
| 210915_PM_x_at | TRBC2 | T cell receptor beta constant 2 | 6.47E−11 |
| 1405_PM_i_at | CCL5 | chemokine (C-C motif) ligand 5 | 8.99E−11 |
| 1555759_PM_a_at | CCL5 | chemokine (C-C motif) ligand 5 | 9.93E−11 |
| 204661_PM_at | CD52 | CD52 molecule | 1.03E−10 |
| 213539_PM_at | CD3D | CD3d molecule, delta (CD3-TCR complex) | 1.14E−10 |
| 204774_PM_at | EVI2A | ecotropic viral integration site 2A | 1.38E−10 |
| 226789_PM_at | EMB | embigin | 1.45E−10 |
| 212588_PM_at | PTPRC | protein tyrosine phosphatase, receptor type, C | 2.06E−10 |
| 205831_PM_at | CD2 | CD2 molecule | 2.10E−10 |
| 224356_PM_x_at | MS4A6A | membrane-spanning 4-domains, subfamily A, member 6A | 2.11E−10 |

TABLE 7-continued

Biopsy Microarray Signatures for subAR using a 2-way 2-Step approach - first step (AR + subAR vs .TX)

| Probeset ID | Gene Symbol | Gene Title | p-value (subAR + cAR Bx vs. TX Bx) |
|---|---|---|---|
| 206011_PM_at | CASP1 | caspase 1, apoptosis-related cysteine peptidase (interleukin 1, beta, convertase) | 2.51E−10 |
| 223280_PM_x_at | MS4A6A | membrane-spanning 4-domains, subfamily A, member 6A | 3.37E−10 |
| 229041_PM_s_at | EST 229041_PM_s_at | — | 4.24E−10 |
| 213566_PM_at | RNASE6 | ribonuclease, RNase A family, k6 | 4.26E−10 |
| 213603_PM_s_at | RAC2 | ras-related C3 botulinum toxin substrate 2 (rho family, small GTP binding protein Rac2) | 4.52E−10 |
| 210972_PM_x_at | TRAC /// TRAJ17 /// TRAV20 | T cell receptor alpha constant /// T cell receptor alpha joining 17 /// T cell receptor | 4.73E−10 |
| 211742_PM_s_at | EVI2B | ecotropic viral integration site 2B | 4.95E−10 |
| 205488_PM_at | GZMA | granzyme A (granzyme 1, cytotoxic T-lymphocyte-associated serine esterase 3) | 5.04E−10 |
| 202957_PM_at | HCLS1 | hematopoietic cell-specific Lyn substrate 1 | 6.04E−10 |
| 223922_PM_x_at | MS4A6A | membrane-spanning 4-domains, subfamily A, member 6A | 6.82E−10 |
| 206978_PM_at | CCR2 | chemokine (C-C motif) receptor 2 | 7.07E−10 |
| 219666_PM_at | MS4A6A | membrane-spanning 4-domains, subfamily A, member 6A | 7.80E−10 |
| 209671_PM_x_at | TRAC | T cell receptor alpha constant | 8.57E−10 |
| 226818_PM_at | MPEG1 | Macrophage expressed 1 | 8.65E−10 |
| 212671_PM_s_at | HLA-DQA1 /// HLA-DQA2 | major histocompatibility complex, class II, DQ alpha 1 /// major histocompatibility com | 9.14E−10 |
| 228532_PM_at | C1orf162 | chromosome 1 open reading frame 162 | 9.60E−10 |
| 204912_PM_at | IL10RA | interleukin 10 receptor, alpha | 1.01E−09 |
| 205821_PM_at | KLRK1 | killer cell lectin-like receptor subfamily K, member 1 | 1.19E−09 |
| 204205_PM_at | APOBEC3G | apolipoprotein B mRNA editing enzyme, catalytic polypeptide-like 3G | 1.19E−09 |
| 214181_PM_x_at | LST1 | leukocyte specific transcript 1 | 1.20E−09 |
| 214470_PM_at | KLRB1 | killer cell lectin-like receptor subfamily B, member 1 | 1.35E−09 |
| 201137_PM_s_at | HLA-DPB1 | major histocompatibility complex, class II, DP beta 1 | 1.35E−09 |
| 211902_PM_x_at | TRD@ | T cell receptor delta locus | 1.50E−09 |
| 210982_PM_s_at | HLA-DRA | major histocompatibility complex, class II, DR alpha | 1.74E−09 |
| 209835_PM_x_at | CD44 | CD44 molecule (indian blood group) | 2.10E−09 |
| 206666_PM_at | GZMK | granzyme K (granzyme 3; tryptase II) | 2.13E−09 |
| 203760_PM_s_at | SLA | Src-like-adaptor | 2.13E−09 |
| 202644_PM_s_at | TNFAIP3 | tumor necrosis factor, alpha-induced protein 3 | 2.24E−09 |
| 204446_PM_s_at | ALOX5 | arachidonate 5-lipoxygenase | 2.34E−09 |
| 213416_PM_at | ITGA4 | integrin, alpha 4 (antigen CD49D, alpha 4 subunit of VLA-4 receptor) | 2.40E−09 |
| 209083_PM_at | CORO1A | coronin, actin binding protein, 1A | 2.41E−09 |
| 225701_PM_at | AKNA | AT-hook transcription factor | 2.49E−09 |
| 224927_PM_at | KIAA1949 | KIAA1949 | 2.95E−09 |
| 211991_PM_s_at | HLA-DPA1 | major histocompatibility complex, class II, DP alpha 1 | 3.00E−09 |
| 235964_PM_x_at | SAMHD1 | SAM domain and HD domain 1 | 3.04E−09 |
| 202207_PM_at | ARL4C | ADP-ribosylation factor-like 4C | 3.09E−09 |
| 210895_PM_s_at | CD86 | CD86 molecule | 3.43E−09 |
| 1555691_PM_a_at | KLRK1 | killer cell lectin-like receptor subfamily K, member 1 | 3.43E−09 |
| 226841_PM_at | MPEG1 | macrophage expressed 1 | 3.66E−09 |
| 205269_PM_at | LCP2 | lymphocyte cytosolic protein 2 (SH2 domain containing leukocyte protein of 76 kDa) | 3.68E−09 |
| 203416_PM_at | CD53 | CD53 molecule | 3.82E−09 |
| 204959_PM_at | MNDA | myeloid cell nuclear differentiation antigen | 3.96E−09 |
| 223322_PM_at | RASSF5 | Ras association (RalGDS/AF-6) domain family member 5 | 4.29E−09 |
| 209970_PM_x_at | CASP1 | caspase 1, apoptosis-related cysteine peptidase (interleukin 1, beta, convertase) | 4.61E−09 |
| 1552703_PM_s_at | CARD16 /// CASP1 | caspase recruitment domain family, member 16 /// caspase 1, apoptosis-related cysteine | 4.62E−09 |
| 221698_PM_s_at | CLEC7A | C-type lectin domain family 7, member A | 4.92E−09 |
| 1559584_PM_a_at | C16orf54 | chromosome 16 open reading frame 54 | 5.09E−09 |
| 205270_PM_s_at | LCP2 | lymphocyte cytosolic protein 2 (SH2 domain containing leukocyte protein of 76 kDa) | 5.11E−09 |
| 209670_PM_at | TRAC | T cell receptor alpha constant | 5.15E−09 |
| 209606_PM_at | CYTIP | cytohesin 1 interacting protein | 5.42E−09 |
| 204891_PM_s_at | LCK | lymphocyte-specific protein tyrosine kinase | 5.54E−09 |
| 1553906_PM_s_at | FGD2 | FYVE, RhoGEF and PH domain containing 2 | 5.99E−09 |
| 223344_PM_s_at | MS4A7 | membrane-spanning 4-domains, subfamily A, member 7 | 6.00E−09 |
| 236295_PM_a_at | NLRC3 | NLR family, CARD domain containing 3 | 6.07E−09 |
| 217733_PM_s_at | TMSB10 | thymosin beta 10 | 6.08E−09 |
| 205081_PM_at | CRIP1 | cysteine-rich protein 1 (intestinal) | 6.14E−09 |

TABLE 7-continued

Biopsy Microarray Signatures for subAR using a 2-way 2-Step approach - first step (AR + subAR vs .TX)

| Probeset ID | Gene Symbol | Gene Title | p-value (subAR + cAR Bx vs. TX Bx) |
|---|---|---|---|
| 208885_PM_at | LCP1 | lymphocyte cytosolic protein 1 (L-plastin) | 6.27E−09 |
| 219161_PM_s_at | CKLF | chemokine-like factor | 6.34E−09 |
| 227346_PM_at | IKZF1 | IKAROS family zinc finger 1 (ikaros) | 6.48E−09 |
| 223620_PM_at | GPR34 | G protein-coupled receptor 34 | 6.60E−09 |
| 213888_PM_s_at | TRAF3IP3 | TRAF3 interacting protein 3 | 6.77E−09 |
| 232024_PM_at | GIMAP2 | GTPase, IMAP family member 2 | 6.89E−09 |
| 206682_PM_at | CLEC10A | C-type lectin domain family 10, member A | 7.07E−09 |
| 208894_PM_at | HLA-DRA | major histocompatibility complex, class II, DR alpha | 7.95E−09 |
| 204971_PM_at | CSTA | cystatin A (stefin A) | 8.19E−09 |
| 202208_PM_s_at | ARL4C | ADP-ribosylation factor-like 4C | 8.47E−09 |
| 226218_PM_at | IL7R | interleukin 7 receptor | 8.48E−09 |
| 211368_PM_s_at | CASP1 | caspase 1, apoptosis-related cysteine peptidase (interleukin 1, beta, convertase) | 8.75E−09 |
| 211366_PM_x_at | CASP1 | caspase 1, apoptosis-related cysteine peptidase (interleukin 1, beta, convertase) | 8.89E−09 |
| 205789_PM_at | CD1D | CD1d molecule | 9.29E−09 |
| 1554240_PM_a_at | ITGAL | integrin, alpha L (antigen CD11A (p180), lymphocyte function-associated antigen 1; alph | 9.60E−09 |
| 211367_PM_s_at | CASP1 | caspase 1, apoptosis-related cysteine peptidase (interleukin 1, beta, convertase) | 1.01E−08 |
| 226525_PM_at | STK17B | serine/threonine kinase 17b | 1.04E−08 |
| 218223_PM_s_at | PLEKHO1 | pleckstrin homology domain containing, family O member 1 | 1.06E−08 |
| 214574_PM_x_at | LST1 | leukocyte specific transcript 1 | 1.10E−08 |
| 209732_PM_at | CLEC2B | C-type lectin domain family 2, member B | 1.10E−08 |
| 210538_PM_s_at | BIRC3 | baculoviral IAP repeat-containing 3 | 1.17E−08 |
| 202157_PM_s_at | CELF2 | CUGBP, Elav-like family member 2 | 1.17E−08 |
| 217456_PM_x_at | HLA-E | major histocompatibility complex, class I, E | 1.23E−08 |
| 211582_PM_x_at | LST1 | leukocyte specific transcript 1 | 1.27E−08 |
| 223451_PM_s_at | CKLF | chemokine-like factor | 1.30E−08 |
| 226474_PM_at | NLRC5 | NLR family, CARD domain containing 5 | 1.31E−08 |
| 229390_PM_at | FAM26F | family with sequence similarity 26, member F | 1.47E−08 |
| 201721_PM_s_at | LAPTM5 | lysosomal protein transmembrane 5 | 1.56E−08 |
| 202206_PM_at | ARL4C | ADP-ribosylation factor-like 4C | 1.64E−08 |
| 201666_PM_at | TIMP1 | TIMP metallopeptidase inhibitor 1 | 1.69E−08 |
| 205898_PM_at | CX3CR1 | chemokine (C-X3-C motif) receptor 1 | 1.74E−08 |
| 204336_PM_s_at | RGS19 | regulator of G-protein signaling 19 | 1.82E−08 |
| 208306_PM_x_at | HLA-DRB1 | Major histocompatibility complex, class II, DR beta 1 | 1.84E−08 |
| 227353_PM_at | TMC8 | transmembrane channel-like 8 | 1.85E−08 |
| 201288_PM_at | ARHGDIB | Rho GDP dissociation inhibitor (GDI) beta | 1.90E−08 |
| 224964_PM_s_at | GNG2 | guanine nucleotide binding protein (G protein), gamma 2 | 1.93E−08 |
| 202643_PM_s_at | TNFAIP3 | tumor necrosis factor, alpha-induced protein 3 | 1.96E−08 |
| 209846_PM_s_at | BTN3A2 | butyrophilin, subfamily 3, member A2 | 2.07E−08 |
| 222858_PM_s_at | DAPP1 | dual adaptor of phosphotyrosine and 3-phosphoinositides | 2.08E−08 |
| 201858_PM_s_at | SRGN | serglycin | 2.30E−08 |
| 204924_PM_at | TLR2 | toll-like receptor 2 | 2.35E−08 |
| 203741_PM_s_at | ADCY7 | adenylate cyclase 7 | 2.37E−08 |
| 213160_PM_at | DOCK2 | dedicator of cytokinesis 2 | 2.38E−08 |
| 213975_PM_s_at | LYZ | lysozyme | 2.39E−08 |
| 1552316_PM_a_at | GIMAP1 | GTPase, IMAP family member 1 | 2.40E−08 |
| 200905_PM_x_at | HLA-E | major histocompatibility complex, class I, E | 2.50E−08 |
| 226219_PM_at | ARHGAP30 | Rho GTPase activating protein 30 | 2.52E−08 |
| 209312_PM_x_at | HLA-DRB1 /// HLA-DRB4 | major histocompatibility complex, class II, DR beta 1 /// major histocompatibility comp | 2.53E−08 |
| 202803_PM_s_at | ITGB2 | integrin, beta 2 (complement component 3 receptor 3 and 4 subunit) | 2.55E−08 |
| 33304_PM_at | ISG20 | interferon stimulated exonuclease gene 20 kDa | 2.56E−08 |
| 228071_PM_at | GIMAP7 | GTPase, IMAP family member 7 | 2.57E−08 |
| 201720_PM_s_at | LAPTM5 | lysosomal protein transmembrane 5 | 2.59E−08 |
| 219033_PM_at | PARP8 | poly (ADP-ribose) polymerase family, member B | 2.70E−08 |
| 200833_PM_s_at | RAP1B | RAP1B, member of RAS oncogene family | 2.72E−08 |
| 227184_PM_at | PTAFR | platelet-activating factor receptor | 2.73E−08 |
| 222217_PM_s_at | SLC27A3 | solute carrier family 27 (fatty acid transporter), member 3 | 2.74E−08 |
| 224451_PM_x_at | ARHGAP9 | Rho GTPase activating protein 9 | 2.76E−08 |
| 206118_PM_at | STAT4 | signal transducer and activator of transcription 4 | 2.78E−08 |
| 229391_PM_s_at | FAM26F | family with sequence similarity 26, member F | 2.81E−08 |
| 218870_PM_at | ARHGAP15 | Rho GTPase activating protein 15 | 2.83E−08 |
| 224916_PM_at | TMEM173 | transmembrane protein 173 | 2.83E−08 |
| 209795_PM_at | CD69 | CD69 molecule | 2.89E−08 |
| 208965_PM_s_at | IFI16 | interferon, gamma-inducible protein 16 | 2.91E−08 |

TABLE 7-continued

Biopsy Microarray Signatures for subAR using a 2-way 2-Step approach - first step (AR + subAR vs .TX)

| Probeset ID | Gene Symbol | Gene Title | p-value (subAR + cAR Bx vs. TX Bx) |
|---|---|---|---|
| 209723_PM_at | SERPINB9 | serpin peptidase inhibitor, clade B (ovalbumin), member 9 | 2.91E−08 |
| 1555852_PM_at | LOC100507463 | hypothetical LOC100507463 | 2.93E−08 |
| 1552701_PM_a_at | CARD16 | caspase recruitment domain family, member 16 | 3.05E−08 |
| 201859_PM_at | SRGN | serglycin | 3.07E−08 |
| 219574_PM_at | MAR1 | membrane-associated ring finger (C3HC4) 1 | 3.20E−08 |
| 230391_PM_at | CD84 | CD84 molecule | 3.30E−08 |
| 235529_PM_x_at | SAMHD1 | SAM domain and HD domain 1 | 3.35E−08 |
| 228055_PM_at | NAPSB | napsin B aspartic peptidase pseudogene | 3.36E−08 |
| 212014_PM_x_at | CD44 | CD44 molecule (indian blood group) | 3.46E−08 |
| 211656_PM_x_at | HLA-DQB1 /// LOC100133583 | major histocompatibility complex, class II, DQ beta 1 /// HLA class II histocompatibili | 3.52E−08 |
| 203761_PM_at | SLA | Src-like-adaptor | 3.53E−08 |
| 209933_PM_s_at | CD300A | CD300a molecule | 3.53E−08 |
| 203233_PM_at | IL4R | interleukin 4 receptor | 3.54E−08 |
| 204563_PM_at | SELL | selectin L | 3.58E−08 |
| 215633_PM_x_at | LST1 | leukocyte specific transcript 1 | 3.61E−08 |
| 234987_PM_at | SAMHD1 | SAM domain and HD domain 1 | 3.61E−08 |
| 242946_PM_at | EST 242946_PM_at | — | 3.63E−08 |
| 235385_PM_at | MAR2 | membrane-associated ring finger (C3HC4) 1 | 3.67E−08 |
| 210113_PM_s_at | NLRP1 | NLR family, pyrin domain containing 1 | 3.67E−08 |
| 228376_PM_at | GGTA1 | glycoprotein, alpha-galactosyltransferase 1 pseudogene | 3.68E−08 |
| 205039_PM_s_at | IKZF1 | IKAROS family zinc finger 1 (ikaros) | 3.69E−08 |
| 217362_PM_x_at | HLA-DRB6 | major histocompatibility complex, class II, DR beta 6 (pseudogene) | 3.71E−08 |
| 209879_PM_at | SELPLG | selectin P ligand | 3.77E−08 |
| 204698_PM_at | ISG20 | interferon stimulated exonuclease gene 20 kDa | 3.87E−08 |
| 215493_PM_x_at | BTN2A1 | butyrophilin, subfamily 2, member A1 | 3.95E−08 |
| 211395_PM_x_at | FCGR2C | Fc fragment of IgG, low affinity IIc, receptor for (CD32) (gene/pseudogene) | 4.15E−08 |
| 223773_PM_s_at | SNHG12 | small nucleolar RNA host gene 12 (non-protein coding) | 4.22E−08 |
| 219279_PM_at | DOCK10 | dedicator of cytokinesis 10 | 4.25E−08 |
| 225353_PM_s_at | C1QC | complement component 1, q subcomponent C chain | 4.33E−08 |
| 216920_PM_s_at | TARP /// TRGC2 | TCR gamma alternate reading frame protein /// T cell receptor gamma constant 2 | 4.35E−08 |
| 207651_PM_at | GPR171 | G protein-coupled receptor 171 | 4.42E−08 |
| 227178_PM_at | CELF2 | CUGBP, Elav-like family member 2 | 4.42E−08 |
| 202510_PM_s_at | TNFAIP2 | tumor necrosis factor, alpha-induced protein 2 | 4.50E−08 |
| 209823_PM_x_at | HLA-DQB1 | major histocompatibility complex, class II, DQ beta 1 | 4.63E−08 |
| 1555756_PM_a_at | CLEC7A | C-type lectin domain family 7, member A | 4.72E−08 |
| 223809_PM_at | RGS18 | regulator of G-protein signaling 18 | 4.72E−08 |
| 243366_PM_s_at | EST 243366_PM_s_at | — | 4.75E−08 |
| 204222_PM_s_at | GLIPR1 | GLI pathogenesis-related 1 | 4.82E−08 |
| 204220_PM_at | GMFG | glia maturation factor, gamma | 4.92E−08 |
| 1557905_PM_s_at | CD44 | CD44 molecule (indian blood group) | 5.25E−08 |
| 229625_PM_at | GBP5 | guanylate binding protein 5 | 5.25E−08 |
| 213414_PM_s_at | RPS19 | ribosomal protein S19 | 5.30E−08 |
| 230499_PM_at | EST 230499_PM_at | — | 5.38E−08 |
| 215193_PM_x_at | HLA-DRB1 /// HLA-DRB3 /// HLA-DRB4 /// HLA-DRB5 /// LOC100133661 /// LOC100294036 /// LOC100509582 /// LOC100510495 /// LOC100510519 | major histocompatibility complex, class II, DR beta 1 /// major histocompatibility comp | 5.40E−08 |
| 232724_PM_at | MS4A6A | membrane-spanning 4-domains, subfamily A, member 6A | 5.40E−08 |
| 210140_PM_at | CST7 | cystatin F (leukocystatin) | 5.42E−08 |
| 224252_PM_s_at | FXYD5 | FXYD domain containing ion transport regulator 5 | 5.47E−08 |
| 219191_PM_s_at | BIN2 | bridging integrator 2 | 5.50E−08 |
| 206991_PM_s_at | CCR5 | chemokine (C-C motif) receptor 5 | 5.54E−08 |
| 208966_PM_x_at | IFI16 | interferon, gamma-inducible protein 16 | 5.60E−08 |
| 210785_PM_s_at | C1orf38 | chromosome 1 open reading frame 38 | 5.62E−08 |
| 242814_PM_at | SERPINB9 | serpin peptidase inhibitor, clade B (ovalbumin), member 9 | 5.71E−08 |
| 232543_PM_x_at | ARHGAP9 | Rho GTPase activating protein 9 | 5.73E−08 |
| 213418_PM_at | HSPA6 | heat shock 70 kDa protein 6 (HSP70B') | 5.80E−08 |

TABLE 7-continued

Biopsy Microarray Signatures for subAR using a 2-way 2-Step approach - first step (AR + subAR vs .TX)

| Probeset ID | Gene Symbol | Gene Title | p-value (subAR + cAR Bx vs. TX Bx) |
|---|---|---|---|
| 212829_PM_at | PIP4K2A | phosphatidylinositol-5-phosphate 4-kinase, type II, alpha | 5.85E−08 |
| 223501_PM_at | TNFSF13B | tumor necrosis factor (ligand) superfamily, member 13b | 5.88E−08 |
| 211581_PM_x_at | LST1 | leukocyte specific transcript 1 | 5.92E−08 |
| 202748_PM_at | GBP2 | guanylate binding protein 2, interferon-inducible | 6.11E−08 |
| 230925_PM_at | APBB1IP | amyloid beta (A4) precursor protein-binding, family B, member 1 interacting protein | 6.25E−08 |
| 209827_PM_s_at | IL16 | interleukin 16 (lymphocyte chemoattractant factor) | 6.49E−08 |
| 204882_PM_at | ARHGAP25 | Rho GTPase activating protein 25 | 7.19E−08 |
| 204319_PM_s_at | RGS10 | regulator of G-protein signaling 10 | 7.27E−08 |
| 217985_PM_s_at | BAZ1A | bromodomain adjacent to zinc finger domain, 1A | 7.33E−08 |
| 212998_PM_x_at | HLA-DQB1 /// LOC100133583 | major histocompatibility complex, class II, DQ beta 1 /// HLA class II histocompatibili | 7.42E−08 |
| 205159_PM_at | CSF2RB | colony stimulating factor 2 receptor, beta, low-affinity (granulocyte-macrophage) | 7.44E−08 |
| 204670_PM_x_at | HLA-DRB1 /// HLA-DRB4 | major histocompatibility complex, class II, DR beta 1 /// major histocompatibility comp | 7.56E−08 |
| 221903_PM_s_at | CYLD | cylindromatosis (turban tumor syndrome) | 7.60E−08 |
| 223343_PM_at | MS4A7 | membrane-spanning 4-domains, subfamily A, member 7 | 7.76E−08 |
| 205285_PM_s_at | FYB | FYN binding protein | 7.83E−08 |
| 220005_PM_at | P2RY13 | purinergic receptor P2Y, G-protein coupled, 13 | 8.02E−08 |
| 218157_PM_x_at | CDC42SE1 | CDC42 small effector 1 | 8.09E−08 |
| 204438_PM_at | MRC1 /// MRC1L1 | mannose receptor, C type 1 /// mannose receptor, C type 1-like 1 | 8.23E−08 |
| 211654_PM_x_at | HLA-DQB1 | major histocompatibility complex, class II, DQ beta 1 | 8.44E−08 |
| 224882_PM_at | ACSS1 | acyl-CoA synthetase short-chain family member 1 | 8.52E−08 |
| 214567_PM_s_at | XCL1 /// XCL2 | chemokine (C motif) ligand 1 /// chemokine (C motif) ligand 2 | 8.56E−08 |
| 223502_PM_s_at | TNFSF13B | tumor necrosis factor (ligand) superfamily, member 13b | 8.61E−08 |
| 228581_PM_at | KCNJ10 | potassium inwardly-rectifying channel, subfamily J, member 10 | 8.69E−08 |
| 229383_PM_at | MAR3 | membrane-associated ring finger (C3HC4) 1 | 8.72E−08 |
| 202649_PM_x_at | RPS19 | ribosomal protein S19 | 8.78E−08 |
| 210889_PM_s_at | FCGR2B | Fc fragment of IgG, low affinity IIb, receptor (CD32) | 8.93E−08 |
| 204174_PM_at | ALOX5AP | arachidonate 5-lipoxygenase-activating protein | 9.16E−08 |
| 204502_PM_at | SAMHD1 | SAM domain and HD domain 1 | 9.17E−08 |
| 223640_PM_at | HCST | hematopoietic cell signal transducer | 9.31E−08 |
| 211597_PM_s_at | HOPX | HOP homeobox | 9.39E−08 |
| 216834_PM_at | RGS1 | regulator of G-protein signaling 1 | 9.57E−08 |
| 212063_PM_at | CD44 | CD44 molecule (indian blood group) | 9.76E−08 |
| 208805_PM_at | PSMA6 | proteasome (prosome, macropain) subunit, alpha type, 6 | 9.90E−08 |
| 210279_PM_at | GPR18 | G protein-coupled receptor 18 | 1.00E−07 |
| 204057_PM_at | IRF8 | interferon regulatory factor 8 | 1.00E−07 |
| 226055_PM_at | ARRDC2 | arrestin domain containing 2 | 1.00E−07 |
| 205758_PM_at | CD8A | CD8a molecule | 1.01E−07 |
| 229723_PM_at | TAGAP | T-cell activation RhoGTPase activating protein | 1.01E−07 |
| 218084_PM_x_at | FXYD5 | FXYD domain containing ion transport regulator 5 | 1.01E−07 |
| 218802_PM_at | CCDC109B | coiled-coil domain containing 109B | 1.02E−07 |
| 205987_PM_at | CD1C | CD1c molecule | 1.04E−07 |
| 205859_PM_at | LY86 | lymphocyte antigen 86 | 1.05E−07 |
| 207794_PM_at | CCR2 | chemokine (C-C motif) receptor 2 | 1.09E−07 |
| 204122_PM_at | TYROBP | TYRO protein tyrosine kinase binding protein | 1.10E−07 |
| 229560_PM_at | TLR8 | toll-like receptor 8 | 1.12E−07 |
| 203923_PM_s_at | CYBB | cytochrome b-245, beta polypeptide | 1.12E−07 |
| 225479_PM_at | LRRC58 | leucine rich repeat containing 58 | 1.17E−07 |
| 222592_PM_s_at | ACSL5 | acyl-CoA synthetase long-chain family member 5 | 1.23E−07 |
| 230550_PM_at | MS4A6A | membrane-spanning 4-domains, subfamily A, member 6A | 1.23E−07 |
| 222859_PM_s_at | DAPP1 | dual adaptor of phosphotyrosine and 3-phosphoinositides | 1.24E−07 |
| 226810_PM_at | OGFRL1 | opioid growth factor receptor-like 1 | 1.28E−07 |
| 221666_PM_s_at | PYCARD | PYD and CARD domain containing | 1.29E−07 |
| 203729_PM_at | EMP3 | epithelial membrane protein 3 | 1.29E−07 |
| 211990_PM_at | HLA-DPA1 | major histocompatibility complex, class II, DP alpha 1 | 1.29E−07 |
| 226136_PM_at | GLIPR1 | GLI pathogenesis-related 1 | 1.32E−07 |
| 201426_PM_s_at | VIM | vimentin | 1.32E−07 |
| 205298_PM_s_at | BTN2A2 | butyrophilin, subfamily 2, member A2 | 1.33E−07 |
| 206332_PM_s_at | IFI16 | interferon, gamma-inducible protein 16 | 1.36E−07 |
| 211339_PM_s_at | ITK | IL2-inducible T-cell kinase | 1.37E−07 |
| 204490_PM_s_at | CD44 | CD44 molecule (indian blood group) | 1.38E−07 |

TABLE 7-continued

Biopsy Microarray Signatures for subAR using a 2-way 2-Step approach - first step (AR + subAR vs .TX)

| Probeset ID | Gene Symbol | Gene Title | p-value (subAR + cAR Bx vs. TX Bx) |
|---|---|---|---|
| 230669_PM_at | RASA2 | RAS p21 protein activator 2 | 1.39E−07 |
| 200003_PM_s_at | RPL28 | ribosomal protein L28 | 1.39E−07 |
| 217478_PM_s_at | HLA-DMA | major histocompatibility complex, class II, DM alpha | 1.40E−07 |
| 236280_PM_at | EST 236280_PM_at | — | 1.41E−07 |
| 222976_PM_s_at | TPM3 | tropomyosin 3 | 1.42E−07 |
| 232311_PM_at | B2M | Beta-2-microglobulin | 1.42E−07 |
| 220577_PM_at | GVINP1 | GTPase, very large interferon inducible pseudogene 1 | 1.43E−07 |
| 238668_PM_at | EST 238668_PM_at | — | 1.44E−07 |
| 232617_PM_at | CTSS | cathepsin S | 1.45E−07 |
| 224833_PM_at | ETS1 | v-ets erythroblastosis virus E26 oncogene homolog 1 (avian) | 1.46E−07 |
| 219014_PM_at | PLAC8 | placenta-specific 8 | 1.49E−07 |
| 219243_PM_at | GIMAP4 | GTPase, IMAP family member 4 | 1.49E−07 |
| 209829_PM_at | FAM65B | family with sequence similarity 65, member B | 1.50E−07 |
| 203471_PM_s_at | PLEK | pleckstrin | 1.53E−07 |
| 211144_PM_x_at | TARP /// TRGC2 | TCR gamma alternate reading frame protein /// T cell receptor gamma constant 2 | 1.54E−07 |
| 211528_PM_x_at | HLA-G | major histocompatibility complex, class I, G | 1.55E−07 |
| 206584_PM_at | LY96 | lymphocyte antigen 96 | 1.57E−07 |
| 231747_PM_at | CYSLTR1 | cysteinyl leukotriene receptor 1 | 1.59E−07 |
| 230735_PM_at | EST 230735_PM_at | — | 1.61E−07 |
| 225604_PM_s_at | GLIPR2 | GLI pathogenesis-related 2 | 1.62E−07 |
| 210072_PM_at | CCL19 | chemokine (C-C motif) ligand 19 | 1.63E−07 |
| 221058_PM_s_at | CKLF | chemokine-like factor | 1.63E−07 |
| 204923_PM_at | SASH3 | SAM and SH3 domain containing 3 | 1.68E−07 |
| 227677_PM_at | JAK3 | Janus kinase 3 | 1.69E−07 |
| 201012_PM_at | ANXA1 | annexin A1 | 1.70E−07 |
| 229155_PM_at | EST 229155_PM_at | — | 1.72E−07 |
| 205101_PM_at | CIITA | class II, major histocompatibility complex, transactivator | 1.74E−07 |
| 216438_PM_s_at | TMSB4X /// TMSL3 | thymosin beta 4, X-linked /// thymosin-like 3 | 1.75E−07 |
| 1552318_PM_at | GIMAP1 | GTPase, IMAP family member 1 | 1.77E−07 |
| 213095_PM_x_at | AIF1 | allograft inflammatory factor 1 | 1.80E−07 |
| 204316_PM_at | RGS10 | regulator of G-protein signaling 10 | 1.82E−07 |
| 203927_PM_at | NFKBIE | nuclear factor of kappa light polypeptide gene enhancer in B-cells inhibitor, epsilon | 1.83E−07 |
| 217523_PM_at | CD44 | CD44 molecule (indian blood group) | 1.84E−07 |
| 209901_PM_x_at | AIF1 | allograft inflammatory factor 1 | 1.84E−07 |
| 203508_PM_at | TNFRSF1B | tumor necrosis factor receptor superfamily, member 1B | 1.85E−07 |
| 208944_PM_at | TGFBR2 | transforming growth factor, beta receptor II (70/80 kDa) | 1.86E−07 |
| 210031_PM_at | CD247 | CD247 molecule | 1.87E−07 |
| 202953_PM_at | C1QB | complement component 1, q subcomponent, B chain | 1.87E−07 |
| 213733_PM_at | MYO1F | myosin 1F | 1.88E−07 |
| 201738_PM_at | EIF1B | eukaryotic translation initiation factor 1B | 1.88E−07 |
| 205884_PM_at | ITGA4 | integrin, alpha 4 (antigen CD49D, alpha 4 subunit of VLA-4 receptor) | 1.93E−07 |
| 204820_PM_s_at | BTN3A2 /// BTN3A3 | butyrophilin, subfamily 3, member A2 /// butyrophilin, subfamily 3, member A3 | 1.99E−07 |
| 218805_PM_at | GIMAP5 | GTPase, IMAP family member 5 | 1.99E−07 |
| 212873_PM_at | HMHA1 | histocompatibility (minor) HA-1 | 1.99E−07 |
| 217979_PM_at | TSPAN13 | tetraspanin 13 | 2.02E−07 |
| 228471_PM_at | ANKRD44 | ankyrin repeat domain 44 | 2.03E−07 |
| 218322_PM_s_at | ACSL5 | acyl-CoA synthetase long-chain family member 5 | 2.03E−07 |
| 215051_PM_x_at | AIF1 | allograft inflammatory factor 1 | 2.04E−07 |
| 213398_PM_s_at | SDR39U1 | short chain dehydrogenase/reductase family 39U, member 1 | 2.04E−07 |
| 206637_PM_at | P2RY14 | purinergic receptor P2Y, G-protein coupled, 14 | 2.05E−07 |

TABLE 8

Biopsy Microarray Signatures for subAR using a 2-way 2-Step approach - second step (AR vs. subAR)

| Probeset ID | Gene Symbol | Gene Title | p-value(cAR Bx vs. subAR Bx) |
|---|---|---|---|
| 227801_PM_at | TRIM59 | tripartite motif-containing 59 | 1.69E−08 |
| 212951_PM_at | GPR116 | G protein-coupled receptor 116 | 6.33E−08 |
| 226668_PM_at | WDSUB1 | WD repeat, sterile alpha motif and U-box domain containing 1 | 7.62E−08 |
| 202357_PM_s_at | CFB | complement factor B | 1.28E−07 |
| 211075_PM_s_at | CD47 | CD47 molecule | 1.32E−07 |
| 204213_PM_at | PIGR | polymeric immunoglobulin receptor | 1.54E−07 |
| 226459_PM_at | PIK3AP1 | phosphoinositide-3-kinase adaptor protein 1 | 1.54E−07 |
| 231779_PM_at | IRAK2 | interleukin-1 receptor-associated kinase 2 | 1.70E−07 |
| 235085_PM_at | SGK223 | homolog of rat pragma of Rnd2 | 1.84E−07 |
| 226714_PM_at | SAMD4B | sterile alpha motif domain containing 4B | 1.98E−07 |
| 202242_PM_at | TSPAN7 | tetraspanin 7 | 2.17E−07 |
| 213857_PM_s_at | CD47 | CD47 molecule | 2.57E−07 |
| 205105_PM_at | MAN2A1 | mannosidase, alpha, class 2A, member 1 | 2.62E−07 |
| 204924_PM_at | TLR2 | toll-like receptor 2 | 2.69E−07 |
| 204470_PM_at | CXCL1 | chemokine (C-X-C motif) ligand 1 (melanoma growth stimulating activity, alpha) | 3.07E−07 |
| 204108_PM_at | NFYA | nuclear transcription factor Y, alpha | 3.20E−07 |
| 236155_PM_at | ZCCHC6 | Zinc finger, CCHC domain containing 6 | 4.22E−07 |
| 212950_PM_at | GPR116 | G protein-coupled receptor 116 | 4.37E−07 |
| 209774_PM_x_at | CXCL2 | chemokine (C-X-C motif) ligand 2 | 5.78E−07 |
| 207966_PM_s_at | GLG1 | golgi glycoprotein 1 | 6.24E−07 |
| 211758_PM_x_at | TXNDC9 | thioredoxin domain containing 9 | 6.38E−07 |
| 238178_PM_at | EST 238178_PM_at | — | 7.69E−07 |
| 202334_PM_s_at | UBE2B | ubiquitin-conjugating enzyme E2B (RAD6 homolog) | 7.75E−07 |
| 231334_PM_at | EST 231334_PM_at | — | 8.26E−07 |
| 223809_PM_at | RGS18 | regulator of G-protein signaling 18 | 8.34E−07 |
| 210405_PM_x_at | TNFRSF10B | tumor necrosis factor receptor superfamily, member 10b | 9.02E−07 |
| 230777_PM_s_at | PRDM15 | PR domain containing 15 | 9.91E−07 |
| 202907_PM_s_at | NBN | nibrin | 1.02E−06 |
| 202621_PM_at | IRF3 | interferon regulatory factor 3 | 1.04E−06 |
| 219938_PM_s_at | PSTPIP2 | proline-serine-threonine phosphatase interacting protein 2 | 1.07E−06 |
| 223047_PM_at | CMTM6 | CKLF-like MARVEL transmembrane domain containing 6 | 1.08E−06 |
| 202018_PM_s_at | LTF | lactotransferrin | 1.10E−06 |
| 233878_PM_s_at | XRN2 | 5'-3' exoribonuclease 2 | 1.19E−06 |
| 244353_PM_s_at | SLC2A12 | solute carrier family 2 (facilitated glucose transporter), member 12 | 1.20E−06 |
| 204785_PM_x_at | IFNAR2 | interferon (alpha, beta and omega) receptor 2 | 1.21E−06 |
| 226000_PM_at | CTTNBP2NL | CTTNBP2 N-terminal like | 1.24E−06 |
| 241891_PM_at | EST 241891_PM_at | — | 1.30E−06 |
| 208791_PM_at | CLU | clusterin | 1.38E−06 |
| 233047_PM_at | FRMD7 | FERM domain containing 7 | 1.39E−06 |
| 226538_PM_at | MAN2A1 | mannosidase, alpha, class 2A, member 1 | 1.44E−06 |
| 208792_PM_s_at | CLU | clusterin | 1.48E−06 |
| 218313_PM_s_at | GALNT7 | UDP-N-acetyl-alpha-D-galactosamine:polypeptide N-acetylgalactosaminyltransferase 7 (Gal | 1.60E−06 |
| 203568_PM_s_at | TRIM38 | tripartite motif-containing 38 | 1.62E−06 |
| 223218_PM_s_at | NFKBIZ | nuclear factor of kappa light polypeptide gene enhancer in B-cells inhibitor, zeta | 1.69E−06 |
| 224358_PM_s_at | MS4A7 | membrane-spanning 4-domains, subfamily A, member 7 | 1.76E−06 |
| 227125_PM_at | IFNAR2 | interferon (alpha, beta and omega) receptor 2 | 1.78E−06 |
| 1552615_PM_at | ACACB | acetyl-CoA carboxylase beta | 1.84E−06 |
| 218865_PM_at | MOSC1 | MOCO sulphurase C-terminal domain containing 1 | 1.87E−06 |
| 210031_PM_at | CD247 | CD247 molecule | 1.91E−06 |
| 212226_PM_s_at | PPAP2B | phosphatidic acid phosphatase type 2B | 1.95E−06 |
| 230912_PM_at | ASPDH | aspartate dehydrogenase domain containing | 2.08E−06 |
| 201042_PM_at | TGM2 | transglutaminase 2 (C polypeptide, protein-glutamine-gamma-glutamyltransferase) | 2.14E−06 |
| 203513_PM_at | SPG11 | spastic paraplegia 11 (autosomal recessive) | 2.39E−06 |
| 243088_PM_at | EST 243088_PM_at | — | 2.58E−06 |
| 204324_PM_s_at | GOLIM4 | golgi integral membrane protein 4 | 2.58E−06 |
| 235905_PM_at | ZNF704 | zinc finger protein 704 | 2.65E−06 |
| 1564679_PM_at | ASB15 | ankyrin repeat and SOCS box-containing 15 | 2.71E−06 |
| 203868_PM_s_at | VCAM1 | vascular cell adhesion molecule 1 | 2.72E−06 |
| 212695_PM_at | CRY2 | cryptochrome 2 (photolyase-like) | 2.77E−06 |
| 223217_PM_s_at | NFKBIZ | nuclear factor of kappa light polypeptide gene enhancer in B-cells inhibitor, zeta | 2.78E−06 |
| 227213_PM_at | ADAT2 | adenosine deaminase, tRNA-specific 2, TAD2 homolog (S. cerevisiae) | 2.91E−06 |

TABLE 8-continued

Biopsy Microarray Signatures for subAR using a 2-way 2-Step approach - second step (AR vs. subAR)

| Probeset ID | Gene Symbol | Gene Title | p-value(cAR Bx vs. subAR Bx) |
|---|---|---|---|
| 206513_PM_at | AIM2 | absent in melanoma 2 | 2.96E−06 |
| 1552749_PM_a_at | KLC3 | kinesin light chain 3 | 2.96E−06 |
| 240413_PM_at | PYHIN1 | pyrin and HIN domain family, member 1 | 3.05E−06 |
| 238960_PM_s_at | LARP4 | La ribonucleoprotein domain family, member 4 | 3.06E−06 |
| 1562966_PM_at | KIAA1217 | KIAA1217 | 3.10E−06 |
| 202898_PM_at | SDC3 | syndecan 3 | 3.16E−06 |
| 229872_PM_s_at | LOC100132999 | hypothetical LOC100132999 | 3.22E−06 |
| 218404_PM_at | SNX10 | sorting nexin 10 | 3.44E−06 |
| 219998_PM_at | HSPC159 | galectin-related protein | 3.50E−06 |
| 211003_PM_x_at | TGM2 | transglutaminase 2 (C polypeptide, protein-glutamine-gamma-glutamyltransferase) | 3.52E−06 |
| 203008_PM_x_at | TXNDC9 | thioredoxin domain containing 9 | 3.59E−06 |
| 213513_PM_x_at | ARPC2 | actin related protein 2/3 complex, subunit 2, 34 kDa | 3.77E−06 |
| 203765_PM_at | GCA | grancalcin, EF-hand calcium binding protein | 3.83E−06 |
| 221510_PM_s_at | GLS | glutaminase | 3.91E−06 |
| 214791_PM_at | SP140L | SP140 nuclear body protein-like | 4.01E−06 |
| 217947_PM_at | CMTM6 | CKLF-like MARVEL transmembrane domain containing 6 | 4.12E−06 |
| 206503_PM_x_at | PML | promyelocytic leukemia | 4.26E−06 |
| 222033_PM_s_at | FLT1 | fms-related tyrosine kinase 1 (vascular endothelial growth factor/vascular permeability | 4.32E−06 |
| 202651_PM_at | LPGAT1 | lysophosphatidylglycerol acyltransferase 1 | 4.48E−06 |
| 237587_PM_at | EST 237587_PM_at | — | 4.55E−06 |
| 209970_PM_x_at | CASP1 | caspase 1, apoptosis-related cysteine peptidase (interleukin 1, beta, convertase) | 4.57E−06 |
| 222976_PM_s_at | TPM3 | tropomyosin 3 | 4.61E−06 |
| 227678_PM_at | XRCC6BP1 | XRCC6 binding protein 1 | 4.64E−06 |
| 209035_PM_at | MDK | midkine (neurite growth-promoting factor 2) | 4.78E−06 |
| 205624_PM_at | CPA3 | carboxypeptidase A3 (mast cell) | 4.78E−06 |
| 203332_PM_s_at | INPP5D | inositol polyphosphate-5-phosphatase, 145 kDa | 4.82E−06 |
| 211917_PM_s_at | PRLR | prolactin receptor | 4.86E−06 |
| 219283_PM_at | C1GALT1C1 | C1GALT1-specific chaperone 1 | 4.94E−06 |
| 239005_PM_at | FLJ39739 | Hypothetical FLJ39739 | 4.99E−06 |
| 228114_PM_x_at | C16orf13 | chromosome 16 open reading frame 13 | 5.00E−06 |
| 205295_PM_at | CKMT2 | creatine kinase, mitochondrial 2 (sarcomeric) | 5.19E−06 |
| 242131_PM_at | ATP6 | ATP synthase F0 subunit 6 | 5.23E−06 |
| 202688_PM_at | TNFSF10 | tumor necrosis factor (ligand) superfamily, member 10 | 5.33E−06 |
| 235536_PM_at | SNORD89 | small nucleolar RNA, C/D box 89 | 5.35E−06 |
| 214212_PM_x_at | FERMT2 | fermitin family member 2 | 5.35E−06 |
| 212148_PM_at | PBX1 | pre-B-cell leukemia homeobox 1 | 5.38E−06 |
| 212504_PM_at | DIP2C | DIP2 disco-interacting protein 2 homolog C (*Drosophila*) | 5.51E−06 |
| 201697_PM_s_at | DNMT1 | DNA (cytosine-5-)-methyltransferase 1 | 5.53E−06 |
| 212501_PM_at | CEBPB | CCAAT/enhancer binding protein (C/EBP), beta | 5.54E−06 |
| 204446_PM_s_at | ALOX5 | arachidonate 5-lipoxygenase | 5.57E−06 |
| 206011_PM_at | CASP1 | caspase 1, apoptosis-related cysteine peptidase (interleukin 1, beta, convertase) | 5.63E−06 |
| 224663_PM_s_at | CFL2 | cofilin 2 (muscle) | 5.75E−06 |
| 201949_PM_x_at | CAPZB | capping protein (actin filament) muscle Z-line, beta | 5.91E−06 |
| 219436_PM_s_at | EMCN | endomucin | 5.96E−05 |
| 220146_PM_at | TLR7 | toll-like receptor 7 | 6.03E−06 |
| 209310_PM_s_at | CASP4 | caspase 4, apoptosis-related cysteine peptidase | 6.11E−06 |
| 207702_PM_s_at | MAGI2 | membrane associated guanylate kinase, WW and PDZ domain containing 2 | 6.12E−06 |
| 204794_PM_at | DUSP2 | dual specificity phosphatase 2 | 6.14E−06 |
| 219202_PM_at | RHBDF2 | rhomboid 5 homolog 2 (*Drosophila*) | 6.28E−06 |
| 233496_PM_s_at | CFL2 | cofilin 2 (muscle) | 6.38E−06 |
| 224578_PM_at | RCC2 | regulator of chromosome condensation 2 | 6.46E−46 |
| 223104_PM_at | JAGN1 | jagunal homolog 1 (*Drosophila*) | 6.54E−06 |
| 219161_PM_s_at | CKLF | chemokine-like factor | 6.57E−06 |
| 226612_PM_at | UBE2QL1 | ubiquitin-conjugating enzyme E2Q family-like 1 | 6.62E−06 |
| 204974_PM_at | RAB3A | RAB3A, member RAS oncogene family | 6.66E−06 |
| 223002_PM_s_at | XRN2 | 5'-3' exoribonuclease 2 | 6.67E−06 |
| 242601_PM_at | HEPACAM2 | HEPACAM family member 2 | 6.71E−06 |
| 205102_PM_at | TMPRSS2 | transmembrane protease, serine 2 | 6.93E−06 |
| 1569926_PM_s_at | SLC34A3 | solute carrier family 34 (sodium phosphate), member 3 | 7.01E−06 |
| 213596_PM_at | CASP4 | caspase 4, apoptosis-related cysteine peptidase | 7.18E−06 |
| 200713_PM_s_at | MAPRE1 | microtubule-associated protein, RP/EB family, member 1 | 7.54E−06 |
| 203132_PM_at | RB1 | retinoblastoma 1 | 7.60E−06 |
| 209752_PM_at | REG1A | regenerating islet-derived 1 alpha | 7.65E−06 |
| 211573_PM_x_at | TGM2 | transglutaminase 2 (C polypeptide, protein-glutamine-gamma-glutamyltransferase) | 7.82E−06 |
| 207213_PM_s_at | USP2 | ubiquitin specific peptidase 2 | 7.87E−06 |
| 217984_PM_at | RNASET2 | ribonuclease T2 | 7.97E−06 |

TABLE 8-continued

Biopsy Microarray Signatures for subAR using a 2-way 2-Step approach - second step (AR vs. subAR)

| Probeset ID | Gene Symbol | Gene Title | p-value(cAR Bx vs. subAR Bx) |
|---|---|---|---|
| 1553304_PM_at | LSM14B | LSM14B, SCD6 homolog B (S. cerevisiae) | 7.97E−06 |
| 229937_PM_x_at | LILRB1 | Leukocyte immunoglobulin-like receptor, subfamily B (with TM and ITIM domains), member | 7.98E−06 |
| 200609_PM_s_at | WDR1 | WD repeat domain 1 | 8.01E−06 |
| 205467_PM_at | CASP10 | caspase 10, apoptosis-related cysteine peptidase | 8.03E−06 |
| 225331_PM_at | CCDC50 | coiled-coil domain containing 50 | 8.05E−06 |
| 1560017_PM_at | TMTC3 | transmembrane and tetratricopeptide repeat containing 3 | 8.07E−06 |
| 200797_PM_s_at | MCL1 | myeloid cell leukemia sequence 1 (BCL2-related) | 8.10E−05 |
| 231337_PM_at | LOC100505498 | hypothetical LOC100505498 | 8.35E−06 |
| 221666_PM_s_at | PYCARD | PYD and CARD domain containing | 8.67E−06 |
| 217733_PM_at | TMSB10 | thymosin beta 10 | 8.89E−06 |
| 220933_PM_s_at | ZCCHC6 | zinc finger, CCHC domain containing 6 | 8.92E−06 |
| 235050_PM_at | SLC2A12 | solute carrier family 2 (facilitated glucose transporter), member 12 | 8.98E−06 |
| 200634_PM_at | PFN1 | profilin 1 | 9.10E−06 |
| 227727_PM_at | MRGPRF | MAS-related GPR, member F | 9.13E−06 |
| 216638_PM_s_at | PRLR | prolactin receptor | 9.14E−06 |
| 207168_PM_s_at | H2AFY | H2A histone family, member Y | 9.63E−06 |
| 226184_PM_at | FMNL2 | formin-like 2 | 9.70E−06 |
| 204846_PM_at | CP | ceruloplasmin (ferroxidase) | 9.71E−06 |
| 210527_PM_x_at | TUBA3C | tubulin, alpha 3c | 9.81E−06 |
| 211368_PM_s_at | CASP1 | caspase 1, apoptosis-related cysteine peptidase (interleukin 1, beta, convertase) | 9.84E−06 |
| 1556656_PM_at | EST 1556656_PM_at | — | 9.89E−06 |
| 223323_PM_x_at | TRPM7 | transient receptor potential cation channel, subfamily M, member 7 | 9.92E−06 |
| 210513_PM_s_at | VEGFA | vascular endothelial growth factor A | 9.95E−06 |
| 1553155_PM_x_at | ATP6V0D2 | ATPase, H+ transporting, lysosomal 38 kDa, V0 subunit d2 | 1.01E−05 |
| 212010_PM_s_at | CDV3 | CDV3 homolog (mouse) | 1.02E−05 |
| 209311_PM_at | BCL2L2 | BCL2-like 2 | 1.02E−05 |
| 201917_PM_s_at | SLC25A36 | solute carrier family 25, member 36 | 1.02E−05 |
| 227396_PM_at | PTPRJ | protein tyrosine phosphatase, receptor type, J | 1.04E−05 |
| 209278_PM_s_at | TFPI2 | tissue factor pathway inhibitor 2 | 1.04E−05 |
| 209903_PM_s_at | ATR | ataxia telangiectasia and Rad3 related | 1.06E−05 |
| 202763_PM_at | CASP3 | caspase 3, apoptosis-related cysteine peptidase | 1.08E−05 |
| 218238_PM_at | GTPBP4 | GTP binding protein 4 | 1.09E−05 |
| 206226_PM_at | HRG | histidine-rich glycoprotein | 1.10E−05 |
| 224462_PM_s_at | CHCHD6 | coiled-coil-helix-coiled-coil-helix domain containing 6 | 1.11E−05 |
| 220603_PM_at | MCTP2 | multiple C2 domains, transmembrane 2 | 1.11E−05 |
| 235161_PM_at | LOC100506451 /// LOC100509094 | hypothetical LOC100506451 /// hypothetical LOC100509094 | 1.11E−05 |
| 211366_PM_x_at | CASP1 | caspase 1, apoptosis-related cysteine peptidase (interleukin 1, beta, convertase) | 1.12E−05 |
| 239636_PM_at | MCF2L | MCF.2 cell line derived transforming sequence-like | 1.12E−05 |
| 228740_PM_at | EST 228740_PM_at | — | 1.12E−05 |
| 216323_PM_x_at | TUBA3C /// TUBA3D /// TUBA3E | tubulin, alpha 3c /// tubulin, alpha 3d /// tubulin, alpha 3e | 1.13E−05 |
| 205068_PM_s_at | ARHGAP26 | Rho GTPase activating protein 26 | 1.13E−05 |
| 217983_PM_s_at | RNASET2 | ribonuclease T2 | 1.14E−05 |
| 206059_PM_at | ZNF91 | zinc finger protein 91 | 1.15E−05 |
| 206944_PM_at | HTR6 | 5-hydroxytryptamine (serotonin) receptor 6 | 1.17E−05 |
| 215264_PM_at | EMX1 | empty spiracles homeobox 1 | 1.18E−05 |
| 213551_PM_x_at | PCGF2 | polycomb group ring finger 2 | 1.18E−05 |
| 218194_PM_at | REXO2 | REX2, RNA exonuclease 2 homolog (S. cerevisiae) | 1.18E−05 |
| 227438_PM_at | ALPK1 | alpha-kinase 1 | 1.19E−05 |
| 1053_PM_at | RFC2 | replication factor C (activator 1) 2, 40 kDa | 1.20E−05 |
| 227874_PM_at | EMCN | endomucin | 1.20E−05 |
| 201918_PM_at | SLC25A36 | solute carrier family 25, member 36 | 1.20E−05 |
| 213355_PM_at | ST3GAL6 | ST3 beta-galactoside alpha-2,3-sialyltransferase 6 | 1.21E−05 |
| 213923_PM_at | RAP2B | RAP2B, member of RAS oncogene family | 1.23E−05 |
| 220990_PM_s_at | MIR21 /// TMEM49 | microRNA 21 /// transmembrane protein 49 | 1.24E−05 |
| 213535_PM_s_at | UBE2I | ubiquitin-conjugating enzyme E2I (UBC9 homolog, yeast) | 1.25E−05 |
| 205910_PM_s_at | CEL /// LOC100508206 | carboxyl ester lipase (bile salt-stimulated lipase) /// bile salt-activated lipase-like | 1.25E−05 |
| 204702_PM_s_at | NFE2L3 | nuclear factor (erythroid-derived 2)-like 3 | 1.27E−05 |
| 230550_PM_at | MS4A6A | membrane-spanning 4-domains, subfamily A, member 6A | 1.29E−05 |
| 205027_PM_s_at | MAP3K8 | mitogen-activated protein kinase kinase kinase 8 | 1.30E−05 |
| 209476_PM_at | TMX1 | thioredoxin-related transmembrane protein 1 | 1.30E−05 |
| 209422_PM_at | PHF20 | PHD finger protein 20 | 1.32E−05 |

TABLE 8-continued

Biopsy Microarray Signatures for subAR using a 2-way 2-Step approach - second step (AR vs. subAR)

| Probeset ID | Gene Symbol | Gene Title | p-value(cAR Bx vs. subAR Bx) |
|---|---|---|---|
| 207754_PM_at | RASSF8 | Ras association (RalGDS/AF-6) domain family (N-terminal) member 8 | 1.33E−05 |
| 35150_PM_at | CD40 | CD40 molecule, TNF receptor superfamily member 5 | 1.34E−05 |
| 41220_PM_at | SEPT9 | septin 9 | 1.35E−05 |
| 227730_PM_at | EST 227730_PM_at | — | 1.40E−05 |
| 206613_PM_s_at | TAF1A | TATA box binding protein (TBP)-associated factor, RNA polymerase I, A, 48 kDa | 1.40E−05 |
| 201179_PM_s_at | GNAI3 | guanine nucleotide binding protein (G protein), alpha inhibiting activity polypeptide 3 | 1.41E−05 |
| 208850_PM_s_at | THY1 | Thy-1 cell surface antigen | 1.43E−05 |
| 217985_PM_s_at | BAZ1A | bromodomain adjacent to zinc finger domain, 1A | 1.44E−05 |
| 200798_PM_x_at | MCL1 | myeloid cell leukemia sequence 1 (BCL2-related) | 1.45E−05 |
| 1555486_PM_a_at | PRR5L | proline rich 5 like | 1.45E−05 |
| 221932_PM_s_at | GLRX5 | glutaredoxin 5 | 1.45E−05 |
| 205079_PM_s_at | MPDZ | multiple PDZ domain protein | 1.46E−05 |
| 241154_PM_x_at | EST 241154_PM_x_at | — | 1.47E−05 |
| 219089_PM_s_at | ZNF576 | zinc finger protein 576 | 1.50E−05 |
| 206219_PM_s_at | VAV1 | vav 1 guanine nucleotide exchange factor | 1.52E−05 |
| 1553153_PM_at | ATP6V0D2 | ATPase, H+ transporting, lysosomal 38 kDa, V0 subunit d2 | 1.54E−05 |
| 208540_PM_x_at | S100A11 | S100 calcium binding protein A11 | 1.56E−05 |
| 223318_PM_s_at | ALKBH7 | alkB, alkylation repair homolog 7 (*E. coli*) | 1.56E−05 |
| 226618_PM_at | UBE2QL1 | ubiquitin-conjugating enzyme E2Q family-like 1 | 1.57E−05 |
| 218092_PM_s_at | AGFG1 | ArfGAP with FG repeats 1 | 1.65E−05 |
| 229041_PM_s_at | EST 229041_PM_s_at | — | 1.66E−05 |
| 214366_PM_s_at | ALOX5 | arachidonate 5-lipoxygenase | 1.66E−05 |
| 226820_PM_at | ZNF362 | zinc finger protein 362 | 1.68E−05 |
| 210426_PM_x_at | RORA | RAR-related orphan receptor A | 1.68E−05 |
| 209545_PM_s_at | RIPK2 | receptor-interacting serine-threonine kinase 2 | 1.68E−05 |
| 214329_PM_x_at | TNFSF10 | tumor necrosis factor (ligand) superfamily, member 10 | 1.69E−05 |
| 210176_PM_at | TLR1 | toll-like receptor 1 | 1.72E−05 |
| 242167_PM_at | EST 242167_PM_at | — | 1.73E−05 |
| 224352_PM_s_at | CFL2 | cofilin 2 (muscle) | 1.73E−05 |
| 223451_PM_s_at | CKLF | chemokine-like factor | 1.76E−05 |
| 202625_PM_at | LYN | v-yes-1 Yamaguchi sarcoma viral related oncogene homolog | 1.79E−05 |
| 202748_PM_at | GBP2 | guanylate binding protein 2, interferon-inducible | 1.81E−05 |
| 209906_PM_at | C3AR1 | complement component 3a receptor 1 | 1.81E−05 |
| 213869_PM_x_at | THY1 | Thy-1 cell surface antigen | 1.84E−05 |
| 225994_PM_at | CPSF2 | cleavage and polyadenylation specific factor 2, 100 kDa | 1.84E−05 |
| 226048_PM_at | MAPK8 | mitogen-activated protein kinase 8 | 1.85E−05 |
| 203828_PM_s_at | IL32 | interleukin 32 | 1.88E−05 |
| 203947_PM_at | CSTF3 | cleavage stimulation factor, 3' pre-RNA, subunit 3, 77 kDa | 1.88E−05 |
| 244811_PM_at | PHIP | pleckstrin homology domain interacting protein | 1.88E−05 |
| 236293_PM_at | RHOH | ras homolog gene family, member H | 1.90E−05 |
| 214467_PM_at | GPR65 | G protein-coupled receptor 65 | 1.91E−05 |
| 235309_PM_at | RPS15A | ribosomal protein S15a | 1.91E−05 |
| 212024_PM_x_at | FLII | flightless 1 homolog (*Drosophila*) | 1.93E−05 |
| 205841_PM_at | JAK2 | Janus kinase 2 | 1.94E−05 |
| 205887_PM_x_at | MSH3 | mutS homolog 3 (*E. coli*) | 1.95E−05 |
| 208743_PM_s_at | YWHAB | tyrosine 3-monooxygenase/tryptophan 5-monooxygenase activation protein, beta polypeptid | 1.98E−05 |
| 238668_PM_at | EST 238668_PM_at | — | 1.98E−05 |
| 205809_PM_s_at | WASL | Wiskott-Aldrich syndrome-like | 1.99E−05 |
| 218008_PM_at | C7orf42 | chromosome 7 open reading frame 42 | 1.99E−05 |
| 204198_PM_s_at | RUNX3 | runt-related transcription factor 3 | 2.00E−05 |
| 201040_PM_at | GNAI2 | guanine nucleotide binding protein (G protein), alpha inhibiting activity polypeptide 2 | 2.01E−05 |
| 223010_PM_s_at | OCIAD1 | OCIA domain containing 1 | 2.03E−05 |
| 225511_PM_at | GPRC5B | G protein-coupled receptor, family C, group 5, member B | 2.04E−05 |
| 226748_PM_at | LYSMD2 | LysM, putative peptidoglycan-binding, domain containing 2 | 2.05E−05 |
| 206150_PM_at | CD27 | CD27 molecule | 2.06E−05 |
| 213136_PM_at | PTPN2 | protein tyrosine phosphatase, non-receptor type 2 | 2.07E−05 |
| 202238_PM_s_at | NNMT | nicotinamide N-methyltransferase | 2.07E−05 |
| 203079_PM_s_at | CUL2 | cullin 2 | 2.07E−05 |
| 201724_PM_s_at | GALNT1 | UDP-N-acetyl-alpha-D-galactosamine:potypeptide N-acetylgalactosaminyltransferase 1 (Gal | 2.08E−05 |
| 226147_PM_s_at | PIGR | polymeric immunoglobulin receptor | 2.08E−05 |

TABLE 8-continued

Biopsy Microarray Signatures for subAR using a 2-way 2-Step approach - second step (AR vs. subAR)

| Probeset ID | Gene Symbol | Gene Title | p-value(cAR Bx vs. subAR Bx) |
|---|---|---|---|
| 203091_PM_at | FUBP1 | far upstream element (FUSE) binding protein 1 | 2.11E−05 |
| 219033_PM_at | PARP8 | poly (ADP-ribose) polymerase family, member 8 | 2.12E−05 |
| 225924_PM_at | FNIP2 | folliculin interacting protein 2 | 2.14E−05 |
| 230565_PM_at | ATP6V1G3 | ATPase, H+ transporting, lysosomal 13 kDa, V1 subunit G3 | 2.14E−05 |
| 1553906_PM_s_at | FGD2 | FYVE, RhoGEF and PH domain containing 2 | 2.16E−05 |
| 208296_PM_x_at | TNFAIP8 | tumor necrosis factor, alpha-induced protein 8 | 2.18E−05 |
| 209787_PM_s_at | HMGN4 | high mobility group nucleosomal binding domain 4 | 2.18E−05 |
| 202957_PM_at | HCLS1 | hematopoietic cell-specific Lyn substrate 1 | 2.19E−05 |
| 210785_PM_s_at | C1orf38 | chromosome 1 open reading frame 38 | 2.20E−05 |
| 228770_PM_at | GPR146 | G protein-coupled receptor 146 | 2.23E−05 |
| 200829_PM_x_at | ZNF207 | zinc finger protein 207 | 2.26E−05 |
| 223344_PM_s_at | MS4A7 | membrane-spanning 4-domains, subfamily A, member 7 | 2.28E−05 |
| 222885_PM_at | EMCN | endomucin | 2.30E−05 |
| 202211_PM_at | ARFGAP3 | ADP-ribosylation factor GTPase activating protein 3 | 2.32E−05 |
| 238581_PM_at | GBP5 | guanylate binding protein 5 | 2.36E−05 |
| 208821_PM_at | SNRPB | small nuclear ribonucleoprotein polypeptides B and B1 | 2.38E−05 |
| 203137_PM_at | WTAP | Wilms tumor 1 associated protein | 2.38E−05 |
| 213102_PM_at | ACTR3 | ARP3 actin-related protein 3 homolog (yeast) | 2.40E−05 |
| 227384_PM_s_at | EST 227384_PM_s_at | — | 2.41E−05 |
| 233632_PM_s_at | XRN1 | 5'-3' exoribonuclease 1 | 2.42E−05 |
| 220742_PM_s_at | NGLY1 | N-glycanase 1 | 2.44E−05 |
| 208642_PM_s_at | XRCC5 | X-ray repair complementing defective repair in Chinese hamster cells 5 (double-strand-b | 2.46E−05 |
| 225814_PM_at | XRN1 | 5'-3' exoribonuclease 1 | 2.46E−05 |
| 209295_PM_at | TNFRSF10B | tumor necrosis factor receptor superfamily, member 10b | 2.47E−05 |
| 218665_PM_at | FZD4 | frizzled homolog 4 (Drosophila) | 2.48E−05 |
| 219023_PM_at | AP1AR | adaptor-related protein complex 1 associated regulatory protein | 2.50E−05 |
| 202510_PM_s_at | TNFAIP2 | tumor necrosis factor, alpha-induced protein 2 | 2.53E−05 |
| 221477_PM_s_at | SOD2 | superoxide dismutase 2, mitochondrial | 2.57E−05 |
| 203182_PM_s_at | SRPK2 | SRSF protein kinase 2 | 2.59E−05 |
| 209189_PM_at | FOS | FBJ murine osteosarcoma viral oncogene homolog | 2.61E−05 |
| 219574_PM_at | MARCH1 | membrane-associated ring finger (C3HC4) 1 | 2.62E−05 |
| 217549_PM_at | EST217549_PM_at | — | 2.62E−05 |
| 210106_PM_at | RDH5 | retinol dehydrogenase 5 (11-cis/9-cis) | 2.64E−05 |
| 33760_PM_at | PEX14 | peroxisomal biogenesis factor 14 | 2.65E−05 |
| 238423_PM_at | SYTL3 | synaptotagmin-like 3 | 2.65E−05 |
| 230176_PM_at | EST 230176_PM_at | — | 2.66E−05 |
| 218546_PM_at | C1orf115 | chromosome 1 open reading frame 115 | 2.70E−05 |
| 1558702_PM_at | TEX10 | testis expressed 10 | 2.75E−05 |
| 212733_PM_at | KIAA0226 | KIAA0226 | 2.75E−05 |
| 229659_PM_s_at | EST 229659_PM_s_at | — | 2.76E−05 |
| 207809_PM_s_at | ATP6AP1 | ATPase, H+ transporting, lysosomal accessory protein 1 | 2.77E−05 |
| 202431_PM_s_at | MYC | v-myc myelocytomatosis viral oncogene homolog (avian) | 2.79E−05 |
| 212433_PM_x_at | RPS2 | ribosomal protein S2 | 2.80E−05 |
| 223086_PM_x_at | MRPL51 | mitochondrial ribosomal protein L51 | 2.81E−05 |
| 228162_PM_at | ESD | esterase D | 2.84E−05 |
| 214770_PM_at | MSR1 | macrophage scavenger receptor 1 | 2.84E−05 |
| 201830_PM_s_at | NET1 | neuroepithelial cell transforming 1 | 2.85E−05 |
| 212314_PM_at | SEL1L3 | sel-1 suppressor of lin-12-like 3 (C. elegans) | 2.86E−05 |
| 209360_PM_s_at | RUNX1 | runt-related transcription factor 1 | 2.89E−05 |
| 221698_PM_s_at | CLEC7A | C-type lectin domain family 7, member A | 2.90E−05 |
| 201359_PM_at | COPB1 | coatomer protein complex, subunit beta 1 | 2.91E−05 |
| 217157_PM_x_at | IGK@ /// IGKC | immunoglobulin kappa locus /// immunoglobulin kappa constant | 2.92E−05 |

TABLE 9

2-Way 2-Step Microarray Analysis (AR v. subAR; AR v. TX; and subAR v. TX) using biopsy samples - Results

| Real | Predicted | | |
|---|---|---|---|
| | TX | SCAR | AR |
| TX | 22 | 2 | 1 |
| SCAR | 0 | 18 | 4 |
| AR | 0 | 2 | 18 |

TABLE 9-continued

2-Way 2-Step Microarray Analysis (AR v. subAR; AR v. TX; and subAR v. TX) using biopsy samples - Results

| Method | Classifies | % Predictive Accuracy | Sensitivity (%) | Specificity (%) | Positive Predictive Value (%) | Negative Predicitve Value (%) | AUC |
|---|---|---|---|---|---|---|---|
| Nearest Centroid | TX vs. AR | 97% | 100% | 94% | 95% | 100% | 0.965 |
| (2 Step Prediction) | TX vs. SCAR | 95% | 100% | 90% | 91% | 100% | 0.947 |
|  | AR vs. SCAR | 86% | 90% | 81% | 81% | 90% | 0.862 |

TABLE 10

3-Way 1-Step NGS Analysis (AR v. subAR v. TX) using biopsy samples - Results

| | Predicted | | |
|---|---|---|---|
| Real | TX | SUBAR | AR |
| TX | 22 | 2 | 1 |
| SCAR | 8 | 11 | 3 |
| AR | 0 | 8 | 11 |

| Method | Classifies | % Predictive Accuracy | Sensitivity (%) | Specificity (%) | Predictive Positive Value (%) | Negative Predicitve Value (%) | AUC |
|---|---|---|---|---|---|---|---|
| Nearest Centroid | TX vs. AR | 97% | 100% | 92% | 95% | 100% | 0.967 |
| (1 Step Prediction) | TX vs. SCAR | 80% | 72% | 83% | 72% | 91% | 0.795 |
|  | AR vs. SCAR | 69% | 58% | 79% | 79% | 59% | 0.689 |

TABLE 11

Biopsy NGS Signatures for subAR using a 2-Step approach (AR + subAR vs. TX and subAR vs TX) - first step: AR + subAR vs. TX

| Column ID | To | Gene Name | p-value(AR + SCAR vs. TX) |
|---|---|---|---|
| 1 | CCR2 | chemokine (C-C motif) receptor 2 | 4.89E−13 |
| 2 | Tbc1d10c | TBC1 domain family, member 10C | 5.04E−11 |
| 3 | Ly9 | lymphocyte antigen 9 | 1.88E−10 |
| 4 | Cd48 | CD48 molecule | 3.78E−10 |
| 5 | Bin2 | bridging integrator 2 | 5.43E−10 |
| 6 | Cd2 | CD2 molecule | 5.64E−10 |
| 7 | ALOX5 | arachidonate 5-lipoxygenase | 7.26E−10 |
| 8 | IKZF3 | IKAROS family zinc finger 3 (Aiolos) | 7.80E−10 |
| 9 | Cd247 | CD247 molecule | 8.24E−10 |
| 10 | CD1D | CD1d molecule | 1.05E−09 |
| 11 | Cd96 | CD96 molecule | 1.27E−09 |
| 12 | Ptprc | protein tyrosine phosphatase, receptor | 1.61E−09 |
| 13 | Ikzf1 | IKAROS family zinc finger 1 (Ikaros) | 2.45E−09 |
| 14 | PTPN22 | protein tyrosine phosphatase, non-recep | 2.51E−09 |
| 15 | EMB | embigin homolog (mouse) | 2.94E−09 |
| 16 | runx3 | runt-related transcription factor 3 | 3.00E−09 |
| 17 | MNDA | myeloid cell nuclear differentiation an | 3.08E−09 |
| 18 | Arl4c | ADP-ribosylation factor-like 4C | 3.41E−09 |
| 19 | IL16 | interleukin 16 (lymphocyte chemoattract | 4.57E−09 |
| 20 | DOCK2 | dedicator of cytokinesis 2 | 5.47E−09 |
| 21 | ITGAL | integrin, alpha L (antigen CD11A (p180) | 6.07E−09 |
| 22 | Fgd2 | FYVE, RhoGEF and PH domain containing 2 | 6.43E−09 |
| 23 | PARVG | parvin, gamma | 6.49E−09 |
| 24 | CD3D | CD3d molecule, delta (CD3-TCR complex) | 6.50E−09 |
| 25 | Mpeg1 | macrophage expressed 1 | 6.53E−09 |
| 26 | LCP1 | lymphocyte cytosolic protein 1 (L-plast | 6.58E−09 |
| 27 | ARHGAP15 | Rho GTPase activating protein 15 | 7.55E−09 |
| 28 | NLRC5 | NLR family, CARD domain containing 5 | 7.70E−09 |
| 29 | GZMK | granzyme K (granzyme 3; tryptase II) | 7.96E−09 |
| 30 | BIRC3 | baculoviral IAP repeat-containing 3 | 8.08E−09 |
| 31 | TMC8 | transmembrane channel-like 8 | 8.56E−09 |
| 32 | RGS18 | regulator of G-protein signaling 18 | 1.00E−08 |
| 33 | Cd3g | CD3g molecule, gamma (CD3-TCR complex) | 1.00E−08 |

TABLE 11-continued

Biopsy NGS Signatures for subAR using a 2-Step approach (AR + subAR vs. TX and subAR vs TX) - first step: AR + subAR vs. TX

| Column ID | To | Gene Name | p-value(AR + SCAR vs. TX) |
|---|---|---|---|
| 34 | Amica1 | adhesion molecule, interacts with CXADR | 1.04E−08 |
| 35 | Il2rg | Interleukin 2 receptor, gamma (severe c | 1.19E−08 |
| 36 | Inpp5d | inositol polyphosphate-5-phosphatase, 1 | 1.25E−08 |
| 37 | cstA | cystatin A (stefin A) | 1.26E−08 |
| 38 | LIMD2 | LIM domain containing 2 | 1.44E−08 |
| 39 | dapp1 | dual adaptor of phosphotyrosine and 3-p | 1.65E−08 |
| 40 | NCKAP1L | NCK-associated protein 1-like | 1.68E−08 |
| 41 | Ms4a7 | membrane-spanning 4-domains, subfamily | 1.80E−08 |
| 42 | TNFAIP3 | tumor necrosis factor, alpha-induced pr | 1.87E−08 |
| 43 | IL7R | interleukin 7 receptor | 1.88E−08 |
| 44 | EVI2B | ecotropic viral integration site 2B | 1.88E−08 |
| 45 | C1orf162 | chromosome 1 open reading frame 162 | 1.98E−08 |
| 46 | SLAMF7 | SLAM family member 7 | 2.09E−08 |
| 47 | RNASE6 | ribonuclease, RNase A family, k6 | 2.20E−08 |
| 48 | CXorf21 | chromosome X open reading frame 21 | 2.38E−08 |
| 49 | SCML4 | sex comb on midleg-like 4 (Drosophila) | 2.42E−08 |
| 50 | CCL5 | chemokine (C-C motif) ligand 5 | 2.44E−08 |
| 51 | EST | EST2 | 2.52E−08 |
| 52 | Pyhin1 | pyrin and HIN domain family, member 1 | 2.64E−08 |
| 53 | Cd8a | CD8a molecule | 2.79E−08 |
| 54 | Cd52 | CD52 molecule | 2.99E−08 |
| 55 | SAMD3 | sterile alpha motif domain containing 3 | 3.16E−08 |
| 56 | btk | Bruton agammaglobulinemia tyrosine kina | 3.18E−08 |
| 57 | IRF4 | interferon regulatory factor 4 | 3.24E−08 |
| 58 | GAB3 | GRB2-associated binding protein 3 | 3.25E−08 |
| 59 | CSF2RA | colony stimulating factor 2 receptor, a | 3.36E−08 |
| 60 | P2RY13 | purinergic receptor P2Y, G-protein coup | 3.46E−08 |
| 61 | FYB | FYN binding protein (FYB-120/130) | 3.58E−08 |
| 62 | TRAF3IP3 | TRAF3 interacting protein 3 | 3.86E−08 |
| 63 | PTAFR | platelet-activating factor receptor | 3.94E−08 |
| 64 | Arhgap25 | Rho GTPase activating protein 25 | 3.99E−08 |
| 65 | myo1f | myosin IF | 4.09E−08 |
| 66 | CELF2 | CUG triplet repeat, RNA binding protein | 4.18E−08 |
| 67 | MS4A6A | membrane-spanning 4-domains, subfamily | 4.18E−08 |
| 68 | kcna3 | potassium voltage-gated channel, shaker | 4.30E−08 |
| 69 | CLIC2 | chloride intracellular channel 2 | 4.33E−08 |
| 70 | IL10RA | interleukin 10 receptor, alpha | 4.73E−08 |
| 71 | NHEDC2 | Na+/H+ exchanger domain containing 2 | 4.76E−08 |
| 72 | THEMIS | thymocyte selection pathway associated | 4.88E−08 |
| 73 | ARHGAP30 | Rho GTPase activating protein 30 | 4.97E−08 |
| 74 | PRKCB | protein kinase C, beta | 5.03E−08 |
| 75 | HCL51 | hematopoietic cell-specific Lyn substra | 5.08E−08 |
| 76 | Rgs10 | regulator of G-protein signaling 10 | 5.66E−08 |
| 77 | Evi2a | ecotropic viral integration site 2A | 5.83E−08 |
| 78 | Spn | sialophorin | 5.84E−08 |
| 79 | IL1B | interleukln 1, beta | 5.88E−08 |
| 80 | LOC100133678 | similar to hCG2042724; similar to HLA c | 6.41E−08 |
| 81 | ITGA4 | integrin, alpha 4 (antigen CD49D, alpha | 6.94E−08 |
| 82 | CCDC109B | coiled-coil domain containing 109B | 7.03E−08 |
| 83 | Gapt | GRB2-binding adaptor protein, transmemb | 7.43E−08 |
| 84 | APBB1IP | amyloid beta (A4) precursor protein-bin | 7.51E−08 |
| 85 | arhgdib | Rho GDP dissociation inhibitor (GDI) be | 7.69E−08 |
| 86 | CD180 | CD180 molecule | 7.79E−08 |
| 87 | PIK3CG | phosphoinositide-3-kinase, catalytic, g | 7.94E−08 |
| 88 | CCR5 | chemokine (C-C motif) receptor 5 | 8.05E−08 |
| 89 | dgkA | diacylglycerol kinase, alpha 80 kDa | 8.25E−08 |
| 90 | RASSF2 | Ras association (RalGDS/AF-6) domain fa | 8.52E−08 |
| 91 | TAGAP | T-cell activation RhoGTPase activating | 8.59E−08 |
| 92 | CASP1 | caspase 1, apoptosis-related cysteine p | 8.74E−08 |
| 93 | LOC606724 | coronin, actln binding protein, 1A pseu | 9.01E−08 |
| 94 | REEP4 | receptor accessory protein 4 | 9.04E−08 |
| 95 | GIMAP7 | GTPase, IMAP family member 7 | 9.16E−08 |
| 96 | KLRB1 | killer cell lectin-like receptor subfam | 9.85E−08 |
| 97 | lcp2 | lymphocyte cytosolic protein 2 (SH2 dom | 9.99E−08 |
| 98 | Lair1 | leukocyte-associated immunoglobulin-lik | 1.01E−07 |
| 99 | CD44 | CD44 molecule (Indian blood group) | 1.02E−07 |
| 100 | GZMA | granzyme A (granzyme 1, cytotoxic T-lym | 1.03E−07 |
| 101 | rac2 | ras-related C3 botulinum toxin substrat | 1.13E−07 |
| 102 | STAMBPL1 | STAM binding protein-like 1 | 1.17E−07 |
| 103 | FAM78A | family with sequence similarity 78, mem | 1.33E−07 |
| 104 | FAIM3 | Fas apoptotic inhibitory molecule 3 | 1.35E−07 |
| 105 | Cd6 | CD6 molecule | 1.39E−07 |
| 106 | EST | EST9 | 1.42E−07 |
| 107 | MAP4K1 | mitogen-activated protein kinase kinase | 1.47E−07 |

TABLE 11-continued

Biopsy NGS Signatures for subAR using a 2-Step approach (AR + subAR vs. TX and subAR vs TX) - first step: AR + subAR vs. TX

| Column ID | To | Gene Name | p-value(AR + SCAR vs. TX) |
|---|---|---|---|
| 108 | CLEC10A | C-type lectin domain family 10, member | 1.52E-07 |
| 109 | SP140 | SP140 nuclear body protein | 1.52E-07 |
| 110 | SELL | selectin L | 1.59E-07 |
| 111 | CRTAM | cytotoxic and regulatory T cell molecul | 1.60E-07 |
| 112 | FCER1G | Fc fragment of IgE, high affinity I, re | 1.64E-07 |
| 113 | CP | ceruloplasmin (ferroxidase) | 1.73E-07 |
| 114 | GPR171 | G protein-coupled receptor 171 | 1.82E-07 |
| 115 | Cx3cr1 | chemokine (C-X3-C motif) receptor 1 | 1.87E-07 |
| 116 | TBXAS1 | thromboxane A synthase 1 (platelet) | 1.87E-07 |
| 117 | SLAMF1 | signaling lymphocytic activation molecu | 1.88E-07 |
| 118 | P2RX7 | purinergic receptor P2X, ligand-gated I | 1.93E-07 |
| 119 | SAMHD1 | SAM domain and HD domain 1 | 1.94E-07 |
| 120 | EST | EST16 | 2.00E-07 |
| 121 | Miat | myocardial infarction associated transc | 2.01E-07 |
| 122 | gmfg | glia maturation factor, gamma | 2.07E-07 |
| 123 | LCK | lymphocyte-specific protein tyrosine ki | 2.11E-07 |
| 124 | SLA | Src-like-adaptor | 2.14E-07 |
| 125 | CARD16 | caspase recruitment domain family, memb | 2.15E-07 |
| 126 | ETS1 | v-ets erythroblastosis virus E26 oncoge | 2.17E-07 |
| 127 | BAZ1A | bromodomain adjacent to zinc finger dom | 2.20E-07 |
| 128 | Selplg | selectin P ligand | 2.28E-07 |
| 129 | IFI16 | interferon, gamma-inducible protein 16 | 2.29E-07 |
| 130 | rassf5 | Ras association (RalGDS/AF-6) domain fa | 2.51E-07 |
| 131 | ADCY7 | adenylate cyclase 7 | 2.58E-07 |
| 132 | PLCB2 | phospholipase c, beta 2 | 2.59E-07 |
| 133 | kcnJ10 | potassium inwardly-rectifying channel, | 2.60E-07 |
| 134 | STAT4 | signal transducer and activator of tran | 2.62E-07 |
| 135 | GPR65 | G protein-coupled receptor 65 | 2.66E-07 |
| 136 | AIM2 | absent in melanoma 2 | 2.69E-07 |
| 137 | SERPINB9 | serpin peptidase inhibitor, clade B (ov | 2.69E-07 |
| 138 | Ccdc88b | coiled-coil domain containing 88B | 2.71E-07 |
| 139 | FECH | ferrochelatase (protoporphyria) | 2.91E-07 |
| 140 | Akna | AT-hook transcription factor | 2.99E-07 |
| 141 | APOBEC3D | apolipoprotein B mRNA editing enzyme, c | 3.00E-07 |
| 142 | BTN3A2 | butyrophilin, subfamily 3, member A2 | 3.01E-07 |
| 143 | ARHGAP9 | Rho GTPase activating protein 9 | 3.20E-07 |
| 144 | pAG1 | phosphoprotein associated with glycosph | 3.23E-07 |
| 145 | SIGLEC10 | sialic acid binding Ig-like lectin 10 | 3.26E-07 |
| 146 | FGL2 | fibrinogen-like 2 | 3.30E-07 |
| 147 | Pou2f2 | POU class 2 homeobox 2 | 3.43E-07 |
| 148 | CYTIP | cytohesin 1 interacting protein | 3.44E-07 |
| 149 | Gad1 | glutamate decarboxylase 1 (brain, 67 kDa | 3.56E-07 |
| 150 | TLR10 | toll-like receptor 10 | 3.56E-07 |
| 151 | WAS | Wiskott-Aldrich syndrome (eczema-thromb | 3.59E-07 |
| 152 | prex1 | phosphatidylinositol-3,4,5-trisphosphat | 3.64E-07 |
| 153 | CD69 | CD69 molecule | 3.68E-07 |
| 154 | SLAMF6 | SLAM family member 6 | 3.74E-07 |
| 155 | CD37 | CD37 molecule | 3.80E-07 |
| 156 | ST8SIA4 | ST8 alpha-N-acetyl-neuraminide alpha-2, | 3.83E-07 |
| 157 | ANKRD44 | ankyrin repeat domain 44 | 3.90E-07 |
| 158 | RASAL3 | RAS protein activator like 3 | 3.92E-07 |
| 159 | KLRD1 | killer cell lectin-like receptor subfam | 3.93E-07 |
| 160 | SMAP2 | small ArfGAP2 | 4.13E-07 |
| 161 | pstpip2 | proline-serine-threonine phosphatase in | 4.24E-07 |
| 162 | FAM65B | family with sequence similarity 65, mem | 4.25E-07 |
| 163 | GIMAP4 | GTPase, IMAP family member 4 | 4.36E-07 |
| 164 | LY86 | lymphocyte antigen 86 | 4.42E-07 |
| 165 | FMNL1 | formin-like 1 | 4.63E-07 |
| 166 | fermt3 | fermitin family homolog 3 (*Drosophila*) | 4.70E-07 |
| 167 | C1s | complement component 1, s subcomponent | 4.78E-07 |
| 168 | BTN2A2 | butyrophilin, subfamily 2, member A2 | 4.78E-07 |
| 169 | EST | EST17 | 4.92E-07 |
| 170 | TLR6 | toll-like receptor 6 | 4.94E-07 |
| 171 | IRF8 | interferon regulatory factor 8 | 4.98E-07 |
| 172 | CD163 | CD163 molecule | 5.02E-07 |
| 173 | LILRB1 | leukocyte immunoglobulin-like receptor, | 5.03E-07 |
| 174 | APOBEC3F | apolipoprotein B mRNA editing enzyme, c | 5.14E-07 |
| 175 | Itgax | Integrin, alpha X (complement component | 5.19E-07 |
| 176 | CTSS | cathepsin S | 5.54E-07 |
| 177 | HCST | hematopoietic cell signal transducer | 5.65E-07 |
| 178 | ccdc69 | coiled-coil domain containing 69 | 5.66E-07 |
| 179 | C1r | complement component 1, r subcomponent | 5.67E-07 |
| 180 | Nkg7 | natural killer cell group 7 sequence | 5.70E-07 |
| 181 | csf1 | colony stimulating factor 1 (macrophage | 5.82E-07 |

TABLE 11-continued

Biopsy NGS Signatures for subAR using a 2-Step approach (AR + subAR vs. TX and subAR vs TX) - first step: AR + subAR vs. TX

| Column ID | To | Gene Name | p-value(AR + SCAR vs. TX) |
|---|---|---|---|
| 182 | pycard | PYD and CARD domain containing | 5.87E−07 |
| 183 | SP140L | SP140 nuclear body protein-like | 5.93E−07 |
| 184 | Cd53 | CD53 molecule | 6.01E−07 |
| 185 | srgn | serglycin | 6.09E−07 |
| 186 | SERPINB8 | serpin peptidase inhibitor, clade B (ov | 6.15E−07 |
| 187 | IL4R | interleukin 4 receptor | 6.30E−07 |
| 188 | GBP2 | guanylate binding protein 2, interferon | 6.39E−07 |
| 189 | Fcgr2b | Fc fragment of IgG, low affinity IIb, r | 6.49E−07 |
| 190 | TIMP1 | TIMP metallopeptidase inhibitor 1 | 6.55E−07 |
| 191 | C17orf87 | chromosome 17 open reading frame 87 | 6.64E−07 |
| 192 | GLIPR2 | GLI pathogenesis-related 2 | 6.65E−07 |
| 193 | LYZ | lysozyme (renal amyloidosis) | 7.18E−07 |
| 194 | KIAA0748 | KIAA0748 | 7.30E−07 |
| 195 | mybl1 | v-myb myeloblastosis viral oncogene hom | 7.48E−07 |
| 196 | CLEC7A | C-type lectin domain family 7, member A | 7.62E−07 |
| 197 | KLHL6 | kelch-like 6 (Drosophila) | 7.67E−07 |
| 198 | IL4I1 | interleukin 4 induced 1 | 7.87E−07 |
| 199 | APOBEC3G | apolipoprotein B mRNA editing enzyme, c | 8.00E−07 |
| 200 | TRANK1 | lupus brain antigen 1 | 8.20E−07 |

TABLE 12

Biopsy NGS Signatures for subAR using a 2-Step approach (AR + subAR vs. TX and AR v. subAR) - second step: AR vs. subAR

| Column ID | To | Gene Name | p-value (cAR vs. subAR) |
|---|---|---|---|
| 4057 | LTF | lactotransferrin | 3.02E−07 |
| 400746 | C1orf130 | chromosome 1 open reading frame 130 | 1.17E−06 |
| 4192 | Mdk | midkine (neurite growth-promoting facto | 1.60E−06 |
| 51705 | EMCN | endomucin | 3.01E−06 |
| 4316 | mmp7 | matrix metallopeptidase 7 (matrilysin, | 4.37E−06 |
| 1056 | Cel | carboxyl ester lipase (bile salt-stimul | 5.01E−06 |
| 140803 | TRPM6 | transient receptor potential cation cha | 5.75E−06 |
| 245973 | ATP6V1C2 | ATPase, H+ transporting, lysosomal 42 kD | 5.97E−06 |
| 55917 | CTTNBP2NL | CTTNBP2 N-terminal like | 7.89E−06 |
| 221395 | Gpr116 | G protein-coupled receptor 116 | 9.47E−06 |
| 5284 | PIGR | polymeric immunoglobulin receptor | 1.05E−05 |
| 6289 | SAA2 | serum amyloid A2 | 1.32E−05 |
| 157285 | SGK223 | homolog of rat pragma of Rnd2 | 1.38E−05 |
| 9021 | socs3 | suppressor of cytokine signaling 3 | 1.39E−05 |
| 56938 | ARNTL2 | aryl hydrocarbon receptor nuclear trans | 1.45E−05 |
| 64332 | NFKBIZ | nuclear factor of kappa light potypepti | 1.47E−05 |
| 51279 | C1RL | complement component 1, r subcomponent- | 1.65E−05 |
| 834 | CASP1 | caspase 1, apoptosis-related cysteine p | 1.69E−05 |
| 1191 | clu | clusterin | 1.91E−05 |
| 10560 | SLC19A2 | solute carrier family 19 (thiamine tran | 1.94E−05 |
| 2321 | FLT1 | fms-related tyrosine kinase 1 (vascular | 2.00E−05 |
| 5452 | Pou2f2 | POU class 2 homeobox 2 | 2.09E−05 |
| 11228 | rassf8 | Ras association (RalGDS/AF-6) domain fa | 2.21E−05 |
| 2919 | CXCL1 | chemokine (C-X-C motif) ligand 1 (melan | 2.34E−05 |
| 7102 | TSPAN7 | tetraspanin 7 | 2.34E−05 |
| 64092 | SAMSN1 | SAM domain, SH3 domain and nuclear loca | 2.50E−05 |
| 9447 | AIM2 | absent in melanoma 2 | 2.54E−05 |
| 133418 | EMB | embigin homolog (mouse) | 2.58E−05 |
| 3455 | IFNAR2 | interferon (alpha, beta and omega) rece | 2.63E−05 |
| 58475 | Ms4a7 | membrane-spanning 4-domains, subfamily | 2.83E−05 |
| 54997 | TESC | tescalcin | 2.84E−05 |
| 6372 | Cxcl6 | chemokine (C-X-C motif) ligand 6 (granu | 2.87E−05 |
| 201633 | TIGIT | T cell immunoreceptor with Ig and ITIM | 2.99E−05 |
| 253012 | HEPACAM2 | HEPACAM family member 2 | 3.26E−05 |
| 118788 | Pik3ap1 | phosphoinositide-3-kinase adaptor prote | 3.32E−05 |
| 245972 | Atp6v0d2 | ATPase, H+ transporting, lysosomal 38 kD | 3.34E−05 |
| 7852 | CXCR4 | chemokine (C-X-C motif) receptor 4 | 3.36E−05 |
| 79668 | PARP8 | poly (ADP-ribose) polymerase family, me | 3.42E−05 |
| 942 | CD86 | CD86 molecule | 3.51E−05 |
| 112597 | LOC541471 | hypothetical LOC541471; non-protein cod | 3.57E−05 |
| 58191 | CXCL16 | chemokine (C-X-C motif) ligand 16 | 3.58E−05 |
| 22982 | dip2c | DIP2 disco-interacting protein 2 homolo | 3.66E−05 |
| 11177 | BAZ1A | bromodomain adjacent to zinc finger dom | 3.79E−05 |

TABLE 12-continued

Biopsy NGS Signatures for subAR using a 2-Step approach (AR + subAR vs. TX and AR v. subAR) - second step: AR vs. subAR

| Column ID | To | Gene Name | p-value (cAR vs. subAR) |
|---|---|---|---|
| 8635 | RNASET2 | ribonuclease T2 | 3.82E−05 |
| 3273 | HRG | histidine-rich glycoprotein | 3.85E−05 |
| 10346 | TRIM22 | tripartite motif-containing 22 | 4.00E−05 |
| 83988 | NCALD | neurocalcin delta | 4.07E−05 |
| 639 | PRDM1 | PR domain containing 1, with ZNF domain | 4.10E−05 |
| 83660 | TLN2 | talin 2 | 4.11E−05 |
| 284996 | Rnf149 | ring finger protein 149 | 4.12E−05 |
| 4773 | NFATC2 | nuclear factor of activated T-cells, cy | 4.20E−05 |
| 5967 | REG1A | regenerating islet-derived 1 alpha; reg | 4.25E−05 |
| 9235 | IL32 | interleukin 32 | 4.45E−05 |
| 27071 | dapp1 | dual adaptor of phosphotyrosine and 3-p | 4.52E−05 |
| 7127 | TNFAIP2 | tumor necrosis factor, alpha-induced pr | 4.64E−05 |
| 4064 | CD180 | CD180 molecule | 4.81E−05 |
| 10859 | LILRB1 | leukocyte immunoglobulin-like receptor, | 4.87E−05 |
| 132160 | PPM1M | protein phosphatase 1M (PP2C domain con | 4.95E−05 |
| 10381 | MC1R | tubulin, beta 3; melanocortin 1 recepto | 4.96E−05 |
| 7049 | Tgfbr3 | transforming growth factor, beta recept | 5.48E−05 |
| 8322 | FZD4 | frizzled homolog 4 (*Drosophila*) | 5.59E−05 |
| 25816 | TNFAIP8 | tumor necrosis factor, alpha-induced pr | 5.72E−05 |
| 3574 | Il7 | interleukin 7 | 5.74E−05 |
| 7097 | TLR2 | toll-like receptor 2 | 5.81E−05 |
| 55016 | 1-Mar | membrane-associated ring finger (C3HC4) | 5.85E−05 |
| 93349 | SP140L | SP140 nuclear body protein-like | 5.86E−05 |
| 3587 | IL10RA | interleukin 10 receptor, alpha | 5.87E−05 |
| 9672 | sdc3 | syndecan 3 | 5.87E−05 |
| 6648 | Sod2 | superoxide dismutase 2, mitochondrial | 5.88E−05 |
| 30817 | EMR2 | egf-like module containing, mucin-like, | 5.92E−05 |
| 5724 | PTAFR | platelet-activating factor receptor | 5.94E−05 |
| 2650 | GCNT1 | glucosaminyl (N-acetyl) transferase 1, | 6.00E−05 |
| 441168 | fam26f | family with sequence similarity 26, mem | 6.06E−05 |
| 56253 | CRTAM | cytotoxic and regulatory T cell molecul | 6.08E−05 |
| 149773 | LOC149773 | hypothetical protein LOC149773 | 6.22E−05 |
| 115761 | ARL11 | ADP-ribosylation factor-like 11 | 6.25E−05 |
| 6775 | STAT4 | signal transducer and activator of tran | 6.39E−05 |
| 7008 | tef | thyrotrophic embryonic factor | 6.44E−05 |
| 222236 | NAPEPLD | N-acyl phosphatidylethanolamine phospho | 6.47E−05 |
| 3158 | HMGCS2 | 3-hydroxy-3-methylglutaryl-Coenzyme A s | 6.52E−05 |
| 1356 | CP | ceruloplasmin (ferroxidase) | 6.55E−05 |
| 57224 | nhsl1 | NHS-like 1 | 6.56E−05 |
| 9535 | gmfg | glia maturation factor, gamma | 7.16E−05 |
| 114905 | C1qtnf7 | C1q and tumor necrosis factor related p | 7.18E−05 |
| 10123 | Arl4c | ADP-ribosylation factor-like 4C | 7.33E−05 |
| 51706 | CYB5R1 | cytochrome b5 reductase 1 | 7.42E−05 |
| 5552 | srgn | serglycin | 7.47E−05 |
| 81619 | TSPAN14 | tetraspanin 14 | 7.64E−05 |
| 151295 | SLC23A3 | solute carrier family 23 (nucleobase tr | 7.72E−05 |
| 55013 | CCDC109B | coiled-coil domain containing 109B | 7.88E−05 |
| 6916 | TBXAS1 | thromboxane A synthase 1 (platelet) | 7.88E−05 |
| 917 | Cd3g | CD3g molecule, gamma (CD3-TCR complex) | 8.00E−05 |
| 55423 | SIRPG | signal-regulatory protein gamma | 8.02E−05 |
| 441108 | C5orf56 | chromosome 5 open reading frame 56 | 8.13E−05 |
| 90826 | PRMT10 | protein arginine methyltransferase 10 ( | 8.32E−05 |
| 23231 | Sell13 | KIAA0746 protein | 8.35E−05 |
| 115330 | GPR146 | G protein-coupled receptor 146 | 8.65E−05 |
| 84465 | Megf11 | multiple EGF-like-domains 11 | 8.72E−05 |
| 2634 | GBP2 | guanylate binding protein 2, interferon | 8.89E−05 |
| 83416 | FCRL5 | Fc receptor-like 5 | 9.17E−05 |
| 1326 | MAP3K8 | mitogen-activated protein kinase kinase | 9.36E−05 |
| 10585 | pomt1 | protein-O-mannosyltransferase 1 | 9.46E−05 |
| 80709 | Akna | AT-hook transcription factor | 9.52E−05 |
| 5583 | PRKCH | protein kinase C, eta | 9.56E−05 |
| 2533 | FYB | FYN binding protein (FYB-120/130) | 0.000101095 |
| 710 | SERPING1 | serpin peptidase inhibitor, clade G (C1 | 0.000101427 |
| 57545 | CC2D2A | coiled-coil and C2 domain containing 2A | 0.000101929 |
| 57477 | Shroom4 | shroom family member 4 | 0.000102322 |
| 27113 | BBC3 | BCL2 binding component 3 | 0.000104668 |
| 257019 | frmd3 | FERM domain containing 3 | 0.000105901 |
| 915 | CD3D | CD3d molecule, delta (CD3-TCR complex) | 0.000108676 |
| 29851 | ICOS | inducible T-cell co-stimulator | 0.000114201 |
| 387357 | THEMIS | thymocyte selection pathway associated | 0.00011469 |
| 4065 | Ly75 | CD302 molecule; lymphocyte antigen 75 | 0.000116227 |
| 4794 | Nfkbie | nuclear factor of kappa light polypepti | 0.000117246 |
| 64407 | RGS18 | regulator of G-protein signaling 18 | 0.000118196 |
| 7052 | tgm2 | transglutaminase 2 (C polypeptide, prot | 0.000120567 |

TABLE 12-continued

Biopsy NGS Signatures for subAR using a 2-Step approach (AR + subAR vs. TX and AR v. subAR) - second step: AR vs. subAR

| Column ID | To | Gene Name | p-value (cAR vs. subAR) |
|---|---|---|---|
| 2857 | GPR34 | G protein-coupled receptor 34 | 0.000120768 |
| 128346 | C1orf162 | chromosome 1 open reading frame 162 | 0.000123894 |
| 3683 | ITGAL | integrin, alpha L (antigen CD11A (p180) | 0.00012454 |
| 2123 | Evi2a | ecotropic viral integration site 2A | 0.000127081 |
| 55784 | MCTP2 | multiple C2 domains, transmembrane 2 | 0.000127734 |
| 919 | Cd247 | CD247 molecule | 0.000130792 |
| 3226 | HOXC10 | homeobox C10 | 0.000133565 |
| 83706 | fermt3 | fermitin family homolog 3 (*Drosophila*) | 0.000135104 |
| 7412 | Vcam1 | vascular cell adhesion molecule 1 | 0.000136061 |
| 9372 | zfyve9 | zinc finger, FYVE domain containing 9 | 0.000136444 |
| 55920 | RCC2 | regulator of chromosome condensation 2 | 0.000136649 |
| 5359 | plscr1 | phospholipid scramblase 1 | 0.000140346 |
| 837 | Casp4 | caspase 4, apoptosis-related cysteine p | 0.000141051 |
| 57585 | CACHD1 | cache domain containing 1 | 0.00014644 |
| 51809 | Galnt7 | UDP-N-acetyl-alpha-D-galactosamine:poly | 0.000149312 |
| 29992 | PILRA | paired immunoglobin-like type 2 recepto | 0.000149525 |
| 259307 | IL4I1 | interleukin 4 Induced 1 | 0.000151253 |
| 162394 | Slfn5 | schlafen family member 5 | 0.000153617 |
| 2124 | EVI2B | ecotropic viral integration site 2B | 0.000154185 |
| 57580 | prex1 | phosphatidylinositol-3,4,5-trisphosphat | 0.000156406 |
| 114614 | MIR155 | microRNA host gene 2 (non-protein codin | 0.000158216 |
| 51411 | Bin2 | bridging integrator 2 | 0.000159986 |
| 4481 | Msr1 | macrophage scavenger receptor 1 | 0.000161335 |
| 26157 | GIMAP2 | GTPase, IMAP family member 2 | 0.000163916 |
| 92241 | Rcsd1 | RCSD domain containing 1 | 0.000164738 |
| 123920 | Cmtm3 | CKLF-like MARVEL transmembrane domain c | 0.000165918 |
| 51284 | TLR7 | toll-like receptor 7 | 0.000170376 |
| 3796 | KIF2A | kinesin heavy chain member 2A | 0.000170538 |
| 961 | CD47 | CD47 molecule | 0.000170747 |
| 54900 | LAX1 | lymphocyte transmembrane adaptor 1 | 0.000173443 |
| 23670 | Tmem2 | transmembrane protein 2 | 0.000174023 |
| 1475 | cstA | cystatin A (stefin A) | 0.00017513 |
| 4067 | LYN | v-yes-1 Yamaguchi sarcoma viral related | 0.000175578 |
| 10406 | WFDC2 | WAP four-disulfide core domain 2 | 0.000180471 |
| 7913 | Dek | DEK oncogene | 0.000180846 |
| 346389 | Macc1 | metastasis associated in colon cancer 1 | 0.000181678 |
| 84230 | LRRC8C | leucine rich repeat containing 8 family | 0.000181977 |
| 10460 | TACC3 | transforming, acidic coiled-coil cental | 0.000182925 |
| 1051 | CEBPB | CCAAT/enhancer binding protein (C/EBP), | 0.000184525 |
| 114793 | FMNL2 | formin-like 2 | 0.000185065 |
| 1794 | DOCK2 | dedicator of cytokinesis 2 | 0.000199278 |
| 7305 | TYROBP | TYRO protein tyrosine kinase binding pr | 0.00019956 |
| 9180 | OSMR | oncostatin M receptor | 0.000202103 |

TABLE 13

2-Way 2-Step NGS Analysis (AR v. subAR; AR v. TX; and subAR v. TX) using biopsy samples - Results

| | Predicted | | |
|---|---|---|---|
| Real | TX | SCAR | AR |
| TX | 23 | 0 | 2 |
| SCAR | 0 | 19 | 3 |
| AR | 0 | 6 | 15 |

| Method | Classifies | % Predictive Accuracy | Sensitivity (%) | Specificity (%) | Positive Predictive Value (%) | Negative Predicitve Value (%) | AUC |
|---|---|---|---|---|---|---|---|
| Nearest Centroid (2 Step Prediction) | TX vs. AR | 95% | 100% | 88% | 92% | 100% | 0.943 |
| | TX vs. SCAR | 100% | 100% | 100% | 100% | 100% | 1.000 |
| | AR vs. SCAR | 79% | 76% | 83% | 83% | 72% | 0.792 |

TABLE 14

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 225640_PM_at | LOC401504 | hypothetical LOC401504 | 2.19E−11 |
| 222562_PM_s_at | TNKS2 | tankyrase, TRF1-interacting ankyrin-related ADP-ribose polymerase 2 | 1.57E−10 |
| 218273_PM_s_at | PDP1 | pyruvate dehydrogenase phosphatase catalytic subunit 1 | 1.44E−09 |
| 206848_PM_at | FAM36A /// HOXA7 | family with sequence similarity 36, member A /// homeobox A7 | 8.49E−09 |
| 207236_PM_at | ZNF345 | zinc finger protein 345 | 1.01E−08 |
| 225565_PM_at | CREB1 | cAMP responsive element binding protein 1 | 1.23E−08 |
| 215342_PM_s_at | RABGAP1L | RAB GTPase activating protein 1-like | 1.85E−08 |
| 235461_PM_at | TET2 | tet oncogene family member 2 | 2.06E−08 |
| 232008_PM_s_at | BBX | bobby sox homolog (*Drosophila*) | 2.53E−08 |
| 230058_PM_at | SDCCAG3 | serologically defined colon cancer antigen 3 | 3.73E−08 |
| 241955_PM_at | HECTD1 | HECT domain containing 1 | 3.86E−08 |
| 240554_PM_at | AKAP8L | A kinase (PRKA) anchor protein 8-like | 4.07E−08 |
| 214499_PM_s_at | BCLAF1 | BCL2-associated transcription factor 1 | 4.21E−08 |
| 216450_PM_x_at | HSP90B1 | heat shock protein 90 kDa beta (Grp94), member 1 | 4.57E−08 |
| 226404_PM_at | RBM39 | RNA binding motif protein 39 | 4.65E−08 |
| 222729_PM_at | FBXW7 | F-box and WD repeat domain containing 7 | 6.21E−08 |
| 222538_PM_s_at | APPL1 | adaptor protein, phosphotyrosine interaction, PH domain and leucine zipper containing 1 | 6.21E−08 |
| 214045_PM_at | LIAS | lipoic acid synthetase | 7.24E−08 |
| 215220_PM_s_at | TPR | translocated promoter region (to activated MET oncogene) | 8.45E−08 |
| 1557193_PM_at | EST1557193_PM_at | — | 9.35E−08 |
| 225551_PM_at | CNST | consortin, connexin sorting protein | 1.06E−07 |
| 235811_PM_at | EST235811_PM_at | — | 1.11E−07 |
| 1558747_PM_at | SMCHD1 | structural maintenance of chromosomes flexible hinge domain containing 1 | 1.22E−07 |
| 214496_PM_x_at | MYST4 | MYST histone acetyltransferase (monocytic leukemia) 4 | 1.35E−07 |
| 222406_PM_s_at | PNRC2 | proline-rich nuclear receptor coactivator 2 | 1.43E−07 |
| 212417_PM_at | SCAMP1 | secretory carrier membrane protein 1 | 1.78E−07 |
| 227144_PM_at | C22orf9 | chromosome 22 open reading frame 9 | 1.98E−07 |
| 244611_PM_at | MED13 | Mediator complex subunit 13 | 2.23E−07 |
| 219024_PM_at | PLEKHA1 | pleckstrin homology domain containing, family A (phosphoinositide binding specific) mem | 2.62E−07 |
| 1559051_PM_s_at | C6orf150 | chromosome 6 open reading frame 150 | 2.78E−07 |
| 231418_PM_at | EST231418_PM_at | — | 2.88E−07 |
| 202818_PM_s_at | TCEB3 | transcription elongation factor B (SIII), polypeptide 3 (110 kDa, elongin A) | 3.30E−07 |
| 201728_PM_s_at | KIAA0100 | KIAA0100 | 3.32E−07 |
| 201083_PM_s_at | BCLAF1 | BCL2-associated transcription factor 1 | 3.64E−07 |
| 208615_PM_s_at | PTP4A2 | protein tyrosine phosphatase type IVA, member 2 | 3.88E−07 |
| 200745_PM_s_at | GNB1 | guanine nucleotide binding protein (G protein), beta polypeptide 1 | 4.45E−07 |
| 215586_PM_at | EST215586_PM_at | — | 4.62E−07 |
| 228801_PM_at | ORMDL1 | ORM1-like 1 (*S. cerevisiae*) | 5.52E−07 |
| 208879_PM_x_at | PRPF6 | PRP6 pre-mRNA processing factor 6 homolog (*S. cerevisiae*) | 5.70E−07 |
| 208003_PM_s_at | NFAT5 | nuclear factor of activated T-cells 5, tonicity-responsive | 6.96E−07 |
| 216449_PM_x_at | HSP90B1 | heat shock protein 90 kDa beta (Grp94), member 1 | 7.21E−07 |
| 201235_PM_s_at | BTG2 | BTG family, member 2 | 8.31E−07 |
| 236484_PM_at | EST236484_PM_at | — | 1.02E−06 |
| 227082_PM_at | EST227082_PM_at | — | 1.21E−06 |
| 236841_PM_at | LOC100134445 | hypothetical LOC100134445 | 1.27E−06 |
| 236207_PM_at | SSFA2 | sperm specific antigen 2 | 1.28E−06 |
| 215282_PM_at | ANAPC13 | anaphase promoting complex subunit 13 | 1.58E−06 |
| 1555568_PM_at | GUSBL1 | glucuronidase, beta-like 1 | 1.60E−06 |
| 236512_PM_at | EST236512_PM_at | — | 1.85E−06 |
| 224687_PM_at | ANKIB1 | ankyrin repeat and IBR domain containing 1 | 2.08E−06 |
| 202719_PM_s_at | TES | testis derived transcript (3 LIM domains) | 2.27E−06 |
| 213311_PM_s_at | TCF25 | transcription factor 25 (basic helix-loop-helix) | 2.29E−06 |
| 229193_PM_at | LUC7L3 | LUC7-like 3 (*S. cerevisiae*) | 2.33E−06 |
| 221905_PM_at | CYLD | cylindromatosis (turban tumor syndrome) | 2.48E−06 |
| 217418_PM_x_at | MS4A1 | membrane-spanning 4-domains, subfamily A, member 1 | 2.73E−06 |
| 217234_PM_s_at | EZR | ezrin | 2.75E−06 |
| 222866_PM_s_at | FLVCR2 | feline leukemia virus subgroup C cellular receptor family, member 2 | 2.78E−06 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 209207_PM_s_at | SEC22B | SEC22 vesicle trafficking protein homolog B (S. cerevisiae) (gene/pseudogene) | 2.80E−06 |
| 232127_PM_at | CLCN5 | chloride channel 5 | 2.82E−06 |
| 243559_PM_at | EST243559_PM_at | — | 3.05E−06 |
| 241668_PM_s_at | EST241668_PM_s_at | — | 3.13E−06 |
| 203145_PM_at | SPAG5 | sperm associated antigen 5 | 3.17E−06 |
| 235430_PM_at | C14orf43 | chromosome 14 open reading frame 43 | 4.05E−06 |
| 222628_PM_s_at | REV1 | REV1 homolog (S. cerevisiae) | 4.08E−06 |
| 209920_PM_at | BMPR2 | bone morphogenetic protein receptor, type II (serine/threonine kinase) | 4.18E−06 |
| 206668_PM_s_at | SCAMP1 | secretory carrier membrane protein 1 | 4.29E−06 |
| 1555562_PM_a_at | ZCCHC7 | zinc finger, CCHC domain containing 7 | 4.31E−06 |
| 1562031_PM_at | JAK2 | Janus kinase 2 | 4.42E−06 |
| 236109_PM_at | EST236109_PM_at | — | 4.50E−06 |
| 200598_PM_s_at | HSP90B1 | heat shock protein 90 kDa beta (Grp94), member 1 | 4.92E−06 |
| 210356_PM_x_at | MS4A1 | membrane-spanning 4-domains, subfamily A, member 1 | 5.02E−06 |
| 240859_PM_at | EST240859_PM_at | — | 5.15E−06 |
| 202173_PM_s_at | VEZF1 | vascular endothelial zinc finger 1 | 5.21E−06 |
| 200900_PM_s_at | M6PR | mannose-6-phosphate receptor (cation dependent) | 5.75E−06 |
| 212027_PM_at | RBM25 | RNA binding motif protein 25 | 5.96E−06 |
| 222915_PM_s_at | BANK1 | B-cell scaffold protein with ankyrin repeats 1 | 6.07E−06 |
| 230028_PM_at | EST230028_PM_at | — | 6.08E−06 |
| 200950_PM_at | ARPC1A | actin related protein 2/3 complex, subunit 1A, 41 kDa | 6.24E−06 |
| 240220_PM_at | EST240220_PM_at | — | 6.48E−06 |
| 204565_PM_at | ACOT13 | acyl-CoA thioesterase 13 | 6.48E−06 |
| 210172_PM_at | SF1 | splicing factor 1 | 6.66E−06 |
| 1554249_PM_a_at | ZNF638 | zinc finger protein 638 | 6.73E−06 |
| 228818_PM_at | EST228818_PM_at | — | 6.88E−06 |
| 212574_PM_x_at | C19orf6 | chromosome 19 open reading frame 6 | 7.23E−06 |
| 239077_PM_at | CSGALNACT2 | chondroitin sulfate N-acetylgalactosaminyltransferase 2 | 7.51E−06 |
| 209281_PM_s_at | ATP2B1 | ATPase, Ca++ transporting, plasma membrane 1 | 7.92E−06 |
| 224989_PM_at | EST224989_PM_at | — | 7.93E−06 |
| 240718_PM_at | LRMP | Lymphoid-restricted membrane protein | 8.17E−06 |
| 229268_PM_at | FAM105B | family with sequence similarity 105, member B | 8.39E−06 |
| 203141_PM_s_at | AP3B1 | adaptor-related protein complex 3, beta 1 subunit | 8.46E−06 |
| 236254_PM_at | VPS13B | vacuolar protein sorting 13 homolog B (yeast) | 8.55E−06 |
| 216263_PM_s_at | NGDN | neuroguidin, EIF4E binding protein | 8.70E−06 |
| 235119_PM_at | TAF3 | TAF3 RNA polymerase II, TATA box binding protein (TBP)-associated factor, 140 kDa | 8.72E−06 |
| 213549_PM_at | SRSF7 | serine/arginine-rich splicing factor 7 | 8.73E−06 |
| 1559485_PM_at | ATG2B | ATG2 autophagy related 2 homolog B (S. cerevisiae) | 9.15E−06 |
| 243414_PM_at | PPIL2 | Peptidylprolyl isomerase (cyclophilin)-like 2 | 9.30E−06 |
| 212658_PM_at | LHFPL2 | lipoma HMGIC fusion partner-like 2 | 9.40E−06 |
| AFFX-r2-Bs-dap-5_at | ESTAFFX-r2-Bs-dap-5_at | — | 9.55E−06 |
| 230466_PM_s_at | EST230466_PM_s_at | — | 9.98E−06 |
| 240690_PM_at | EST240690_PM_at | — | 1.01E−05 |
| 236414_PM_at | EST236414_PM_at | — | 1.02E−05 |
| 241702_PM_at | EST241702_PM_at | — | 1.07E−05 |
| 202631_PM_s_at | APPBP2 | amyloid beta precursor protein (cytoplasmic tail) binding protein 2 | 1.15E−05 |
| 224350_PM_at | EST224350_PM_at | — | 1.16E−05 |
| 217896_PM_s_at | FAM192A | family with sequence similarity 192, member A | 1.17E−05 |
| 239046_PM_at | EST239046_PM_at | — | 1.20E−05 |
| 1564063_PM_a_at | ATP11B | ATPase, class VI, type 11B | 1.23E−05 |
| 243206_PM_at | EST243205_PM_at | — | 1.24E−05 |
| 238506_PM_at | LRRC58 | leucine rich repeat containing 58 | 1.27E−05 |
| 210042_PM_s_at | CTSZ | cathepsin Z | 1.32E−05 |
| 227410_PM_at | FAM43A | family with sequence similarity 43, member A | 1.37E−05 |
| 1557529_PM_at | C12orf51 | chromosome 12 open reading frame 51 | 1.39E−05 |
| 1552978_PM_a_at | SCAMP1 | secretory carrier membrane protein 1 | 1.39E−05 |
| 213272_PM_s_at | TMEM159 | transmembrane protein 159 | 1.39E−05 |
| 244090_PM_at | EST244090_PM_at | — | 1.40E−05 |
| 229033_PM_at | MUM1 | melanoma associated antigen (mutated) 1 | 1.42E−05 |
| 1565852_PM_at | EST1565852_PM_at | — | 1.52E−05 |
| 216069_PM_at | EST216069_PM_at | — | 1.53E−05 |
| 216915_PM_s_at | PTPN12 | protein tyrosine phosphatase, non-receptor type 12 | 1.60E−05 |
| 1557895_PM_at | FLJ35934 | FLJ35934 | 1.66E−05 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
| --- | --- | --- | --- |
| 240613_PM_at | JAK1 | Janus kinase 1 | 1.73E−05 |
| 241755_PM_at | UQCRC2 | ubiquinol-cytochrome c reductase core protein II | 1.74E−05 |
| 1561058_PM_at | EST1561058_PM_at | — | 1.75E−05 |
| 222633_PM_at | TBL1XR1 | transducin (beta)-like 1 X-linked receptor 1 | 1.78E−05 |
| 207318_PM_s_at | CDK13 | cyclin-dependent kinase 13 | 1.82E−05 |
| 203823_PM_at | RGS3 | regulator of G-protein signaling 3 | 1.83E−05 |
| 242049_PM_s_at | NBAS | neuroblastoma amplified sequence | 1.83E−05 |
| 1559397_PM_s_at | PRR14 | proline rich 14 | 1.87E−05 |
| 1555185_PM_x_at | TERF2 | telomeric repeat binding factor 2 | 1.96E−05 |
| 204199_PM_at | RALGPS1 | Ral GEF with PH domain and SH3 binding motif 1 | 2.00E−05 |
| 217818_PM_s_at | ARPC4 | actin related protein 2/3 complex, subunit 4, 20 kDa | 2.04E−05 |
| 230404_PM_at | FLJ44606 | glutaredoxin-like protein YDR286C homolog | 2.05E−05 |
| 237184_PM_at | EST237184_PM_at | — | 2.11E−05 |
| 219498_PM_s_at | BCL11A | B-cell CLL/lymphoma 11A (zinc finger protein) | 2.11E−05 |
| 213688_PM_at | CALM1 | calmodulin 1 (phosphorylase kinase, delta) | 2.13E−05 |
| 201777_PM_s_at | KIAA0494 | KIAA0494 | 2.15E−05 |
| 213235_PM_at | C16orf38 | chromosome 16 open reading frame 88 | 2.15E−05 |
| 236524_PM_at | EST236524_PM_at | — | 2.16E−05 |
| 235547_PM_at | N4BP2L2 | NEDD4 binding protein 2-like 2 | 2.20E−05 |
| 224684_PM_at | SNX12 | sorting nexin 12 | 2.22E−05 |
| 212467_PM_at | DNAJC13 | DnaJ (Hsp40) homolog, subfamily C, member 13 | 2.23E−05 |
| 1553304_PM_at | LSM14B | LSM14B, SCD6 homolog B (S. cerevisiae) | 2.44E−05 |
| 215489_PM_x_at | HOMER3 | homer homolog 3 (Drosophila) | 2.44E−05 |
| 220843_PM_s_at | DCAF13 | DDB1 and CUL4 associated factor 13 | 2.52E−05 |
| 223217_PM_s_at | NFKBIZ | nuclear factor of kappa light polypeptide gene enhancer in B-cells inhibitor, zeta | 2.59E−05 |
| 232323_PM_s_at | TTC17 | tetratricopeptide repeat domain 17 | 2.60E−05 |
| 232353_PM_s_at | STYXL1 | serine/threonine/tyrosine interacting-like 1 | 2.65E−05 |
| 1563674_PM_at | FCRL2 | Fc receptor-like 2 | 2.69E−05 |
| 208325_PM_at | AKAP13 | A kinase (PRKA) anchor protein 13 | 2.71E−05 |
| 1560814_PM_a_at | C15orf57 | chromosome 15 open reading frame 57 | 2.77E−05 |
| 201085_PM_s_at | SON | SON DNA binding protein | 2.77E−05 |
| 1568680_PM_s_at | YTHDC2 | YTH domain containing 2 | 2.80E−05 |
| 217979_PM_at | TSPAN13 | tetraspanin 13 | 2.82E−05 |
| 241237_PM_at | EST241237_PM_at | — | 2.85E−05 |
| 243739_PM_at | EST243739_PM_at | — | 5.74E−05 |
| 212022_PM_s_at | MKI67 | antigen identified by monoclonal antibody Ki-67 | 3.10E−05 |
| 236562_PM_at | ZNF439 | zinc finger protein 439 | 3.12E−05 |
| 214869_PM_x_at | GAPVD1 | GTPase activating protein and VPS9 domains 1 | 3.14E−05 |
| 1553961_PM_s_at | SNX21 | sorting nexin family member 21 | 3.17E−05 |
| 203958_PM_s_at | ZBTB40 | zinc finger and BTB domain containing 40 | 3.24E−05 |
| 240593_PM_x_at | EST240593_PM_x_at | — | 3.31E−05 |
| 216901_PM_s_at | IKZF1 | IKAROS family zinc finger 1 (Ikaros) | 3.34E−05 |
| 225878_PM_at | KIF1B | kinesin family member 1B | 3.42E−05 |
| 224818_PM_at | SORT1 | sortilin 1 | 3.47E−05 |
| 225240_PM_at | MSI2 | musashi homolog 2 (Drosophila) | 3.51E−05 |
| 222522_PM_x_at | MRPS10 | mitochondrial ribosomal protein S10 | 3.56E−05 |
| 228147_PM_at | EST228147_PM_at | — | 3.62E−05 |
| 222575_PM_at | SETD5 | SET domain containing 5 | 3.75E−05 |
| 214474_PM_at | PRKAB2 | protein kinase, AMP-activated, beta 2 non-catalytic subunit | 3.80E−05 |
| 233409_PM_at | RHBDL3 | rhomboid, veinlet-like 3 (Drosophila) | 3.84E−05 |
| 239815_PM_at | EST239815_PM_at | — | 3.95E−05 |
| 213998_PM_s_at | DDX17 | DEAD (Asp-Glu-Ala-Asp) box polypeptide 17 | 4.03E−05 |
| AFFX-DapX-5_at | ESTAFFX-DapX-5_at | — | 4.20E−05 |
| 1567045_PM_at | EST1567045_PM_at | — | 4.23E−05 |
| 204324_PM_s_at | GOLIM4 | golgi integral membrane protein 4 | 4.27E−05 |
| 208835_PM_s_at | LUC7L3 | LUC7-like 3 (S. cerevisiae) | 4.40E−05 |
| 210214_PM_s_at | BMPR2 | bone morphogenetic protein receptor, type II (serine/threonine kinase) | 4.41E−05 |
| 210282_PM_at | ZMYM2 | zinc finger, MYM-type 2 | 4-44E−05 |
| 222873_PM_s_at | EHMT1 | euchromatic histone-lysine N-methyltransferase 1 | 4.44E−05 |
| 243932_PM_at | EST243932_PM_at | — | 4.63E−05 |
| 1568907_PM_at | EST1568907_PM_at | — | 4.65E−05 |
| 208797_PM_s_at | GOLGA8A | golgin A8 family, member A | 4.69E−05 |
| 218393_PM_at | SMU1 | smu-1 suppressor of mec-8 and unc-52 homolog (C. elegans) | 4.69E−05 |
| 239027_PM_at | DOCK8 | dedicator of cytokinesis 8 | 4.74E−05 |
| 215894_PM_at | PTGDR | prostaglandin D2 receptor (DP) | 4.82E−05 |
| 208114_PM_s_at | ISG20L2 | interferon stimulated exonuclease gene 20 kDa-like 2 | 4.83E−05 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
| --- | --- | --- | --- |
| 212076_PM_at | MLL | myeloid/lymphoid or mixed-lineage leukemia (trithorax homolog, Drosophila) | 4.90E−05 |
| 222326_PM_at | EST222326_PM_at | — | 5.04E−05 |
| 215603_PM_x_at | GGT2 | gamma-glutamyltransferase 2 | 5.04E−05 |
| 224933_PM_s_at | JMJD1C | jumonji domain containing 1C | 5.08E−05 |
| 242197_PM_x_at | CD36 | CD36 molecule (thrombospondin receptor) | 5.28E−05 |
| 230629_PM_s_at | EP400 | E1A binding protein p400 | 5.31E−05 |
| 243361_PM_at | SREK1 | splicing regulatory glutamine/lysine-rich protein 1 | 5.32E−05 |
| 237884_PM_X_at | TRPM7 | transient receptor potential cation channel, subfamily M, member 7 | 5.35E−05 |
| 236557_PM_at | ZBTB38 | zinc finger and BTB domain containing 38 | 5.36E−05 |
| 223307_PM_at | CDCA3 | cell division cycle associated 3 | 5.42E−05 |
| 218321_PM_x_at | STYXL1 | serine/threonine/tyrosine interacting-like 1 | 5.48E−05 |
| 205179_PM_s_at | ADAM8 | ADAM metallopeptidase domain 8 | 5.49E−05 |
| 227329_PM_at | ZBTB46 | zinc finger and BTB domain containing 46 | 5.67E−05 |
| 222395_PM_s_at | UBE2Z | ubiquitin-conjugating enzyme E2Z | 5.69E−05 |
| 201488_PM_x_at | KHDRBS1 | KH domain containing, RNA binding, signal transaction associated 1 | 5.72E−05 |
| 200806_PM_s_at | HSPD1 | heat shock 60 kDa protein 1 (chaperonin) | 5.73E−05 |
| 244233_PM_at | C18orf10 | chromosome 18 open reading frame 10 | 0.000168658 |
| 225098_PM_at | ABI2 | abl-interactor 2 | 5.74E−05 |
| 222540_PM_s_at | RSF1 | remodeling and spacing factor 1 | 5.82E−05 |
| 242422_PM_at | G3BP1 | GTPase activating protein (SH3 domain) binding protein 1 | 5.85E−05 |
| 206371_PM_at | FOLR3 | folate receptor 3 (gamma) | 5.98E−05 |
| 204270_PM_at | SKI | v-ski sarcoma viral oncogene homolog (avian) | 5.99E−05 |
| 207826_PM_s_at | ID3 | inhibitor of DNA binding 3, dominant negative helix-loop-helix protein | 6.00E−05 |
| 235216_PM_at | ESCO1 | establishment of cohesion 1 homolog 1 (S. cerevisiae) | 6.01E−05 |
| 1558088_PM_a_at | UBE2I | ubiquitin-conjugating enzyme E2I (UBC9 homolog, yeast) | 6.18E−05 |
| 206521_PM_s_at | GTF2A1 | general transcription factor IIA, 1, 19/37 kDa | 6.21E−05 |
| 210693_PM_at | SPPL2B | signal peptide peptidase-like 2B | 6.27E−05 |
| 202953_PM_at | C1QB | complement component 1, q subcomponent, B chain | 6.31E−05 |
| 227918_PM_s_at | ZYG11B | zyg-11 homolog B (C. elegans) | 6.37E−05 |
| 223569_PM_at | PPAPDC1B | phosphatidic acid phosphatase type 2 domain containing 1B | 6.43E−05 |
| 215667_PM_x_at | LOC441259 /// PMS2L2 /// PMS2P1 /// PMS2P6 | PMS2 postmeiotic segregation increased 2 (S. cerevisiae like /// postmeiotic segregati | 6.50E−05 |
| 222563_PM_s_at | TNKS2 | tankyrase, TRF1-interacting ankyrin-related ADP-ribose polymerase 2 | 6.50E−05 |
| 209076_PM_s_at | WDR45L | WDR45-like | 6.56E−05 |
| 233261_PM_at | EBF1 | Early B-cell factor 1 | 6.68E−05 |
| 229389_PM_at | ATG16L2 | ATG16 autophagy related 16-like 2 (S. cerevisiae) | 6.70E−05 |
| 223969_PM_s_at | RETNLB | resistin like beta | 6.72E−05 |
| 228868_PM_x_at | CDT1 | Chromatin licensing and DNA replication factor 1 | 6.80E−05 |
| 1558173_PM_a_at | LUZP1 | leucine zipper protein 1 | 6.90E−05 |
| 243319_PM_at | EST243319_PM_at | — | 6.92E−05 |
| 203479_PM_s_at | OTUD4 | OTU domain containing 4 | 7.03E−05 |
| 35201_PM_at | HNRNPL | heterogeneous nuclear ribonucleoprotein L | 7.13E−05 |
| 244696_PM_at | EST244696_PM_at | — | 7.18E−05 |
| 202705_PM_at | CCNB2 | cyclin B2 | 7.25E−05 |
| 239154_PM_at | EST239154_PM_at | — | 7.31E−05 |
| 230270_PM_at | PRPF38B | PRP38 pre-mRNA processing factor 38 (yeast) domain containing B | 7.31E−05 |
| 209583_PM_s_at | CD200 | CD200 molecule | 7.37E−05 |
| 214250_PM_at | NUMA1 | nuclear mitotic apparatus protein 1 | 7.37E−05 |
| 222508_PM_s_at | ARGLU1 | arginine and glutamate rich 1 | 7.38E−05 |
| 201347_PM_x_at | GRHPR | glyoxylate reductase/hydroxypyruvate reductase | 7.44E−05 |
| 1552812_PM_a_at | SENP1 | SUMO1/sentrin specific peptidase 1 | 7.83E−05 |
| 202773_PM_s_at | SFSWAP | splicing factor, suppressor of white-apricot homolog (Drosophila) | 8.00E−05 |
| AFFX-r2-Bs-dap-M_at | ESTAFFX-r2-Bs-dap-M_at | — | 8.02E−05 |
| 218474_PM_s_at | KCTD5 | potassium channel tetramerisation domain containing 5 | 0.000187936 |
| 209582_PM_s_at | CD200 | CD200 molecule | 8.08E−05 |
| 211417_PM_x_at | GGT1 | gamma-glutamyltransferase 1 | 8.10E−05 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 201996_PM_s_at | SPEN | spen homolog, transcriptional regulator (*Drosophila*) | 8.45E−05 |
| 222996_PM_s_at | CXXC5 | CXXC finger protein 5 | 8.51E−05 |
| 215937_PM_at | PTGDR | prostaglandin D2 receptor (DP) | 8.56E−05 |
| 230424_PM_at | C5orf13 | chromosome 5 open reading frame 13 | 8.66E−05 |
| 203796_PM_s_at | BCL7A | B-cell CLL/lymphoma 7A | 8.88E−05 |
| 241619_PM_at | CALM1 | calmodulin 1 (phosphorylase kinase, delta) | 8.90E−05 |
| 238277_PM_at | EST238277_PM_at | — | 9.06E−05 |
| 208268_PM_at | ADAM28 | ADAM metallopeptidase domain 28 | 9.25E−05 |
| 226079_PM_at | FLYWCH2 | FLYWCH family member 2 | 9.43E−05 |
| 212119_PM_at | RHOQ | ras homolog gene family, member Q | 9.49E−05 |
| 235956_PM_at | KIAA1377 | KIAA1377 | 9.61E−05 |
| 230245_PM_s_at | LOC283663 | hypothetical LOC283663 | 9.61E−05 |
| 1559589_PM_a_at | EST1559589_PM_a_at | — | 9.62E−05 |
| AFFX-M27830_5_at | ESTAFFX-M27830_5_at | — | 9.63E−05 |
| 219751_PM_at | SETD6 | SET domain containing 6 | 9.94E−05 |
| 207655_PM_s_at | BLNK | B-cell linker | 0.000100294 |
| 227849_PM_at | RP9 | Retinitis pigmentosa 9 (autosomal dominant) | 0.000100349 |
| 243236_PM_at | EST243236_PM_at | — | 0.000100441 |
| 1556983_PM_a_at | EST1556983_PM_a_at | — | 0.000101358 |
| 201537_PM_s_at | DUSP3 | dual specificity phosphatase 3 | 0.000102353 |
| 203276_PM_at | LMNB1 | lamin B1 | 0.000103605 |
| 1555913_PM_at | GON4L | gon-4-lite (*C. elegans*) | 0.00010638 |
| 244011_PM_at | PPM1K | protein phosphatase, Mg2+/Mn2+ dependent, 1K | 0.000106418 |
| 226647_PM_at | TMEM25 | transmembrane protein 25 | 0.000107452 |
| 221220_PM_s_at | SCYL2 | SCY1-like 2 (*S. cerevisiae*) | 0.000109068 |
| 227101_PM_at | ZNF800 | zinc finger protein 800 | 0.000109971 |
| 231235_PM_at | NKTR | natural killer-tumor recognition sequence | 0.000112022 |
| 235112_PM_at | EST235112_PM_at | — | 0.000112143 |
| 215270_PM_at | LFNG | LFNG O-fucosylpeptide 3-beta-N-acetylglucosaminyltransferase | 0.000113268 |
| 224918_PM_x_at | MGST1 | microsomal glutathione S-transferase 1 | 0.000120191 |
| 243381_PM_at | EST243381_PM_at | — | 0.000121699 |
| 227173_PM_s_at | BACH2 | BTB and CNC homology 1, basic leucine zipper transcription factor 2 | 0.000122183 |
| 201236_PM_s_at | BTG2 | BTG family, member 2 | 0.000124084 |
| 235003_PM_at | UHMK1 | U2AF homology motif (UHM) kinase 1 | 0.000124901 |
| 206983_PM_at | CCR6 | chemokine (C-C motif) receptor 6 | 0.000129751 |
| 206708_PM_at | FOXN2 | forkhead box N2 | 0.000130568 |
| 233955_PM_x_at | CXXC5 | CXXC finger protein 5 | 0.000132557 |
| 238743_PM_at | EST238743_PM_at | — | 0.000133124 |
| 239130_PM_at | MIR101-1 | microRNA 101-1 | 0.000133903 |
| 208478_PM_s_at | BAX | BCL2-associated X protein | 0.000134313 |
| 213315_PM_x_at | CXorf40A | chromosome X open reading frame 40A | 0.000134499 |
| 227894_PM_at | WDR90 | WD repeat domain 90 | 0.000134921 |
| 212382_PM_at | TCF4 | transcription factor 4 | 0.000135201 |
| 209773_PM_s_at | RRM2 | ribonucleotide reductase M2 | 0.000137305 |
| 1561872_PM_at | EST1561872_PM_at | — | 0.000138018 |
| 212961_PM_x_at | CXorf40B | chromosome X open reading frame 40B | 0.000140653 |
| 240521_PM_at | EST240521_PM_at | — | 0.000142199 |
| 222922_PM_at | KCNE3 | potassium voltage-gated channel, Isk-related family, member 3 | 0.000142431 |
| 232070_PM_at | LOC100499193 | hypothetical LOC100499193 | 0.000144063 |
| 217230_PM_at | EZR | ezrin | 0.000144366 |
| 233252_PM_s_at | STRBP | spermatid perinuclear RNA binding protein | 0.000145405 |
| 228643_PM_at | EST228643_PM_at | — | 0.000147578 |
| 214352_PM_s_at | KRAS | v-Ki-ras2 Kirsten rat sarcoma viral oncogene homolog | 0.000148531 |
| AFFX-DapX-M_at | ESTAFFX-DapX-M_at | — | 0.000148867 |
| 235376_PM_at | EST235376_PM_at | — | 0.000150505 |
| 223701_PM_at | USP47 | ubiquitin specific peptidase 47 | 0.000151065 |
| 231823_PM_s_at | SH3PXD2B | SH3 and PX domains 2B | 0.000151285 |
| 222891_PM_s_at | BCL11A | B-cell CLL/lymphoma 11A (zinc finger protein) | 0.000151761 |
| 207629_PM_s_at | ARHGEF2 | Rho/Rac guanine nucleotide exchange factor (GEF) 2 | 0.000153859 |
| 1558662_PM_s_at | BANK1 | B-cell scaffold protein with ankyrin repeats 1 | 0.000156425 |
| 243798_PM_at | EST243798_PM_at | — | 0.000157554 |
| 222787_PM_s_at | TMEM106B | transmembrane protein 106B | 0.000158414 |
| 215621_PM_s_at | IGHD | immunoglobulin heavy constant delta | 0.000158835 |
| 236820_PM_at | EST236820_PM_at | — | 0.000159122 |
| 221962_PM_s_at | UBE2H | ubiquitin-conjugating enzyme E2H (UBC8 homolog, yeast) | 0.000159574 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
| --- | --- | --- | --- |
| 229072_PM_at | EST229072_PM_at | — | 0.000160113 |
| 223568_PM_s_at | PPAPDC1B | phosphatidic acid phosphatase type 2 domain containing 1B | 0.000160614 |
| 224472_PM_x_at | SDF4 | stromal cell derived factor 4 | 0.000164081 |
| 239497_PM_at | EST239497_PM_at | — | 0.000164848 |
| 224592_PM_x_at | HP1BP3 | heterochromatin protein 1, binding protein 3 | 0.000165271 |
| 235288_PM_at | EST235288_PM_at | — | 0.000165435 |
| 205419_PM_at | GPR183 | G protein-coupled receptor 183 | 0.000166502 |
| 241205_PM_at | EST241205_PM_at | — | 0.000167418 |
| 209926_PM_at | LOC729991 | hypothetical protein LOC729991 | 0.000168054 |
| 202004_PM_x_at | SDHC | succinate dehydrogenase complex, subunit C, integral membrane protein, 15 kDa | 0.000168296 |
| 201918_PM_at | SLC25A36 | solute carrier family 25, member 36 | 0.000168448 |
| 225179_PM_at | UBE2K | ubiquitin-conjugating enzyme E2K (UBC1 homolog, yeast) | 0.000308015 |
| 237340_PM_at | SLC26A8 | solute carrier family 26, member 8 | 0.000170412 |
| 212807_PM_s_at | SORT1 | sortilin 1 | 0.000170978 |
| 208814_PM_at | HSPA4 | heat shock 70 kDa protein 4 | 0.000175793 |
| 236198_PM_at | EST236198_PM_at | — | 0.000181184 |
| 236375_PM_at | EST236375_PM_at | — | 0.000182487 |
| 223860_PM_at | EST223860_PM_at | — | 0.000183192 |
| 217606_PM_at | EST217606_PM_at | — | 0.000183954 |
| 202082_PM_s_at | SEC14L1 | SEC14-like 1 (*S. cerevisiae*) | 0.000184816 |
| 216401_PM_x_at | EST216401_PM_x_at | — | 0.000184974 |
| 226975_PM_at | RNPC3 | RNA-binding region (RNP1, RRM) containing 3 | 0.0004054 |
| 229353_PM_s_at | NUCKS1 | nuclear casein kinase and cyclin-dependent kinase substrate 1 | 0.000188103 |
| 239292_PM_at | EST239292_PM_at | — | 0.000188651 |
| 200921_PM_s_at | BTG1 | B-cell translation gene 1, anti-proliferative | 0.000189007 |
| 242225_PM_at | EST242225_PM_at | — | 0.000191962 |
| 231736_PM_x_at | MGST1 | microsomal glutathione S-transferase 1 | 0.000192368 |
| 207165_PM_at | HMMR | hyaluronan-mediated motility receptor (RHAMM) | 0.000192879 |
| 1555978_PM_s_at | EST1555978_PM_s_at | — | 0.000201472 |
| 226879_PM_at | HVCN1 | hydrogen voltage-gated channel 1 | 0.00020194 |
| 221234_PM_s_at | BACH2 | BTB and CNC homology 1, basic leucine zipper transcription factor 2 | 0.000202403 |
| AFFX-r2-Bs-lys-3_at | ESTAFFX-r2-Bs-lys-3_at | — | 0.000203767 |
| 226968_PM_at | KIF1B | kinesin family member 1B | 0.000204386 |
| 210384_PM_at | PRMT2 | protein arginine methyltransferase 2 | 0.000207517 |
| 219667_PM_s_at | BANK1 | B-cell scaffold protein with ankyrin repeats 1 | 0.000209859 |
| 202723_PM_s_at | FOXO1 | forkhead box O1 | 0.000210019 |
| 211217_PM_s_at | KCNQ1 | potassium voltage-gated channel, KQT-like subfamily, member 1 | 0.000210371 |
| 238511_PM_at | LOC440288 | similar to FLJ16518 protein | 0.000211154 |
| 221601_PM_s_at | FAIM3 | Fas apoptotic inhibitory molecule 3 | 0.000212934 |
| 219806_PM_s_at | C11orf75 | chromosome 11 open reading frame 75 | 0.000213004 |
| 210596_PM_at | MAGT1 | magnesium transporter 1 | 0.000217053 |
| 226008_PM_at | NDNL2 | necdin-like 2 | 0.000219345 |
| 213517_PM_at | PCBP2 | poly(rC) binding protein 2 | 0.000220506 |
| 1569894_PM_at | PPP2R3C | protein phosphatase 2, regulatory subunit B", gamma | 0.000220967 |
| 211074_PM_at | FOLR1 | folate receptor 1 (adult) | 0.000225092 |
| 226094_PM_at | PIK3C2A | phosphoinositide-3-kinase, class 2, alpha polypeptide | 0.0002278 |
| 202371_PM_at | TCEAL4 | transcription elongation factor A (SII)-like 4 | 0.000228612 |
| 201072_PM_s_at | SMARCC1 | SWI/SNF related, matrix associated, actin dependent regulator of chromatin, subfamily c | 0.000229302 |
| 215457_PM_at | EST215457_PM_at | — | 0.000230542 |
| 220436_PM_at | CNTNAP3B | similar to cell recognition molecule CASPR3 | 0.000231163 |
| 200810_PM_s_at | CIRBP | cold inducible RNA binding protein | 0.000233312 |
| 201073_PM_s_at | SMARCC1 | SWI/SNF related, matrix associated, actin dependent regulator of chromatin, subfamily c | 0.000233789 |
| 235852_PM_at | STON2 | Stonin 2 | 0.000236399 |
| 1569385_PM_s_at | TET2 | tet oncogene family member 2 | 0.000237687 |
| 228592_PM_at | MS4A1 | membrane-spanning 4-domains, subfamily A, member 1 | 0.000238044 |
| 205726_PM_at | DIAPH2 | diaphanous homolog 2 (*Drosophila*) | 0.000239122 |
| 223766_PM_at | LOC100133130 | PRO1102 | 0.000240505 |
| 228487_PM_s_at | EST228487_PM_s_at | — | 0.000243645 |
| 231340_PM_at | EST231340_PM_at | — | 0.000244821 |
| 222228_PM_s_at | ALKBH4 | alkB, alkylation repair homolog 4 (*E. coli*) | 0.000246256 |
| 202072_PM_at | HNRNPL | heterogeneous nuclear ribonucleoprotein L | 0.000246632 |
| 206881_PM_s_at | LILRA3 | leukocyte immunoglobulin-like receptor, subfamily A (without TM domain), member 3 | 0.000247423 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 230128_PM_at | IGL@ | immunoglobulin lambda locus | 0.000247531 |
| 209060_PM_x_at | NCOA3 | nuclear receptor coactivator 3 | 0.000247993 |
| 1557270_PM_at | EST1557270_PM_at | — | 0.000249224 |
| 233078_PM_at | API5 | apoptosis inhibitor 5 | 0.000253409 |
| 1553793_PM_a_at | KIAA1109 | KIAA1109 | 0.000254467 |
| 215339_PM_at | NKTR | natural killer-tumor recognition sequence | 0.000255637 |
| 1556314_PM_a_at | EST1556314_PM_a_at | — | 0.000255826 |
| 208079_PM_s_at | AURKA | aurora kinase A | 0.000257743 |
| 218300_PM_at | C16orf53 | chromosome 16 open reading frame 53 | 0.000258687 |
| 1556461_PM_at | EST1556461_PM_at | — | 0.000259468 |
| 1558733_PM_at | ZBTB38 | zinc finger and BTB domain containing 36 | 0.000260942 |
| 225742_PM_at | MDM4 | Mdm4 p53 binding protein homolog (mouse) | 0.000264828 |
| 204028_PM_s_at | RABGAP1 | RAB GTPase activating protein 1 | 0.000265807 |
| 1559618_PM_at | LOC100129447 | hypothetical protein LOC100129147 | 0.000268803 |
| 1564494_PM_s_at | P4HB | protyl 4-hydroxylase, beta polypeptide | 0.000269853 |
| 212452_PM_x_at | MYST4 | MYST histone acetyltransferase (monocytic leukemia) 4 | 0.000270084 |
| 201960_PM_s_at | MYCBP2 | MYC binding protein 2 | 0.000275031 |
| 1561286_PM_a_at | DIP2A | DIP2 disco-interacting protein 2 homolog A (Drosophila) | 0.000276434 |
| 219581_PM_at | TSEN2 | tRNA splicing endonuclease 2 homolog (S. cerevisiae) | 0.000276518 |
| 242946_PM_at | EST242946_PM_at | — | 0.000277157 |
| 212684_PM_at | ZNF3 | zinc finger protein 3 | 0.00028112 |
| 214669_PM_x_at | IGK@ /// IGKC | immunoglobulin kappa locus /// immunoglobulin kappa constant | 0.000282936 |
| 217613_PM_at | TMEM144 | transmembrane protein 144 | 0.000285003 |
| 238811_PM_at | ATP11B | ATPase, class VI, type 11B | 0.000286178 |
| 218039_PM_at | NUSAP1 | nucleolar and spindle associated protein 1 | 0.000287635 |
| 225095_PM_at | SPTLC2 | serine palmitoyltransferase, long chain base subunit 2 | 0.000289913 |
| 208799_PM_at | PSMB5 | proteasome (prosome, macropain) subunit, beta type, 5 | 0.00029164 |
| 230897_PM_at | CCDC30 /// LOC1000507214 | coiled-coil domain containing 30 /// hypothetical LOC100507214 | 0.000292704 |
| 214735_PM_at | IPCEF1 | interaction protein for cytohesin exchange factors 1 | 0.00029714 |
| 239545_PM_at | EST239545_PM_at | — | 0.000297175 |
| 243780_PM_at | EST243780_PM_at | — | 0.000297494 |
| 201689_PM_s_at | TPD52 | tumor protein D52 | 0.000298768 |
| 209919_PM_x_at | GGT1 | gamma-glutamyltransferase 1 | 0.000299895 |
| 210052_PM_s_at | TPX2 | TPX2, microtubule-associated, homolog (Xenopus laevis) | 0.000301428 |
| 209994_PM_s_at | ABCB1 /// ABCB4 | ATP-binding cassette, sub-family B (MDR/TAP), member 1 /// ATP-binding cassette, sub-fa | 0.000302891 |
| 227466_PM_at | FAM200B | family with sequence similarity 200, member B | 0.000303971 |
| 209797_PM_at | CNPY2 | canopy 2 homolog (zebrafish) | 0.000304017 |
| 229157_PM_at | LOC100505483 | hypothetical LOC100505483 | 0.000307218 |
| 201805_PM_at | PRKAG1 | protein kinase, AMP-activated, gamma 1 non-catalytic subunit | 0.000307861 |
| AFFX-r2-P1-cre-3_at | ESTAFFX-r2-P1-cre-3_at | — | 0.000472245 |
| 200607_PM_s_at | RAD21 | RAD21 homolog (S. pombe) | 0.00031137 |
| 212113_PM_at | ATXN7L3B | ataxin 7-like 3B | 0.000314652 |
| 236327_PM_at | EST236327_PM_at | — | 0.000315612 |
| 224795_PM_x_at | IGK@ /// IGKC | immunoglobulin kappa locus /// immunoglobulin kappa constant | 0.000316664 |
| 240826_PM_at | EST240826_PM_at | — | 0.000318564 |
| 237560_PM_at | MRPS5 | Mitochondrial ribosomal protein S5 | 0.000320215 |
| 239902_PM_at | EST239902_PM_at | — | 0.000322709 |
| 201825_PM_s_at | SCCPDH | saccharopine dehydrogenase (putative) | 0.00032353 |
| 240965_PM_at | EST240965_PM_at | — | 0.000324754 |
| 217813_PM_s_at | SPIN1 | spindlin 1 | 0.00032924 |
| 205770_PM_at | GSR | glutathione reductase | 0.000330346 |
| 214263_PM_x_at | POLR2C | polymerase (RNA) II (DNA directed) polypeptide C, 33 kDa | 0.000331556 |
| 214677_PM_x_at | IGL@ /// LOC100287927 | immunoglobulin lambda locus /// Hypothetical protein LOC100287927 | 0.000332453 |
| 244456_PM_at | EST244456_PM_at | — | 0.000333092 |
| 221651_PM_x_at | IGK@ /// IGKC | immunoglobulin kappa locus /// immunoglobulin kappa constant | 0.000333367 |
| 236650_PM_at | EST236650_PM_at | — | 0.000337191 |
| 220946_PM_s_at | SETD2 | SET domain containing 2 | 0.000337367 |
| 224516_PM_s_at | CXXC5 | CXXC finger protein 5 | 0.000337471 |
| 212581_PM_x_at | GAPDH | glyceraldehyde-3-phosphate dehydrogenase | 0.000338308 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 212492_PM_s_at | KDM4B | lysine (K)-specific demethylase 4B | 0.000338683 |
| 221969_PM_at | PAX5 | paired box 5 | 0.000340498 |
| 242498_PM_x_at | EST242498_PM_x_at | — | 0.000342507 |
| 222737_PM_s_at | BRD7 | bromodomain containing 7 | 0.00034288 |
| 204714_PM_s_at | F5 | coagulation factor V (proaccelerin, labile factor) | 0.000343146 |
| 203671_PM_at | TPMT | thiopurlne S-methyltransferase | 0.000344362 |
| 225353_PM_s_at | C1QC | complement component 1, q subcomponent, C chain | 0.000345493 |
| 225709_PM_at | ARL6IP6 | ADP-ribosylation-like factor 6 interacting protein 6 | 0.000345892 |
| 237040_PM_at | CWF19L2 | CWF19-like 2, cell cycle control (S. pombe) | 0.000346442 |
| 226731_PM_at | ITGA1 | integrin, alpha 1 | 0.000348057 |
| AFFX-r2-Bs-phe-5_at | ESTAFFX-r2-Bs-phe-5_at | — | 0.000348063 |
| 205467_PM_at | CASP10 | caspase 10, apoptosis-related cysteine peptidase | 0.000348547 |
| 209001_PM_s_at | ANAPC13 | anaphase promoting complex subunit 13 | 0.000349407 |
| 233982_PM_x_at | STYXL1 | serine/threonine/tyrosine interacting-like 1 | 0.000350724 |
| 239040_PM_at | HNRNPD | Heterogeneous nuclear ribonucleoprotein D (AU-rich element RNA binding protein 1, 37 kDa | 0.00035153 |
| 205756_PM_s_at | F8 | coagulation factor VIII, procoagulant component | 0.000357136 |
| 1554229_PM_at | C5orf41 | chromosome 5 open reading frame 41 | 0.00035719 |
| 1568877_PM_a_at | ACBD5 | acyl-CoA binding domain containing 5 | 0.000360867 |
| 207707_PM_s_at | SEC13 | SEC13 homolog (S. cerevisiae) | 0.000360921 |
| 241403_PM_at | CLK4 | CDC-like kinase4 | 0.00036609 |
| 208664_PM_s_at | TTC3 | tetratricopeptide repeat domain 3 | 0.000366897 |
| 225206_PM_s_at | MTRF1L | mitochondrial translational release factor 1-like | 0.000367409 |
| 201336_PM_at | VAMP3 | vesicle-associated membrane protein 3 (cellubrevin) | 0.000371211 |
| 215121_PM_x_at | IGLC7 /// IGLV1-44 /// LOC100290481 | immunoglobulin lambda constant 7 /// immunoglobulln lambda variable 1-44 /// immunoglob | 0.000374949 |
| 210996_PM_s_at | YWHAE | tyrosine 3-monooxygenase/tryptophan 5-monoaoxygenase activation protein, epsilon polypep | 0.000377721 |
| 220590_PM_at | ITFG2 | integrin alpha FG-GAP repeat containing 2 | 0.000378104 |
| 1554745_PM_at | RALGPS1 | Ral GEF with PH domain and SH3 binding motif 1 | 0.000379212 |
| 239833_PM_at | EST239833_PM_at | — | 0.000379421 |
| 1553107_PM_s_at | C5orf24 | chromosome 5 open reading frame 24 | 0.000381869 |
| 216843_PM_x_at | LOC441259 /// PMS2L2 /// PMS2P1 /// PMS2P5 /// PMS2P6 | PMS2 postmeiotic segregation increased 2 (S. cerevisiae)-like /// postmeiotic segregati | 0.000384462 |
| 202262_PM_x_at | DDAH2 | dimethylarginine dimethylaminohydrolase 2 | 0.000385193 |
| 236428_PM_at | EST236428_PM_at | — | 0.000385729 |
| 230648_PM_at | LOC283663 | hypothetical LOC283663 | 0.000386276 |
| 243745_PM_at | EST243745_PM_at | — | 0.000392422 |
| 212827_PM_at | IGHM | immunoglobulin heavy constant mu | 0.000397367 |
| 212547_PM_at | BRD3 | bromodomain containing 3 | 0.000397485 |
| 214901_PM_at | ZNF8 | zinc finger protein 8 | 0.000397826 |
| 233031_PM_at | ZEB2 | zinc finger E-box binding homeobox 2 | 0.000401666 |
| 206370_PM_at | PIK3CG | phosphoinositide-3-kinase, catalytic, gamma polypeptide | 0.000403616 |
| 243005_PM_at | EST243005_PM_at | — | 0.000404995 |
| 204562_PM_at | IRF4 | interferon regulatory factor 4 | 0.000405376 |
| AFFX-r2-P1-cre-5_at | ESTAFFX-r2-P1-cre-5_at | — | 0.000692881 |
| 1553313_PM_s_at | SLC5A3 | solute carrier family 5 (sodium/myo-inositol cotransporter), member 3 | 0.000406242 |
| 239645_PM_at | EST239645_PM_at | — | 0.00040727 |
| 35160_PM_at | LDB1 | LIM domain binding 1 | 0.000410024 |
| 225920_PM_at | LOC148413 | hypothetical LOC148413 | 0.000410869 |
| 205611_PM_at | TNFSF12 | tumor necrosis factor (ligand) superfamily, member 12 | 0.000410968 |
| 227055_PM_at | METTL7B | methyltransferase like 7B | 0.000413609 |
| 216308_PM_x_at | GRHPR | glyoxylate reductase/hydroxypyruvate reductase | 0.000414211 |
| 222858_PM_s_3t | DAPP1 | dual adaptor of phosphotyrosine and 3-phosphoinositides | 0.000415151 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
| --- | --- | --- | --- |
| 1565162_PM_s_at | MGST1 | microsomal glutathione S-transferase 1 | 0.000421907 |
| 221602_PM_s_at | FAIM3 | Fas apoptotic inhibitory molecule 3 | 0.000427899 |
| 221671_PM_x_at | IGK@ /// IGKC | immunoglobulin kappa locus /// immunoglobulin kappa constant | 0.000428838 |
| 215176_PM_x_at | IGK@ /// IGKC | immunoglobulin kappa locus /// immunoglobulin kappa constant | 0.000431177 |
| 239001_PM_at | MGST1 | Microsomal glutathione S-transferase 1 | 0.000438289 |
| 232095_PM_at | EST232095_PM_at | — | 0.00044223 |
| 1557780_PM_at | EST1557780_PM_at | — | 0.000447614 |
| 221586_PM_s_at | E2F5 | E2F transcription factor 5, p130-binding | 0.000451682 |
| 215359_PM_x_at | ZNF44 | zinc finger protein 44 | 0.000459167 |
| 205863_PM_at | S100A12 | S100 calcium binding protein A12 | 0.000462242 |
| 209226_PM_s_at | TNPO1 | transportin 1 | 0.000464987 |
| 215338_PM_s_at | NKTR | natural killer-tumor recognition sequence | 0.000468526 |
| 201674_PM_s_at | AKAP1 | A kinase (PRKA) anchor protein 1 | 0.0004691 |
| 216591_PM_s_at | SDHC | succinate dehydrogenase complex, subunit C, integral membrane protein, 15 kDa | 0.000471684 |
| 1555779_PM_a_at | CD79A | CD79a molecule, immunoglobulin-associated alpha | 0.000473019 |
| 207983_PM_s_at | STAG2 | stromal antigen 2 | 0.00047413 |
| 1554696_PM_s_at | TYMS | thymidylate synthetase | 0.000477028 |
| 226286_PM_at | ELMOD3 | ELMO/CED-12 domain containing 3 | 0.000481236 |
| 213986_PM_s_at | C19orf6 | chromosome 19 open reading frame 6 | 0.000485839 |
| 222343_PM_at | BCL2L11 | BCL2-like 11 (apoptosis facilitator) | 0.000486282 |
| 218078_PM_s_at | ZDHHC3 | zinc finger, DHHC-type containing 3 | 0.000490729 |
| 223488_PM_s_at | GNB4 | guanine nucleotide binding protein (G protein), beta polypeptide 4 | 0.000490757 |
| 206034_PM_at | SERPINB8 | serpin peptidase inhibitor, clade B (ovalbumin), member 8 | 0.000490816 |
| 243771_PM_at | EST243771_PM_at | — | 0.000491776 |
| 244804_PM_at | SQSTM1 | sequestosome 1 | 0.000491966 |
| 215012_PM_at | ZNF451 | zinc finger protein 451 | 0.000492264 |
| 225447_PM_at | GPD2 | glycerol-3-phosphate dehydrogenase 2 (mitochondrial) | 0.000494271 |
| 239651_PM_at | ANAPC5 | anaphase promoting complex subunit 5 | 0.000497135 |
| 222728_PM_s_at | TAF1D | TATA box binding protein (TBP)-associated factor, RNA polymerase I, D, 41 kDa | 0.000499059 |
| 1563253_PM_s_at | ERBB3 | v-erb-b2 erythroblastic leukemia viral oncogene homolog 3 (avian) | 0.000499088 |
| 224969_PM_at | ATXN7L3 | ataxin 7-like 3 | 0.000501076 |
| 235984_PM_at | EST235984_PM_at | — | 0.000504457 |
| 231939_PM_s_at | BDP1 | B double prime 1, subunit of RNA polymerase III transcription initiation factor IIIB | 0.000505035 |
| 219420_PM_s_at | C1orf163 | chromosome 1 open reading frame 163 | 0.000505672 |
| 212804_PM_s_at | GAPVD1 | GTPase activating protein and VP59 domains 1 | 0.000505681 |
| 243434_PM_at | EST243434_PM_at | — | 0.000506264 |
| 201291_PM_s_at | TOP2A | topoisomerase (DNA) II alpha 170 kDa | 0.000507872 |
| 209138_PM_x_at | IGL@ | Immunoglobulin lambda locus | 0.000508704 |
| 1559263_PM_s_at | PPIL4 /// ZC3H12D | peptidylprolyl isomerase (cyclophilin)-like 4 /// zinc finger CCCH-type containing 12D | 0.000511201 |
| 212994_PM_at | THOC2 | THO complex 2 | 0.000512681 |
| 209013_PM_x_at | TRIO | triple functional domain (PTPRF interacting) | 0.000514112 |
| 208936_PM_x_at | LGALS8 | lectin, galactoside-binding, soluble, 8 | 0.000514485 |
| 215357_PM_s_at | POLDIP3 | polymerase (DNA-directed), delta interacting protein 3 | 0.000516138 |
| 204970_PM_s_at | MAFG | v-maf musculoaponeurotic fibrosarcoma oncogene homolog G (avian) | 0.00051907 |
| 239780_PM_at | EST239780_PM_at | — | 0.000519847 |
| 213648_PM_at | EXOSC7 | exosome component 7 | 0.000522394 |
| 238365_PM_s_at | C1orf228 | chromosome 1 open reading frame 228 | 0.000524946 |
| 238627_PM_at | TRAPPC2L | trafficking protein particle complex 2-like | 0.000531608 |
| 224563_pM_at | WASF2 | WAS protein family, member 2 | 0.000531756 |
| 211310_PM_at | EZH1 | enhancer of zeste homolog 1 (Drosophila) | 0.000535033 |
| 219497_PM_s_at | BCL11A | B-cell CLL/lymphoma 11A (zinc finger protein) | 0.000536239 |
| 242115_PM_at | EST242115_PM_at | — | 0.000536939 |
| 239486_PM_at | EST239486_PM_at | — | 0.000538967 |
| 227057_PM_at | ARHGAP27 | Rho GTPase activating protein 27 | 0.000558167 |
| 243490_PM_at | EST243490_PM_at | — | 0.000559582 |
| 208752_PM_x_at | NAP1L1 | nucleosome assembly protein 1-like 1 | 0.000559875 |
| 1554822_PM_at | PHTF2 | putative homeodomain transcription factor 2 | 0.000562813 |
| 33148_PM_at | ZFR | zinc finger RNA binding protein | 0.000563495 |
| 226384_PM_at | PPAPDC1B | phosphatidic acid phosphatase type 2 domain containing 1B | 0.000567195 |
| 222158_PM_s_at | PPPDE1 | PPPDE peptidase domain containing 1 | 0.000568969 |
| AFFX-r2-Bs-dap-3_at | ESTAFFX-r2-Bs-dap-3_at | — | 0.00056963 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 242916_PM_at | CEP110 | centrosomal protein 110 kDa | 0.000570647 |
| 224877_PM_s_at | MRP55 | mitochondrial ribosomal protein S5 | 0.000570714 |
| 235728_PM_at | ZFP3 | zinc finger protein 3 homolog (mouse) | 0.000574739 |
| 233089_PM_at | QRSL1 | glutaminyl-tRNA synthase (glutamine-hydrolyzing)-like 1 | 0.000574905 |
| 238602_PM_at | DIS3L2 | DIS3 mitotic control homolog (*S. cerevisiae*)-like 2 | 0.000575483 |
| 207131_PM_x_at | GGT1 | gamma-glutamyltransferase 1 | 0.000581613 |
| 215942_PM_s_at | GTSE1 | G-2 and S-phase expressed 1 | 0.000584379 |
| 203485_PM_at | RTN1 | reticulon 1 | 0.000586494 |
| 1562364_PM_at | GVIN1 | GTPase, very large interferon inducible 1 | 0.000587505 |
| 224733_PM_at | CMTM3 | CKLF-like MARVEL transmembrane domain containing 3 | 0.000589647 |
| 217898_PM_at | C15orf24 | chromosome 15 open reading frame 24 | 0.00059102 |
| 201401_PM_s_at | ADRBK1 | adrenergic, beta, receptor kinase 1 | 0.000595924 |
| 240174_PM_at | EST240174_PM_at | — | 0.000598439 |
| 200623_PM_s_at | CALM3 | calmodulin 3 (phosphorylase kinase, delta) | 0.000601157 |
| 206562_PM_s_at | CSNK1A1 | casein kinase 1, alpha 1 | 0.000602948 |
| 215495_PM_s_at | SAMD4A | sterile alpha motif domain containing 4A | 0.000606 |
| 215293_PM_s_at | PGAP2 | post-GPI attachment to proteins 2 | 0.000609566 |
| 202971_PM_s_at | DYRK2 | dual-specificity tyrosine-(Y)-phosphorylation regulated kinase 2 | 0.000611919 |
| 229571_PM_at | EST229571_PM_at | — | 0.000616179 |
| 210787_PM_s_at | CAMKK2 | calcium/calmodulin-dependent protein kinase kinase 2, beta | 0.000616474 |
| 1569089_PM_a_at | FLJ35390 | hypothetical LOC255031 | 0.000619243 |
| 201739_PM_at | SGK1 | serum/glucocorticoid regulated kinase 1 | 0.000619837 |
| 221079_PM_s_at | METTL2A /// METTL2B | methyltransferase like 2A /// methyltransferase like 2B | 0.000620397 |
| 235792_PM_x_at | PIK3C2A | phosphoinositide-3-kinase, class 2, alpha potypeptide | 0.000623715 |
| AFFX-HUMGAPDH/M33197_3_at | GAPDH | glyceraldehyde-3-phosphate dehydrogenase | 0.000625862 |
| 243182_PM_at | EST243182_PM_at | — | 0.000626437 |
| 230735_PM_at | EST230735_PM_at | — | 0.000630009 |
| 1555301_PM_a_at | DIP2A | DIP2 disco-interacting protein 2 homolog A (*Drosophila*) | 0.000632511 |
| 211721_PM_s_at | ZNF551 | zinc finger protein 551 | 0.000632559 |
| 1560020_PM_at | DNAJC13 | DnaJ (Hsp40) homolog, subfamily C, member 13 | 0.000634502 |
| 229327_PM_s_at | EST229327_PM_s_at | — | 0.000644805 |
| 236237_PM_at | EST236237_PM_at | — | 0.000644857 |
| 204214_PM_s_at | RAB32 | RAB32, member RAS oncogene family | 0.000647569 |
| 227108_PM_at | STARD9 | StAR-related lipid transfer (START) domain containing 9 | 0.000649001 |
| 227152_PM_at | C12orf35 | chromosome 12 open reading frame 35 | 0.000649869 |
| 213286_PM_at | ZFR | zinc finger RNA binding protein | 0.000650155 |
| 210943_PM_s_at | LYST | lysosomal trafficking regulator | 0.000652166 |
| 210281_PM_s_at | ZMYM2 | zinc finger, MYM-type 2 | 0.000655464 |
| 210131_PM_x_at | SDHC | succinate dehydrogenase complex, subunit C, integral membrane protein, 15 kDa | 0.000560271 |
| 219073_PM_s_at | OSBPL10 | oxysterol binding protein-like 10 | 0.000660978 |
| 201733_PM_at | CLCN3 | chloride channel 3 | 0.000662473 |
| 242732_PM_at | EST242732_PM_at | — | 0.000665353 |
| 223997_PM_at | FNIP1 | folliculin interacting protein 1 | 0.000668942 |
| 228762_PM_at | LFNG | LFNG O-fucosylpeptide 3-beta-N-acetylglucosaminyltransferase | 0.000671686 |
| 216525_PM_x_at | PMS2P3 | postmeiotic segregation increased 2 pseudogene 3 | 0.000677006 |
| 226456_PM_at | C16orf75 | chromosome 16 open reading frame 75 | 0.000677438 |
| 209113_PM_s_at | HMG20B | high-mobility group 20B | 0.000679675 |
| 224854_PM_s_at | SLAIN2 | SLAIN motif family, member 2 | 0.000682615 |
| 239235_PM_at | EST239235_PM_at | — | 0.000683667 |
| 228718_PM_at | ZNF44 | zinc finger protein 44 | 0.000688863 |
| 217785_PM_s_at | YKT6 | YKT6 v-SNARE homolog (*S. cerevisiae*) | 0.00069086 |
| 218240_PM_at | NKIRAS2 | NFKB inhibitor interacting Ras-like 2 | 0.000690947 |
| 236796_PM_at | BACH2 | BTB and CNC homology 1, basic leucine zipper transcription factor 2 | 0.000691868 |
| 238893_PM_at | LOC338758 | hypothetical LOC338758 | 2.94E−05 |
| 212178_PM_s_at | POM121 /// POM121C | POM121 membrane glycoprotein /// POM121 membrane glycoprotein C | 0.000695226 |
| 229243_PM_at | EST229243_PM_at | — | 0.000699175 |
| 231188_PM_at | ZSCAN2 | zinc finger and SCAN domain containing 2 | 0.000705941 |
| 236408_PM_at | EST236408_PM_at | — | 0.000706706 |
| 202954_PM_at | UBE2C | ubiquitin-conjugating enzyme E2C | 0.00070987 |
| 241995_PM_at | DGUOK | deoxyguanosine kinase | 0.00071203 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 213132_PM_s_at | MCAT | malonyl CoA:ACP acyltransferase (mitochondrial) | 0.000713197 |
| 243461_PM_at | EST243461_PM_at | — | 0.000714864 |
| 209374_PM_s_at | IGHM | immunoglobulin heavy constant m u | 0.000716721 |
| 1559587_PM_at | SYMPK | symplekin | 0.000720074 |
| 239864_PM_at | LOC100130175 | hypothetical protein LOC100130175 | 0.000722172 |
| 226150_PM_at | PPAPDC1B | phosphatidic acid phosphatase type 2 domain containing 1B | 0.000722764 |
| 224227_PM_s_at | BDP1 | B double prime 1, subunit of RNA polymerase III transcription initiation factor IIIB | 0.000724793 |
| 202535_PM_at | FADD | Fas (TNFRSF6)-associated via death domain | 0.000725868 |
| 243072_PM_at | EST243072_PM_at | — | 0.00072676 |
| 226798_PM_at | BCL2L13 | BCL2-like 13 (apoptosis facilitator) | 0.000726832 |
| 210218_PM_s_at | SP100 | SP100 nuclear antigen | 0.000728004 |
| 224414_PM_s_at | CARD6 | caspase recruitment domain family, member 6 | 0.000729842 |
| 213453_PM_x_at | GAPDH | glyceraldehyde-3-phosphate dehydrogenase | 0.000732584 |
| 240124_PM_at | EST240124_PM_at | — | 0.000735862 |
| 234258_PM_3t | EST234258_PM_at | — | 0.000737628 |
| 200972_PM_at | TSPAN3 | tetraspanin 3 | 0.000738686 |
| 221521_PM_s_at | GINS2 | GINS complex subunit 2 (Psf2 homolog) | 0.000740977 |
| 229563_PM_s_at | RPL10A | ribosomal protein L10a | 0.000743036 |
| 243690_PM_at | TRIOBP | TRIO and F-actin binding protein | 0.000754519 |
| 228040_PM_at | MGC21881 | hypothetical locus MGC21881 | 0.000758151 |
| 214836_PM_x_at | IGK@ /// IGKC /// IGKV1-5 | immunoglobulin kappa locus /// immunoglobulin kappa constant /// immunoglobulin kappa v | 0.00076237 |
| 228813_PM_at | HDAC4 | histone deacetylase 4 | 0.000762977 |
| 216984_PM_x_at | IGLV2-23 | immunoglobulin lambda variable 2-23 | 0.000765219 |
| 243474_PM_at | EST243474_PM_at | — | 0.000768017 |
| 240704_PM_at | EST240704_PM_at | — | 0.000768307 |
| 209023_PM_s_at | STAG2 | stromal antigen 2 | 0.000770382 |
| 227198_PM_at | AFF3 | AF4/FMR2 family, member 3 | 0.00077081 |
| 211672_PM_s_at | ARPC4 | actin related protein 2/3 complex, subunit 4, 20 kDa | 0.000773643 |
| 201536_PM_at | DUSP3 | dual specificity phosphatase 3 | 0.000774485 |
| 201840_PM_at | NEDD8 | neural precursor cell expressed, developmentally down-regulated 8 | 0.000777605 |
| 1554453_PM_at | HNRPLL | heterogeneous nuclear ribonucleoprotein L-like | 0.000778138 |
| 1554516_PM_at | LOC100288109 /// LOC203274 | Hypothetical protein LOC100288109 /// Hypothetical protein LOC203274 | 0.000779538 |
| 233745_PM_at | EST233745_PM_at | — | 0.000780591 |
| 230370_PM_x_at | STYXL1 | serine/threonine/tyrosine interacting-like 1 | 0.000781146 |
| 211611_PM_s_at | ATF6B /// TNXB | activating transcription factor 6 beta /// tenascin XB | 0.000784184 |
| 206114_PM_at | EPHA4 | EPH receptor A4 | 0.00078538 |
| 225880_PM_at | TOR1AIP2 | torsin A interacting protein 2 | 0.000786899 |
| 217198_PM_x_at | IGHA2 /// IGHD /// IGHG1 /// LOC100126583 /// LOC100510361 | immunoglobulin heavy constant alpha 2 (A2m marker) /// immunoglobulin heavy constant de | 0.000788023 |
| 215379_PM_x_at | IGLC7 /// IGLV1-44 | immunoglobulin lambda constant 7 /// immunoglobulln lambda variable 1-44 | 0.000796455 |
| 208757_PM_at | TMED9 | transmembrane emp24 protein transport domain containing 9 | 0.000796492 |
| 212979_PM_s_at | FAM115A | family with sequence similarity 115, member A | 0.000796767 |
| 213450_PM_s_at | ICOSLG | inducible T-cell co-stimulator ligand | 0.000801819 |
| 244429_PM_at | EST244429_PM_at | — | 0.000801949 |
| 211453_PM_s_at | AKT2 | v-akt murine thymoma viral oncogene homolog 2 | 0.00080311 |
| 211352_PM_s_at | NCOA3 | nuclear receptor coactivator 3 | 0.000805416 |
| 239450_PM_at | EST239450_PM_at | — | 0.000808718 |
| 226679_PM_at | SLC26A11 | solute carrier family 26, member 11 | 0.000810101 |
| 209567_PM_at | RRS1 | RRS1 ribosome biogenesis regulator homolog (S. cerevisiae) | 0.000810395 |
| 244498_PM_x_at | LOC100505679 | hypothetical protein LOC100505679 | 0.0008122 |
| 205731_PM_s_at | NCOA2 | nuclear receptor coactivator 2 | 0.000813451 |
| 212421_PM_at | C22orf9 | chromosome 22 open reading frame 9 | 0.000819733 |
| 1568702_PM_a_at | PAAF1 | proteasomal ATPase-associated factor 1 | 0.000820736 |
| 226160_PM_at | H6PD | hexose-6-phosphate dehydrogenase (glucose 1-dehydrogenase) | 0.000829239 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 227882_PM_at | FKRP | fukutin related protein | 0.000831453 |
| 211275_PM_s_at | GYG1 | glycogenin 1 | 0.000837756 |
| 240392_PM_at | EST240392_PM_at | — | 0.000837778 |
| 214615_PM_at | P2RY10 | purinergic receptor P2Y, G-protein coupled, 10 | 0.000839839 |
| 219933_PM_at | GLRX2 | glutaredoxin 2 | 0.000844012 |
| 210264_PM_at | GPR35 | G protein-coupled receptor 35 | 0.000844817 |
| 236250_PM_at | AFG3L1P | AFG3 ATPase family gene 3-like 1 (*S. cerevisiae*), pseudogene | 0.000853458 |
| 201690_PM_s_at | TPD52 | tumor protein D52 | 0.000856129 |
| 230434_PM_at | PHOSPHO2 | phosphatase, orphan 2 | 0.000856483 |
| 205267_PM_at | POU2AF1 | POU class 2 associating factor 1 | 0.000857053 |
| 223234_PM_at | MAD2L2 | MAD2 mitotic arrest deficient-like 2 (yeast) | 0.000860917 |
| 201259_PM_s_at | SYPL1 | synaptophysin-like 1 | 0.000861326 |
| 222387_PM_s_at | VPS35 | vacuolar protein sorting 35 homolog (*S. cerevisiae*) | 0.000862194 |
| 1555896_PM_a_at | ADAM15 | ADAM metallopeptidase domain 15 | 0.00086724 |
| 220112_PM_at | ANKRD55 | ankyrin repeat domain 55 | 0.000868721 |
| 212229_PM_s_at | FBXO21 | F-box protein 21 | 0.000873958 |
| 219737_PM_s_at | PCDH9 | protocadherin 9 | 0.000879071 |
| 212386_PM_at | TCF4 | transcription factor 4 | 0.000884201 |
| 223819_PM_x_at | COMMD5 | COMM domain containing 5 | 0.000886611 |
| 238477_PM_at | KIF1C | kinesin family member 1C | 0.000886757 |
| 1554452_PM_a_at | C7orf68 | chromosome 7 open reading frame 68 | 0.000891429 |
| 242279_PM_at | EST242279_PM_at | — | 0.000896083 |
| 202095_PM_s_at | BIRC5 | baculoviral IAP repeat-containing 5 | 0.000914017 |
| 228693_PM_at | CCDC50 | coiled-coil domain containing 50 | 0.000917681 |
| 225626_PM_at | PAG1 | phosphoprotein associated with glycosphingolipid microdomains 1 | 0.00091903 |
| 1557117_PM_at | EST1557117_PM_at | — | 0.00092373 |
| 208621_PM_s_at | EZR | ezrin | 0.000926268 |
| 239213_PM_at | SERPINB1 | serpin peptidase inhibitor, clade B (ovalbumin), member 1 | 0.000926276 |
| 206116_PM_s_at | TPM1 | tropomyosin 1 (alpha) | 0.00092976 |
| 202689_PM_at | RBM15B | RNA binding motif protein 15B | 0.000940032 |
| 242352_PM_at | NIPBL | Nipped-B homolog (*Drosophila*) | 0.000940617 |
| 228364_PM_at | ZNF784 | zinc finger protein 784 | 0.000940805 |
| 241614_PM_at | EST241614_PM_at | — | 0.000943349 |
| 201432_PM_at | CAT | catalase | 0.000947049 |
| 218009_PM_s_at | PRC1 | protein regulator of cytokinesis 1 | 0.00095654 |
| 218862_PM_at | ASB13 | ankyrin repeat and SOCS box-containing 13 | 0.000957234 |
| 212392_PM_s_at | PDE4DIP | phosphodiesterase 4D interacting protein | 0.000959054 |
| 215451_PM_s_at | AFF1 | AF4/FMR2 family, member 1 | 0.000961327 |
| 219267_PM_at | GLTP | glycolipid transfer protein | 0.000963785 |
| 228377_PM_at | KLHL14 | kelch-like 14 (*Drosophila*) | 0.000971257 |
| 226365_PM_at | EST226365_PM_at | — | 0.000974061 |
| 227937_PM_at | MYPOP | Myb-related transcription factor, partner of profilin | 0.000983015 |
| 217148_PM_x_at | EST217148_PM_x_at | — | 0.00098494 |
| AFFX-HUMRGE/M10098_3_at | ESTAFFX-HUMRGE/M10098_3_at | — | 0.000987735 |
| 239061_PM_at | TPRXL | tetra-peptide repeat homeobox-like | 0.000989572 |
| 1570021_PM_at | EST1570021_PM_at | — | 0.000995573 |
| 205781_PM_at | C16orf7 | chromosome 16 open reading frame 7 | 0.000995722 |
| 1557388_PM_at | RTTN | rotatin | 0.00099729 |
| 236215_PM_at | EST236215_PM_at | — | 0.00100332 |
| 221239_PM_s_at | FCRL2 | Fc receptor-like 2 | 0.00100594 |
| 209680_PM_s_at | KIFC1 | Kinesin family member C1 | 0.00101262 |
| 1560922_PM_s_at | ZNF169 | zinc finger protein 169 | 0.00101809 |
| 39318_PM_at | TCL1A | T-cell leukemia/lymphoma 1A | 0.0010181 |
| 222292_PM_at | CD40 | CD40 molecule, TNF receptor superfamily member 5 | 0.00102743 |
| 217398_PM_x_at | GAPDH | glyceraldehyde-3-phosphate dehydrogenase | 0.00102797 |
| 228599_PM_at | MS4A1 | membrane-spanning 4-domains, subfamily A, member 1 | 0.00103001 |
| 240861_PM_at | EST240861_PM_at | — | 0.00103147 |
| 202065_PM_s_at | PPFIA1 | protein tyrosine phosphatase, receptor type, f polypeptide (PTPRF), interacting protein | 0.0010369 |
| 234488_PM_s_at | GMCL1 /// GMCL1L | germ cell-less homolog 1 (*Drosophila*) /// germ cell-less homolog 1 (*Drosophila*)-like | 0.00104025 |
| 233375_PM_at | EFCAB2 | EF-hand calcium binding domain 2 | 0.00104248 |
| 1560724_PM_at | EST1560724_PM_at | — | 0.00104357 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
| --- | --- | --- | --- |
| 209006_PM_s_at | C1orf63 | chromosome 1 open reading frame 63 | 0.00104379 |
| 214992_PM_s_at | DNASE2 | deoxyribonuclease II, lysosomal | 0.00104413 |
| 218391_PM_at | SNF8 | SNF8, ESCRT-II complex subunit, homolog (*S. cerevisiae*) | 0.00104546 |
| 242288_PM_s_at | EMILIN2 | elastin microfibril interfacer 2 | 0.00104673 |
| 239926_PM_at | EST239926_PM_at | — | 0.00105049 |
| 243699_PM_at | LOC100507006 | hypothetical LOC100507006 | 0.00105279 |
| 202016_PM_at | MEST | mesoderm specific transcript homolog (mouse) | 0.00105615 |
| 201211_PM_s_at | DDX3X | DEAD (Asp-Glu-Ala-Asp) box polypeptide 3, X-linked | 0.00105627 |
| 238130_PM_at | NFATC2IP | nuclear factor of activated T-cells, cytoplasmic, calcineurin-dependent 2 interacting p | 0.00105997 |
| 217378_PM_x_at | EST217378_PM_x_at | — | 0.00106017 |
| 200868_PM_s_at | RNF114 | ring finger protein 114 | 0.00106168 |
| 209699_PM_x_at | AKR1C2 | aldo-keto reductase family 1, member C2 (dihydrodiol dehydrogenase 2; bile acid binding | 0.00106498 |
| 225052_PM_at | TMEM203 | transmembrane protein 203 | 0.00106532 |
| 237464_PM_at | EST237464_PM_at | — | 0.00106804 |
| 201944_PM_at | HEXB | hexosaminidase B (beta polypeptide) | 0.00107107 |
| 234764_PM_x_at | IGLV1-36 | immunoglobulin lambda variable 1-36 | 0.00107144 |
| 223393_PM_s_at | TSHZ3 | teashirt zinc finger homeobox 3 | 0.00107465 |
| 240652_PM_at | EST240652_PM_at | — | 0.00108224 |
| 231672_PM_at | EST231672_PM_at | — | 0.00108448 |
| 230486_PM_at | EST230486_PM_at | — | 0.00108996 |
| 212967_PM_x_at | NAP1L1 | nucleosome assembly protein 1-like 1 | 0.00109982 |
| 220068_PM_at | VPREB3 | pre-B lymphocyte 3 | 0.0011043 |
| 228250_PM_at | FNIP1 | folliculin interacting protein 1 | 0.00111525 |
| 222388_PM_s_at | VPS35 | vacuolar protein sorting 35 homolog (*S. cerevisiae*) | 0.00111739 |
| 241885_PM_at | EST241885_PM_at | — | 0.00111828 |
| 229852_PM_at | NMNAT1 | nicotinamide nucleotide adenylyltransferase 1 | 0.0011245 |
| 232906_PM_at | EST232906_PM_at | — | 0.00112623 |
| 213082_PM_s_at | SLC35D2 | solute carrier family 35, member D2 | 0.00112801 |
| 1569189_PM_at | TTC9C | tetratricopeptide repeat domain 9C | 0.00113081 |
| 200709_PM_at | FKBP1A | FK506 binding protein 1A, 12 kDa | 0.00113213 |
| 238860_PM_at | C6orf130 | chromosome 6 open reading frame 130 | 0.00113294 |
| 218149_PM_s_at | ZNF395 | zinc finger protein 395 | 0.00113365 |
| 226663_PM_at | ANKRD10 | ankyrin repeat domain 10 | 0.00113647 |
| 221837_PM_at | KLHL22 | kelch-like 22 (*Drosophila*) | 0.00113942 |
| 222193_PM_at | C2orf43 | chromosome 2 open reading frame 43 | 0.00114481 |
| 201698_PM_s_at | SRSF9 | serine/arginine-rich splicing factor 9 | 0.00115792 |
| 209042_PM_s_at | UBE2G2 | ubiquitin-conjugating enzyme E2G 2 (UBC7 homolog, yeast) | 0.00115961 |
| 235231_PM_at | ZNF789 | zinc finger protein 789 | 0.00116259 |
| 236799_PM_at | EST236799_PM_at | — | 0.00116393 |
| 235409_PM_at | MGA | MAX gene associated | 0.00116667 |
| 201456_PM_s_at | BUB3 | budding uninhibited by benzimidazoles 3 homolog (yeast) | 0.00116683 |
| 226825_PM_s_at | TMEM165 | transmembrane protein 165 | 0.00117042 |
| 1556462_PM_a_at | EST1556462_PM_a_at | — | 0.00117146 |
| 243667_PM_at | EST243667_PM_at | — | 0.00117303 |
| 1566824_PM_at | EST1566824_PM_at | — | 0.00117375 |
| 217078_PM_s_at | CD300A | CD300a molecule | 0.00117516 |
| 208610_PM_s_at | SRRM2 | serine/arginine repetitive matrix 2 | 0.00117811 |
| 215954_PM_s_at | C19orf29 | chromosome 19 open reading frame 29 | 0.00117964 |
| 219443_PM_at | TASP1 | taspase, threonine aspartase, 1 | 0.00118869 |
| 207188_PM_at | CDK3 | cyclin-dependent kinase 3 | 0.00119927 |
| 235526_PM_at | SOX6 | SRY (sex determining region Y)-box 6 | 0.00119931 |
| 217927_PM_at | SPCS1 | signal peptidase complex subunit 1 homolog (*S. cerevisiae*) | 0.00120191 |
| 203096_PM_s_at | RAPGEF2 | Rap guanine nucleotide exchange factor (GEF) 2 | 0.00120412 |
| 243968_PM_x_at | FCRL1 | Fc receptor-like 1 | 0.00120435 |
| 235469_PM_at | FAM133B /// LOC728066 | family with sequence similarity 133, member B /// family with sequence similarity 133, | 0.00120671 |
| 205297_PM_s_at | CD79B | CD79b molecule, immunoglobulin-associated beta | 0.00121583 |
| 212177_PM_at | SFRS18 | splicing factor, arginine/serine-rich 18 | 0.00122218 |
| 203554_PM_x_at | PTTG1 | pituitary tumor-transforming 1 | 0.00122388 |
| 230533_PM_at | ZMYND8 | zinc finger, MYND-type containing 8 | 0.00122749 |
| 223161_PM_at | KIAA1147 | KIAA1147 | 0.00122827 |
| 208652_PM_at | PPP2CA | protein phosphatase 2, catalytic subunit, alpha isozyme | 0.0012327 |

TABLE 14-continued

Blood Microarray Signatures for subAR using a 3-Way 1-Step approach
(AR vs. subAR vs. TX): full gene list (818 genes) at FDR < 5%

| Probeset ID | Gene Symbol | Gene Title | p-value |
|---|---|---|---|
| 235577_PM_at | ZNF652 | zinc finger protein 652 | 0.00123352 |
| 203222_PM_s_at | TLE1 | transducin-like enhancer of split 1 (E(sp1)) homolog, *Drosophila*) | 0.001235 |
| 202871_PM_at | TRAF4 | TNF receptor-associated factor 4 | 0.00123923 |
| 223887_PM_at | GPR132 | G protein-coupled receptor 132 | 0.00123983 |
| 244015_PM_at | EST244015_PM_at | — | 0.00124998 |
| 1558438_PM_a_at | IGHA1 | Immunoglobulin heavy constant alpha 1 | 0.00125035 |
| 202696_PM_at | OXSR1 | oxidative-stress responsive 1 | 0.00125038 |
| 228083_PM_at | CACNA2D4 | calcium channel, voltage-dependent, alpha 2/delta subunit 4 | 0.00125662 |
| 242712_PM_x_at | RANBP2 /// RGPD1 /// RGPD2 /// RGPD3 /// RGPD4 /// RGPD5 /// RGPD6 /// RGPD8 | RAN binding protein 2 /// RANBP2-like and GRIP domain containing 1 /// RANBP2-like and | 0.00126544 |
| 221850_PM_x_at | AGAP4 /// AGAP6 /// AGAP7 /// AGAP8 | ArfGAP with GTPase domain, ankyrin repeat and PH domain 4 /// ArfGAP with GTPase domain | 0.00126719 |
| 236700_PM_at | EIF3C | eukaryotic translation initiation factor 3, subunit C | 0.00126801 |
| 208466_PM_at | RAB3D | RAB3D, member RAS oncogene family | 0.00127517 |
| 243492_PM_at | THEM4 | thioesterase superfamily member 4 | 0.0012775 |
| 213448_PM_at | EST213448_PM_at | — | 0.00128088 |
| 222800_PM_at | TRNAU1AP | tRNA selenocysteine 1 associated protein 1 | 0.00128375 |
| 232236_PM_at | EST232236_PM_at | — | 0.00129017 |
| 213891_PM_s_at | TCF4 | transcription factor 4 | 0.00129164 |
| 202166_PM_s_at | PPP1R2 | protein phosphatase 1, regulatory (inhibitor) subunit 2 | 0.00129303 |
| 228273_PM_at | PRR11 | proline rich 11 | 0.00129725 |
| 206896_PM_s_at | GNG7 | guanine nucleotide binding protein (G protein), gamma 7 | 0.00129953 |
| 227616_PM_at | BCL9L | B-cell CLL/lymphoma 9-like | 0.00130003 |
| 237778_PM_at | EST237778_PM_at | — | 0.00130027 |
| 235662_PM_at | EST235662_PM_at | — | 0.00130307 |
| 1554670_PM_at | GGA1 | golgi-associated, gamma adaptin ear containing, ARF binding protein 1 | 0.00130507 |
| 236621_PM_at | RPS27 | ribosomal protein S27 | 0.00130665 |
| 214052_PM_x_at | BAT2L2 | HLA-B associated transcript 2-like 2 | 0.00130805 |
| 219382_PM_at | SERTAD3 | SERTA domain containing 3 | 0.00131171 |
| 211645_PM_x_at | EST211645_PM_x_at | — | 0.00131608 |
| 242261_PM_at | EST242261_PM_at | — | 0.00131609 |
| 201896_PM_s_at | PSRC1 | proline/serine-rich coiled-coil 1 | 0.00132007 |
| 202589_PM_at | TYMS | thymidylate synthetase | 0.00132608 |
| 225602_PM_at | GLIPR2 | GLI pathogenesis-related 2 | 0.0013347 |
| 239760_PM_at | EST239760_PM_at | — | 0.00133591 |
| 230000_PM_at | RNF213 | ring finger protein 213 | 0.00133665 |
| 238485_PM_at | EST238485_PM_at | — | 0.00133773 |
| 1569320_PM_at | GPBP1L1 | GC-rich promoter binding protein 1-like 1 | 0.00134606 |
| 224766_PM_at | LOC100506548 /// RPL37 | hypothetical LOC100506548 /// ribosomal protein L37 | 0.0013474 |
| 227062_PM_at | EST227062_PM_at | — | 0.00134993 |
| 243919_PM_at | EST243919_PM_at | — | 0.00135277 |
| 202942_PM_at | ETFB | electron-transfer-flavoprotein, beta polypeptide | 0.00135862 |
| 239266_PM_at | EST239266_PM_at | — | 0.00135979 |
| 225259_PM_at | RAB6B | RAB6B, member RAS oncogene family | 0.00136 |
| 239764_PM_at | EST239764_PM_at | — | 0.00137061 |
| 234767_PM_at | FAR1 | fatty acyl CoA reductase 1 | 8.02E−05 |

TABLE 15

Blood Microarray Signatures for subAR using a 3-Way 1-Step approach (AR vs. subAR vs. TX): best performing gene signature (61 genes)

| Probe Set ID | Gene Symbol | Gene Title |
|---|---|---|
| 1559249_PM_at | ATXN1 | ataxin 1 |
| 1559391_PM_s_at | EST20 | — |
| 1570299_PM_at | EST1 | — |
| 201015_PM_s_at | JUP | junction plakoglobin |
| 201876_PM_at | PON2 | paraoxonase 2 |
| 203137_PM_at | WTAP | Wilms tumor 1 associated protein |
| 204185_PM_x_at | PPID | peptidylprolyl isomerase D |
| 206366_PM_x_at | XCL1 | chemokine (C motif) ligand 1 |
| 208249_PM_s_at | TGDS | TDP-glucose 4,6-dehydratase |
| 209833_PM_at | CRADD | CASP2 and RIPK1 domain containing adaptor with death domain |
| 211360_PM_s_at | ITPR2 | inositol 1,4,5-trisphosphate receptor, type 2 |
| 212872_PM_s_at | MED20 | mediator complex subunit 20 |
| 214567_PM_s_at | XCL1 /// XCL2 | chemokine (C motif) ligand 1 /// chemokine (C motif) ligand 2 |
| 215092_PM_s_at | NFAT5 | nuclear factor of activated T-cells 5, tonicity-responsive |
| 215707_PM_s_at | PRNP | prion protein |
| 215887_PM_at | ZNF277 | zinc finger protein 277 |
| 215933_PM_s_at | HHEX | hematopoietically expressed homeobox |
| 217703_PM_x_at | EST2 | — |
| 217982_PM_s_at | MORF4L1 | mortality factor 4 like 1 |
| 218178_PM_s_at | CHMP1B | charged multivesicular body protein 1B |
| 218474_PM_s_at | KCTD5 | potassium channel tetramerization domain containing 5 |
| 220127_PM_s_at | FBXL12 | F-box and leucine-rich repeat protein 12 |
| 220221_PM_at | VPS13D | vacuolar protein sorting 13 homolog D (*S. cerevisiae*) |
| 221579_PM_s_at | NUDT3 /// RPS10-NUDT3 | nudix (nucleoside diphosphate linked moiety X)-type motif 3 /// RPS10-NUDT3 readthrough |
| 222489_PM_s_at | WRNIP1 | Werner helicase interacting protein 1 |
| 223819_PM_x_at | COMMD5 /// LOC101928879 /// ZNF250 | COMM domain containing 5 /// COMM domain-containing protein 5-like /// zinc finger protein 250 |
| 223937_PM_at | FOXP1 | forkhead box P1 |
| 225091_PM_at | ZCCHC3 | zinc finger, CCHC domain containing 3 |
| 225179_PM_at | UBE2K | ubiquitin-conjugating enzyme E2K |
| 225399_PM_at | TSEN15 | TSEN15 tRNA splicing endonuclease subunit |
| 225509_PM_at | SAP30L | SAP30-like |
| 226975_PM_at | RNPC3 | RNA-binding region (RNP1, RRM) containing 3 |
| 227410_PM_at | FAM43A | family with sequence similarity 43, member A |
| 228476_PM_at | KIAA1407 | KIAA1407 |
| 229243_PM_at | RP11-111M22.4 | — |
| 230505_PM_at | LOC145474 | uncharacterized LOC145474 |
| 232031_PM_s_at | EPG5 | ectopic P-granules autophagy protein 5 homolog (*C. elegans*) |
| 232284_PM_at | PSMD6-AS2 | PSMD6 antisense RNA 2 |
| 236168_PM_at | EST3 | — |
| 236404_PM_at | EST4 | — |
| 236883_PM_at | EST5 | — |
| 237176_PM_at | EST6 | — |
| 237544_PM_at | CTD-2165H16.3 | — |
| 238317_PM_x_at | EST7 | — |
| 239227_PM_at | EST8 | — |
| 239404_PM_at | EST9 | — |
| 239600_PM_at | EST10 | — |
| 240498_PM_at | EST11 | — |
| 241688_PM_at | EST12 | — |
| 242060_PM_x_at | PHF11 | PHD finger protein 11 |
| 242352_PM_at | NIPBL | Nipped-B homolog (*Drosophila*) |
| 242390_PM_at | EST13 | — |
| 242824_PM_at | EST14 | — |
| 242877_PM_at | EST15 | — |
| 243739_PM_at | EST16 | — |
| 244233_PM_at | TPGS2 | tubulin polyglutamylase complex subunit 2 |
| 244840_PM_x_at | DOCK4 | dedicator of cytokinesis 4 |
| AFFX-CreX-5_at | EST17 | — |
| AFFX-r2-P1-cre-3_at | EST18 | — |
| AFFX-r2-P1-cre-5_at | EST19 | — |

TABLE 16

Blood Microarray analysis results for subAR using a 3-Way 1-Step approach (AR vs. subAR vs. TX)

|  | TX | SCAR | AR |
|---|---|---|---|
| TX | 19 | 3 | 3 |
| SCAR | 1 | 21 | 1 |
| AR | 1 | 3 | 17 |

| Method | Classifies | % Predictive Accuracy | Sensitivity (%) | Specificity (%) | Positive Predictive Value (%) | Negative Predictive Value (%) | AUC |
|---|---|---|---|---|---|---|---|
| Nearest Centroid (1 Step Prediction) | TX vs. AR | 90% | 95% | 85% | 86% | 94% | 0.898 |
|  | TX vs. SCAR | 91% | 95% | 87% | 86% | 95% | 0.912 |
|  | AR vs. SCAR | 91% | 88% | 94% | 95% | 85% | 0.905 |

TABLE 17

Blood PAXgene NGS Signatures for subAR using a 3-Way 1-Step approach
(AR vs. subAR vs. TX): full gene list (123 genes) at p < 0.01

| Probeset ID | Gene Symbol | Transcript | p-value |
| --- | --- | --- | --- |
| NM_001123228>TMEM14E | TMEM14E | NM_001123228 | 1.79E−06 |
| NM_001375>DNASE2 | DNASE2 | NM_001375 | 6.30E−06 |
| NM_003107>SOX4 | SOX4 | NM_003107 | 1.77E−05 |
| NM_148901>TNFRSF18 | TNFRSF18 | NM_148901 | 0.00014023 |
| NR_109780>LOC100506860 | LOC100506860 | NR_109780 | 0.00019178 |
| NM_001336>CTSZ | CTSZ | NM_001336 | 0.00043567 |
| NR_109851>LINC-PINT | LINC-PINT | NR_109851 | 0.00045431 |
| NM_021991>JUP | JUP | NM_021991 | 0.00047653 |
| NR_022011>PWARSN | PWARSN | NR_022011 | 0.00073955 |
| NM_001146190>ZNF407 | ZNF407 | NM_001146190 | 0.00081929 |
| NM_130771>OSCAR | OSCAR | NM_130771 | 0.00087193 |
| NM_133168>OSCAR | OSCAR | NM_133168 | 0.00087195 |
| NM_133169>OSCAR | OSCAR | NM_133169 | 0.00087211 |
| NM_032955>AIF1 | AIF1 | NM_032955 | 0.00096137 |
| NM_001286473>C14orf159 | C14orf159 | NM_001286473 | 0.00096319 |
| NM_020979>SH2B2 | SH2B2 | NM_020979 | 0.00097423 |
| NM_006428>MRPL28 | MRPL28 | NM_006428 | 0.00098373 |
| NM_001271819>ORAI2 | ORAI2 | NM_001271819 | 0.00100025 |
| NM_005798>TRIM13 | TRIM13 | NM_005798 | 0.00104837 |
| NM_001025238>TSPAN4 | TSPAN4 | NM_001025238 | 0.0011929 |
| NM_001284237>ZFYVE16 | ZFYVE16 | NM_001284237 | 0.00139031 |
| NR_047701>COA1 | COA1 | NR_047701 | 0.00140464 |
| NR_003140.7>SNORD117 | SNORD117 | NR_003140.7 | 0.00145813 |
| NM_001040440>CCDC112 | CCDC112 | NM_001040440 | 0.0015703 |
| NM_001243878>FHL3 | FHL3 | NM_001243878 | 0.00172631 |
| NM_001290222>NQO2 | NQO2 | NM_001290222 | 0.00181379 |
| NR_029478>MIRLET7A3 | MIRLET7A3 | NR_029478 | 0.00183984 |
| NM_001197234>BTN2A1 | BTN2A1 | NM_001197234 | 0.00193406 |
| NR_002605>DLEU1 | DLEU1 | NR_002605 | 0.00195495 |
| NR_028505>MIR22HG | MIR22HG | NR_028505 | 0.00200373 |
| NR_051980>MINOS1P1 | MINOS1P1 | NR_051980 | 0.00201321 |
| NM_001244898>PTBP3 | PTBP3 | NM_001244898 | 0.00217963 |
| NM_152889>CHST13 | CHST13 | NM_152889 | 0.00224819 |
| NM_001277224>TAGLN2 | TAGLN2 | NM_001277224 | 0.00229155 |
| NR_037937>SCNM1 | SCNM1 | NR_037937 | 0.00233534 |
| NM_138730>HMGN3 | HMGN3 | NM_138730 | 0.00235072 |
| NM_148962>OXER1 | OXER1 | NM_148962 | 0.00240808 |
| NM_002729>HHEX | HHEX | NM_002729 | 0.00254469 |
| NR_040030>CFLAR-AS1 | CFLAR-AS1 | NR_040030 | 0.00289549 |
| NR_110146>VNN2 | VNN2 | NR_110146 | 0.00294559 |
| NM_018993>RIN2 | RIN2 | NM_018993 | 0.00302295 |
| NM_002514>NOV | NOV | NM_002514 | 0.00304015 |
| NM_173527>REM2 | REM2 | NM_173527 | 0.00356599 |
| NR_103549>LUCAT1 | LUCAT1 | NR_103549 | 0.00379271 |
| NR_036503>PRKCQ-AS1 | PRKCQ-AS1 | NR_036503 | 0.00382665 |
| NM_001666>ARHGAP4 | ARHGAP4 | NM_001666 | 0.00392569 |
| NM_001164741>ARHGAP4 | ARHGAP4 | NM_001164741 | 0.00392606 |
| NR_120600>PRMT5-AS1 | PRMT5-AS1 | NR_120600 | 0.00399138 |
| NM_001012959>DISC1 | DISC1 | NM_001012959 | 0.00412158 |
| NM_003104>SORD | SORD | NM_003104 | 0.00440187 |
| NM_005461>MAFB | MAFB | NM_005461 | 0.00461273 |
| NM_207354>ANKRD13D | ANKRD13D | NM_207354 | 0.00462185 |
| NM_017723>TOR4A | TOR4A | NM_017723 | 0.00473781 |
| NM_001567>INPPL1 | INPPL1 | NM_001567 | 0.00513417 |
| NM_002068>GNA15 | GNA15 | NM_002068 | 0.00516178 |
| NM_006480>RGS14 | RGS14 | NM_006480 | 0.00528027 |
| NR_003042>SNORD45C | SNORD45C | NR_003042 | 0.00533478 |
| NM_014098>PRDX3 | PRDX3 | NM_014098 | 0.00534763 |
| NM_153690>FAM43A | FAM43A | NM_153690 | 0.0053505 |
| NM_001127586>ING4 | ING4 | NM_001127586 | 0.00547331 |
| NM_017628>TET2 | TET2 | NM_017628 | 0.00547411 |
| NM_182491>ZFAND2A | ZFAND2A | NM_182491 | 0.00559846 |
| NM_032353>VPS25 | VPS25 | NM_032353 | 0.00564435 |
| NM_016538>SIRT7 | SIRT7 | NM_016538 | 0.00570906 |
| NM_001242831>ELOVL5 | ELOVL5 | NM_001242831 | 0.00579687 |
| NR_120485>IL7R | IL7R | NR_120485 | 0.00603421 |
| NM_001289406>MFSD1 | MFSD1 | NM_001289406 | 0.0061122 |
| NR_038975>MIR181A2HG | MIR181A2HG | NR_038975 | 0.00612369 |
| NM_005999>TSNAX | TSNAX | NM_005999 | 0.00613635 |
| NR_030767>ANKRD13D | ANKRD13D | NR_030767 | 0.00621972 |
| NM_025080>ASRGL1 | ASRGL1 | NM_025080 | 0.00626114 |
| NM_003656>CAMK1 | CAMK1 | NM_003656 | 0.00631752 |
| NM_001291478>AKAP8L | AKAP8L | NM_001291478 | 0.00634315 |
| NM_001286766>KIAA0226L | KIAA0226L | NM_001286766 | 0.00638614 |
| NM_005793>PRDX3 | PRDX3 | NM_006793 | 0.00639539 |

TABLE 17-continued

Blood PAXgene NGS Signatures for subAR using a 3-Way 1-Step approach
(AR vs. subAR vs. TX): full gene list (123 genes) at p < 0.01

| Probeset ID | Gene Symbol | Transcript | p-value |
|---|---|---|---|
| NR_103791>LINC01127 | LINC01127 | NR_103791 | 0.00640001 |
| NR_036514>C17orf62 | C17orf62 | NR_036514 | 0.00656751 |
| NM_001278243>ZFAND5 | ZFAND5 | NM_001278243 | 0.00657954 |
| NM_001040059>CD68 | CD68 | NM_001040059 | 0.00664828 |
| NM_001287060>RABGEF1 | RABGEF1 | NM_001287060 | 0.00680239 |
| NM_001113738.2>ARL17A | ARL17A | NM_001113738.2 | 0.00682141 |
| NM_152288>ORAI3 | ORAI3 | NM_152288 | 0.00700377 |
| NM_001167903>MFSD1 | MFSD1 | NM_001167903 | 0.00705708 |
| NM_021134>MRPL23 | MRPL23 | NM_021134 | 0.00707961 |
| NM_001012727>AGPAT2 | AGPAT2 | NM_001012727 | 0.00714772 |
| NM_018370>DRAM1 | DRAM1 | NM_018370 | 0.00733689 |
| NM_022898>BCL11B | BCL11B | NM_022898 | 0.00735164 |
| NM_001282238>BCL11B | BCL11B | NM_001282238 | 0.00735456 |
| NM_006720>ABLIM1 | ABLIM1 | NM_006720 | 0.00741649 |
| NR_027330>SND1-IT1 | SND1-IT1 | NR_027330 | 0.00753502 |
| NM_152581>MOSPD2 | MOSPD2 | NM_152581 | 0.00761177 |
| NM_001985>ETFB | ETFB | NM_001985 | 0.00762131 |
| NM_016243>CYB5R1 | CYB5R1 | NM_016243 | 0.00764199 |
| NM_203458>NOTCH2NL | NOTCH2NL | NM_203458 | 0.00765447 |
| NM_004907>IER2 | IER2 | NM_004907 | 0.00767968 |
| NM_001278245>ZFAND5 | ZFAND5 | NM_001278245 | 0.00780399 |
| NM_024832>RIN3 | RIN3 | NM_024832 | 0.00799293 |
| NR_103518>LILRB1 | LILRB1 | NR_103518 | 0.00799882 |
| NM_145030>PPP1R35 | PPP1R35 | NM_145030 | 0.00804432 |
| NM_002555>SLC22A18 | SLC22A18 | NM_002555 | 0.00805737 |
| NM_001142391>SLC10A3 | SLC10A3 | NM_001142391 | 0.00826523 |
| NM_017607>PPP1R12C | PPP1R12C | NM_017607 | 0.0083532 |
| NM_033313>CDC14A | CDC14A | NM_033313 | 0.00835701 |
| NM_001271618>PPP1R12C | PPP1R12C | NM_001271618 | 0.00836024 |
| NM_173804>TMEM86B | TMEM86B | NM_173804 | 0.00852912 |
| NR_034140>LINC00612 | LINC00612 | NR_034140 | 0.00856223 |
| NM_080590>CAPS | CAPS | NM_080590 | 0.00868781 |
| NR_046591>DPYD-AS2 | DPYD-AS2 | NR_046591 | 0.00887841 |
| NM_020170>NCLN | NCLN | NM_020170 | 0.00906534 |
| NM_023935>DDRGK1 | DDRGK1 | NM_023935 | 0.00910211 |
| NR_102308>CACNG6 | CACNG6 | NR_102308 | 0.00910804 |
| NR_027154>SMG1P1 | SMG1P1 | NR_027154 | 0.00911855 |
| NR_102405>NBPF8 | NBPF8 | NR_102405 | 0.00916001 |
| NM_183233>SLC22A18 | SLC22A18 | NM_183233 | 0.0091612 |
| NR_036512>LOC100129917 | LOC100129917 | NR_036512 | 0.00924015 |
| NM_002223>ITPR2 | ITPR2 | NM_002223 | 0.00932503 |
| NM_001282948>JMJD1C | JMJD1C | NM_001282948 | 0.00945087 |
| NM_001270483>TST | TST | NM_001270483 | 0.00949873 |
| NM_024537>CARS2 | CARS2 | NM_024537 | 0.00957495 |
| NM_174958>ATP2A3 | ATP2A3 | NM_174958 | 0.0096019 |
| NM_001669>ARSD | ARSD | NM_001669 | 0.00974531 |
| NM_001042572>CHD2 | CHD2 | NM_001042572 | 0.0098763 |

TABLE 18

Blood PAXgene NGS for subAR using a 3-Way 1-Step approach (AR vs. subAR vs. TX): best performing gene signature (53 genes)

| Gene ID | Gene Symbol | Transcript |
|---|---|---|
| NM_001123228>TMEM14E | TMEM14E | NM_001123228 |
| NM_001375>DNASE2 | DNASE2 | NM_001375 |
| NM_003107>SOX4 | SOX4 | NM_003107 |
| NM_148901>TNFRSF18 | TNFRSF18 | NM_148901 |
| NR_109780>LOC100506860 | LOC100506860 | NR_109780 |
| NM_001336>CTSZ | CTSZ | NM_001336 |
| NR_109851>LINC-PINT | LINC-PINT | NR_109851 |
| NM_021991>JUP | JUP | NM_021991 |
| NR_022011>PWARSN | PWARSN | NR_022011 |
| NM_001146190>ZNF407 | ZNF407 | NM_001146190 |
| NM_130771>OSCAR | OSCAR | NM_130771 |
| NM_133168>OSCAR | OSCAR | NM_133168 |
| NM_133169>OSCAR | OSCAR | NM_133169 |
| NM_032955>AIF1 | AIF1 | NM_032955 |
| NM_001286473>C14orf159 | C14orf159 | NM_001286473 |
| NM_020979>SH2B2 | SH2B2 | NM_020979 |
| NM_006428>MRPL28 | MRPL28 | NM_006428 |
| NM_001271819>ORAI2 | ORAI2 | NM_001271819 |
| NM_005798>TRIM13 | TRIM13 | NM_005798 |
| NM_001025238>TSPAN4 | TSPAN4 | NM_001025238 |
| NM_001284237>ZFYVE16 | ZFYVE16 | NM_001284237 |
| NR_047701>COA1 | COA1 | NR_047701 |
| NR_003140.7>SNORD117 | SNORD117 | NR_003140.7 |
| NM_001040440>CCDC112 | CCDC112 | NM_001040440 |
| NM_001243878>FHL3 | FHL3 | NM_001243878 |
| NM_001290222>NQO2 | NQO2 | NM_001290222 |
| NR_029478>MIRLET7A3 | MIRLET7A3 | NR_029478 |
| NM_001197234>BTN2A1 | BTN2A1 | NM_001197234 |
| NR_002605>DLEU1 | DLEU1 | NR_002605 |
| NR_028505>MIR22HG | MIR22HG | NR_028505 |
| NR_051980>MINOS1P1 | MINOS1P1 | NR_051980 |
| NM_001244898>PTBP3 | PTBP3 | NM_001244898 |
| NM_152889>CHST13 | CHST13 | NM_152889 |
| NM_001277224>TAGLN2 | TAGLN2 | NM_001277224 |

TABLE 18-continued

Blood PAXgene NGS for subAR using a 3-Way 1-Step approach (AR vs. subAR vs. TX): best performing gene signature (53 genes)

| Gene ID | Gene Symbol | Transcript |
|---|---|---|
| NR_037937>SCNM1 | SCNM1 | NR_037937 |
| NM_138730>HMGN3 | HMGN3 | NM_138730 |
| NM_148962>OXER1 | OXER1 | NM_148962 |
| NM_002729>HHEX | HHEX | NM_002729 |
| NR_040030>CFLAR-AS1 | CFLAR-AS1 | NR_040030 |
| NR_110146>VNN2 | VNN2 | NR_110146 |
| NM_018993>RIN2 | RIN2 | NM_018993 |
| NM_002514>NOV | NOV | NM_002514 |
| NM_173527>REM2 | REM2 | NM_173527 |
| NR_103549>LUCAT1 | LUCAT1 | NR_103549 |
| NR_036503>PRKCQ-AS1 | PRKCQ-AS1 | NR_036503 |
| NM_001666>ARHGAP4 | ARHGAP4 | NM_001666 |
| NM_001164741>ARHGAP4 | ARHGAP4 | NM_001164741 |
| NR_120600>PRMT5-AS1 | PRMT5-AS1 | NR_120600 |
| NM_001012959>DISC1 | DISCI | NM_001012959 |
| NM_003104>SORD | SORD | NM_003104 |
| NM_005461>MAFB | MAFB | NM_005461 |
| NM_207354>ANKRD13D | ANKRD13D | NM_207354 |
| NM_017723>TOR4A | TOR4A | NM_017723 |

TABLE 19

Blood PAXgene NGS analysis results for subAR using a 3-Way 1-Step approach (AR vs. subAR vs. TX)

| Method | Classifies | % Predictive Accuracy | Sensitivity (%) | Specificity (%) | Positive Predictive Value (%) | Negative Predicitve Value (%) | AUC |
|---|---|---|---|---|---|---|---|
| Nearest Centroid (1 Step Prediction) | TX vs. AR | 92% | 95% | 90% | 90% | 95% | 0.921 |
| | TX vs. SCAR | 83% | 83% | 82% | 83% | 82% | 0.829 |
| | AR vs. SCAR | 93% | 94% | 95% | 94% | 95% | 0.943 |

| | TX | SCAR | AR |
|---|---|---|---|
| TX | 19 | 4 | 2 |
| SCAR | 4 | 18 | 1 |
| AR | 1 | 1 | 19 |

We claim:

1. A method of treating a transplant recipient on an immunosuppressive drug comprising:
   (a) obtaining nucleic acids of interest, wherein the nucleic acids of interest comprise mRNA derived from a blood sample from the transplant recipient or cDNA complements of mRNA derived from a blood sample from the transplant recipient wherein the transplant recipient has a serum creatinine level that is stable and less than 2.3 mg/dL;
   (b) performing a microarray assay or Next Generation sequencing assay on the nucleic acids of interest obtained in (a) to detect expression levels of at least five genes, wherein the at least five genes are capable of specifically detecting subclinical acute rejection (subAR) in a transplant patient with stable serum creatinine levels;
   (c) detecting subclinical acute rejection in the transplant recipient that has the serum creatinine level that is stable and less than 2.3 mg/dL based on the expression levels detected in (b); and
   (d) administering a new immunosuppressive drug or a higher dose of the immunosuppressive drug to the transplant recipient in order to treat the subclinical acute rejection detected in (c).

2. The method of claim 1, wherein the transplant recipient that has the serum creatinine level that is stable and less than 2.3 mg/dL also has normal serum creatinine levels.

3. The method of claim 1, further comprising contacting the nucleic acids of interest with probes, wherein the probes are specific for the at least five genes selected in (b).

4. The method of claim 1, wherein the method is repeated at different times on the transplant recipient that has the serum creatinine level that is stable and less than 2.3 mg/dL.

5. The method of claim 1, wherein the transplant recipient that has the serum creatinine level that is stable and less than 2.3 mg/dL is a kidney transplant recipient.

6. The method of claim 1, wherein the blood sample in (a) comprises whole blood, peripheral blood, serum, plasma, peripheral blood lymphocytes (PBLs), peripheral blood mononuclear cells (PBMCs), T cells, CD4 T cells, CD8 T cells, or macrophages.

7. The method of claim 1, comprising administering the new immunosuppressive drug to the transplant recipient that has the serum creatinine level that is stable and less than 2.3 mg/dL based on the expression levels detected in (b).

8. The method of claim 1, further comprising performing a kidney biopsy or serum creatinine test to detect subAR or risk thereof based on the expression levels detected in (b).

9. The method of claim 1, comprising performing the Next Generation sequencing assay on the nucleic acids of interest obtained in (a).

10. The method of claim 1, comprising performing the microarray assay on the nucleic acids of interest obtained in (a) wherein the performing the microarray assay on the nucleic acids of interest obtained in (a) comprises hybridizing the mRNA or DNA complements of mRNA from the transplant recipient that has the serum creatinine level that is stable and less than 2.3 mg/dL to a probe set, wherein the probe set comprises one or more oligonucleotides and wherein the probe set specifically detects subAR in a transplant patient with stable serum creatinine levels.

11. The method of claim 1, wherein the transplant recipient that has the serum creatinine level that is stable and less than 2.3 mg/dL has a normal or stable eGFR.

12. The method of claim 1, wherein the transplant recipient that has the serum creatinine level that is stable and less than 2.3 mg/dL has a serum creatinine not exceeding 20% of a baseline value of the kidney transplant recipient.

13. The method of claim 1, additionally comprising reporting the subclinical acute rejection detected in (c) or the expression levels detected in (b) to a caregiver.

14. The method of claim 1, wherein the immunosuppressive drug or the new immunosuppressive drug is a calcineurin inhibitor, an mTOR inhibitor, an anti-proliferative, a corticosteroid, or an anti-T-cell antibody.

15. The method of claim 1, wherein the immunosuppressive drug or new immunosuppressive drug is cyclosporine, tacrolimus, sirolimus, everolimus, azathioprine, mycophenolic acid, prednisone, hydrocortisone, basiliximab, daclizumab, Orthoclone, anti-thymocyte globulin or anti-lymphocyte globulin.

16. The method of claim 1, further comprising repeating (a)-(c) after administration of the new immunosuppressive drug or higher dose of the immunosuppressive drug.

17. The method of claim 1, comprising administering a new immunosuppressive drug in (d).

18. The method of claim 17, comprising terminating administration of the new immunosuppressive drug after repeating (a)-(c).

19. The method of claim 1, comprising detecting expression levels of at least five genes capable of specifically detecting subclinical acute rejection selected from the group consisting of the genes recited in Tables 2, 3, 4, 7, 8, 11, 12, 14, 15, 17, and 18.

20. The method of claim 1, comprising performing the microarray assay on the nucleic acids of interest obtained in (a).

* * * * *

UNITED STATES PATENT AND TRADEMARK OFFICE
CERTIFICATE OF CORRECTION

| | | |
|---|---|---|
| PATENT NO. | : 10,443,100 B2 | Page 1 of 1 |
| APPLICATION NO. | : 15/358390 | |
| DATED | : October 15, 2019 | |
| INVENTOR(S) | : Salomon et al. | |

It is certified that error appears in the above-identified patent and that said Letters Patent is hereby corrected as shown below:

In the Specification

Column 1, Lines 20-25, the paragraph STATEMENT CONCERNING GOVERNMENT SUPPORT should be changed to:
-- STATEMENT OF GOVERNMENT LICENSE RIGHTS
This invention was made with government support under grant numbers AI063603, AI084146, and AI052349 awarded by the National Institutes of Health. The government has certain rights in the invention. --

Signed and Sealed this
Seventh Day of April, 2020

Andrei Iancu
*Director of the United States Patent and Trademark Office*